(12) United States Patent
Feutrill et al.

(10) Patent No.: US 12,215,112 B2
(45) Date of Patent: Feb. 4, 2025

(54) CD151 INHIBITORS

(71) Applicant: ESFAM BIOTECH PTY LTD, Melbourne (AU)

(72) Inventors: John Thomas Feutrill, Rosanna (AU); Jean-Marc Garnier, Ocean Grove (AU); Albert George Frauman, Melbourne (AU)

(73) Assignee: ESFAM BIOTECH PTY LTD, Melbourne (AU)

( * ) Notice: Subject to any disclaimer, the term of this patent is extended or adjusted under 35 U.S.C. 154(b) by 83 days.

(21) Appl. No.: 18/006,978

(22) PCT Filed: Jul. 27, 2021

(86) PCT No.: PCT/AU2021/050816
§ 371 (c)(1),
(2) Date: Jan. 26, 2023

(87) PCT Pub. No.: WO2022/020888
PCT Pub. Date: Feb. 3, 2022

(65) Prior Publication Data
US 2023/0365567 A1    Nov. 16, 2023

(30) Foreign Application Priority Data
Jul. 27, 2020  (AU) ................................ 2020902630

(51) Int. Cl.
*C07D 487/04* (2006.01)
(52) U.S. Cl.
CPC ................. *C07D 487/04* (2013.01)

(58) Field of Classification Search
CPC ............................ C07D 235/18; C07D 487/04
See application file for complete search history.

(56) References Cited

FOREIGN PATENT DOCUMENTS

| WO | WO 2005/063755 A1 | 7/2005 | |
|---|---|---|---|
| WO | WO 2009/123986 A1 | 10/2009 | |
| WO | WO-2018145080 A1 * | 8/2018 | ......... A61K 31/4365 |
| WO | WO 2022/020887 A1 | 2/2022 | |
| WO | WO 2022/020889 A1 | 2/2022 | |
| WO | WO 2022/020890 A1 | 2/2022 | |
| WO | WO 2022/020891 A1 | 2/2022 | |

OTHER PUBLICATIONS

Pubchem CID 46975591. Indexed Nov. 25, 2010 (Year: 2010).*
Dawane et al., "Design, Synthesis, and Characterization of Some Novel Pyrazolo [1,5-a] Pyrimidines as Potent Antimicrobial Agents", *Journal of Heterocyclic Chemistry* 47(5):1250-1254 (2010).
International Search Report and Written Opinion for International Application No. PCT/AU2021/050816, mailed Aug. 26, 2021, 9 pages.
Shaikh, et al., "PEG-400: prompted eco-friendly synthesis of some novel pyrazolo [1, 5-a] pyrimidine derivatives and their in vitro antimicrobial evaluation", *Journal of Chemical and Pharmaceutical Research* 3(2):435-443 (2011).
Extended European Search Report for Application No. 21849186.8 dated Aug. 1, 2024, 7 pages.

* cited by examiner

*Primary Examiner* — Theodore R. Howell
*Assistant Examiner* — George W Kosturko
(74) *Attorney, Agent, or Firm* — Lathrop GPM LLP; Brian C. Trinque

(57) ABSTRACT

The present invention relates to compounds of formula (I) that have the ability to inhibit CD151.

19 Claims, 1 Drawing Sheet

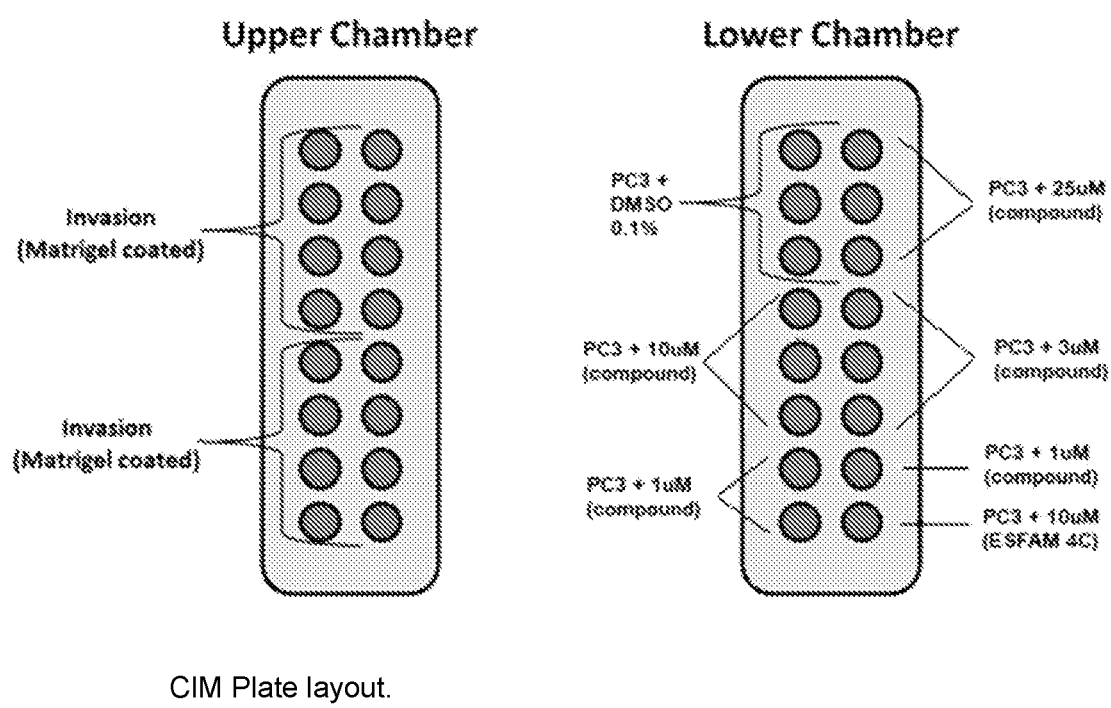
CIM Plate layout.

CD151 INHIBITORS

TECHNICAL FIELD

The present invention relates to compounds that the applicant has found to be inhibitors of CD151. As a result of this activity these compounds can be used in the treatment of medical indications associated with this transmembrane domain cell surface protein. Accordingly, the compounds may find application in the treatment of cancers as well as asthma, multiple sclerosis and inflammatory bowel disease by way of example. The compounds may also find application in the treatment of certain animal diseases also associated with CD151.

BACKGROUND OF INVENTION

In the last 200 years there has been significant progress made in medical research such that average life expectancy has dramatically increased as effective medical treatments have been developed for a significant number of diseases/conditions.

Nevertheless, there is still an ongoing drive to provide treatments for those diseases and conditions for which no effective treatment is available. Accordingly, there is significant research conducted into biological targets that may be implicated in many of the medical conditions of interest.

One area of interest are the tetraspanins. The tetraspanins are a superfamily of four transmembrane domain cell surface proteins and include the tumour suppressor KAI1/CD82 and the tumour promoter CD151. Tetraspanins are expressed in a wide variety of cell types and are of relevance to cancer progression. In particular, tetraspanins may be involved in cellular adhesion, cell motility and tumour suppression or activation. The tetraspanins are thought to regulate their activities via the organisation of a cell surface membrane microdomain which facilitates their interaction with a range of other proteins such as integrins, immunoreceptors and signalling molecules.

CD151 is a member of the tetraspanin super family, which associates with integrins, membrane receptors, intracellular signaling molecules (such as P14K and PKC), immunoglobulins and other tetraspanins; such tetraspanin-enriched microdomains (TEMs) act as molecular facilitators (Kumari S et al, Biomarkers in Cancer 2015; 7: 7-11).

CD151 is responsible for maintaining wound healing, platelet aggregation, epithelial cell integrity, cell migration, angiogenesis and tumor metastasis. Its expression is ubiquitous, but it is frequently over-expressed in cancer cells where it is associated with cancer progression and metastasis.

The over-expression of CD151 has been associated with a large range of common human cancers including prostate (Ang J et al, Cancer Epidemiol Biomarkers Prev 2004; 13(11 Pt 1): 1717-1721), breast (Yang X H et al, Cancer Res 2008; 68: 3204-3213), pancreas (Zhu G H et al, Dig Dis Sci 2011; 56: 1090-1098), colonic cancer (Hashida H et al, Br J Cancer 2003; 89: 158-167) and non-small cell lung cancer (Tokuhara T et al, Clin Cancer Res 2001; 7: 4109-4114). Other cancers where CD151 is over-expressed are hepatocellular (Ke A W et al, Hepatology 2009; 49: 491-503), intrahepatic cholangiocarcinoma (Huang X Y et al, Cancer 2010; 116: 5440-5451), renal cell carcinoma (Yoo S H et al, Histopathology 2011; 58: 191-197), endometrial carcinoma (Voss M A et al, Br J Cancer 2011; 104: 1611-1618), oesophageal carcinoma (Suzuki S et al, Ann Surg Oncol 2011; 18: 888-893), squamous cell carcinoma (Li Q et al, Oncogene 2013; 32: 1772-1783), glioblastoma multiforme (Lee D et al, J Surg Oncol 2013; 107: 646-652), melanoma (Saito N et al, Pigment Cell Melanoma Res 2009; 22: 601-610) and ovarian carcinoma (Medrano M et al, Cell Rep 2017; 18: 2343-2358).

A number of non-cancerous medical conditions are also associated with over-expression of CD151, e.g. asthma (Qiao Y et al, J Allergy Clin Immunol 2017; 139: 82-92), inflammatory bowel disease(Zelman-Toister E et al, Inflamm Bowel Dis 2016; 22: 257-267), multiple sclerosis Lombardo, S. D.; Mazzon, E.; Basile, M. S.; Campo, G.; Corsico, F.; Presti, M.; Bramanti, P.; Mangano, K; Petralia, M. C.; Nicoletti, F; Fagone, P. Modulation of Tetraspanin 32 (TSPAN32) Expression in T Cell-Mediated Immune Responses and in Multiple Sclerosis, Int. J. Mol. Sci. 2019, 20, 4323.and cytomegalovirus infection (Hochdorfer D et al, Journal of Virology 2016; 90: 6430-6442), as well as human papillomavirus type 16 infection (linked to carcinoma of the female genital tract) (Spoden G et al, PLoS One 2008; 3: 1-15) Other infective agents associated with CD151 include *Neisseria meningitidis*, the agent responsible for meningococcal meningitis (Hauck C R et al, Curr Opin Microbiol 2003; 6: 43-49 and Green L R et al, Infect Immun 2001; 79: 2241-2249) and the influenza virus (Qiao Y et al, J Allergy Clin Immunol 2018; 141: 1799-1817.

As such there is significant interest in developing inhibitors of CD151 as it would be anticipated that compounds with this ability would be useful in the treatment of these disorders.

SUMMARY OF THE INVENTION

The present applicants have therefore studied the expression of CD151 with a view to identifying inhibitors of its function that may find application in the treatment of conditions in which over-expression is implicated.

As a result of these studies the applicants have identified compounds that inhibit CD151.

Accordingly, in one embodiment the present invention provides a compound of Formula (I):

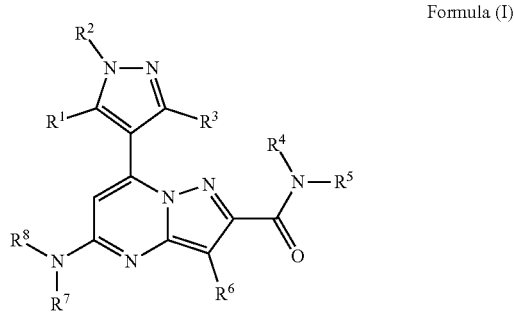

Formula (I)

wherein $R^1$, $R^2$ and $R^3$ are each independently selected from the group consisting of H and $C_1$-$C_{12}$alkyl;

$R^4$ is selected from the group consisting of H and $C_1$-$C_{12}$alkyl;

$R^5$ is selected from the group consisting of H, optionally substituted $C_6$-$C_{18}$aryl, optionally substituted $C_1$-$C_{18}$heteroaryl, optionally substituted $C_6$-$C_{18}$aryl$C_1$-$C_{12}$alkyl-, and optionally substituted $C_1$-$C_{18}$heteroaryl$C_1$-$C_{12}$alkyl-;

$R^6$ is selected from the group consisting of H, $C_1$-$C_{12}$alkyl, $C_3$-$C_6$ cycloalkyl and $C_1$-$C_5$ heterocyloalkyl;

$R^7$ is selected from the group consisting of H and $C_1$-$C_{12}$alkyl;

$R^8$ is selected from the group consisting of H, $C_1$-$C_{12}$alkyl, optionally substituted $C_6$-$C_{18}$aryl optionally substituted $C_1$-$C_{18}$heteroaryl, optionally substituted $C_6$-$C_{18}$aryl$C_1$-$C_{12}$alkyl-, and optionally substituted $C_1$-$C_{18}$heteroaryl$C_1$-$C_{12}$alkyl-;

or $R^7$ and $R^8$ when taken together with the nitrogen atom to which they are attached form a $C_2$-$C_{12}$heterocyclic group;

or a pharmaceutically acceptable salt thereof.

The compounds of the present invention have been found to have the ability to inhibit CD151 in humans and are thus able to be used in the treatment of conditions associated with expression of this gene.

In yet an even further aspect the present invention provides a pharmaceutical composition comprising a compound according to Formula (I) and a pharmaceutically acceptable diluent, excipient or carrier.

BRIEF DESCRIPTION OF THE DRAWINGS

FIG. 1 is a schematic diagram of a 16-well ACEA Cell invasion/migration (CIM) plate layout that was used in conjunction with an XCELLigence® real-time cell analysis (RTCA) instrument from ACEA Biosciences to measure cell invasion over 72 hours.

DETAILED DESCRIPTION

In this specification a number of terms are used that are well known to a skilled addressee. Nevertheless, for the purposes of clarity a number of terms will be defined.

Throughout the description and the claims of this specification the word "comprise" and variations of the word, such as "comprising" and "comprises" is not intended to exclude other additives, components, integers or steps.

The term "inhibit" and variations thereof such as "inhibiting" means to prevent, block or reduce the function of the thing being inhibited. The term does not require complete inhibition with a reduction of activity at least 50% being considered inhibition.

In the definitions of a number of substituents below it is stated that "the group may be a terminal group or a bridging group". This is intended to signify that the use of the term is intended to encompass the situation where the group is a linker between two other portions of the molecule as well as where it is a terminal moiety. Using the term alkyl as an example, some publications would use the term "alkylene" for a bridging group and hence in these other publications there is a distinction between the terms "alkyl" (terminal group) and "alkylene" (bridging group). In the present application no such distinction is made and most groups may be either a bridging group or a terminal group.

In this specification terms are used which are well known to a skilled addressee. Nevertheless, for the purposes of clarity a number of these terms will be defined.

As used herein, the term "unsubstituted" means that there is no substituent or that the only substituents are hydrogen.

The term "optionally substituted" as used throughout the specification denotes that the group may or may not be further substituted or fused (so as to form a condensed polycyclic system), with one or more non-hydrogen substituent groups. If an optional substituent is present then the substituent groups are one or more groups independently selected from the group consisting of halogen, =O, =S, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, heteroarylalkyl, arylalkyl, cycloalkylalkenyl, heterocycloalkylalkenyl, arylalkenyl, heteroarylalkenyl, cycloalkylheteroalkyl, heterocycloalkylheteroalkyl, arylheteroalkyl, heteroarylheteroalkyl, hydroxy, hydroxyalkyl, alkyloxy, alkyloxyalkyl, alkyloxycycloalkyl, alkyloxyheterocycloalkyl, alkyloxyaryl, alkyloxyheteroaryl, alkyloxycarbonyl, alkylaminocarbonyl, alkenyloxy, alkynyloxy, cycloalkyloxy, cycloalkenyloxy, heterocycloalkyloxy, heterocycloalkenyloxy, aryloxy, phenoxy, benzyloxy, heteroaryloxy, arylalkyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, alkylsulfinyl, arylsulfinyl, aminosulfinylaminoalkyl, —C(=O)OH, —C(=O)R$^e$, —C(=O)OR$^e$, C(=O)NR$^e$R$^f$, C(=NOH)R$^e$, C(=NR$^e$)NR$^f$R$^g$, NR$^e$R$^f$, NR$^e$C(=O)R$^f$, NR$^e$C(=O)OR$^f$, NR$^e$C(=O)NR$^f$R$^g$, NR$^e$C(=NR$^f$)NR$^g$R$^h$, NR$^e$SO$_2$R$^f$, —SR$^e$, SO$_2$NR$^e$R$^f$, —OR$^e$, OC(=O)NR$^e$R$^f$, OC(=O)R$^e$ and acyl.

wherein R$^e$, R$^f$, R$^g$ and R$^h$ are each independently selected from the group consisting of H, $C_1$-$C_{12}$alkyl, $C_1$-$C_{12}$haloalkyl, $C_2$-$C_{12}$alkenyl, $C_2$-$C_{12}$alkynyl, $C_1$-$C_{10}$heteroalkyl, $C_3$-$C_{12}$cycloalkyl, $C_3$-$C_{12}$cycloalkenyl, $C_1$-$C_{12}$heterocycloalkyl, $C_1$-$C_{12}$heterocycloalkenyl, $C_6$-$C_{18}$aryl, $C_1$-$C_{18}$heteroaryl, and acyl, or any two or more of R$^a$, R$^b$, R$^c$ and R$^d$, when taken together with the atoms to which they are attached form a heterocyclic ring system with 3 to 12 ring atoms.

In some embodiments each optional substituent is independently selected from the group consisting of: halogen, =O, =S, —CN, —NO$_2$, —CF$_3$, —OCF$_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, hydroxy, hydroxyalkyl, alkyloxy, alkyloxyalkyl, alkyloxyaryl, alkyloxyheteroaryl, alkenyloxy, alkynyloxy, cycloalkyloxy, cycloalkenyloxy, heterocycloalkyloxy, heterocycloalkenyloxy, aryloxy, heteroaryloxy, arylalkyl, heteroarylalkyl, arylalkyloxy, amino, alkylamino, acylamino, aminoalkyl, arylamino, sulfonyl, alkylsulfonyl, arylsulfonyl, aminosulfonyl, aminoalkyl, —COOH, —SH, and acyl.

Examples of particularly suitable optional substituents include F, Cl, Br, I, CH$_3$, CH$_2$CH$_3$, OH, OCH$_3$, CF$_3$, OCF$_3$, NO$_2$, NH$_2$, and CN.

"Acyl" means an R—C(=O)— group in which the R group may be an alkyl, cycloalkyl, heterocycloalkyl, aryl or heteroaryl group as defined herein. Examples of acyl include acetyl and benzoyl. The group may be a terminal group or a bridging group. If the group is a terminal group, it is bonded to the remainder of the molecule through the carbonyl carbon.

"Acylamino" means an R—C(=O)—NH— group in which the R group may be an alkyl, cycloalkyl, heterocycloalkyl, aryl or heteroaryl group as defined herein. The group may be a terminal group or a bridging group. If the group is a terminal group, it is bonded to the remainder of the molecule through the nitrogen atom.

"Alkenyl" as a group or part of a group denotes an aliphatic hydrocarbon group containing at least one carbon-carbon double bond and which may be straight or branched preferably having 2-12 carbon atoms, more preferably 2-10 carbon atoms, most preferably 2-6 carbon atoms, in the normal chain. The group may contain a plurality of double bonds in the normal chain and the orientation about each is independently E or Z. The alkenyl group is preferably a 1-alkenyl group. Exemplary alkenyl groups include, but are not limited to, ethenyl, propenyl, butenyl, pentenyl, hexenyl, heptenyl, octenyl and nonenyl. The group may be a terminal group or a bridging group.

"Alkenyloxy" refers to an alkenyl-O— group in which alkenyl is as defined herein. Preferred alkenyloxy groups are $C_1$-$C_6$alkenyloxy groups. The group may be a terminal group or a bridging group. If the group is a terminal group, it is bonded to the remainder of the molecule through the oxygen atom.

"Alkyl" as a group or part of a group refers to a straight or branched aliphatic hydrocarbon group, preferably a $C_1$-$C_{12}$ alkyl, more preferably a $C_1$-$C_{10}$ alkyl, most preferably $C_1$-$C_6$ unless otherwise noted. Examples of suitable straight and branched $C_1$-$C_6$ alkyl substituents include methyl, ethyl, n-propyl, 2-propyl, n-butyl, sec-butyl, t-butyl, hexyl, and the like. The group may be a terminal group or a bridging group.

"Alkylamino" includes both mono-alkylamino and dialkylamino, unless specified. "Mono-alkylamino" means an Alkyl-NH— group, in which alkyl is as defined herein. "Dialkylamino" means a (alkyl)$_2$N-group, in which each alkyl may be the same or different and are each as defined herein for alkyl. The alkyl group is preferably a $C_1$-$C_6$alkyl group. The group may be a terminal group or a bridging group. If the group is a terminal group, it is bonded to the remainder of the molecule through the nitrogen atom.

"Alkylaminocarbonyl" refers to a group of the formula (Alkyl)$_x$(H)$_y$NC(=O)— in which alkyl is as defined herein, x is 1 or 2, and the sum of X+Y=2. The group may be a terminal group or a bridging group. If the group is a terminal group, it is bonded to the remainder of the molecule through the carbonyl carbon.

"Alkyloxy" refers to an alkyl-O— group in which alkyl is as defined herein. Preferably the alkyloxy is a $C_1$-$C_6$alkyloxy. Examples include, but are not limited to, methoxy and ethoxy. The group may be a terminal group or a bridging group.

"Alkyloxyalkyl" refers to an alkyloxy-alkyl-group in which the alkyloxy and alkyl moieties are as defined herein. The group may be a terminal group or a bridging group. If the group is a terminal group, it is bonded to the remainder of the molecule through the alkyl group.

"Alkyloxyaryl" refers to an alkyloxy-aryl- group in which the alkyloxy and aryl moieties are as defined herein. The group may be a terminal group or a bridging group. If the group is a terminal group, it is bonded to the remainder of the molecule through the aryl group.

"Alkyloxycarbonyl" refers to an alkyl-O—C(=O)— group in which alkyl is as defined herein. The alkyl group is preferably a $C_1$-$C_6$ alkyl group. Examples include, but are not limited to, methoxycarbonyl and ethoxycarbonyl. The group may be a terminal group or a bridging group. If the group is a terminal group, it is bonded to the remainder of the molecule through the carbonyl carbon.

"Alkyloxycycloalkyl" refers to an alkyloxy-cycloalkyl- group in which the alkyloxy and cycloalkyl moieties are as defined herein. The group may be a terminal group or a bridging group. If the group is a terminal group, it is bonded to the remainder of the molecule through the cycloalkyl group.

"Alkyloxyheteroaryl" refers to an alkyloxy-heteroaryl- group in which the alkyloxy and heteroaryl moieties are as defined herein. The group may be a terminal group or a bridging group. If the group is a terminal group, it is bonded to the remainder of the molecule through the heteroaryl group.

"Alkyloxyheterocycloalkyl" refers to an alkyloxy-heterocycloalkyl- group in which the alkyloxy and heterocycloalkyl moieties are as defined herein. The group may be a terminal group or a bridging group. If the group is a terminal group, it is bonded to the remainder of the molecule through the heterocycloalkyl group.

"Alkylsulfinyl" means an alkyl-S—(=O)— group in which alkyl is as defined herein. The alkyl group is preferably a $C_1$-$C_6$ alkyl group. Exemplary alkylsulfinyl groups include, but not limited to, methylsulfinyl and ethylsulfinyl. The group may be a terminal group or a bridging group. If the group is a terminal group, it is bonded to the remainder of the molecule through the sulfur atom.

"Alkylsulfonyl" refers to an alkyl-S(=O)$_2$— group in which alkyl is as defined above. The alkyl group is preferably a $C_1$-$C_6$alkyl group. Examples include, but not limited to methylsulfonyl and ethylsulfonyl. The group may be a terminal group or a bridging group. If the group is a terminal group, it is bonded to the remainder of the molecule through the sulfur atom.

"Alkynyl" as a group or part of a group means an aliphatic hydrocarbon group containing a carbon-carbon triple bond and which may be straight or branched preferably having from 2-12 carbon atoms, more preferably 2-10 carbon atoms, more preferably 2-6 carbon atoms in the normal chain. Exemplary structures include, but are not limited to, ethynyl and propynyl. The group may be a terminal group or a bridging group.

"Alkynyloxy" refers to an alkynyl-O— group in which alkynyl is as defined herein. Preferred alkynyloxy groups are $C_1$-$C_6$alkynyloxy groups. The group may be a terminal group or a bridging group. If the group is a terminal group, it is bonded to the remainder of the molecule through the oxygen atom.

"Aminoalkyl" means an NH$_2$-alkyl- group in which the alkyl group is as defined herein. The group may be a terminal group or a bridging group. If the group is a terminal group, it is bonded to the remainder of the molecule through the alkyl group.

"Aminosulfonyl" means an NH$_2$—S(=O)$_2$— group. The group may be a terminal group or a bridging group. If the group is a terminal group, it is bonded to the remainder of the molecule through the sulfur atom.

"Aryl" as a group or part of a group denotes (i) an optionally substituted monocyclic, or fused polycyclic, aromatic carbocycle (ring structure having ring atoms that are all carbon) preferably having from 5 to 12 atoms per ring. Examples of aryl groups include phenyl, naphthyl, and the like; (ii) an optionally substituted partially saturated bicyclic aromatic carbocyclic moiety in which a phenyl and a $C_{5-7}$cycloalkyl or $C_{5-7}$cycloalkenyl group are fused together to form a cyclic structure, such as tetrahydronaphthyl, indenyl or indanyl. The group may be a terminal group or a bridging group. Typically, an aryl group is a $C_6$-$C_{18}$ aryl group.

"Arylalkenyl" means an aryl-alkenyl- group in which the aryl and alkenyl are as defined herein. Exemplary arylalkenyl groups include phenylallyl. The group may be a terminal group or a bridging group. If the group is a terminal group, it is bonded to the remainder of the molecule through the alkenyl group.

"Arylalkyl" means an aryl-alkyl- group in which the aryl and alkyl moieties are as defined herein. Preferred arylalkyl groups contain a $C_{1-5}$alkyl moiety. Exemplary arylalkyl groups include benzyl, phenethyl, 1-naphthalenemethyl and 2-naphthalenemethyl. The group may be a terminal group or a bridging group. If the group is a terminal group, it is bonded to the remainder of the molecule through the alkyl group.

"Arylalkyloxy" refers to an aryl-alkyl-O— group in which the alkyl and aryl are as defined herein. The group may be a terminal group or a bridging group. If the group is a terminal group it is bonded to the remainder of the molecule through the oxygen atom.

"Arylamino" includes both mono-arylamino and di-arylamino unless specified. Mono-arylamino means a group of formula arylNH—, in which aryl is as defined herein. Di-arylamino means a group of formula (aryl)$_2$N- where each aryl may be the same or different and are each as defined herein for aryl. The group may be a terminal group or a bridging group. If the group is a terminal group, it is bonded to the remainder of the molecule through the nitrogen atom.

"Arylheteroalkyl" means an aryl-heteroalkyl- group in which the aryl and heteroalkyl moieties are as defined herein. The group may be a terminal group or a bridging group. If the group is a terminal group, it is bonded to the remainder of the molecule through the heteroalkyl group.

"Aryloxy" refers to an aryl-O— group in which the aryl is as defined herein. Preferably the aryloxy is a $C_6$-$C_{18}$aryloxy, more preferably a $C_6$-$C_{10}$aryloxy. The group may be a terminal group or a bridging group. If the group is a terminal group, it is bonded to the remainder of the molecule through the oxygen atom.

"Arylsulfonyl" means an aryl-S(=O)$_2$— group in which the aryl group is as defined herein. The group may be a terminal group or a bridging group. If the group is a terminal group, it is bonded to the remainder of the molecule through the sulfur atom.

A "bond" is a linkage between atoms in a compound or molecule. The bond may be a single bond, a double bond, or a triple bond.

"Cycloalkenyl" means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl. The cycloalkenyl group may be substituted by one or more substituent groups. A cycloalkenyl group typically is a $C_3$-$C_{12}$ alkenyl group. The group may be a terminal group or a bridging group.

"Cycloalkyl" refers to a saturated monocyclic or fused or spiro polycyclic, carbocycle preferably containing from 3 to 9 carbons per ring, such as cyclopropyl, cyclobutyl, cyclopentyl, cyclohexyl and the like, unless otherwise specified. It includes monocyclic systems such as cyclopropyl and cyclohexyl, bicyclic systems such as decalin, and polycyclic systems such as adamantane. A cycloalkyl group typically is a $C_3$-$C_{12}$ alkyl group. The group may be a terminal group or a bridging group.

"Cycloalkylalkyl" means a cycloalkyl-alkyl- group in which the cycloalkyl and alkyl moieties are as defined herein. Exemplary monocycloalkylalkyl groups include cyclopropylmethyl, cyclopentylmethyl, cyclohexylmethyl and cycloheptylmethyl. The group may be a terminal group or a bridging group. If the group is a terminal group, it is bonded to the remainder of the molecule through the alkyl group.

"Cycloalkylalkenyl" means a cycloalkyl-alkenyl- group in which the cycloalkyl and alkenyl moieties are as defined herein. The group may be a terminal group or a bridging group. If the group is a terminal group, it is bonded to the remainder of the molecule through the alkenyl group.

"Cycloalkylheteroalkyl" means a cycloalkyl-heteroalkyl- group in which the cycloalkyl and heteroalkyl moieties are as defined herein. The group may be a terminal group or a bridging group. If the group is a terminal group, it is bonded to the remainder of the molecule through the heteroalkyl group.

"Cycloalkyloxy" refers to a cycloalkyl-O— group in which cycloalkyl is as defined herein. Preferably the cycloalkyloxy is a $C_1$-$C_6$cycloalkyloxy. Examples include, but are not limited to, cyclopropanoxy and cyclobutanoxy. The group may be a terminal group or a bridging group. If the group is a terminal group, it is bonded to the remainder of the molecule through the oxygen atom.

"Cycloalkenyloxy" refers to a cycloalkenyl-O— group in which the cycloalkenyl is as defined herein. Preferably the cycloalkenyloxy is a $C_1$-$C_6$cycloalkenyloxy. The group may be a terminal group or a bridging group. If the group is a terminal group, it is bonded to the remainder of the molecule through the oxygen atom.

"Haloalkyl" refers to an alkyl group as defined herein in which one or more of the hydrogen atoms has been replaced with a halogen atom selected from the group consisting of fluorine, chlorine, bromine and iodine. A haloalkyl group typically has the formula $C_nH_{(2n+1-m)}X_m$ wherein each X is independently selected from the group consisting of F, Cl, Br and I. In groups of this type n is typically from 1 to 10, more preferably from 1 to 6, most preferably 1 to 3. m is typically 1 to 6, more preferably 1 to 3. Examples of haloalkyl include fluoromethyl, difluoromethyl and trifluoromethyl.

"Haloalkenyl" refers to an alkenyl group as defined herein in which one or more of the hydrogen atoms has been replaced with a halogen atom independently selected from the group consisting of F, Cl, Br and I.

"Haloalkynyl" refers to an alkynyl group as defined herein in which one or more of the hydrogen atoms has been replaced with a halogen atom independently selected from the group consisting of F, Cl, Br and I.

"Halogen" represents chlorine, fluorine, bromine or iodine.

"Heteroalkyl" refers to a straight- or branched-chain alkyl group preferably having from 2 to 12 carbons, more preferably 2 to 6 carbons in the chain, in which one or more of the carbon atoms (and any associated hydrogen atoms) are each independently replaced by a heteroatomic group selected from S, O, P and NR' where R' is selected from the group consisting of H, optionally substituted $C_1$-$C_{12}$alkyl, optionally substituted $C_3$-$C_{12}$cycloalkyl, optionally substituted $C_6$-$C_{18}$aryl, and optionally substituted $C_1$-$C_{18}$heteroaryl. Exemplary heteroalkyls include alkyl ethers, secondary and tertiary alkyl amines, amides, alkyl sulfides, and the like. Examples of heteroalkyl also include hydroxy$C_1$-$C_6$alkyl, $C_1$-$C_6$alkyloxy$C_1$-$C_6$alkyl, amino$C_1$-$C_6$alkyl, $C_1$-$C_6$alkylamino$C_1$-$C_6$alkyl, and di($C_1$-$C_6$alkyl)amino$C_1$-$C_6$alkyl. The group may be a terminal group or a bridging group.

"Heteroalkyloxy" refers to a heteroalkyl-O— group in which heteroalkyl is as defined herein. Preferably the heteroalkyloxy is a $C_2$-$C_6$heteroalkyloxy. The group may be a terminal group or a bridging group.

"Heteroaryl" either alone or part of a group refers to groups containing an aromatic ring (preferably a 5 or 6 membered aromatic ring) having one or more heteroatoms as ring atoms in the aromatic ring with the remainder of the ring atoms being carbon atoms. Suitable heteroatoms include nitrogen, oxygen and sulphur. The group may be a monocyclic or bicyclic heteroaryl group. Examples of heteroaryl include thiophene, benzothiophene, benzofuran, benzimidazole, benzoxazole, benzothiazole, benzisothiazole, naphtho[2,3-b]thiophene, furan, isoindolizine, xantholene, phenoxatine, pyrrole, imidazole, pyrazole, pyridine, pyrazine, pyrimidine, pyridazine, tetrazole, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, 2-, 3- or 4- pyridyl, 2-, 3-, 4-, 5-, or 8-quinolyl, 1-, 3-, 4-, or 5-isoquinolinyl 1-, 2-, or 3-indolyl, and 2-, or 3-thienyl. A heteroaryl group is typically a $C_1$-$C_{18}$, sheteroaryl group. The group may be a terminal group or a bridging group.

"Heteroarylalkyl" means a heteroaryl-alkyl group in which the heteroaryl and alkyl moieties are as defined herein. Preferred heteroarylalkyl groups contain a lower alkyl moiety. Exemplary heteroarylalkyl groups include pyridylmethyl. The group may be a terminal group or a bridging group. If the group is a terminal group it is bonded to the remainder of the molecule through the alkyl group.

"Heteroarylalkenyl" means a heteroaryl-alkenyl- group in which the heteroaryl and alkenyl moieties are as defined herein. The group may be a terminal group or a bridging group. If the group is a terminal group it is bonded to the remainder of the molecule through the alkenyl group.

"Heteroarylheteroalkyl" means a heteroaryl-heteroalkyl-group in which the heteroaryl and heteroalkyl moieties are as defined herein. The group may be a terminal group or a bridging group. If the group is a terminal group, it is bonded to the remainder of the molecule through the heteroalkyl group.

"Heteroaryloxy" refers to a heteroaryl-O— group in which the heteroaryl is as defined herein. Preferably the heteroaryloxy is a $C_1$-$C_{18}$heteroaryloxy. The group may be a terminal group or a bridging group. If the group is a terminal group, it is bonded to the remainder of the molecule through the oxygen atom.

"Heterocyclic" refers to saturated, partially unsaturated or fully unsaturated monocyclic, bicyclic or polycyclic ring system containing at least one heteroatom selected from the group consisting of nitrogen, sulfur and oxygen as a ring atom. Examples of heterocyclic moieties include heterocycloalkyl, heterocycloalkenyl and heteroaryl.

"Heterocycloalkenyl" refers to a heterocycloalkyl group as defined herein but containing at least one double bond. A heterocycloalkenyl group typically is a $C_2$-$C_{12}$heterocycloalkenyl group. The group may be a terminal group or a bridging group.

"Heterocycloalkyl" refers to a saturated monocyclic, bicyclic, or polycyclic ring containing at least one heteroatom selected from nitrogen, sulfur, oxygen, preferably from 1 to 3 heteroatoms in at least one ring. Each ring is preferably from 3 to 10 membered, more preferably 4 to 7 membered. Examples of suitable heterocycloalkyl substituents include pyrrolidyl, tetrahydrofuryl, tetrahydrothiofuranyl, piperidyl, piperazyl, tetrahydropyranyl, morphilino, 1,3-diazapane, 1,4-diazapane, 1,4-oxazepane, and 1,4-oxathiapane. A heterocycloalkyl group typically is a $C_2$-$C_{12}$heterocycloalkyl group. The group may be a terminal group or a bridging group.

"Heterocycloalkylalkyl" refers to a heterocycloalkyl-alkyl- group in which the heterocycloalkyl and alkyl moieties are as defined herein. Exemplary heterocycloalkylalkyl groups include (2-tetrahydrofuryl)methyl, (2-tetrahydrothiofuranyl) methyl. The group may be a terminal group or a bridging group. If the group is a terminal group, it is bonded to the remainder of the molecule through the alkyl group.

"Heterocycloalkylalkenyl" refers to a heterocycloalkyl-alkenyl- group in which the heterocycloalkyl and alkenyl moieties are as defined herein. The group may be a terminal group or a bridging group. If the group is a terminal group, it is bonded to the remainder of the molecule through the alkenyl group.

"Heterocycloalkylheteroalkyl" means a heterocycloalkyl-heteroalkyl- group in which the heterocycloalkyl and heteroalkyl moieties are as defined herein. The group may be a terminal group or a bridging group. If the group is a terminal group, it is bonded to the remainder of the molecule through the heteroalkyl group.

"Heterocycloalkyloxy" refers to a heterocycloalkyl-O— group in which the heterocycloalkyl is as defined herein. Preferably the heterocycloalkyloxy is a $C_1$-$C_6$heterocycloalkyloxy. The group may be a terminal group or a bridging group. If the group is a terminal group, it is bonded to the remainder of the molecule through the oxygen atom.

"Heterocycloalkenyloxy" refers to a heterocycloalkenyl-O— group in which heterocycloalkenyl is as defined herein. Preferably the Heterocycloalkenyloxy is a $C_1$-$C_6$Heterocycloalkenyloxy. The group may be a terminal group or a bridging group. If the group is a terminal group, it is bonded to the remainder of the molecule through the oxygen atom.

"Hydroxyalkyl" refers to an alkyl group as defined herein in which one or more of the hydrogen atoms has been replaced with an OH group. A hydroxyalkyl group typically has the formula $C_nH_{(2n+1-x)}(OH)_x$. In groups of this type n is typically from 1 to 10, more preferably from 1 to 6, most preferably 1 to 3. x is typically 1 to 6, more preferably 1 to 3.

"Sulfinyl" means an R—S(=O)— group in which the R group may be OH, alkyl, cycloalkyl, heterocycloalkyl; aryl or heteroaryl group as defined herein. The group may be a terminal group or a bridging group. If the group is a terminal group, it is bonded to the remainder of the molecule through the sulfur atom.

"Sulfinylamino" means an R—S(=O)—NH— group in which the R group may be OH, alkyl, cycloalkyl, heterocycloalkyl; aryl or heteroaryl group as defined herein. The group may be a terminal group or a bridging group. If the group is a terminal group, it is bonded to the remainder of the molecule through the nitrogen atom.

"Sulfonyl" means an R—S(=O)$_2$— group in which the R group may be OH, alkyl, cycloalkyl, heterocycloalkyl; aryl or heteroaryl group as defined herein. The group may be a terminal group or a bridging group. If the group is a terminal group, it is bonded to the remainder of the molecule through the sulfur atom.

"Sulfonylamino" means an R—S(=O)$_2$—NH— group. The group may be a terminal group or a bridging group. If the group is a terminal group, it is bonded to the remainder of the molecule through the nitrogen atom.

It is understood that included in the family of compounds of Formula (I) are isomeric forms including diastereoisomers, enantiomers, tautomers, and geometrical isomers in "E" or "Z" configurational isomer or a mixture of E and Z isomers. It is also understood that some isomeric forms such as diastereomers, enantiomers, and geometrical isomers can be separated by physical and/or chemical methods and by those skilled in the art. For those compounds where there is the possibility of geometric isomerism the applicant has drawn the isomer that the compound is thought to be although it will be appreciated that the other isomer may be the correct structural assignment.

Some of the compounds of the disclosed embodiments may exist as single stereoisomers, racemates, and/or mixtures of enantiomers and/or diastereomers. All such single stereoisomers, racemates and mixtures thereof, are intended to be within the scope of the subject matter described and claimed.

Additionally, Formula (I) is intended to cover, where applicable, solvated as well as unsolvated forms of the compounds. Thus, each formula includes compounds having the indicated structure, including the hydrated as well as the non-hydrated forms.

The term "pharmaceutically acceptable salts" refers to salts that retain the desired biological activity of the above-identified compounds and include pharmaceutically acceptable acid addition salts and base addition salts. Suitable pharmaceutically acceptable acid addition salts of compounds of Formula (I) may be prepared from an inorganic acid or from an organic acid. Examples of such inorganic acids are hydrochloric, sulfuric, and phosphoric acid. Appropriate organic acids may be selected from aliphatic, cycloaliphatic, aromatic, heterocyclic carboxylic and sulfonic classes of organic acids, examples of which are formic, acetic, propanoic, succinic, glycolic, gluconic, lactic, malic, tartaric, citric, fumaric, maleic, alkyl sulfonic, arylsulfonic. In a similar vein base addition salts may be prepared by ways well known in the art using organic or inorganic bases. Example of suitable organic bases include simple amines such as methylamine, ethylamine, triethylamine and the like. Examples of suitable inorganic bases include NaOH, KOH, and the like. Additional information on pharmaceutically acceptable salts can be found in Remington's Pharmaceutical Sciences, 19th Edition, Mack Publishing Co., Easton, P A 1995. In the case of agents that are solids, it is understood by those skilled in the art that the inventive compounds, agents and salts may exist in different crystalline or polymorphic forms, all of which are intended to be within the scope of the present invention and specified formulae.

The term "therapeutically effective amount" or "effective amount" is an amount sufficient to effect beneficial or desired clinical results. An effective amount can be administered in one or more administrations. An effective amount is typically sufficient to palliate, ameliorate, stabilize, reverse, slow or delay the progression of the disease state.

As stated above the compounds of the invention have the formula (I):

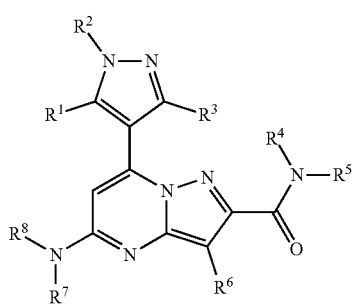

Formula (I)

or a pharmaceutically acceptable salt thereof

As with any group of structurally related compounds which possess a particular utility, certain embodiments of variables of the compounds of the Formula (I), are particularly useful in their end use application.

In the compounds of the invention $R^1$, $R^2$ and $R^3$ are each independently selected from the group consisting of H and $C_1$-$C_{12}$alkyl.

In some embodiments $R^1$ is H. In some embodiments $R^1$ is $C_1$-$C_{12}$alkyl. In some embodiments $R^1$ is selected from the group consisting of methyl, ethyl, isopropyl, propyl, 2-ethyl-propyl, 3,3-dimethyl-propyl, butyl, isobutyl, 3,3-dimethyl-butyl, 2-ethyl-butyl, pentyl, 2-methyl, pentyl, and hexyl.

In some embodiments $R^2$ is H. In some embodiments $R^2$ is $C_1$-$C_{12}$alkyl. In some embodiments $R^2$ is selected from the group consisting of methyl, ethyl, isopropyl, propyl, 2-ethyl-propyl, 3,3-dimethyl-propyl, butyl, isobutyl, 3,3-dimethyl-butyl, 2-ethyl-butyl, pentyl, 2-methyl, pentyl, and hexyl.

In some embodiments $R^3$ is H. In some embodiments $R^3$ is $C_1$-$C_{12}$alkyl. In some embodiments $R^3$ is selected from the group consisting of methyl, ethyl, isopropyl, propyl, 2-ethyl-propyl, 3,3-dimethyl-propyl, butyl, isobutyl, 3,3-dimethyl-butyl, 2-ethyl-butyl, pentyl, 2-methyl, pentyl, and hexyl.

In some embodiments of the compounds of the invention $R^1$ is H, and this provides compounds of formula (Ia):

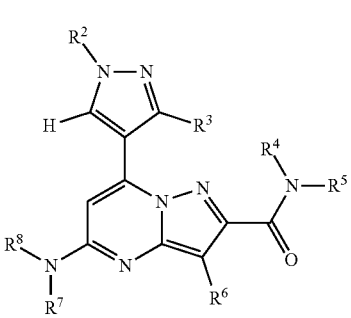

Formula (Ia)

or a pharmaceutically acceptable salt thereof;
wherein $R^2$, $R^3$, $R^4$, $R^5$, $R^6$, $R^7$ and $R^8$ are as described above.

In some embodiments of the compounds of the invention $R^2$ is H, and this provides compounds of formula (Ib):

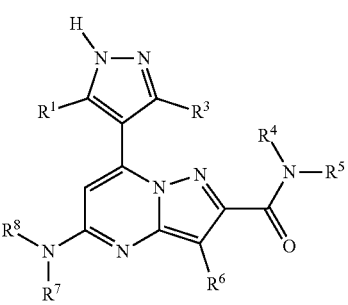

Formula (Ib)

or a pharmaceutically acceptable salt thereof;
wherein $R^1$, $R^3$, $R^4$, $R^5$, $R^6$, $R^7$ and $R^8$ are as described above.

In some embodiments of the compounds of the invention $R^3$ is H, and this provides compounds of formula (Ic):

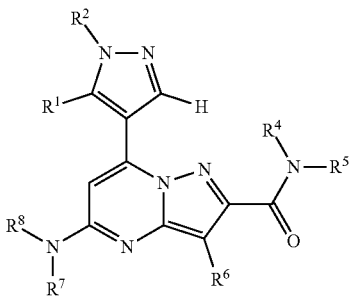

Formula (Ic)

or a pharmaceutically acceptable salt thereof;
wherein $R^1$, $R^2$, $R^4$, $R^5$, $R^6$, $R^7$ and $R^8$ are as described above.

In some embodiments of the compounds of the invention $R^1$ is H, $R^2$ is H and $R^3$ is H and this provides compounds of formula (II):

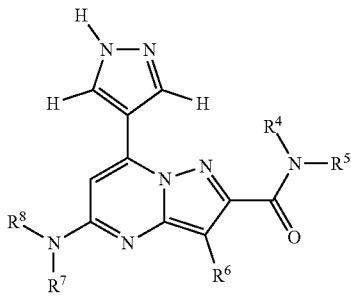

Formula (II)

or a pharmaceutically acceptable salt thereof;
wherein, $R^4$, $R^5$, $R^6$, $R^7$ and $R^8$ are as described above.

$R^4$ is selected from the group consisting of H and $C_1$-$C_{12}$alkyl. In some embodiments $R^4$ is H. In some embodiments $R^4$ is $C_1$-$C_{12}$alkyl. In some embodiments $R^4$ is selected from the group consisting of methyl, ethyl, isopropyl, propyl, 2-ethyl-propyl, 3,3-dimethyl-propyl, butyl, isobutyl, 3,3-dimethyl-butyl, 2-ethyl-butyl, pentyl, 2-methyl, pentyl, and hexyl.

In some embodiments of the compounds of the invention $R^1$ is H, $R^2$ is H, $R^3$ is H and $R^4$ is H and this provides compounds of formula (III):

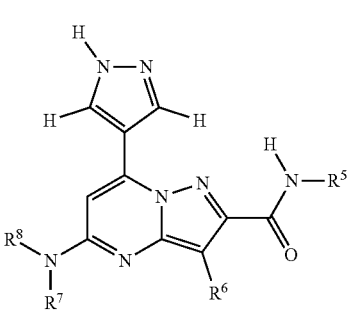

Formula (III)

or a pharmaceutically acceptable salt thereof;
wherein, $R^5$, $R^6$, $R^7$ and $R^8$ are as described above.

In the compounds of the invention $R^5$ is selected from the group consisting of H, optionally substituted $C_6$-$C_{18}$aryl, optionally substituted $C_1$-$C_{18}$heteroaryl, optionally substituted $C_6$-$C_{18}$aryl$C_1$-$C_{12}$alkyl-, and optionally substituted $C_1$-$C_{18}$heteroaryl$C_1$-$C_{12}$alkyl-.

In some embodiments $R^5$ is H. In some embodiments $R^5$ is optionally substituted $C_6$-$C_{18}$aryl. In some embodiments $R^5$ is optionally substituted $C_1$-$C_{18}$heteroaryl. In some embodiments $R^5$ is optionally substituted $C_6$-$C_{18}$aryl$C_1$-$C_{12}$alkyl-. In some embodiments $R^5$ is optionally substituted $C_1$-$C_{18}$heteroaryl$C_1$-$C_{12}$alkyl-.

In some embodiments $R^5$ is an optionally substituted $C_6$-$C_{18}$aryl. Examples of this group include optionally substituted phenyl and optionally substituted naphthyl. In some embodiments $R^5$ is optionally substituted phenyl.

In some embodiments $R^5$ is optionally substituted phenyl moiety of the formula A:

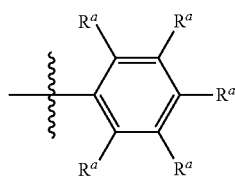

Formula A wherein each $R^a$ is independently selected from the group consisting of H, halogen, OH, $NO_2$, CN, SH, $NH_2$, $CF_3$, $OCF_3$, optionally substituted $C_1$-$C_{12}$alkyl, optionally substituted $C_1$-$C_{12}$haloalkyl optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$aryloxy, optionally substituted $C_1$-$C_{18}$heteroaryloxy, optionally substituted $C_1$-$C_{12}$alkylamino, $SR^9$, $SO_3H$, $SO_2NR^9R^{10}$, $SO_2R^9$, $SONR^9R^{10}$, $SOR^9$, $COR^9$, COOH, $COOR^9$, $CONR^9R^{10}$, $NR^9COR^{10}$, $NR^9COOR^{10}$, $NR^9SO_2R^{10}$, $NR^9CONR^9R^{10}$, $NR^9R^{10}$, and acyl,
wherein $R^9$ and $R^{10}$ are each independently selected from the group consisting of H and $C_1$-$C_{12}$alkyl.

In some embodiments $R^5$ is optionally substituted phenyl moiety selected from the group consisting of:

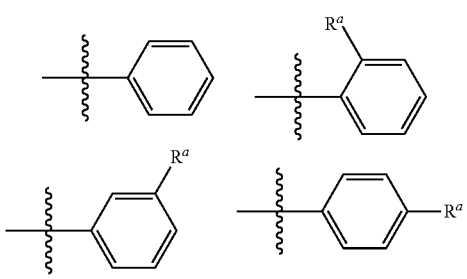

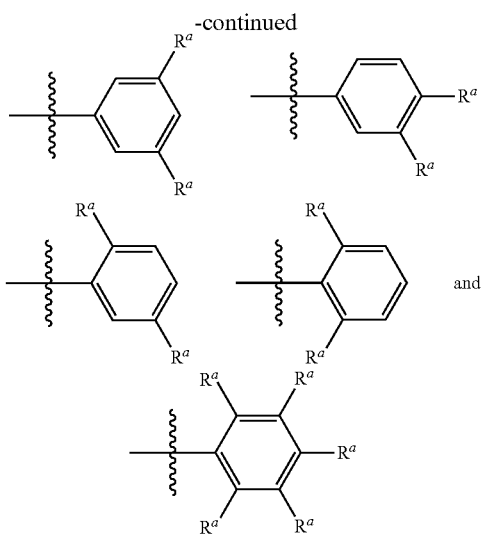

where each $R^a$ is as defined above.

In some embodiments of the invention each $R^a$ is independently selected from the group consisting of H, halogen, OH, $NO_2$, CN, SH, $NH_2$, $NHCOCH_3$, $CF_3$, $OCHF_2$, $OCF_3$, $C_1$-$C_{12}$alkyl and $C_1$-$C_{12}$alkyloxy.

In some embodiments each $R^a$ is independently selected from the group consisting of H, $CH_3$, $CH_2CH_3$, $CH_2CH_2CH_3$, $CH(CH_3)_2$, $(CH_2)_3CH_3$, Cl, Br, F, I, OH, $NO_2$, $NH_2$, $N(CH_3)_2$, $NHCOCH_3$, $NHSO_2CH_3$, $NHSO_2CH_2CH_2CH_3$, CN, $OCH_3$, $OCH_2CH_3$, $OCH_2CH_2CH_3$, $OCH(CH_3)_2$, $OCH_2CH_2OCH_3$, $OC_6H_5$, $OCH_2C(CH_3)_3$, $OCH_2$cycloproply, O-tetrahydropyran, piperazine, 4-methyl piperazine, 4-acyl-piperazine, morpholine, $CF_3$, $OCHF_2$, and $OCF_3$.

In some embodiments of the compounds of the invention $R^1$ is H, $R^2$ is H, $R^3$ is H, $R^4$ is H and $R^5$ is a moiety of the formula A and this provides compounds of formula (IV):

Formula (IV)

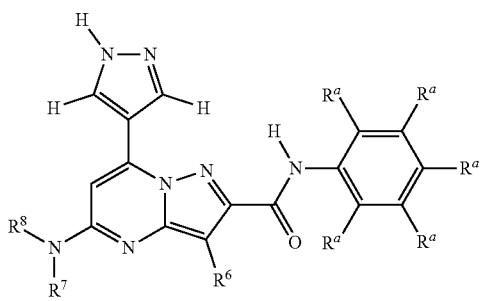

or a pharmaceutically acceptable salt thereof.
wherein, $R^a$, $R^6$, $R^7$ and $R^8$ are as described above.

In some embodiments the group $R^5$ is an optionally substituted $C_1$-$C_{18}$ heteroaryl group. Suitable heteroaryl groups include thiophene, benzothiophene, benzofuran, benzimidazole, benzoxazole, benzothiazole, benzisothiazole, naphtho[2,3-b]thiophene, furan, isoindolizine, xantholene, phenoxatine, pyrrole, imidazole, pyrazole, pyridine, pyrazine, pyrimidine, pyridazine, tetrazole, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, pyridyl, quinolyl, isoquinolinyl, indolyl, and thienyl. In each instance where there is the possibility of multiple sites of substitution on the heteroaryl ring all possible attachment points are contemplated. Merely by way of example if the heteroaryl is a pyridyl moiety it may be a 2-pyridyly, a 3-pyridyl or a 4-pyridyl.

In some embodiments $R^5$ is selected from the group consisting of:

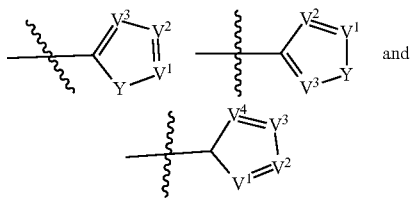

wherein each $V^1$, $V^2$, $V^3$ and $V^4$ are independently selected from the group consisting of N and $CR^B$;
wherein each $R^B$ is independently selected from the group consisting of H, halogen, OH, $NO_2$, CN, SH, $NH_2$, $CF_3$, $OCF_3$, optionally substituted $C_1$-$C_{12}$alkyl, optionally substituted $C_1$-$C_{12}$haloalkyl optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$aryloxy, optionally substituted $C_1$-$C_{18}$heteroaryloxy, optionally substituted $C_1$-$C_{12}$alkylamino, $SR^9$, $SO_3H$, $SO_2NR^9R^{10}$, $SO_2R^9$, $SONR^9R^{10}$, $SOR^9$, $COR^9$, COOH, $COOR^9$, $CONR^9R^{10}$, $NR^9COR^{10}$, $NR^9COOR^{10}$, $NR^9SO_2R^{10}$, $NR^9CONR^9R^{10}$, $NR^9R^{10}$, and acyl;
wherein $R^9$ and $R^{10}$ are each independently selected from the group consisting of H and $C_1$-$C_{12}$alkyl.
Y is selected from the group consisting of S, O, and NH.
In one embodiment $R^5$ is selected from the group consisting of:

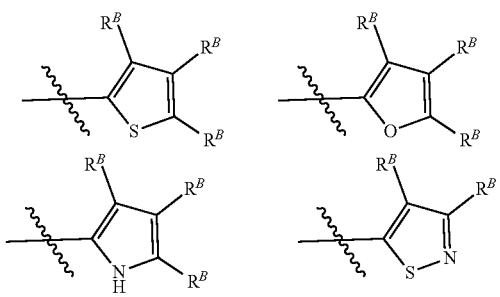

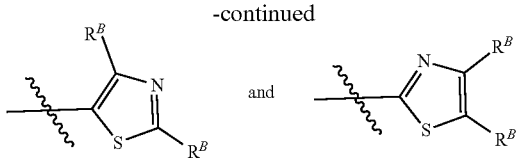

wherein $R^B$ is as described above.

In one embodiment $R^5$ is selected from the group consisting of:

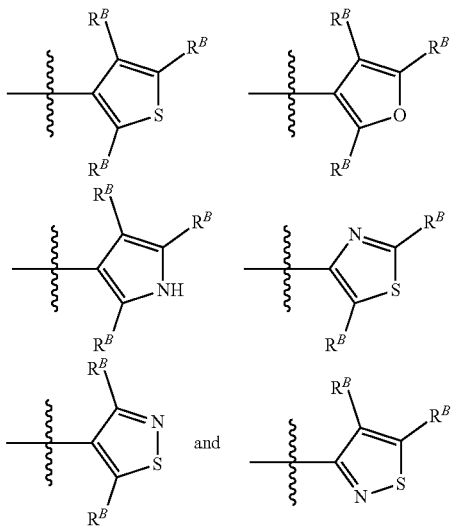

where each $R^B$ is as defined above.

In some embodiments of the invention each $R^B$ is independently selected from the group consisting of H, halogen, OH, $NO_2$, CN, SH, $NH_2$, $NHCOCH_3$, $CF_3$, $OCHF_2$, $OCF_3$, $C_1$-$C_{12}$alkyl and $C_1$-$C_{12}$alkyloxy.

In some embodiments each $R^B$ is independently selected from the group consisting of H, $CH_3$, $CH_2CH_3$, $CH_2CH_2CH_3$, $CH(CH_3)_2$, $(CH_2)_3CH_3$, Cl, Br, F, I, OH, $NO_2$, $NH_2$, $NHSO_2CH_2CH_2CH_3$, CN, $OCH_3$, $OCH_2CH_3$, $OCH_2CH_2CH_3$, $OCH(CH_3)_2$, $OC_6H_5$, $OCH_2CCH$, $OCH_2$cycloproply, $CF_3$, $OCHF_2$, and $OCF_3$.

In some embodiments of the invention $R^5$ is optionally substituted $C_6$-$C_{18}$aryl$C_1$-$C_{12}$alkyl-. In these embodiments the optionally substituted $C_6$-$C_{18}$aryl is as described above for $R^5$. The alkyl is typically selected from the group consisting of methyl, ethyl, isopropyl, propyl, 2-ethyl-propyl, 3,3-dimethyl-propyl, butyl, isobutyl, 3,3-dimethyl-butyl, 2-ethyl-butyl, pentyl, 2-methyl, pentyl, and hexyl.

In some embodiments of the invention $R^5$ is substituted $C_1$-$C_{18}$heteroaryl $C_1$-$C_{12}$alkyl-. In these embodiments the optionally substituted $C_1$-$C_{18}$heteroaryl is as described above for $R^5$. The alkyl is typically selected from the group consisting of methyl, ethyl, isopropyl, propyl, 2-ethyl-propyl, 3,3-dimethyl-propyl, butyl, isobutyl, 3,3-dimethyl-butyl, 2-ethyl-butyl, pentyl, 2-methyl, pentyl, and hexyl.

In the compounds of the invention $R^6$ is selected from the group consisting of H, $C_1$-$C_{12}$alkyl, $C_3$-$C_6$ cycloalkyl; $C_1$-$C_5$ heterocycloalkyl. In one embodiment $R^6$ is H. In one embodiment $R^6$ is $C_1$-$C_{12}$alkyl. In one embodiment $R^6$ is $C_3$-$C_6$ cycloalkyl. In one embodiment $R^6$ is $C_1$-$C_5$ heterocycloalkyl.

In one specific embodiment $R^6$ is $C_1$-$C_{12}$alkyl. Examples of suitable values of $R^6$ include methyl, ethyl, isopropyl, propyl, 2-ethyl-propyl, 3,3-dimethyl-propyl, butyl, isobutyl, 3,3-dimethyl-butyl, 2-ethyl-butyl, pentyl, 2-methyl, pentyl, and hexyl. A particularly preferred value of $R^6$ is isopropyl.

In one specific embodiment $R^6$ is $C_3$-$C_6$ cycloalkyl. Examples of suitable values of $R^6$ include cyclopropyl, cyclobutyl, cyclopentyl and cyclohexyl.

In one specific embodiment $R^6$ is $C_1$-$C_5$ heterocycloalkyl. Examples of suitable values of $R^6$ include azetidine, oxetane, thietane, pyrrolidine, oxolane, thiolane, piperidine, oxane, and thiane.

In the compounds of the invention $R^7$ is selected from the group consisting of H and $C_1$-$C_{12}$alkyl, or $R^7$ and $R^8$ when taken together with the nitrogen atom to which they are attached form a monocyclic or bicyclic $C_2$-$C_{12}$heterocycloalkyl group.

In one embodiment $R^7$ is H.

In one embodiment $R^7$ is $C_1$-$C_{12}$alkyl. Examples of suitable values of $R^7$ include methyl, ethyl, isopropyl, propyl, 2-ethyl-propyl, 3,3-dimethyl-propyl, butyl, isobutyl, 3,3-dimethyl-butyl, 2-ethyl-butyl, pentyl, 2-methyl, pentyl, and hexyl. In one preferred embodiment $R^7$ is Methyl.

In the compounds of the invention $R^a$ is selected from the group consisting of H, $C_1$-$C_{12}$alkyl, optionally substituted $C_6$-$C_{18}$aryl, optionally substituted $C_1$-$C_{18}$heteroaryl, optionally substituted $C_6$-$C_{18}$aryl$C_1$-$C_{12}$alkyl-, and optionally substituted $C_1$-$C_{18}$heteroaryl$C_1$-$C_{12}$alkyl-.

In one embodiment $R^8$ is H.

In one embodiment $R^8$ is $C_1$-$C_{12}$alkyl. Examples of suitable values of $R^8$ include methyl, ethyl, isopropyl, propyl, 2-ethyl-propyl, 3,3-dimethyl-propyl, butyl, isobutyl, 3,3-dimethyl-butyl, 2-ethyl-butyl, pentyl, 2-methyl, pentyl, and hexyl. In one preferred embodiment $R_8$ is Methyl.

In one embodiment $R^8$ is optionally substituted $C_6$-$C_{18}$aryl. Examples of this group include optionally substituted phenyl and optionally substituted naphthyl. In some embodiments $R^8$ is optionally substituted phenyl.

In some embodiments $R^8$ is optionally substituted phenyl moiety of the formula B:

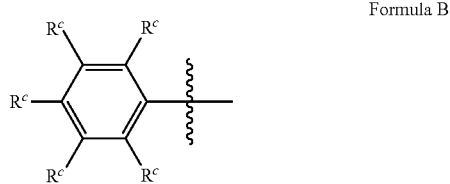

Formula B wherein each $R^c$ is independently selected from the group consisting of H, halogen, OH, $NO_2$, CN, SH, $NH_2$, $CF_3$, $OCF_3$, optionally substituted $C_1$-$C_{12}$alkyl, optionally substituted $C_1$-$C_{12}$haloalkyl optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted C$_2$-C$_{12}$heterocycloalkenyloxy, optionally substituted C$_6$-C$_{18}$aryloxy, optionally substituted C$_1$-C$_{18}$heteroaryloxy, optionally substituted C$_1$-C$_{12}$alkylamino, SR$^9$, SO$_3$H, SO$_2$NR$^9$R$^{10}$, SO$_2$R$^9$, SONR$^9$R$^{10}$, SOR$^9$, COR$^9$, COOH, COOR$^9$, CONR$^9$R$^{10}$, NR$^9$COR$^{10}$, NR$^9$COOR$^{10}$, NR$^9$SO$_2$R$^{10}$, NR$^9$CONR$^9$R$^{10}$, NR$^9$R$^{10}$, and acyl, wherein R$^9$ and R$^{10}$ are each independently selected from the group consisting of H and C$_1$-C$_{12}$alkyl.

In some embodiments R$^8$ is optionally substituted phenyl moiety of the selected from the group consisting of:

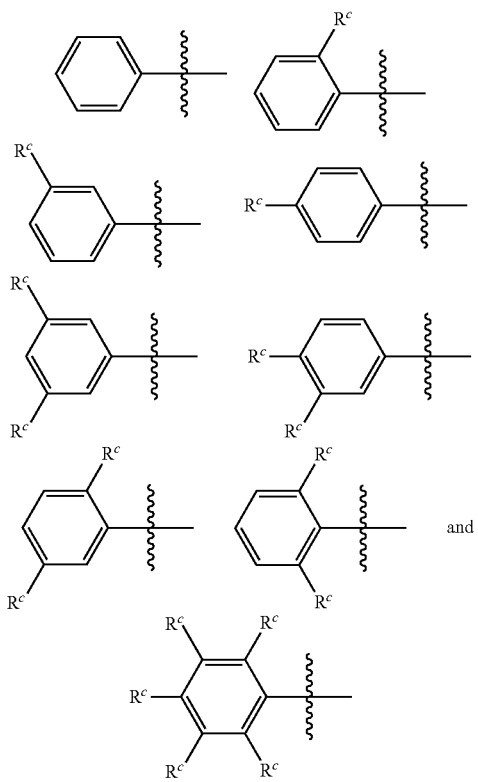

where each R$^c$ is as defined above.

In some embodiments of the invention each R$^c$ is independently selected from the group consisting of H, halogen, OH, NO$_2$, CN, SH, NH$_2$, NHCOCH$_3$, CF$_3$, OCHF$_2$, OCF$_3$, C$_1$-C$_{12}$alkyl and C$_1$-C$_{12}$alkyloxy.

In some embodiments each R$^c$ is independently selected from the group consisting of H, CH$_3$, CH$_2$CH$_3$, CH$_2$CH$_2$CH$_3$, CH(CH$_3$)$_2$, (CH$_2$)$_3$CH$_3$, Cl, Br, F, I, OH, NO$_2$, NH$_2$, NHSO$_2$CH$_2$CH$_2$CH$_3$, CN, OCH$_3$, OCH$_2$CH$_3$, OCH$_2$CH$_2$CH$_3$, OCH(CH$_3$)$_2$, OC$_6$H$_5$, OCH$_2$CCH, OCH$_2$cycloproply, CF$_3$, OCHF$_2$, and OCF$_3$.

In one embodiment R$^8$ is optionally substituted C$_1$-C$_{18}$heteroaryl. Suitable heteroaryl groups include thiophene, benzothiophene, benzofuran, benzimidazole, benzoxazole, benzothiazole, benzisothiazole, naphtho[2,3-b]thiophene, furan, isoindolizine, xantholene, phenoxatine, pyrrole, imidazole, pyrazole, pyridine, pyrazine, pyrimidine, pyridazine, tetrazole, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, pyridyl, quinolyl, isoquinolinyl, indolyl, and thienyl. In each instance where there is the possibility of multiple sites of substitution on the heteroaryl ring all possible attachment points are contemplated. Merely by way of example if the heteroaryl is a pyridyl moiety it may be a 2-pyridyly, a 3-pyridyl or a 4-pyridyl.

In some embodiments R$^8$ is selected from the group consisting of:

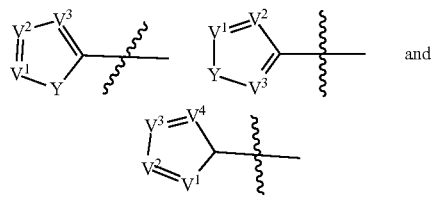

wherein each V$^1$, V$^2$, V$^3$ and V$^4$ are independently selected from the group consisting of N and CR$^D$;

wherein each R$^D$ is independently selected from the group consisting of H, halogen, OH, NO$_2$, CN, SH, NH$_2$, CF$_3$, OCF$_3$, optionally substituted C$_1$-C$_{12}$alkyl, optionally substituted C$_1$-C$_{12}$haloalkyl optionally substituted C$_2$-C$_{12}$alkenyl, optionally substituted C$_2$-C$_{12}$alkynyl, optionally substituted C$_2$-C$_{12}$heteroalkyl, optionally substituted C$_3$-C$_{12}$cycloalkyl, optionally substituted C$_3$-C$_{12}$cycloalkenyl, optionally substituted C$_2$-C$_{12}$heterocycloalkyl, optionally substituted C$_2$-C$_{12}$heterocycloalkenyl, optionally substituted C$_6$-C$_{18}$aryl, optionally substituted C$_1$-C$_{18}$heteroaryl, optionally substituted C$_1$-C$_{12}$alkyloxy, optionally substituted C$_2$-C$_{12}$alkenyloxy, optionally substituted C$_2$-C$_{12}$alkynyloxy, optionally substituted C$_2$-C$_{18}$heteroalkyloxy, optionally substituted C$_3$-C$_{12}$cycloalkyloxy, optionally substituted C$_3$-C$_{12}$cycloalkenyloxy, optionally substituted C$_2$-C$_{12}$heterocycloalkyloxy, optionally substituted C$_2$-C$_{12}$heterocycloalkenyloxy, optionally substituted C$_1$-C$_{18}$aryloxy, optionally substituted C$_1$-C$_{18}$heteroaryloxy, optionally substituted C$_1$-C$_{12}$alkylamino, SR$^9$, SO$_3$H, SO$_2$NR$^9$R$^{10}$, SO$_2$R$^9$, SONR$^9$R$^{10}$, SOR$^9$, COR$^9$, COOH, COOR$^9$, CONR$^9$R$^{10}$, NR$^9$COR$^{10}$, NR$^9$COOR$^{10}$, NR$^9$SO$_2$R$^{10}$, NR$^9$CONR$^9$R$^{10}$, NR$^9$R$^{10}$, and acyl, wherein R$^9$ and R$^{10}$ are each independently selected from the group consisting of H and C$_1$-C$_{12}$alkyl.

Y is selected from the group consisting of S, O, and NH.

In one embodiment R$^8$ is selected from the group consisting of:

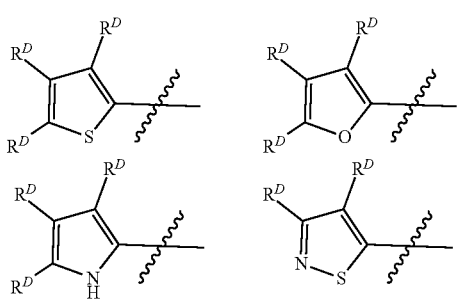

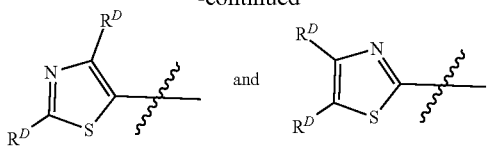

wherein $R^D$ is as described above.

In one embodiment $R^8$ is selected from the group consisting of:

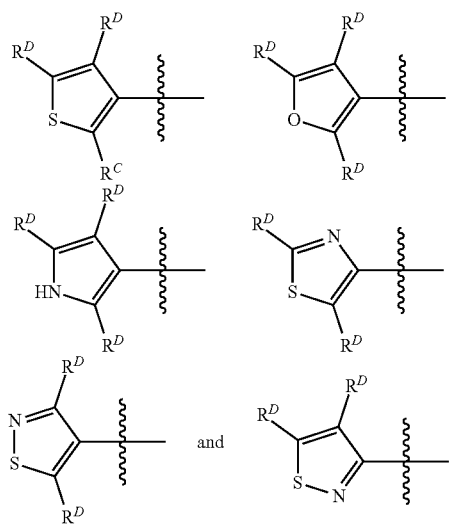

where each $R^D$ is as defined above.

In some embodiments of the invention each $R^D$ is independently selected from the group consisting of H, halogen, OH, $NO_2$, CN, SH, $NH_2$, $NHCOCH_3$, $CF_3$, $OCHF_2$, $OCF_3$, $C_1$-$C_{12}$alkyl and $C_1$-$C_{12}$alkyloxy.

In some embodiments each $R^D$ is independently selected from the group consisting of H, $CH_3$, $CH_2CH_3$, $CH_2CH_2CH_3$, $CH(CH_3)_2$, $(CH_2)_3CH_3$, Cl, Br, F, I, OH, $NO_2$, $NH_2$, $NHSO_2CH_2CH_2CH_3$, CN, $OCH_3$, $OCH_2CH_3$, $OCH_2CH_2CH_3$, $OCH(CH_3)_2$, $OC_6H_5$, $OCH_2CCH$, $OCH_2$cycloproply, $CF_3$, $OCHF_2$, and $OCF_3$.

In some embodiments of the invention $R^8$ is optionally substituted $C_6$-$C_{18}$aryl$C_1$-$C_{12}$alkyl-. In these embodiments the optionally substituted $C_6$-$C_{18}$aryl is as described above for $R^8$. The alkyl is typically selected from the group consisting of methyl, ethyl, isopropyl, propyl, 2-ethyl-propyl, 3,3-dimethyl-propyl, butyl, isobutyl, 3,3-dimethyl-butyl, 2-ethyl-butyl, pentyl, 2-methyl, pentyl, and hexyl. In one particular embodiment the alkyl is methyl such that the alkyl is a methylene group joining the aryl group to the nitrogen.

In some embodiments of the invention $R^8$ is optionally substituted $C_1$-$C_{18}$heteroaryl $C_1$-$C_{12}$alkyl-. In these embodiments the optionally substituted $C_1$-$C_{18}$heteroaryl is as described above for $R^8$. The alkyl is typically selected from the group consisting of methyl, ethyl, isopropyl, propyl, 2-ethyl-propyl, 3,3-dimethyl-propyl, butyl, isobutyl, 3,3-dimethyl-butyl, 2-ethyl-butyl, pentyl, 2-methyl, pentyl, and hexyl.

In some embodiments $R^7$ and $R^8$ when taken together with the nitrogen atom to which they are attached form a a $C_2$-$C_{12}$heterocyclic group. The a $C_2$-$C_{12}$heterocyclic group may be any suitable $C_2$-$C_{12}$heterocyclic group and may be monocyclic or bicyclic heterocyclic group. In one embodiment the a $C_2$-$C_{12}$heterocyclic group is monocyclic. In one embodiment the a $C_2$-$C_{12}$heterocyclic group is bicyclic.

The $C_2$-$C_{12}$ heterocyclic group may consist of fully saturated rings, fully unsaturated rings or combinations thereof. For example, it may contain one saturated ring and one unsaturated ring.

In one embodiment the $C_2$-$C_{12}$ heterocyclic group is a group of the formula C:

Formula C

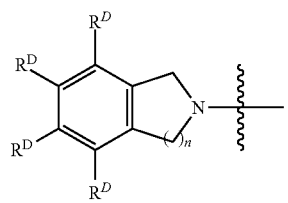

wherein each $R^D$ is independently selected from the group consisting of H, halogen, OH, $NO_2$, CN, SH, $NH_2$, $CF_3$, $OCF_3$, optionally substituted $C_1$-$C_{12}$alkyl, optionally substituted $C_1$-$C_{12}$haloalkyl optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{12}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$aryloxy, optionally substituted $C_1$-$C_{18}$heteroaryloxy, optionally substituted $C_1$-$C_{12}$alkylamino, $SR^9$, $SO_3H$, $SO_2NR^9R^{10}$, $SO_2R^9$, $SONR^9R^{10}$, $SOR^9$, $COR^9$, COOH, $COOR^9$, $CONR^9R^{10}$, $NR^9COR^{10}$, $NR^9COOR^{10}$, $NR^9SO_2R^{10}$, $NR^9CONR^9R^{10}$, $NR^9R^{10}$, and acyl, wherein each $R^9$ and $R^{10}$ are independently selected from the group consisting of H and $C_1$-$C_{12}$alkyl;

n is an integer selected from 1 and 2.

In one embodiment the $C_2$-$C_{12}$ heterocyclic group is a group of the formula D:

Formula D

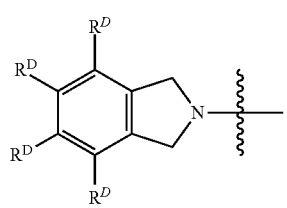

In one embodiment the $C_2$-$C_{12}$ heterocyclic group is a group of the formula E:

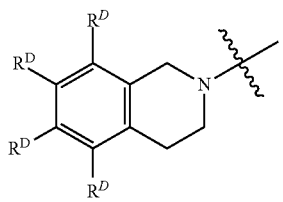

Formula E

In some embodiments of the compounds of formula D and E each $R_D$ is independently selected from the group consisting of H, $CH_3$, $CH_2CH_3$, $CH_2CH_2CH_3$, $CH(CH_3)_2$, $(CH_2)_3CH_3$, Cl, Br, F, I, OH, $NO_2$, $NH_2$, $NHSO_2CH_2CH_2CH_3$, CN, $OCH_3$, $OCH_2CH_3$, $OCH_2CH_2CH_3$, $OCH(CH_3)_2$, $OCH_5$, $OCH_2C(CH_3)_3$, $OCH_2$cycloproply, $CF_3$, $OCHF_2$, and $OCF_3$.

In some embodiments of the compounds of the invention containing an $R^9$ group, the $R^9$ group is selected from the group consisting of H, methyl, ethyl, isopropyl, propyl, 3,3-dimethyl-propyl, butyl, isobutyl, 3,3-dimethyl-butyl, 2-ethyl-butyl, pentyl, and hexyl. In some embodiments $R^9$ is selected from the group consisting of H, methyl and ethyl. In some embodiments $R^9$ is H. In some embodiments $R^9$ is methyl. In some embodiments $R^9$ is ethyl.

In some embodiments of the compounds of the invention containing an $R^{10}$ group, the $R^{10}$ group is selected from the group consisting of H, methyl, cyclopropylmethyl, ethyl, isopropyl, propyl, cyclopropyl, 3,3-dimethyl-propyl, butyl, isobutyl, cyclobutyl, 3,3-dimethyl-butyl, 2-ethyl-butyl, pentyl, hexyl, phenyl and pyridine-2-yl. In some embodiments $R^{10}$ is selected from the group consisting of H, methyl and ethyl. In some embodiments $R^{10}$ is H. In some embodiments $R^{10}$ is methyl. In some embodiments $R^{10}$ is ethyl.

Many if not all of the variables discussed above may be optionally substituted. If the variable is optionally substituted then each optional substituent is independently selected from the group consisting of halogen, =O, =S, —CN, —$NO_2$, —$CF_3$, —$OCF_3$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, heteroarylalkyl, arylalkyl, cycloalkylalkenyl, heterocycloalkylalkenyl, arylalkenyl, heteroarylalkenyl, cycloalkylheteroalkyl, heterocycloalkylheteroalkyl, arylheteroalkyl, heteroarylheteroalkyl, hydroxy, hydroxyalkyl, alkyloxy, alkyloxyalkyl, alkyloxycycloalkyl, alkyloxyheterocycloalkyl, alkyloxyaryl, alkyloxyheteroaryl, alkyloxycarbonyl, alkylaminocarbonyl, alkenyloxy, alkynyloxy, cycloalkyloxy, cycloalkenyloxy, heterocycloalkyloxy, heterocycloalkenyloxy, aryloxy, phenoxy, benzyloxy, heteroaryloxy, arylalkyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, alkylsulfinyl, arylsulfinyl, aminosulfinylaminoalkyl, —C(=O)OH, —C(=O)$R^e$, —C(=O)$OR^e$, C(=O)$NR^eR^f$, C(=NOH)$R^e$, C(=$NR^e$)$NR^fR^g$, $NR^eR^f$, $NR^eC(=O)R^f$, $NR^eC(=O)OR^f$, $NR^eC(=O)NR^fR^g$, $NR^eC(=NR^f)NR^gR^h$, $NR^eSO_2R^f$, —$SR^e$, $SO_2NR^eR^f$, —$OR^e$, $OC(=O)NR^eR^f$, $OC(=O)R^e$ and acyl;

wherein $R^e$, $R^f$, $R^g$ and $R^h$ are each independently selected from the group consisting of H, $C_1$-$C_{12}$alkyl, $C_1$-$C_{12}$haloalkyl, $C_2$-$C_{12}$alkenyl, $C_2$-$C_{12}$alkynyl, $C_1$-$C_{10}$heteroalkyl, $C_3$-$C_{12}$cycloalkyl, $C_3$-$C_{12}$cycloalkenyl, $C_1$-$C_{12}$heterocycloalkyl, $C_1$-$C_{12}$heterocycloalkenyl, $C_6$-$C_{18}$aryl, $C_1$-$C_{18}$heteroaryl, and acyl, or any two or more of $R^a$, $R^b$, $R^c$ and $R^d$, when taken together with the atoms to which they are attached form a heterocyclic ring system with 3 to 12 ring atoms.

In some embodiments each optional substituent is independently selected from the group consisting of: F, Cl, Br, =O, =S, —CN, —$NO_2$, alkyl, alkenyl, heteroalkyl, haloalkyl, alkynyl, aryl, cycloalkyl, heterocycloalkyl, heteroaryl, hydroxy, hydroxyalkyl, alkoxy, alkylamino, aminoalkyl, acylamino, phenoxy, alkoxyalkyl, benzyloxy, alkylsulfonyl, arylsulfonyl, aminosulfonyl, —C(O)$OR^a$, COOH, SH, and acyl.

In some embodiments each optional substituent is independently selected from the group consisting of: F, Br, Cl, =O, =S, —CN methyl, trifluoro-methyl, ethyl, 2,2,2-trifluoroethyl, isopropyl, propyl, 2-ethyl-propyl, 3,3-dimethyl-propyl, butyl, isobutyl, 3,3-dimethyl-butyl, 2-ethyl-butyl, pentyl, 2-methyl-pentyl, pent-4-enyl, hexyl, heptyl, octyl, phenyl, $NH_2$, —$NO_2$, phenoxy, hydroxy, methoxy, trifluoro-methoxy, ethoxy, and methylenedioxy.

In some embodiments each optional substituent is independently selected from the group consisting of H, $CH_3$, $CH_2CH_3$, $CH_2CH_2CH_3$, $CH(CH_3)_2$, $(CH_2)_3CH_3$, Cl, Br, F, I, OH, $NO_2$, $NH_2$, CN, $OCH_3$, $OCH_2CH_2CH_3$, $CF_3$, and $OCF_3$.

Alternatively, two optional substituents on the same moiety when taken together may be joined to form a fused cyclic substituent attached to the moiety that is optionally substituted. Accordingly, the term optionally substituted includes a fused ring such as a cycloalkyl ring, a heterocycloalkyl ring, an aryl ring or a heteroaryl ring.

Examples of specific compounds of Formula (I) of the present invention include:

1

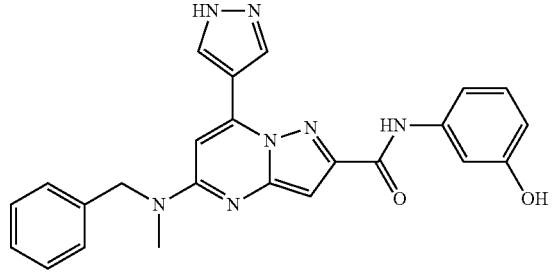

2 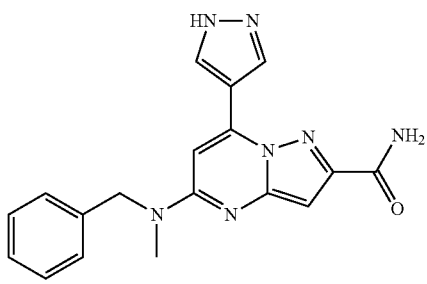 [SMILES: CN(Cc1ccccc1)c1cc(-c2cn[nH]c2)n2nc(C(N)=O)cc2n1]
3 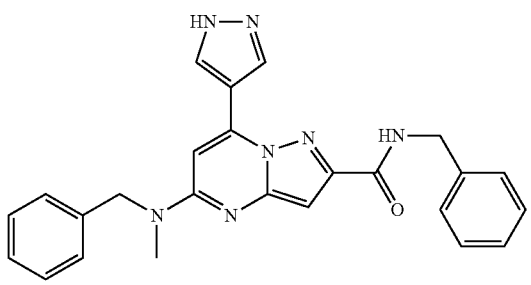 [SMILES: CN(Cc1ccccc1)c1cc(-c2cn[nH]c2)n2nc(C(=O)NCc3ccccc3)cc2n1]
4 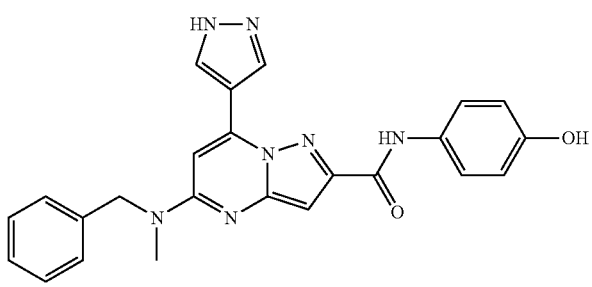
5 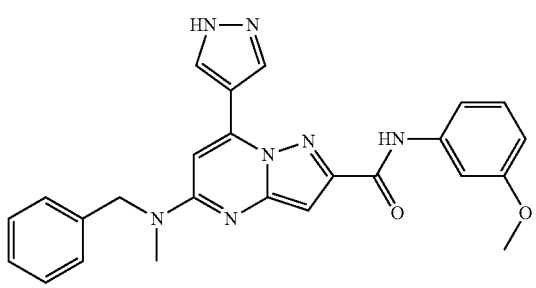
6 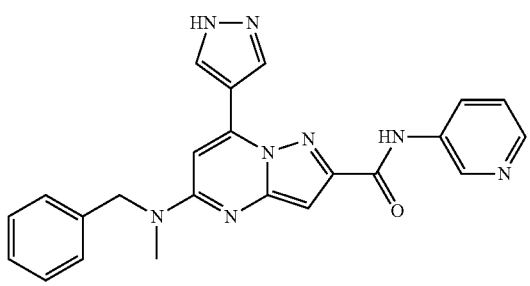 [SMILES: CN(Cc1ccccc1)c1cc(-c2cn[nH]c2)n2nc(C(=O)Nc3cccnc3)cc2n1]

| | |
|---|---|
| 7 | 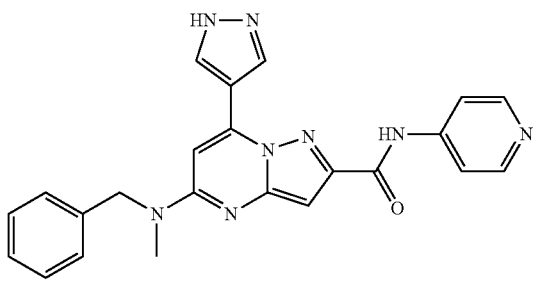 [SMILES: CN(Cc1ccccc1)c1cc(-c2cn[nH]c2)n2nc(C(=O)Nc3ccncc3)cc2n1] |
| 8 | 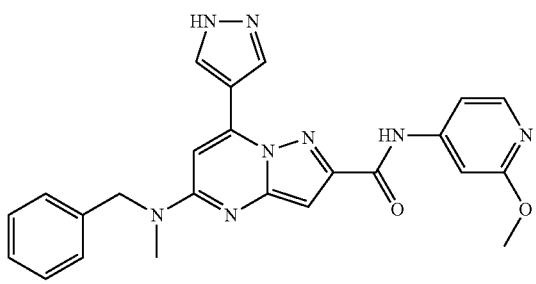 [SMILES: COc1cc(NC(=O)c2cc3nc(N(C)Cc4ccccc4)cc(-c4cn[nH]c4)n3n2)ccn1] |
| 9 | 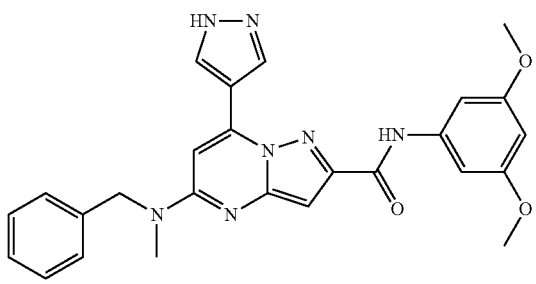 [SMILES: COc1cc(NC(=O)c2cc3nc(N(C)Cc4ccccc4)cc(-c4cn[nH]c4)n3n2)cc(OC)c1] |
| 10 | 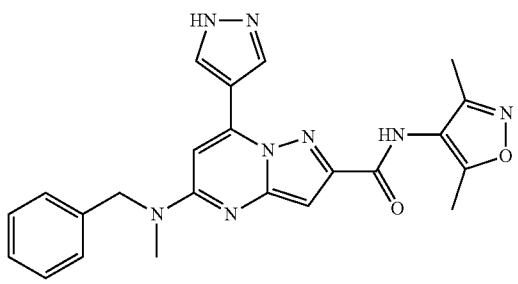 [SMILES: Cc1noc(C)c1NC(=O)c1cc2nc(N(C)Cc3ccccc3)cc(-c3cn[nH]c3)n2n1] |
| 11 | 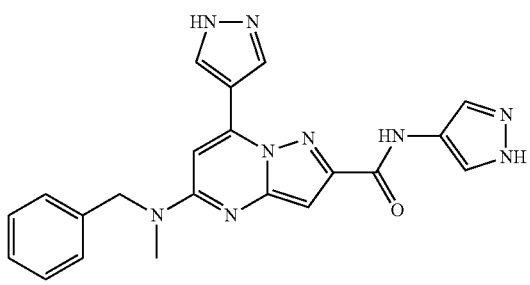 [SMILES: CN(Cc1ccccc1)c1cc(-c2cn[nH]c2)n2nc(C(=O)Nc3cn[nH]c3)cc2n1] |

-continued
12
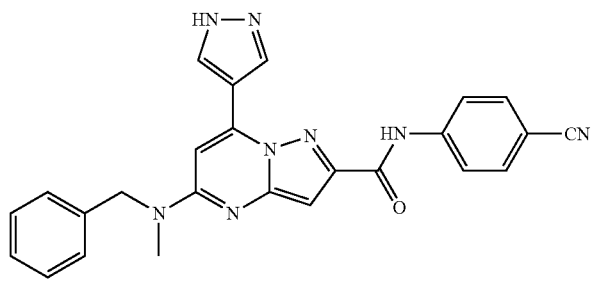 [SMILES: CN(Cc1ccccc1)c1cc(-c2cn[nH]c2)n2nc(C(=O)Nc3ccc(C#N)cc3)cc2n1]
13
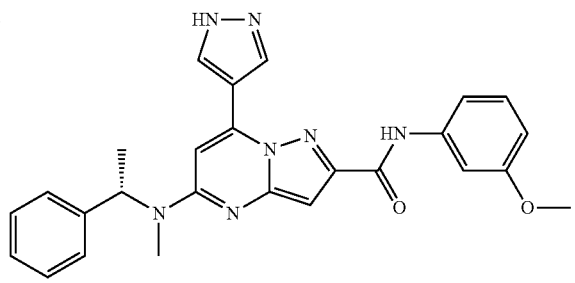
14
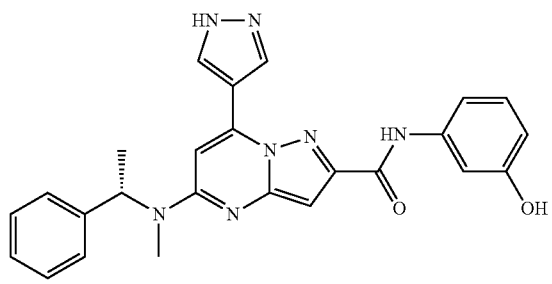 [SMILES: CN(Cc1ccccc1)c1cc(-c2cn[nH]c2)n2nc(C(=O)Nc3cccc(C#N)c3)cc2n1]
15
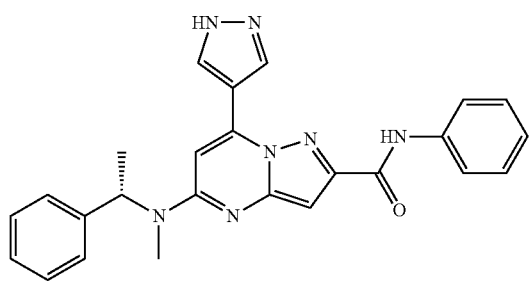 [SMILES: C[C@@H](c1ccccc1)N(C)c1cc(-c2cn[nH]c2)n2nc(C(=O)Nc3ccccc3)cc2n1]
16

-continued
| | |
|---|---|
| 17 | 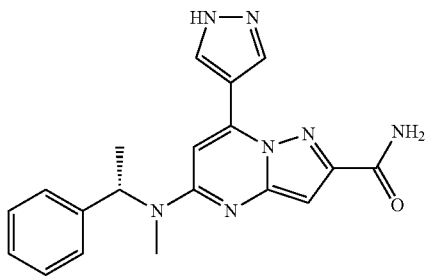 [SMILES: C[C@@H](c1ccccc1)N(C)c1cc(-c2cn[nH]c2)n2nc(C(N)=O)cc2n1] |
| 18 | 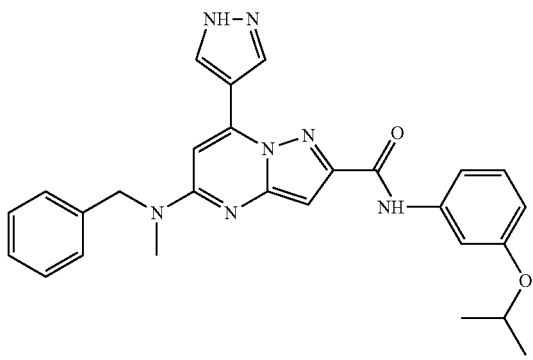 [SMILES: CC(C)Oc1cccc(NC(=O)c2cc3nc(N(C)Cc4ccccc4)cc(-c4cn[nH]c4)n3n2)c1] |
| 19 | 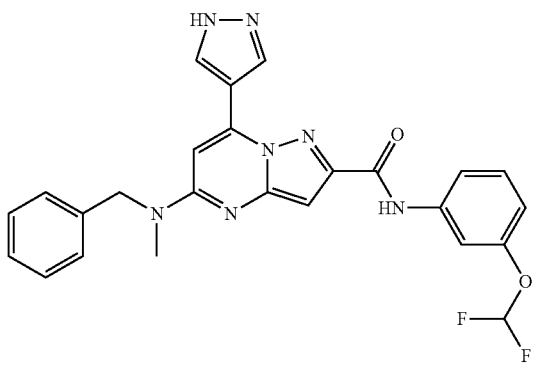 [SMILES: CN(Cc1ccccc1)c1cc(-c2cn[nH]c2)n2nc(C(=O)Nc3cccc(OC(F)F)c3)cc2n1] |
| 20 | 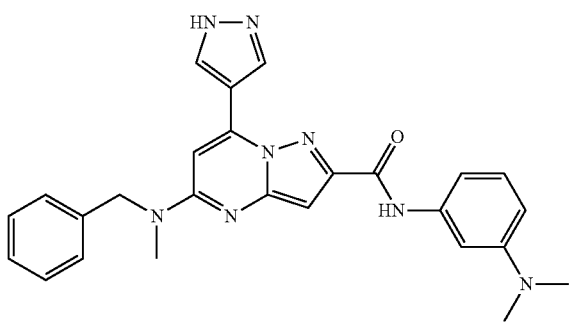 [SMILES: CN(C)c1cccc(NC(=O)c2cc3nc(N(C)Cc4ccccc4)cc(-c4cn[nH]c4)n3n2)c1] |
| 21 | 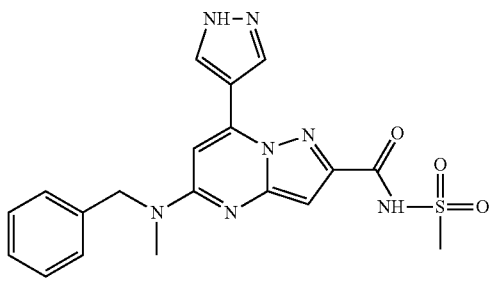 [SMILES: CN(Cc1ccccc1)c1cc(-c2cn[nH]c2)n2nc(C(=O)NS(C)(=O)=O)cc2n1] |

| | |
|---|---|
| 22 | 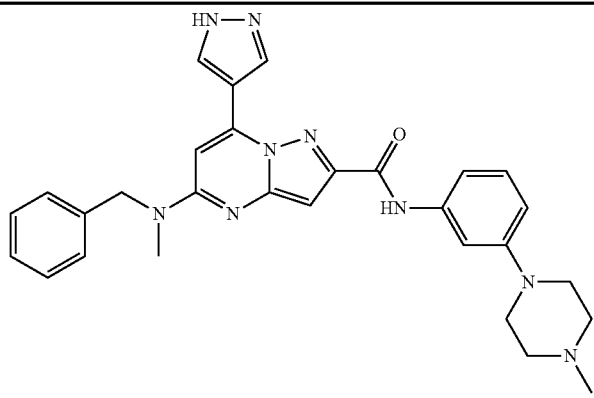 |
| 23 | 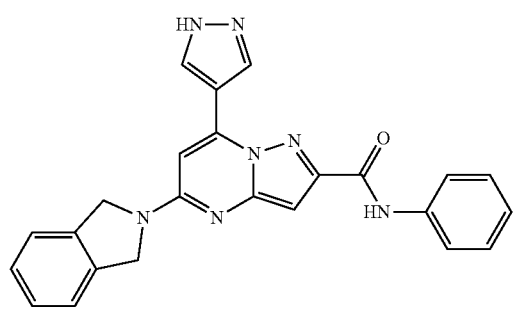 [SMILES: O=C(Nc1ccccc1)c1cc2nc(N3Cc4ccccc4C3)cc(-c3cn[nH]c3)n2n1] |
| 24 | 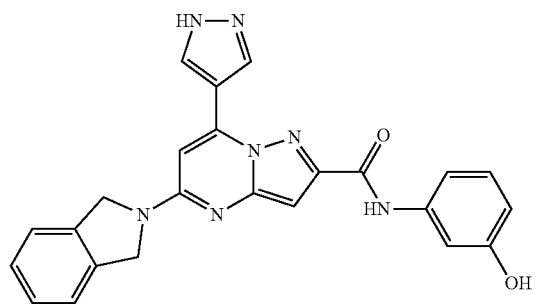 [SMILES: O=C(Nc1cccc(O)c1)c1cc2nc(N3Cc4ccccc4C3)cc(-c3cn[nH]c3)n2n1] |
| 25 | 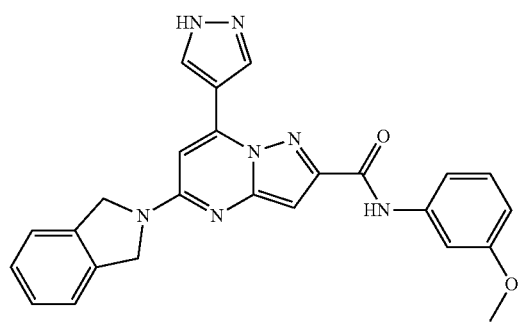 [SMILES: COc1cccc(NC(=O)c2cc3nc(N4Cc5ccccc5C4)cc(-c4cn[nH]c4)n3n2)c1] |
| 26 | 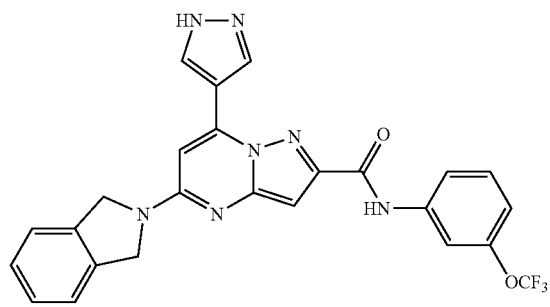 [SMILES: O=C(Nc1cccc(OC(F)(F)F)c1)c1cc2nc(N3Cc4ccccc4C3)cc(-c3cn[nH]c3)n2n1] |

27 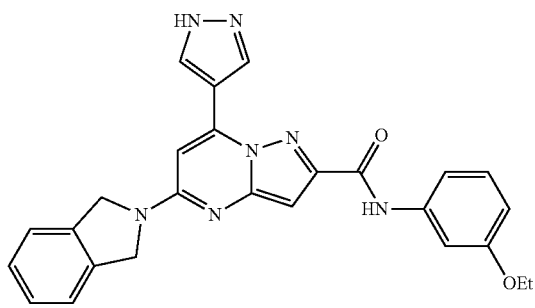 [SMILES: CCOc1cccc(NC(=O)c2cc3nc(N4Cc5ccccc5C4)cc(-c4cn[nH]c4)n3n2)c1]
28 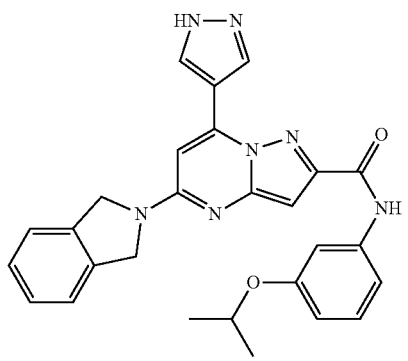 [SMILES: CC(C)Oc1cccc(NC(=O)c2cc3nc(N4Cc5ccccc5C4)cc(-c4cn[nH]c4)n3n2)c1]
29 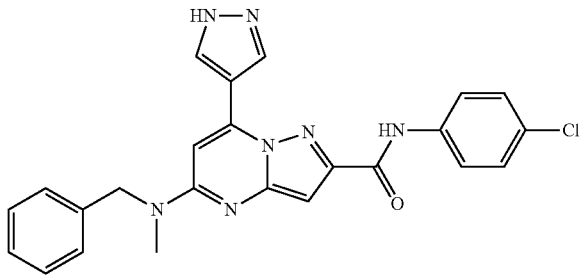 [SMILES: CN(Cc1ccccc1)c1cc(-c2cn[nH]c2)n2nc(C(=O)Nc3ccc(Cl)cc3)cc2n1]
30 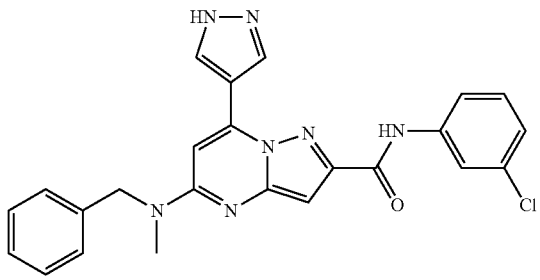 [SMILES: CN(Cc1ccccc1)c1cc(-c2cn[nH]c2)n2nc(C(=O)Nc3cccc(Cl)c3)cc2n1]
31 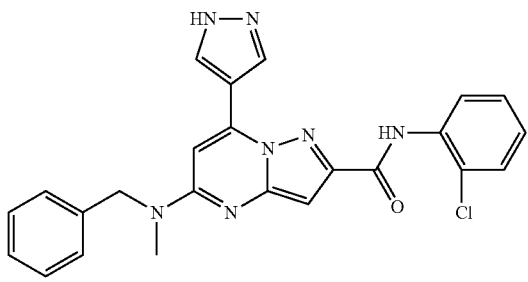

-continued
32
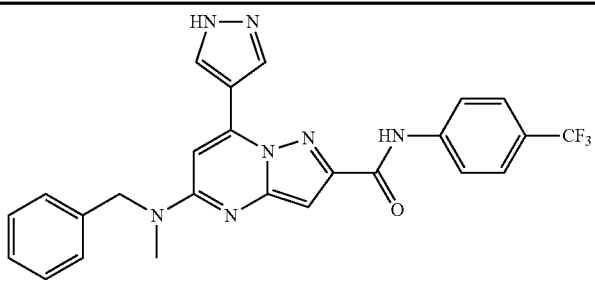
33
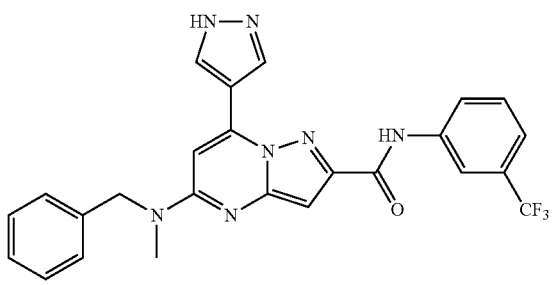 [SMILES: CN(Cc1ccccc1)c1cc(-c2cn[nH]c2)n2nc(C(=O)Nc3cccc(C(F)(F)F)c3)cc2n1]
34
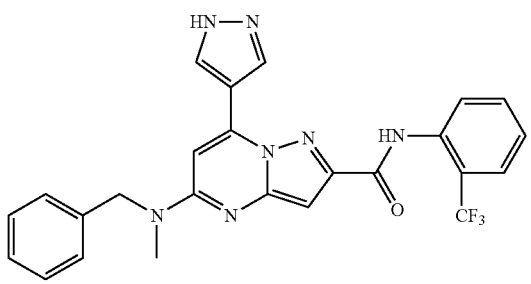 [SMILES: CN(Cc1ccccc1)c1cc(-c2cn[nH]c2)n2nc(C(=O)Nc3ccccc3C(F)(F)F)cc2n1]
35
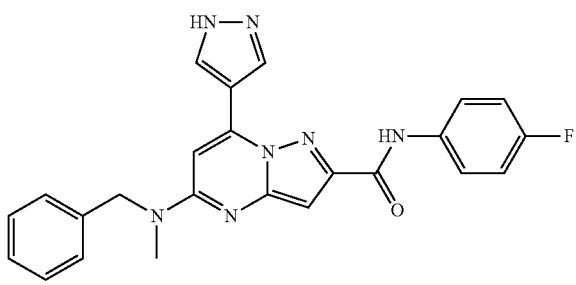 [SMILES: CN(Cc1ccccc1)c1cc(-c2cn[nH]c2)n2nc(C(=O)Nc3ccc(F)cc3)cc2n1]
36
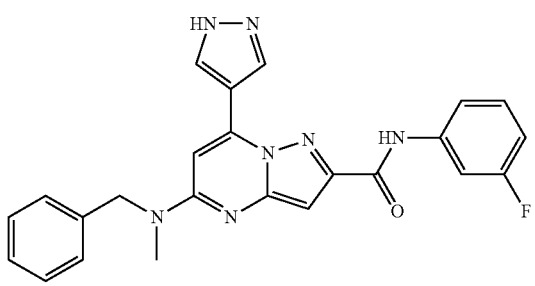 [SMILES: CN(Cc1ccccc1)c1cc(-c2cn[nH]c2)n2nc(C(=O)Nc3cccc(F)c3)cc2n1]

| | |
|---|---|
| 37 | 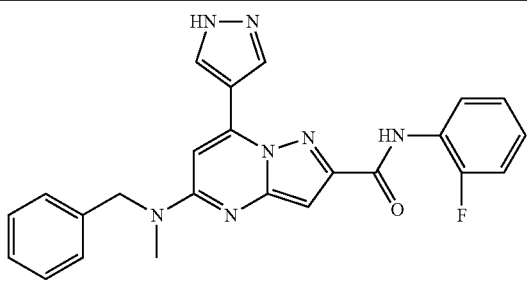 |
| 38 | 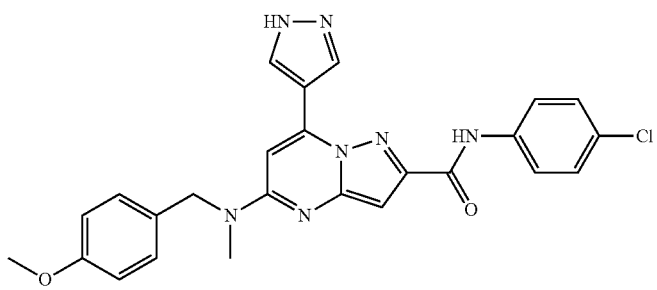 [SMILES: COc1ccc(CN(C)c2cc(-c3cn[nH]c3)n3nc(C(=O)Nc4ccc(Cl)cc4)cc3n2)cc1] |
| 39 | 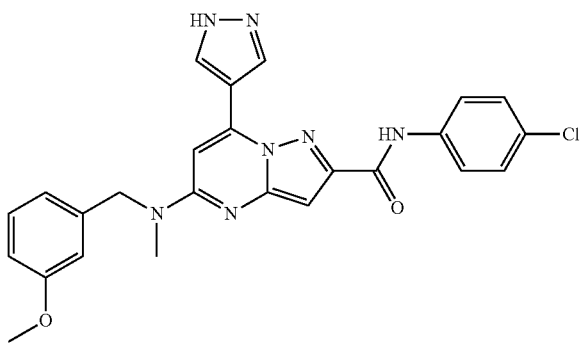 [SMILES: COc1cccc(CN(C)c2cc(-c3cn[nH]c3)n3nc(C(=O)Nc4ccc(Cl)cc4)cc3n2)c1] |
| 40 | 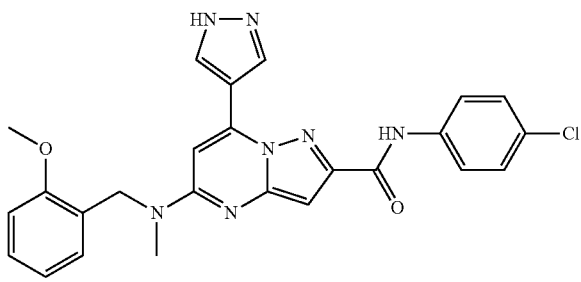 [SMILES: COc1ccccc1CN(C)c1cc(-c2cn[nH]c2)n2nc(C(=O)Nc3ccc(Cl)cc3)cc2n1] |
| 41 | 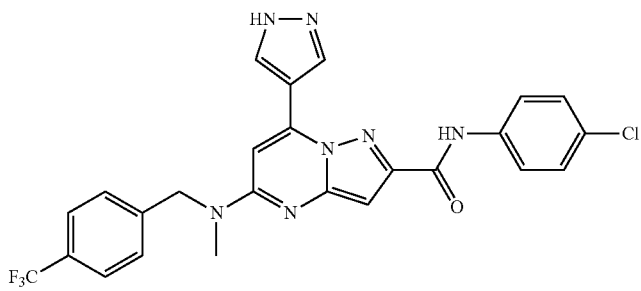 [SMILES: CN(Cc1ccc(C(F)(F)F)cc1)c1cc(-c2cn[nH]c2)n2nc(C(=O)Nc3ccc(Cl)cc3)cc2n1] |

-continued
42
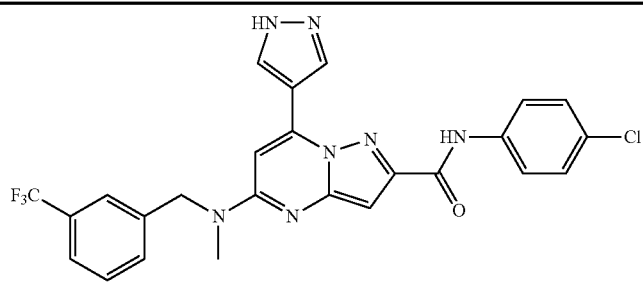
43
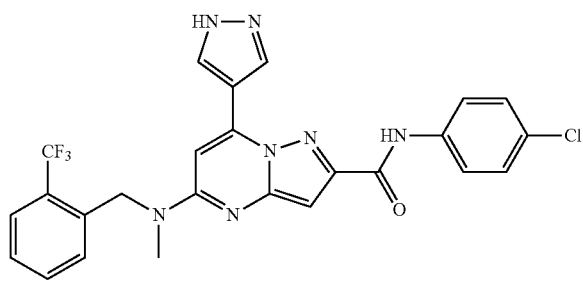 [SMILES: CN(Cc1ccccc1C(F)(F)F)c1cc(-c2cn[nH]c2)n2nc(C(=O)Nc3ccc(Cl)cc3)cc2n1]
44
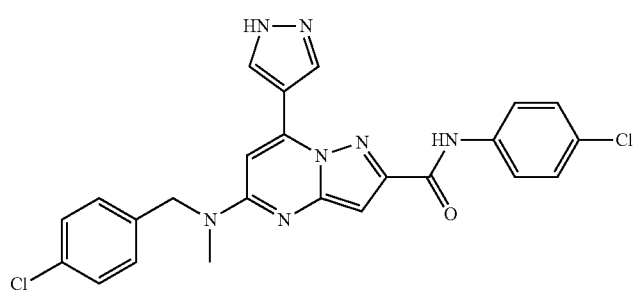 [SMILES: CN(Cc1ccc(Cl)cc1)c1cc(-c2cn[nH]c2)n2nc(C(=O)Nc3ccc(Cl)cc3)cc2n1]
45
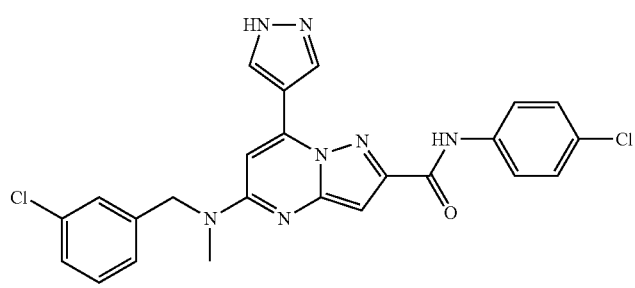 [SMILES: CN(Cc1cccc(Cl)c1)c1cc(-c2cn[nH]c2)n2nc(C(=O)Nc3ccc(Cl)cc3)cc2n1]
46
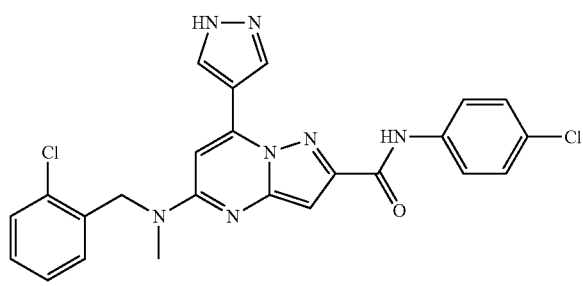 [SMILES: CN(Cc1ccccc1Cl)c1cc(-c2cn[nH]c2)n2nc(C(=O)Nc3ccc(Cl)cc3)cc2n1]

-continued
47 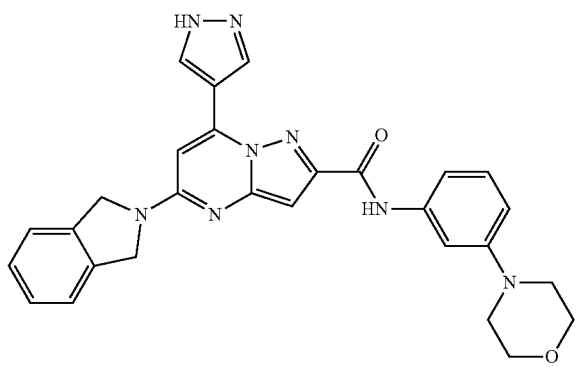 [SMILES: O=C(Nc1cccc(N2CCOCC2)c1)c1cc2nc(N3Cc4ccccc4C3)cc(-c3cn[nH]c3)n2n1]
48 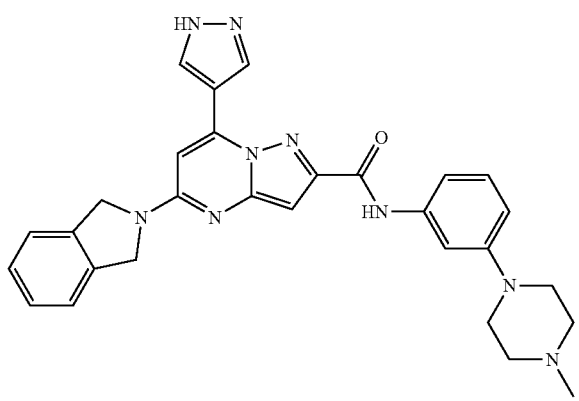 [SMILES: CN1CCN(c2cccc(NC(=O)c3cc4nc(N5Cc6ccccc6C5)cc(-c5cn[nH]c5)n4n3)c2)CC1]
49 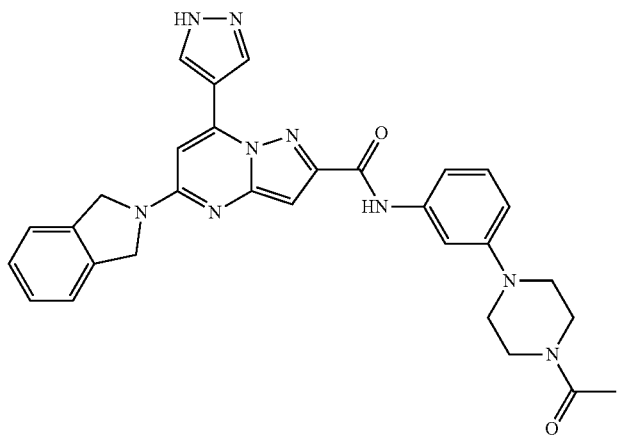 [SMILES: CC(=O)N1CCN(c2cccc(NC(=O)c3cc4nc(N5Cc6ccccc6C5)cc(-c5cn[nH]c5)n4n3)c2)CC1]
50 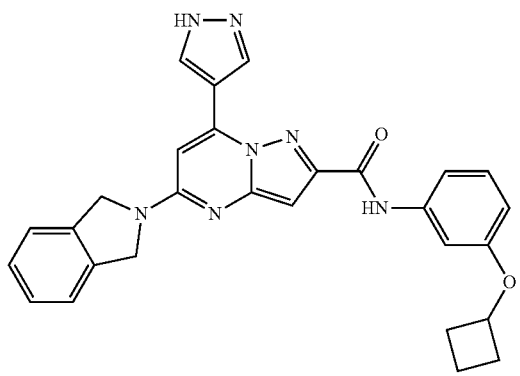 [SMILES: O=C(Nc1cccc(OC2CCC2)c1)c1cc2nc(N3Cc4ccccc4C3)cc(-c3cn[nH]c3)n2n1]

51 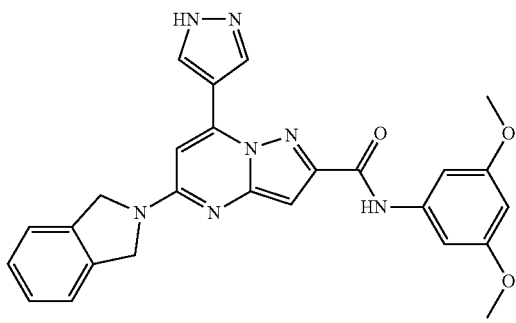 [SMILES: COc1cc(NC(=O)c2cc3nc(N4Cc5ccccc5C4)cc(-c4cn[nH]c4)n3n2)cc(OC)c1]
52 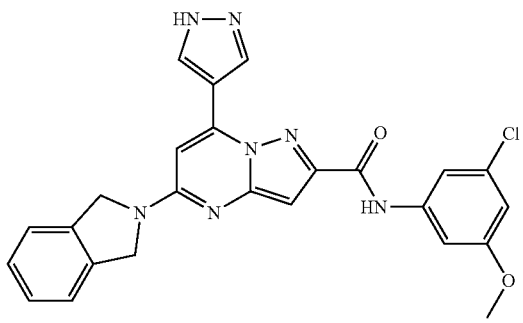 [SMILES: COc1cc(Cl)cc(NC(=O)c2cc3nc(N4Cc5ccccc5C4)cc(-c4cn[nH]c4)n3n2)c1]
53 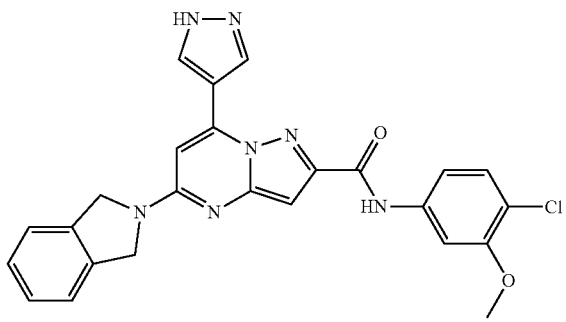 [SMILES: COc1cc(NC(=O)c2cc3nc(N4Cc5ccccc5C4)cc(-c4cn[nH]c4)n3n2)ccc1Cl]
54 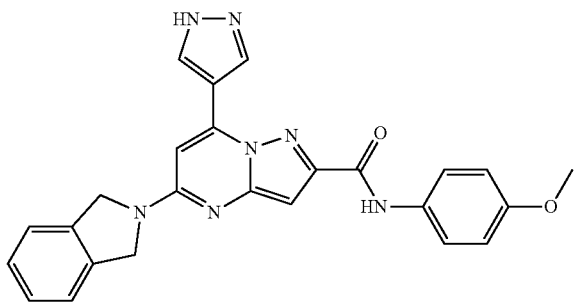 [SMILES: COc1ccc(NC(=O)c2cc3nc(N4Cc5ccccc5C4)cc(-c4cn[nH]c4)n3n2)cc1]
55 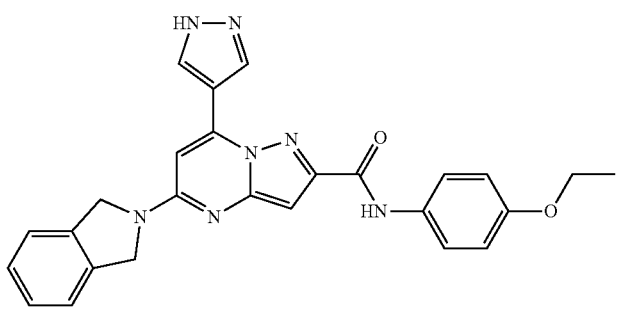

-continued
56 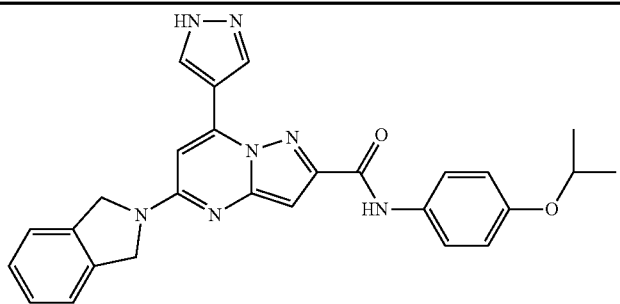
57 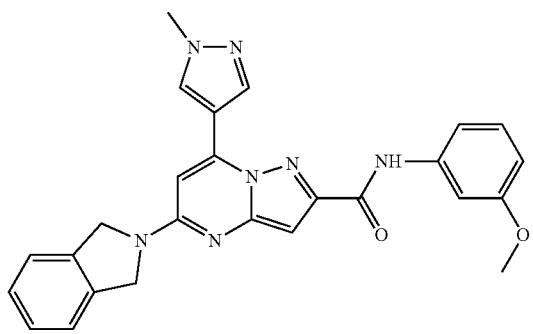 [SMILES: COc1cccc(NC(=O)c2cc3nc(N4Cc5ccccc5C4)cc(-c4cnn(C)c4)n3n2)c1]
58 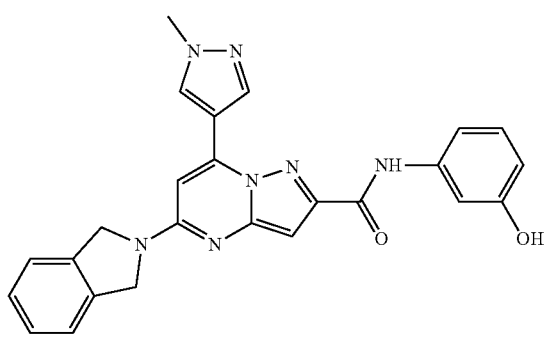 [SMILES: Cn1cc(-c2cc(N3Cc4ccccc4C3)nc3cc(C(=O)Nc4cccc(O)c4)nn23)cn1]
59 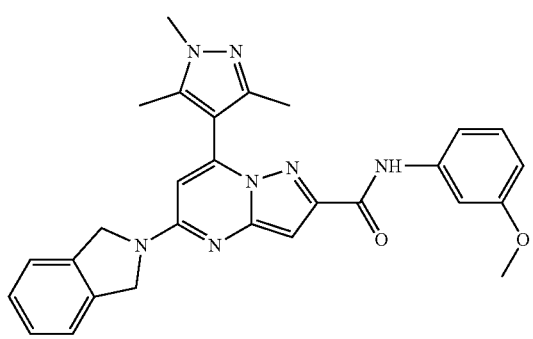 [SMILES: COc1cccc(NC(=O)c2cc3nc(N4Cc5ccccc5C4)cc(-c4c(C)nn(C)c4C)n3n2)c1]
60 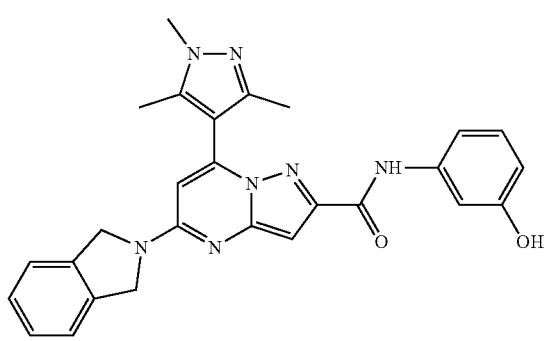 [SMILES: Cc1nn(C)c(C)c1-c1cc(N2Cc3ccccc3C2)nc2cc(C(=O)Nc3cccc(O)c3)nn12]

-continued
61 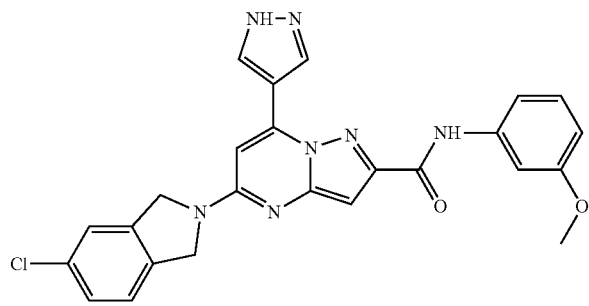 [SMILES: COc1cccc(NC(=O)c2cc3nc(N4Cc5ccc(Cl)cc5C4)cc(-c4cn[nH]c4)n3n2)c1]
62 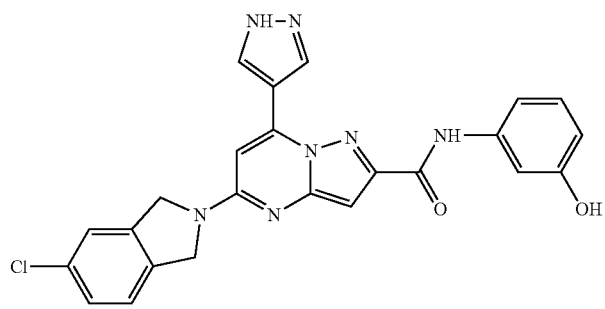 [SMILES: O=C(Nc1cccc(O)c1)c1cc2nc(N3Cc4ccc(Cl)cc4C3)cc(-c3cn[nH]c3)n2n1]
63 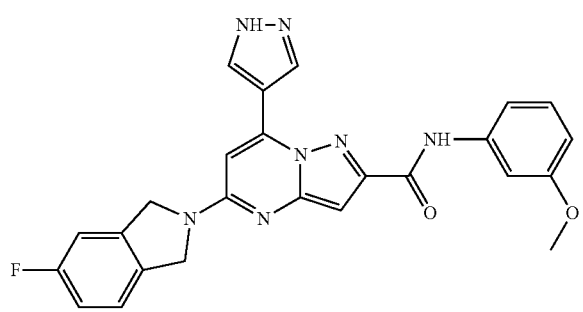 [SMILES: COc1cccc(NC(=O)c2cc3nc(N4Cc5ccc(F)cc5C4)cc(-c4cn[nH]c4)n3n2)c1]
64 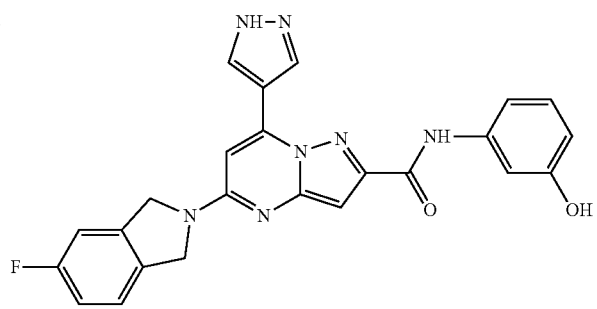 [SMILES: O=C(Nc1cccc(O)c1)c1cc2nc(N3Cc4ccc(F)cc4C3)cc(-c3cn[nH]c3)n2n1]
65 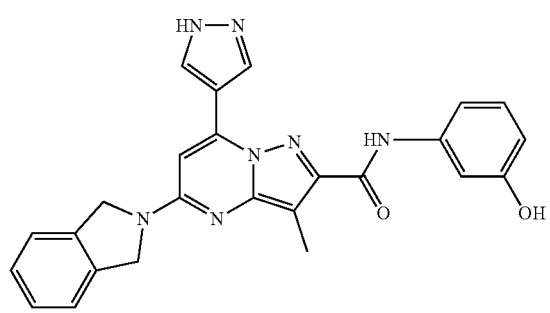 [SMILES: Cc1c(C(=O)Nc2cccc(O)c2)nn2c(-c3cn[nH]c3)cc(N3Cc4ccccc4C3)nc12]

66 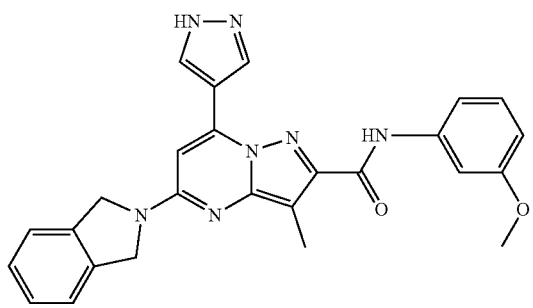 [SMILES: COc1cccc(NC(=O)c2nn3c(-c4cn[nH]c4)cc(N4Cc5ccccc5C4)nc3c2C)c1]
67 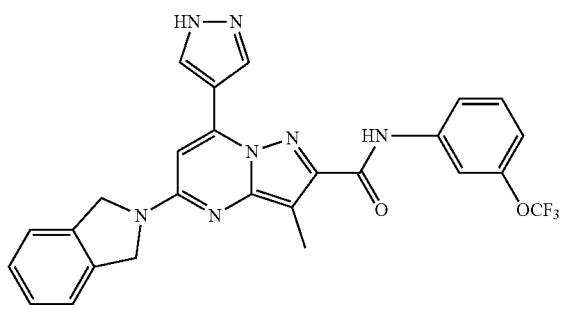 [SMILES: Cc1c(C(=O)Nc2cccc(OC(F)(F)F)c2)nn2c(-c3cn[nH]c3)cc(N3Cc4ccccc4C3)nc12]
68 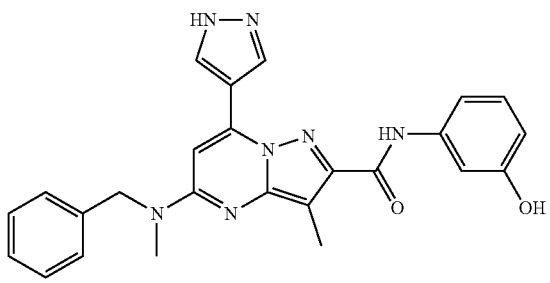
69 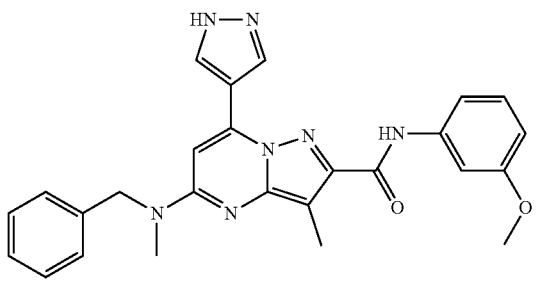 [SMILES: COc1cccc(NC(=O)c2nn3c(-c4cn[nH]c4)cc(N(C)Cc4ccccc4)nc3c2C)c1]
70 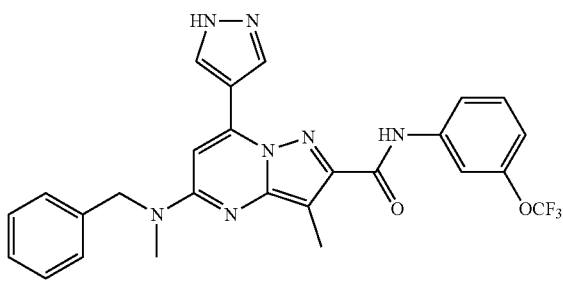 [SMILES: Cc1c(C(=O)Nc2cccc(OC(F)(F)F)c2)nn2c(-c3cn[nH]c3)cc(N(C)Cc3ccccc3)nc12]

71 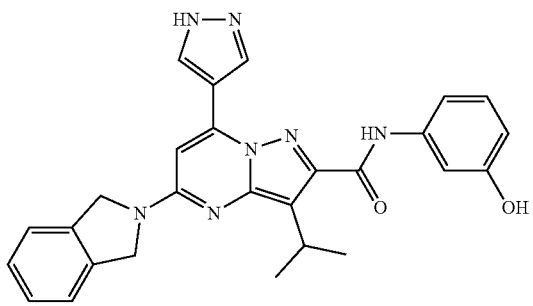 [SMILES: CC(C)c1c(C(=O)Nc2cccc(O)c2)nn2c(-c3cn[nH]c3)cc(N3Cc4ccccc4C3)nc12]
72 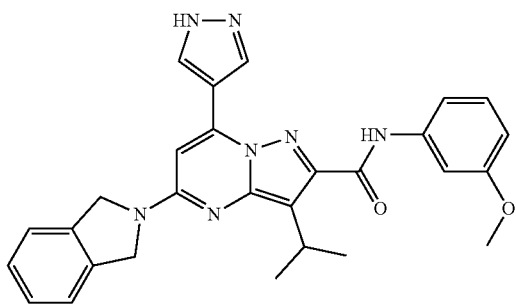 [SMILES: COc1cccc(NC(=O)c2nn3c(-c4cn[nH]c4)cc(N4Cc5ccccc5C4)nc3c2C(C)C)c1]
73 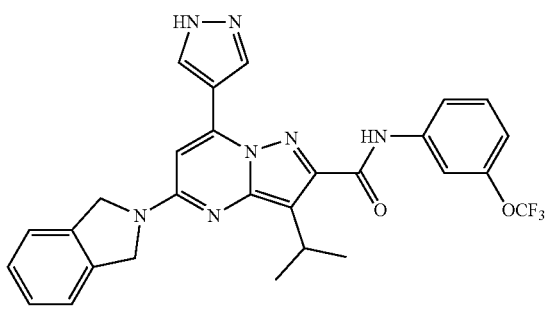 [SMILES: CC(C)c1c(C(=O)Nc2cccc(OC(F)(F)F)c2)nn2c(-c3cn[nH]c3)cc(N3Cc4ccccc4C3)nc12]
74 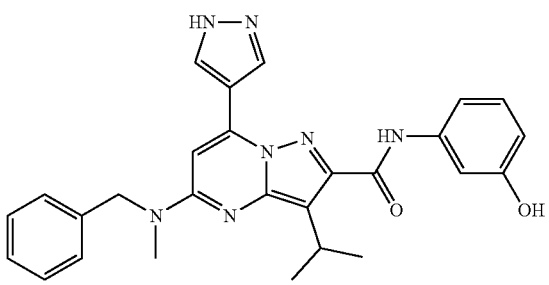 [SMILES: CC(C)c1c(C(=O)Nc2cccc(O)c2)nn2c(-c3cn[nH]c3)cc(N(C)Cc3ccccc3)nc12]
75 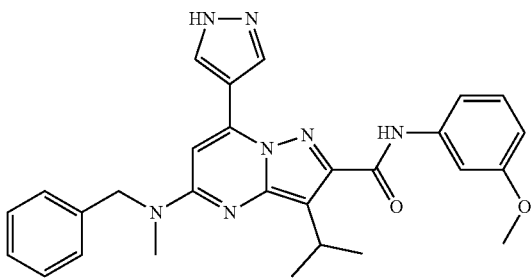 [SMILES: COc1cccc(NC(=O)c2nn3c(-c4cn[nH]c4)cc(N(C)Cc4ccccc4)nc3c2C(C)C)c1]

-continued
76
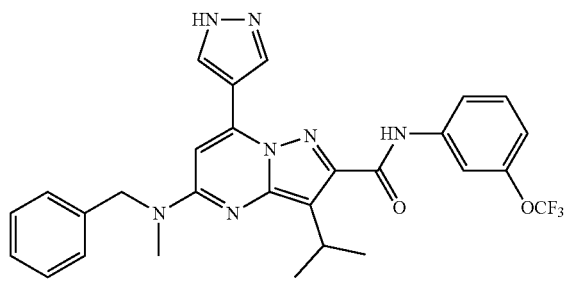 [SMILES: CC(C)c1c(C(=O)Nc2cccc(OC(F)(F)F)c2)nn2c(-c3cn[nH]c3)cc(N(C)Cc3ccccc3)nc12]
77
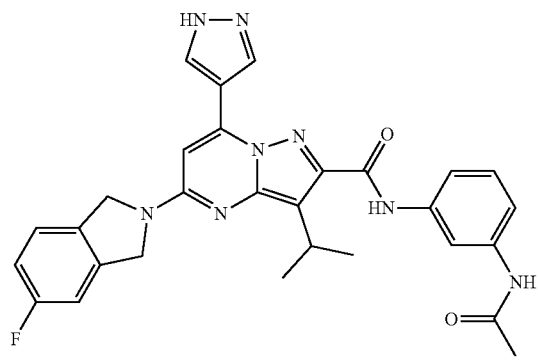 [SMILES: CC(=O)Nc1cccc(NC(=O)c2nn3c(-c4cn[nH]c4)cc(N4Cc5ccc(F)cc5C4)nc3c2C(C)C)c1]
78
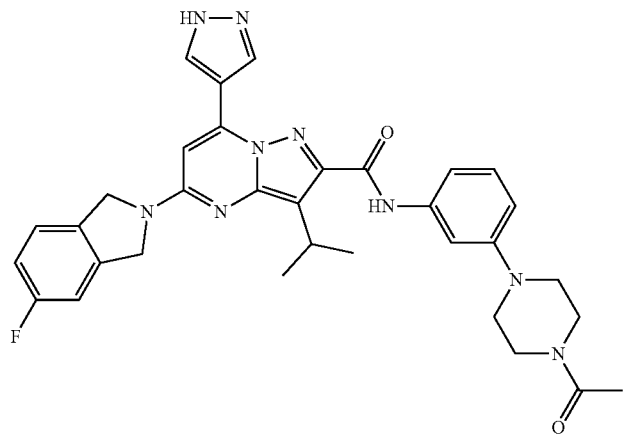 [SMILES: CC(=O)N1CCN(c2cccc(NC(=O)c3nn4c(-c5cn[nH]c5)cc(N5Cc6ccc(F)cc6C5)nc4c3C(C)C)c2)CC1]
79

80
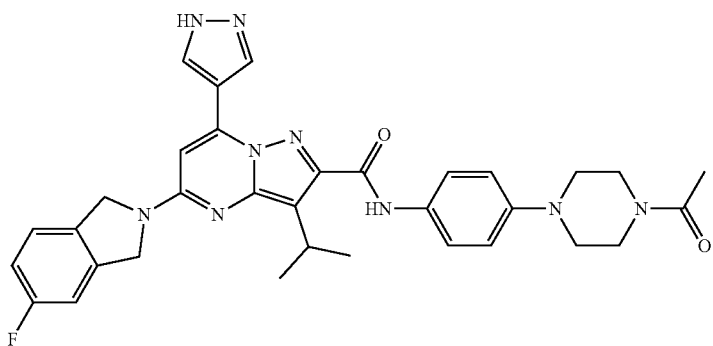 [SMILES: CC(=O)N1CCN(c2ccc(NC(=O)c3nn4c(-c5cn[nH]c5)cc(N5Cc6ccc(F)cc6C5)nc4c3C(C)C)cc2)CC1]
81
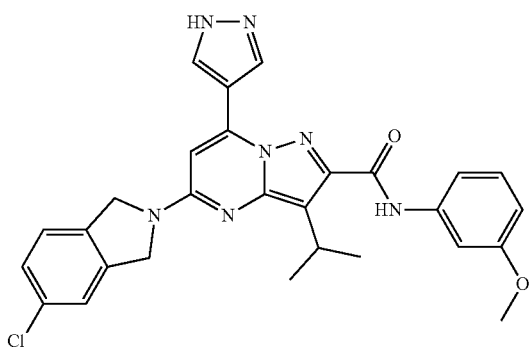 [SMILES: COc1cccc(NC(=O)c2nn3c(-c4cn[nH]c4)cc(N4Cc5ccc(Cl)cc5C4)nc3c2C(C)C)c1]
82
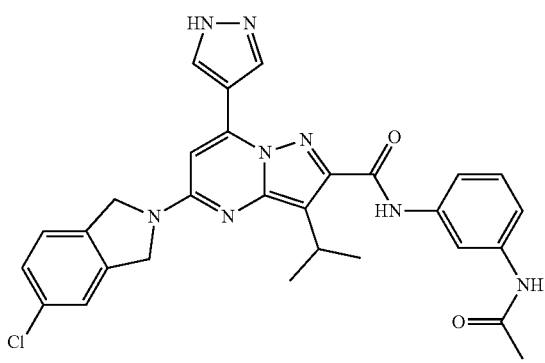 [SMILES: CC(=O)Nc1cccc(NC(=O)c2nn3c(-c4cn[nH]c4)cc(N4Cc5ccc(Cl)cc5C4)nc3c2C(C)C)c1]
83
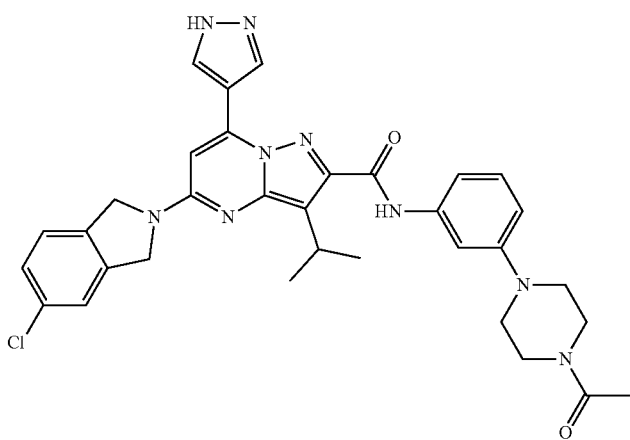 [SMILES: CC(=O)N1CCN(c2cccc(NC(=O)c3nn4c(-c5cn[nH]c5)cc(N5Cc6ccc(Cl)cc6C5)nc4c3C(C)C)c2)CC1]

-continued
84
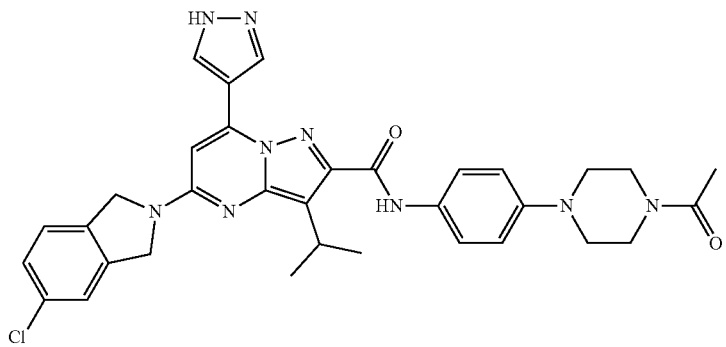 [SMILES: CC(=O)N1CCN(c2ccc(NC(=O)c3nn4c(-c5cn[nH]c5)cc(N5Cc6ccc(Cl)cc6C5)nc4c3C(C)C)cc2)CC1]
85
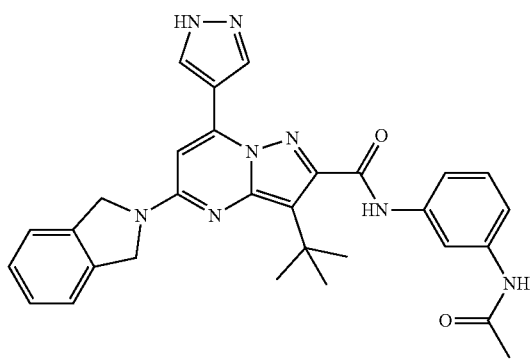 [SMILES: CC(=O)Nc1cccc(NC(=O)c2nn3c(-c4cn[nH]c4)cc(N4Cc5ccccc5C4)nc3c2C(C)(C)C)c1]
86
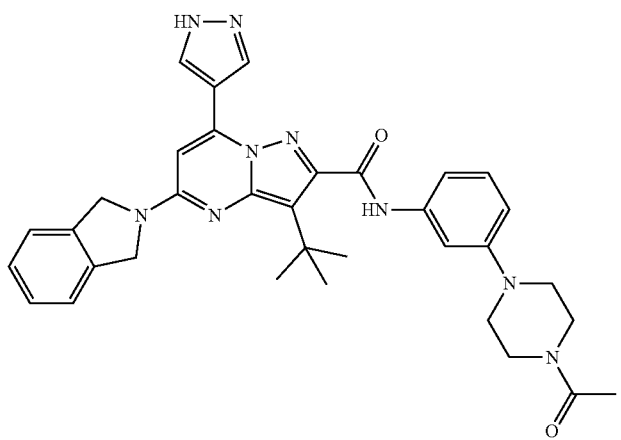 [SMILES: CC(=O)N1CCN(c2cccc(NC(=O)c3nn4c(-c5cn[nH]c5)cc(N5Cc6ccccc6C5)nc4c3C(C)(C)C)c2)CC1]
87

-continued
88
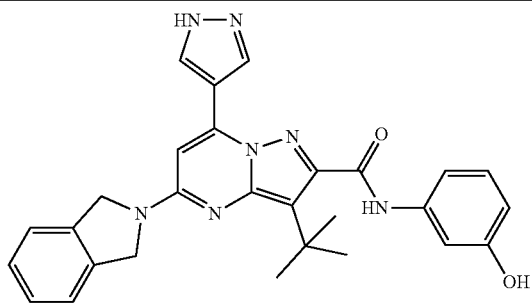
89
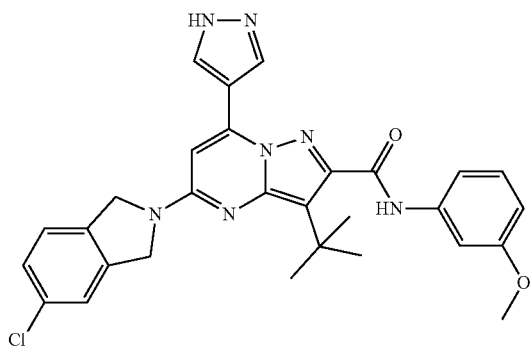 [SMILES: COc1cccc(NC(=O)c2nn3c(-c4cn[nH]c4)cc(N4Cc5ccc(Cl)cc5C4)nc3c2C(C)(C)C)c1]
90
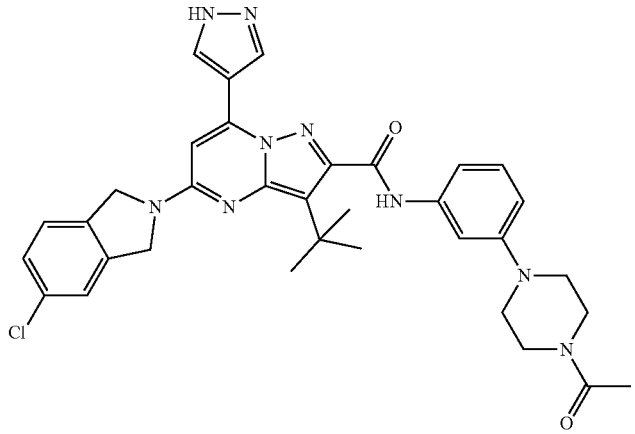 [SMILES: CC(=O)N1CCN(c2cccc(NC(=O)c3nn4c(-c5cn[nH]c5)cc(N5Cc6ccc(Cl)cc6C5)nc4c3C(C)(C)C)c2)CC1]
91
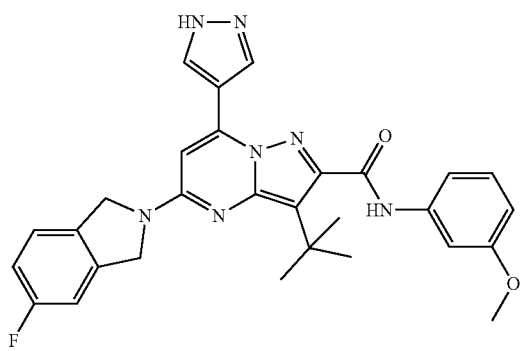

92
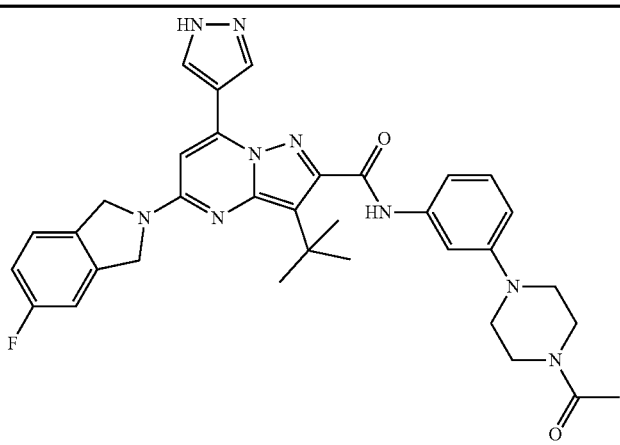
93
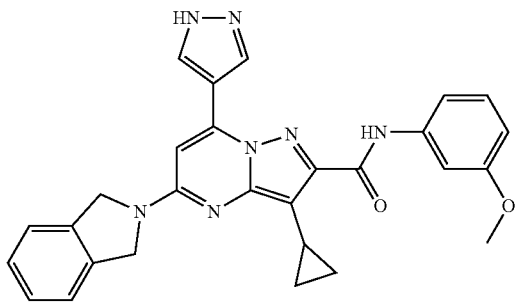 [SMILES: COc1cccc(NC(=O)c2nn3c(-c4cn[nH]c4)cc(N4Cc5ccccc5C4)nc3c2C2CC2)c1]
94
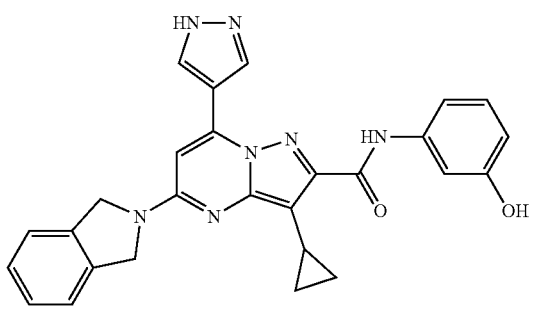 [SMILES: O=C(Nc1cccc(O)c1)c1nn2c(-c3cn[nH]c3)cc(N3Cc4ccccc4C3)nc2c1C1CC1]
95
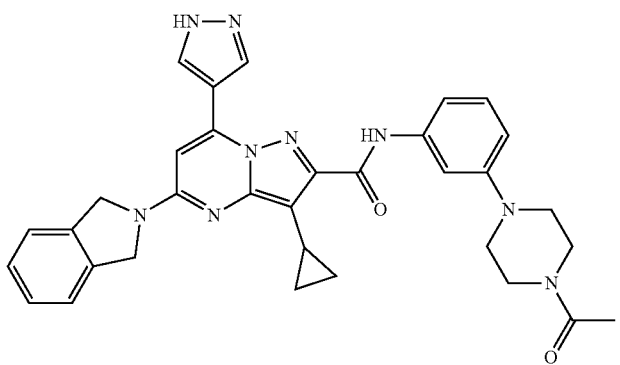 [SMILES: CC(=O)N1CCN(c2cccc(NC(=O)c3nn4c(-c5cn[nH]c5)cc(N5Cc6ccccc6C5)nc4c3C3CC3)c2)CC1]

| | |
|---|---|
| 96 | 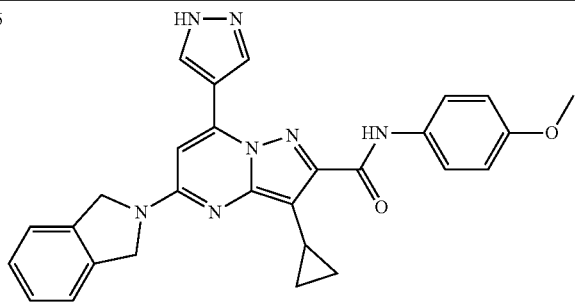 |
| 97 | 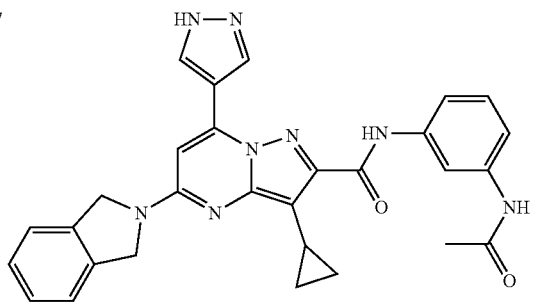 |
| 98 | 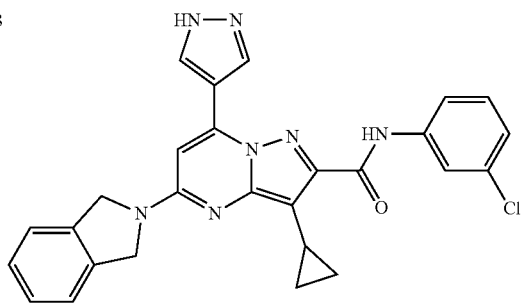 |
| 99 | 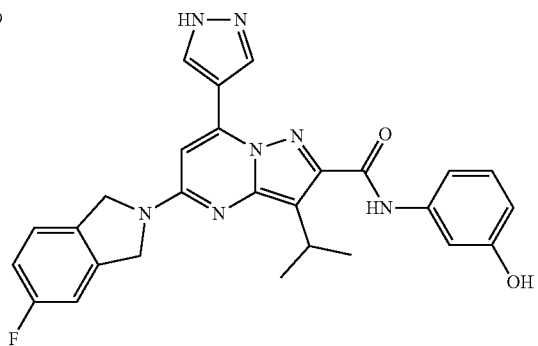 [SMILES: CC(C)c1c(C(=O)Nc2cccc(O)c2)nn2c(-c3cn[nH]c3)cc(N3Cc4ccc(Cl)cc4C3)nc12] |
| 100 | 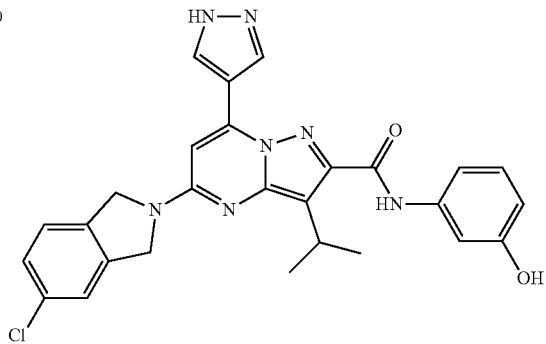 |

-continued
101
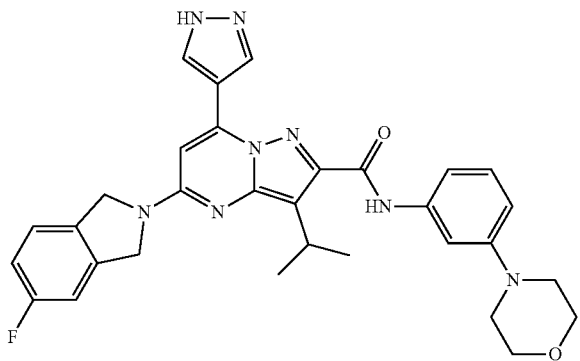 [SMILES: CC(C)c1c(C(=O)Nc2cccc(N3CCOCC3)c2)nn2c(-c3cn[nH]c3)cc(N3Cc4ccc(F)cc4C3)nc12]
102
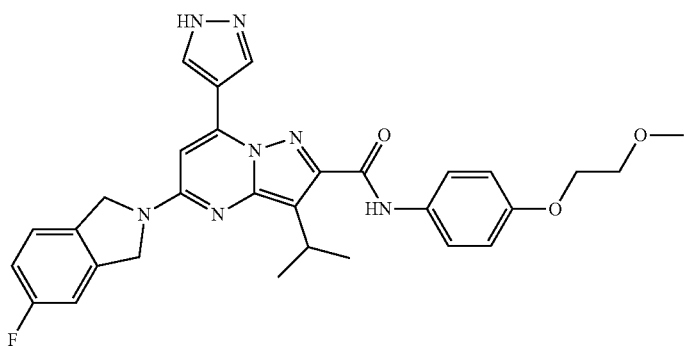
103
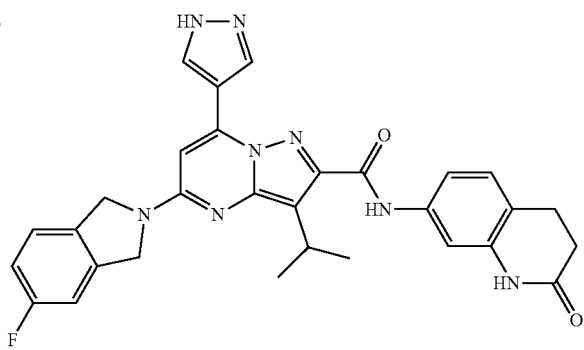 [SMILES: CC(C)c1c(C(=O)Nc2ccc3c(c2)NC(=O)CC3)nn2c(-c3cn[nH]c3)cc(N3Cc4ccc(F)cc4C3)nc12]
104
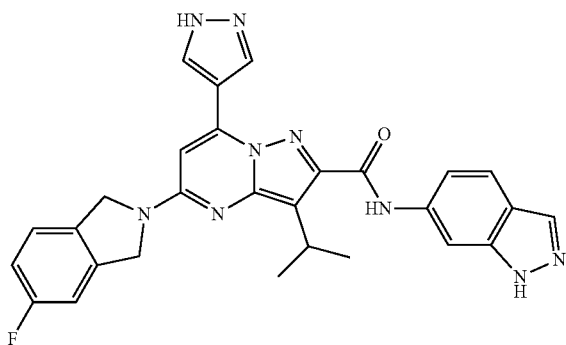 [SMILES: CC(C)c1c(C(=O)Nc2ccc3cn[nH]c3c2)nn2c(-c3cn[nH]c3)cc(N3Cc4ccc(F)cc4C3)nc12]

-continued
105
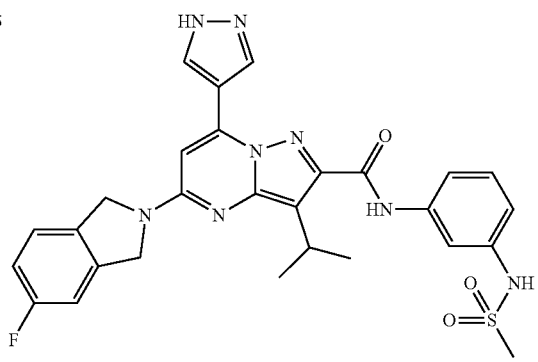
106
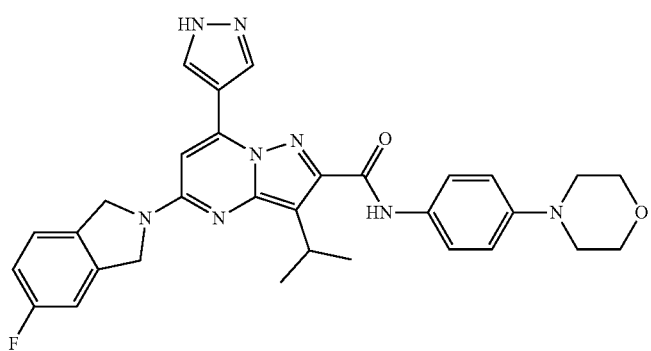 [SMILES: CC(C)c1c(C(=O)Nc2ccc(N3CCOCC3)cc2)nn2c(-c3cn[nH]c3)cc(N3Cc4ccc(F)cc4C3)nc12]
107
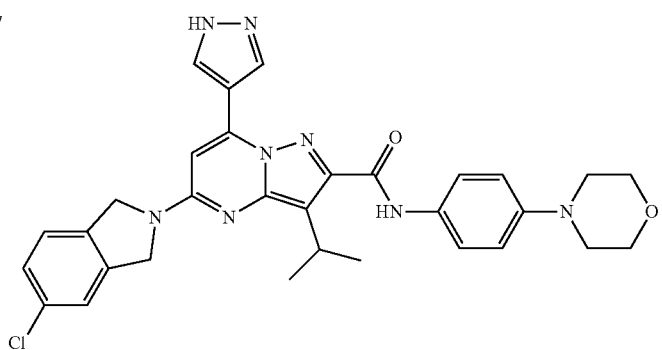
108
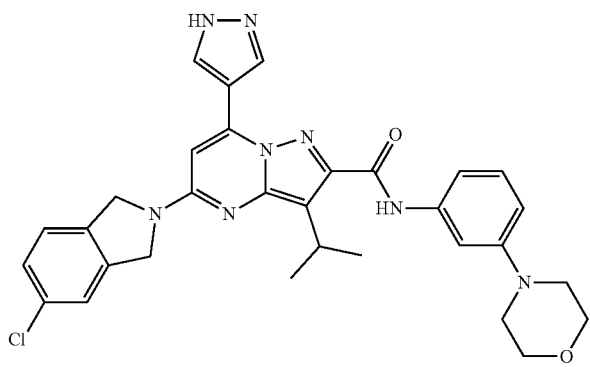 [SMILES: CC(C)c1c(C(=O)Nc2cccc(N3CCOCC3)c2)nn2c(-c3cn[nH]c3)cc(N3Cc4ccc(Cl)cc4C3)nc12]

-continued
109
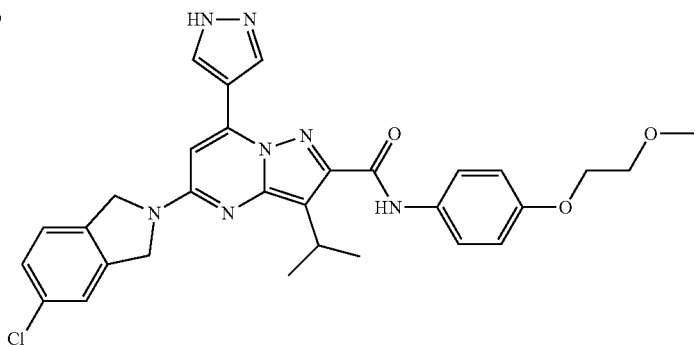
110
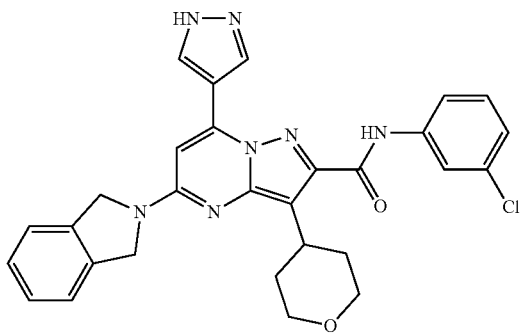 [SMILES: O=C(Nc1cccc(Cl)c1)c1nn2c(-c3cn[nH]c3)cc(N3Cc4ccccc4C3)nc2c1C1CCOCC1]
111
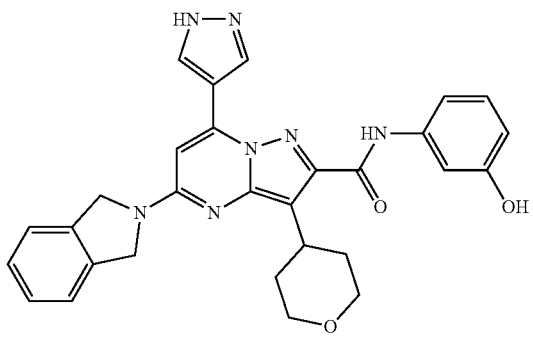 [SMILES: O=C(Nc1cccc(O)c1)c1nn2c(-c3cn[nH]c3)cc(N3Cc4ccccc4C3)nc2c1C1CCOCC1]
112
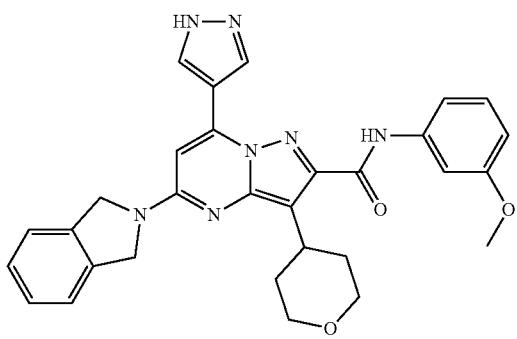 [SMILES: COc1cccc(NC(=O)c2nn3c(-c4cn[nH]c4)cc(N4Cc5ccccc5C4)nc3c2C2CCOCC2)c1]

113 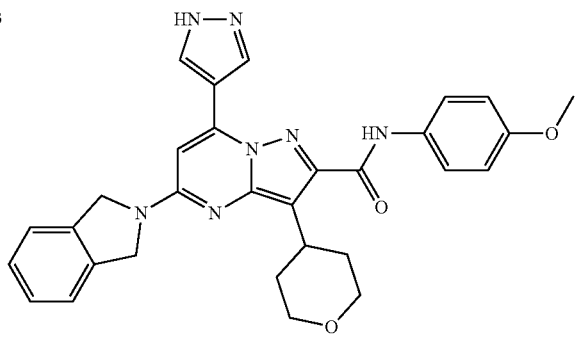
114 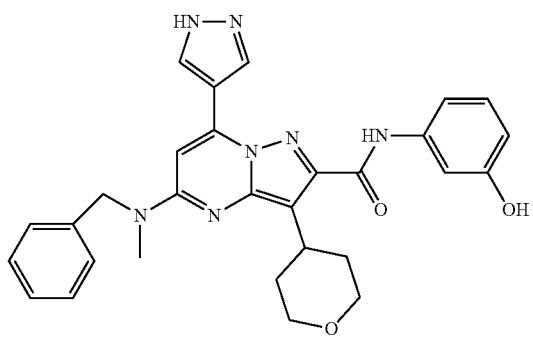 [SMILES: CN(Cc1ccccc1)c1cc(-c2cn[nH]c2)n2nc(C(=O)Nc3cccc(O)c3)c(C3CCOCC3)c2n1]
115 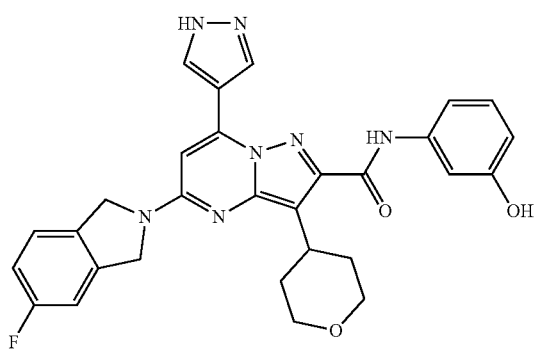 [SMILES: O=C(Nc1cccc(O)c1)c1nn2c(-c3cn[nH]c3)cc(N3Cc4ccc(F)cc4C3)nc2c1C1CCOCC1]
116 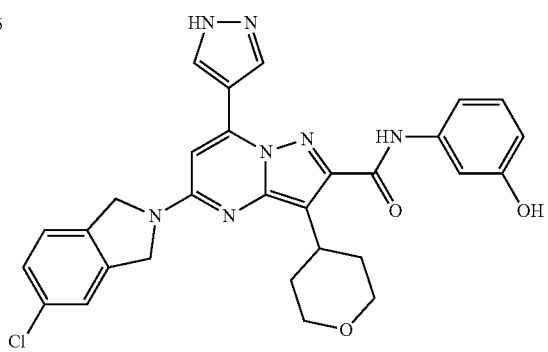

117
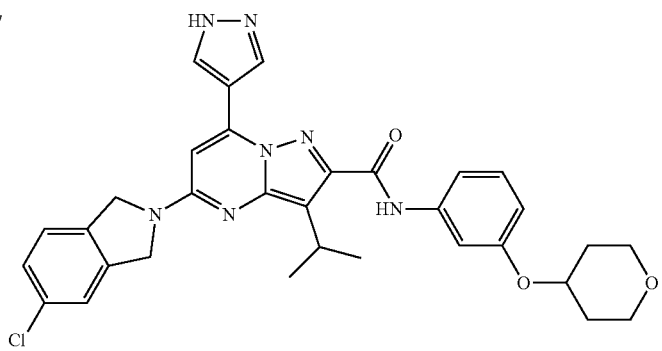
118
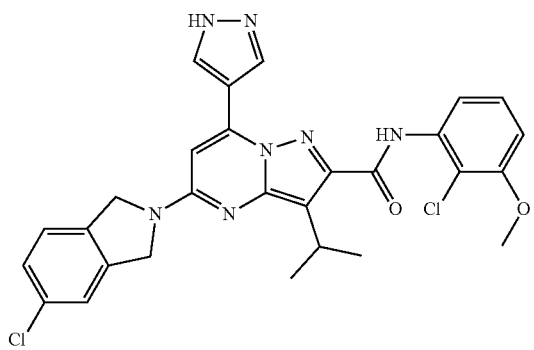 [SMILES: COc1cccc(NC(=O)c2nn3c(-c4cn[nH]c4)cc(N4Cc5ccc(Cl)cc5C4)nc3c2C(C)C)c1Cl]
119
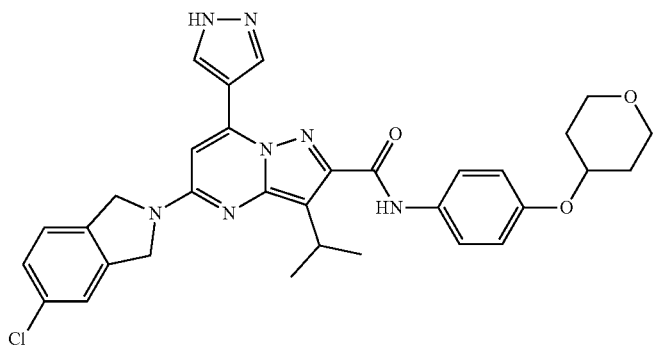 [SMILES: CC(C)c1c(C(=O)Nc2ccc(OC3CCOCC3)cc2)nn2c(-c3cn[nH]c3)cc(N3Cc4ccc(Cl)cc4C3)nc12]
120
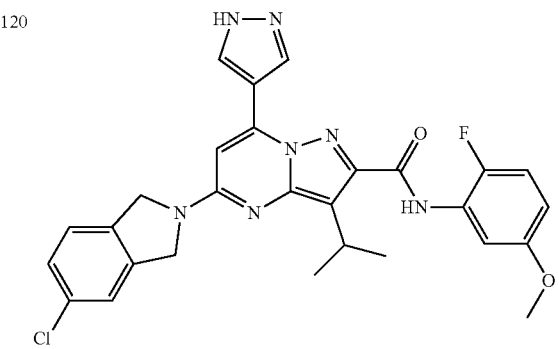

121
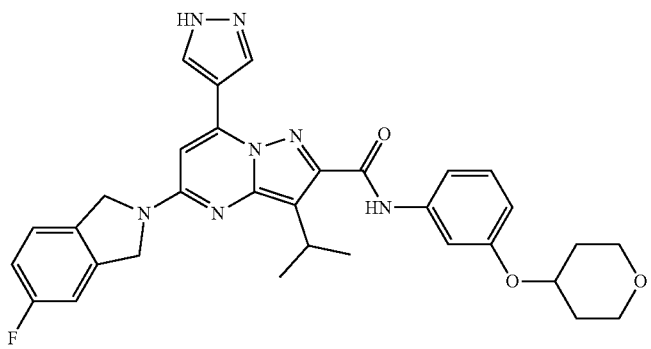 [SMILES: CC(C)c1c(C(=O)Nc2cccc(OC3CCOCC3)c2)nn2c(-c3cn[nH]c3)cc(N3Cc4ccc(F)cc4C3)nc12]
122
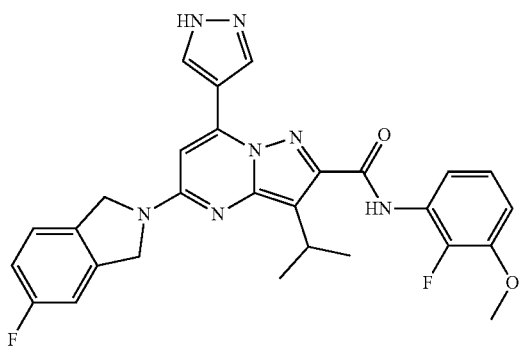
123
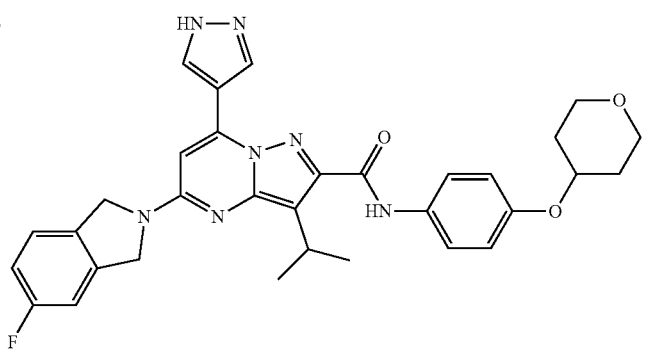 [SMILES: CC(C)c1c(C(=O)Nc2ccc(OC3CCOCC3)cc2)nn2c(-c3cn[nH]c3)cc(N3Cc4ccc(F)cc4C3)nc12]
124
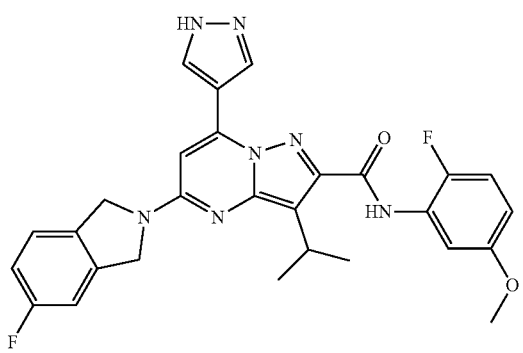

125 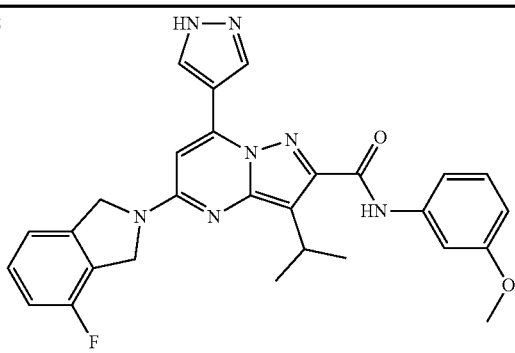

126 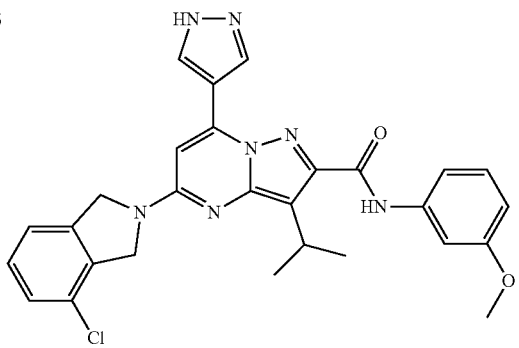

127 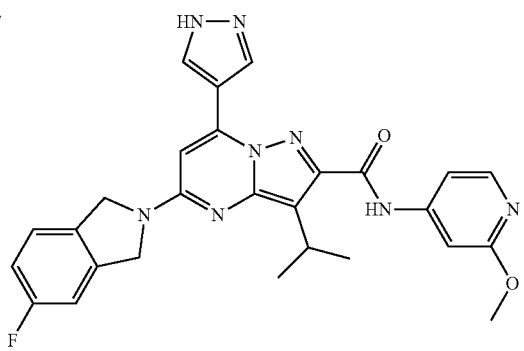

or a pharmaceutically acceptable salt thereof.

The compounds have the ability to inhibit CD151. The ability to inhibit CD151 may be a result of the compounds acting directly and solely on the CD151 to modulate/potentiate biological activity. However, it is understood that the compounds may also act at least partially on other factors associated with CD151 activity.

The inhibition of CD151 may be carried out in any of a number of ways known in the art. For example, if inhibition of CD151 in vitro is desired an appropriate amount of the compound may be added to a solution containing the CD151. In circumstances where it is desired to inhibit CD151 in a humam, the inhibition of the CD151 typically involves administering the compound to a human containing the CD151.

Accordingly, the compounds may find a multiple number of applications in which their ability to inhibit CD151 mentioned above can be utilised.

Accordingly compounds of the invention would be expected to have useful therapeutic properties especially in relation to conditions such as cancer. Examples of cancers that have been associated with CD151 activity include prostate cancer, breast cancer, pancreas cancer, colonic cancer, non-small cell lung cancer, hepatocellular carcinoma, intrahepatic cholangiocarcinoma, renal cell carcinoma, endometrial carcinoma, oesophageal carcinoma, carcinoma of the oesophagus/gastro-oesophageal junction, osteosarcoma, Wilms tumour, mesothelioma, squamous cell carcinoma, glioblastoma multiforme, melanoma and ovarian carcinoma.

CD151 activity has also been associated with conditions such as asthma, multiple sclerosis and inflammatory bowel disease.

Expression of CD151 has also been associated with infection by an infectious agent. As such inhibition of CD151 can assist in the treatment of conditions mediated by an infectious agent. Examples of infectious agents of this type include human papilloma virus, influenza virus, and the bacterium *Neisseria meningitidis*.

Administration of compounds within Formula (I) to humans can be by any of the accepted modes for enteral administration such as oral or rectal, or by parenteral administration such as subcutaneous, intramuscular, intravenous and intradermal routes. Injection can be bolus or via constant or intermittent infusion. The active compound is typically included in a pharmaceutically acceptable carrier or diluent and in an amount sufficient to deliver to the patient a therapeutically effective dose. In various embodiments the activator compound may be selectively toxic or more toxic to rapidly proliferating cells, e.g. cancerous tumours, than to normal cells.

The compounds of the invention can be administered in any form or mode which makes the compound bioavailable. One skilled in the art of preparing formulations can readily select the proper form and mode of administration depending upon the particular characteristics of the compound selected, the condition to be treated, the stage of the condition to be treated and other relevant circumstances. We refer the reader to Remingtons Pharmaceutical Sciences, $19^{th}$ edition, Mack Publishing Co. (1995) for further information.

The compounds of the present invention can be administered alone or in the form of a pharmaceutical composition in combination with a pharmaceutically acceptable carrier, diluent or excipient. The compounds of the invention, while effective themselves, are typically formulated and administered in the form of their pharmaceutically acceptable salts as these forms are typically more stable, more easily crystallised and have increased solubility.

The compounds are, however, typically used in the form of pharmaceutical compositions which are formulated depending on the desired mode of administration. As such in some embodiments the present invention provides a pharmaceutical composition including a compound of Formula (I) and a pharmaceutically acceptable carrier, diluent or excipient. The compositions are prepared in manners well known in the art.

The invention in other embodiments provides a pharmaceutical pack or kit comprising one or more containers filled with one or more of the ingredients of the pharmaceutical compositions of the invention. In such a pack or kit can be found a container having a unit dosage of the agent(s). The kits can include a composition comprising an effective agent either as concentrates (including lyophilized compositions), which can be diluted further prior to use or they can be provided at the concentration of use, where the vials may include one or more dosages. Conveniently, in the kits, single dosages can be provided in sterile vials so that the physician can employ the vials directly, where the vials will have the desired amount and concentration of agent(s). Associated with such container(s) can be various written materials such as instructions for use, or a notice in the form prescribed by a governmental agency regulating the manufacture, use or sale of pharmaceuticals or biological products, which notice reflects approval by the agency of manufacture, use or sale for human administration.

The compounds of the invention may be used or administered in combination with one or more additional drug(s) for the treatment of the disorder/diseases mentioned. The components can be administered in the same formulation or in separate formulations. If administered in separate formulations the compounds of the invention may be administered sequentially or simultaneously with the other drug(s).

In addition to being able to be administered in combination with one or more additional drugs, the compounds of the invention may be used in a combination therapy. When this is done the compounds are typically administered in combination with each other. Thus, one or more of the compounds of the invention may be administered either simultaneously (as a combined preparation) or sequentially in order to achieve a desired effect. This is especially desirable where the therapeutic profile of each compound is different such that the combined effect of the two drugs provides an improved therapeutic result.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of micro-organisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents that delay absorption such as aluminium monostearate and gelatin.

If desired, and for more effective distribution, the compounds can be incorporated into slow release or targeted delivery systems such as polymer matrices, liposomes, and microspheres.

The injectable formulations can be sterilized, for example, by filtration through a bacterial-retaining filter, or by incorporating sterilizing agents in the form of sterile solid compositions that can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminium metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Dosage forms for topical administration of a compound of this invention include powders, patches, sprays, ointments and inhalants. The active compound is mixed under sterile conditions with a pharmaceutically acceptable carrier and any needed preservatives, buffers, or propellants which may be required.

The amount of compound administered will preferably treat and reduce or alleviate the condition. A therapeutically effective amount can be readily determined by an attending diagnostician using conventional techniques and by observing results obtained under analogous circumstances. In determining the therapeutically effective amount a number of factors are to be considered including but not limited to, the species of animal, its size, age and general health, the specific condition involved, the severity of the condition, the response of the patient to treatment, the particular compound administered, the mode of administration, the bioavailability of the preparation administered, the dose regime selected, the use of other medications and other relevant circumstances.

A preferred dosage will be a range from about 0.01 to 300 mg per kilogram of body weight per day. A more preferred dosage will be in the range from 0.1 to 100 mg per kilogram of body weight per day, more preferably from 0.2 to 80 mg per kilogram of body weight per day, even more preferably 0.2 to 50 mg per kilogram of body weight per day. A suitable dose can be administered in multiple sub-doses per day.
Synthesis of Compounds of the Invention The compounds for use in the methods of the present invention may be prepared using known organic synthesis techniques and can be synthesized according to any of numerous possible synthetic routes including the reaction routes and synthesis schemes as described below, employing the techniques available in the art using starting materials that are readily available. The preparation of compounds of the embodiments is described in detail in the following examples, but the artisan will recognize that the chemical reactions described may be readily adapted to prepare other agents of the various embodiments.

The reactions for preparing compounds of the invention can be carried out in suitable solvents, which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., 1H or 13C), infrared spectroscopy, spectrophotometry (e.g., UV-visible), or mass spectrometry, or by chromatography such as high-performance liquid chromatography (HPLC) or thin layer chromatography.

The expressions, "ambient temperature," "room temperature," and "r.t.", as used herein, are understood in the art, and refer generally to a temperature, e.g. a reaction temperature, that is about the temperature of the room in which the reaction is carried out, for example, a temperature from about 20° C. to about 30° C.

The invention will now be illustrated by way of examples; however, the examples are not to be construed as being limitations thereto. Additional compounds, other than those described below, may be prepared using methods and synthetic protocols or appropriate variations or modifications thereof, as described herein.

EXAMPLES

Definitions

AcOH (acetic acid);
atm (atmosphere);
Boc$_2$O (di-tert-butyl dicarbonate);
c-Hex (cyclohexane);
CDCl$_3$ (deuterated chloroform);
CD$_3$OD (deuterated methanol);
CHCl$_3$ (chloroform);
conc. (concentrated);
DCM (dichloromethane);
DIPEA (N,N-diisopropylethylamine);
DMAP (4-dimethylaminopyridine);
DMSO (dimethyl sulfoxide);
DMSO-d$_6$ (deuterated dimethyl sulfoxide);
eq (equivalent);

ES-API (electrospray atmospheric pressure ionization);
Et₃N (triethylamine);
Et₂O (diethyl ether);
EtOAc (ethyl acetate);
EtOH (ethanol);
g (gram);
h (hour);
HATU (1-[bis(dimethylamino)methylene]-1H-1,2,3-triazolo[4,5-b]pyridinium 3-oxide hexafluorophosphate);
HCl (hydrochloric acid/hydrogen chloride);
$^1$H NMR (proton nuclear magnetic resonance);
Hz (hertz);
L (litre);
LCMS (liquid chromatography-mass spectrometry);
LiHMDS (lithium bis(trimethylsilyl)amide);
M (molar);
MeOH (methanol);
mg (milligrams);
MHz (megahertz);
min (min);
mL (millilitres);
mmol (millimoles);
MsCl (methanesulfonyl chloride);
n-BuLi (n-butyllithium);
NaH (sodium hydride);
NaHCO₃ (sodium bicarbonate);
NaOH (sodium hydroxide);
Na₂SO₄ (sodium sulphate);
Pd(dppf)Cl₂ ([1,1'-Bis(diphenylphosphino)ferrocene]dichloropalladium(II), complex with DCM);
PE (Petroleum Ether);
ppm (parts per million);
RT (room temperature);
TFA (trifluoroacetic acid);
THF (tetrahydrofuran).

The majority of the materials were purchased commercially as reagent grade.

Nuclear magnetic resonance (NMR) spectra were obtained on a Bruker Avance-400 spectrometer ($^1$H at 400.13 MHz and $^{13}$C at 100.62 MHz). Proton chemical shifts are reported in ppm from an internal standard of residual chloroform (7.26 ppm), dimethylsulfoxide (2.50 ppm) or methanol (3.31 ppm). Each resonance was assigned according to the following convention; chemical shift (δ) (multiplicity, coupling constant(s) in Hz, integration). Carbon chemical shifts are reported in parts per million (ppm) using an internal standard of residual chloroform (77.16 ppm), dimethylsulfoxide (39.52 ppm) or methanol (49.00 ppm). Chemical shifts were reported as δ values in parts per million (ppm). The following abbreviations have been used upon reporting spectral data: s, singlet; d, doublet; t, triplet; q, quartet; quin, quintet; sext, sextet; m, multiplet; app, apparent; and br, broad.

Electrospray mass spectroscopy (MS) was carried out using the following methods;

Method A: 1. Equipment Information, LC model: Aqilent 1200 (Pump type: Binary Pump, Detector type: DAD) MS model: Aqilent G6110A Quadrupole.

Parameters of LCMS-LC: Column: Xbridge-C18, 3.5 μm, 2.1×50 mm, Column temperature: 30° C., Acquisition of wavelength: 214 nm, 254 nm, Mobile phase: A: 0.05% HCOOH aqueous solution, B: CAN, Run time: 5 min, MS: Ion source: ES+ (or ES−) MS range: 70~900 m/z, Fragmentor: 60, Drying gas flow: 12~13 L/min, Nebulizer pressure: 35 psi, Drying gas temperature: 350° C., Vcap: 3.5 kV.

| Gradient Table | | | | |
|---|---|---|---|---|
| | | Gradient | | |
| Method Name (LCMS) | Flow (ml/min) | T (min) | A (%) | B (%) |
| SYN-P-M (ES+) | 0.6 | 0.00 | 90 | 10 |
| or | 0.6 | 0.50 | 90 | 10 |
| SYN-N-M (ES−) | 0.6 | 4.00 | 10 | 90 |
| (for medium | 0.6 | 4.50 | 0 | 100 |
| polarity samples) | 0.6 | 4.51 | 90 | 10 |
| | 0.6 | 5.00 | 90 | 10 |
| SYN-P-L (ES+) | 0.6 | 0.00 | 97 | 3 |
| or | 0.6 | 0.50 | 97 | 3 |
| SYN-N-L (ES−) | 0.6 | 4.00 | 30 | 70 |
| (for large polarity | 0.6 | 4.50 | 0 | 100 |
| samples) | 0.6 | 4.51 | 97 | 3 |
| | 0.6 | 5.00 | 97 | 3 |
| SYN-P-S (ES+) | 0.6 | 0.00 | 45 | 55 |
| or | 0.6 | 0.50 | 45 | 55 |
| SYN-N-S (ES−) | 0.6 | 4.00 | 90 | 10 |
| (for small polarity | 0.6 | 4.50 | 45 | 55 |
| samples) | 0.6 | 5.00 | 45 | 55 |

Method B: 1) LC: Agilent Technologies 1290 series, Binary Pump, Diode Array Detector. Colum: Agilent EclipsePlus RRHD C18, 1.8 μm, 3.0×50 mm. Mobile phase: A: 0.05% Formate in water (v/v), B: 0.05% Formate in MeCN(v/v). Flow Rate: 1.0 mL/min at 40° C. Detector: 214 nm, 254 nm.

Gradient stop time, 3.0 min. Timetable:

| T (min) | A (%) | B (%) |
|---|---|---|
| 0.00 | 60 | 40 |
| 2.65 | 0 | 100 |
| 3.00 | 0 | 100 |

MS: G6120A, Quadrupole LC/MS; Ion Source: ESI, Signal: positive, TIC: 70~1000 m/z, Fragmentor: 60, Threshold: 5, Gain: 1, Drying gas flow: 10 L/min, Nebulizer pressure: 35 psi, LCMS-P2-3 min-1) LC: Agilent Technologies 1290 series, Binary Pump, Diode Array Detector. Colum: Agilent EclipsePlus RRHD C18, 1.8 μm, 3.0×50 mm. Mobile phase: A: 0.05% Formate in water (v/v), B: 0.05% Formate in MeCN(v/v). Flow Rate: 1.0 mL/min at 40° C. Detector: 214 nm, 254 nm.

Gradient stop time, 3.0 min. Timetable:

| T (min) | A (%) | B (%) |
|---|---|---|
| 0.00 | 80 | 20 |
| 2.65 | 20 | 80 |
| 3.00 | 20 | 80 |

MS: G6120A, Quadrupole LC/MS, Ion Source: ESI, Signal: positive, TIC: 70~1000 m/z, Fragmentor: 60, Threshold: 5, Gain: 1, Drying gas flow: 10 L/min, Nebulizer pressure: 35 psi Method C—LC model: Waters 2695 alliance, (Pump: Quaternary Pump, Detector: 2996 Photodiode Array Detector), MS model: Micromass ZQ. Parameters of LCMS-LC: Column: Xbridge-C18, 2.5 μm, 2.1×30 mm, Column temperature: 30° C. Acquisition of wavelength: 214 nm, 254 nm. Mobile phase: A: 0.05% HCOOH aqueous solution, B: CAN. Run time: 5 min. MS: Ion source: ES+(or ES−) MS range: 50~900 m/z. Capillary: 3 0.5 kV Cone: 35 V Extractor: 3 V. Drying gas flow: 350 L/hr cone: 50 L/hr. Desolvation temperature: 300° C. Source temperature: 120° C. Run time: 5 min

| MS method | Name | LC method | | | |
|---|---|---|---|---|---|
| | | Gradient | | | |
| | | Flow (ml/min) | T (min) | A (%) | B (%) |
| MS-POS-8 MIN (ES+) or POS-NEG-8 MIN (ES+ & ES−) | LC-5 min (for medium polarity samples) | 0.5 | 0.0 | 70 | 30 |
| | | 0.5 | 0.3 | 70 | 30 |
| | | 0.5 | 0.6 | 50 | 50 |
| | | 0.5 | 0.9 | 40 | 60 |
| | | 0.5 | 1.2 | 30 | 70 |
| | LC-5 min-L (for large polarity samples) | 0.5 | 3.2 | 5 | 95 |
| | | 0.5 | 3.5 | 5 | 95 |
| | | 0.5 | 4.0 | 70 | 30 |
| | | 0.5 | 5.0 | 70 | 30 |
| | | 0.5 | 0.0 | 90 | 10 |
| | | 0.5 | 0.4 | 90 | 10 |
| | | 0.5 | 0.8 | 80 | 20 |
| | | 0.5 | 1.2 | 70 | 30 |
| | | 0.5 | 2.0 | 55 | 45 |
| | | 0.5 | 2.8 | 40 | 60 |
| | | 0.5 | 3.3 | 5 | 95 |
| | | 0.5 | 3.7 | 5 | 95 |
| | | 0.5 | 4.0 | 90 | 10 |
| | | 0.5 | 5.0 | 90 | 10 |
| | LC-5 min-S (for small polarity samples) | 0.5 | 0.0 | 70 | 30 |
| | | 0.5 | 0.3 | 70 | 30 |
| | | 0.5 | 0.5 | 40 | 60 |
| | | 0.5 | 1.0 | 15 | 85 |
| | | 0.5 | 3.2 | 5 | 95 |
| | | 0.5 | 3.7 | 5 | 95 |
| | | 0.5 | 4.0 | 70 | 30 |
| | | 0.5 | 5.0 | 70 | 30 |

Sample preparation—The sample was dissolved in methanol, the concentration about 1~10 mg/mL, then filtered through the syringes filter with 0.22 μm. (Injection volume: 1~10 μL).

Method 0 LC model: Waters 2695 alliance, (Pump: Quaternary Pump, Detector: 2996 Photodiode Array Detector), MS model: Micromass ZQ, Parameters of LCMS-LC: Column: Xbridge-C18, 3.5 μm, 2.1×50 mm. Column temperature: 20° C. Acquisition of wavelength: 214 nm, 254 nm. Mobile phase: A: 0.05% HCOOH aqueous solution, B: CAN. Run time: 8 min MS: Ion source: ES+(or ES−) MS range: 100-1000 m/z. Capillary: 3 kV Cone: 40 V Extractor: 3 V.Drying gas flow: 800 L/hr cone: 50 L/hr. Desolvation temperature: 500° C. Source temperature: 120° C. Run time: 8 min

| MS method | Name | LC method | | | |
|---|---|---|---|---|---|
| | | Gradient | | | |
| | | Flow (ml/min) | T (min) | A (%) | B (%) |
| MS-POS-8 MIN (ES+) or POS-NEG-8 MIN (ES+ & ES−) | LC-8 min (for medium polarity samples) | 0.7 | 0.00 | 90 | 10 |
| | | 0.7 | 1.00 | 90 | 10 |
| | | 0.7 | 6.00 | 10 | 90 |
| | | 0.7 | 7.00 | 0 | 100 |
| | | 0.7 | 7.01 | 90 | 10 |
| | | 0.7 | 8.00 | 90 | 10 |
| | LC-8 min-L (for large polarity samples) | 0.7 | 0.00 | 97 | 3 |
| | | 0.7 | 0.50 | 97 | 3 |
| | | 0.7 | 4.50 | 60 | 40 |
| | | 0.7 | 5.00 | 50 | 50 |
| | | 0.7 | 6.50 | 10 | 90 |
| | | 0.7 | 7.00 | 97 | 3 |
| | | 0.7 | 8.00 | 97 | 3 |
| | LC-8 min-S (for small polarity samples) | 0.7 | 0.00 | 50 | 50 |
| | | 0.7 | 1.00 | 50 | 50 |
| | | 0.7 | 6.00 | 0 | 100 |
| | | 0.7 | 7.00 | 0 | 100 |
| | | 0.7 | 7.10 | 50 | 50 |
| | | 0.7 | 8.00 | 50 | 50 |

Sample preparation—The sample was dissolved in methanol, the concentration about 1~10 mg/mL, then filtered through the syringes filter with 0.22 μm. (Injection volume: 1~10 μL).

Thin layer chromatography (TLC) was used to monitor reactions and chromatographic fractions on Merck Kieselgel 60 F254 aluminium backed plates. Silica gel 60 F254 was used as the stationary phase to perform flash chromatography. Gradient elution using ethyl acetate (EtOAc) and hexane, analytical grade were used unless otherwise stated.

All glassware used in reactions requiring anhydrous conditions, was oven-dried (120° C.) and then cooled under nitrogen prior to use.

A general scheme for the formation of a number of compounds of the inventions is shown in Schemes 1 and 2 below which can be modified as appropriate to produce a number of compounds of the invention. As shown in scheme 1 a typical first step is to synthesise the heteroaromatic core molecule (in circumstances where this is not readily available)

In general, the appropriately protected diacid moiety (1) is reacted with the appropriately functionalized acetylene in the presence of a strong base to form II. Compound II is then reacted with hydrazine to form the 5 membered heterocyclic ring compound (III). Compound III is then reacted with a suitably substituted diacid to form the amide IV which is then cyclised to form the bicyclic heteroaromatic compound V. Finally, compound V is then reacted with $POCl_3$ to insert chloro groups for further elaboration of the substituents of the ring (compound VI). As will be appreciated by a skilled worker in the field this scheme depicts one mode of formation of an advanced intermediate for the synthesis of compounds of the invention. Variation of the R group on the acetylene and the ester group on the starting diacid allows for a number of different advanced intermediates to be made using this technique.

Scheme 1

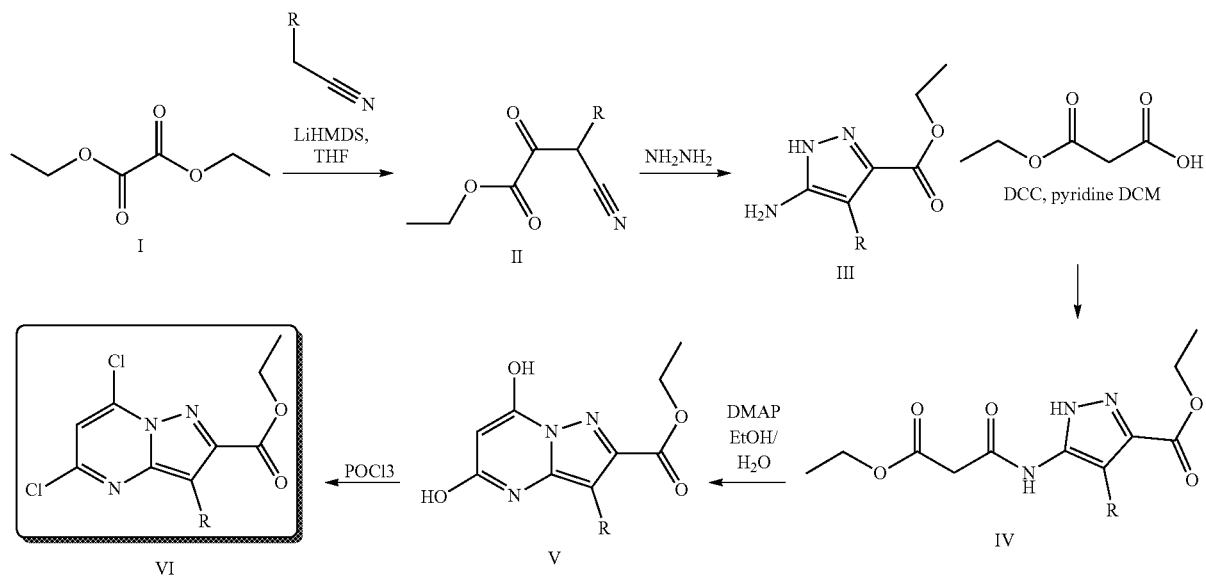

Once the advanced intermediate VI has been produced using the procedure shown in scheme 1 it can be elaborated to compounds of the invention using the procedure in scheme 2 as shown below. Typically, a compound of formula VI is subjected to a Suzuki coupling with a suitable heteroaromatic boronic acid to introduce the heteroaromatic group and form compounds of formula VII. Reaction of compound VII with a suitably substituted diamine leads to compounds of formula VIII which are then saponified to remove the acid protecting group to produce the free acid IX. This is then subjected to an amide coupling with a suitable aromatic amine to form compounds of formula X.

Scheme 2

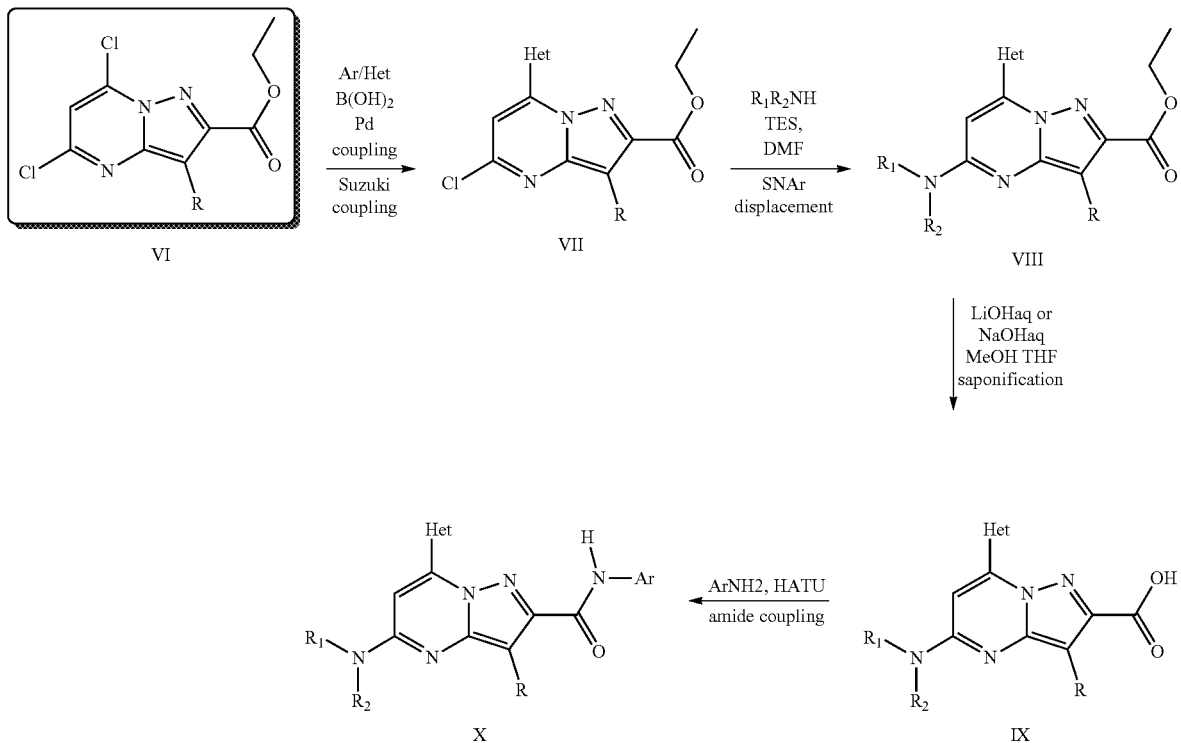

As will be appreciated by a skilled worker in the field the procedure outlined in schemes 1 and 2 may be modified using methodology well known in the art to arrive at a significant number of compounds of the invention. In addition, in the following examples modifications of the reactions depicted in these schemes is provided as exemplars of how this can be done.

Synthesis of Compounds

Example 1—5-(benzyl(methyl)amino)-N-(3-hydroxyphenyl)-7-(1H-pyrazol-4-yl)pyrazolo[1,5-a]pyrimidine-2-carboxamide (1)

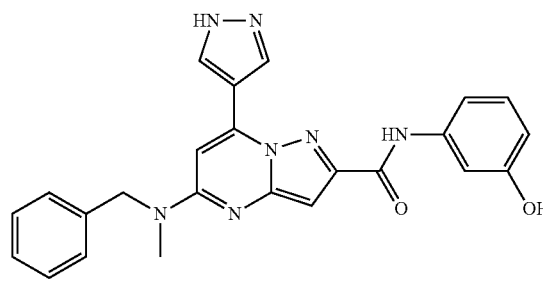

(1)

Compound 1 was synthesised using the procedure shown in Scheme 3.

Scheme 3.

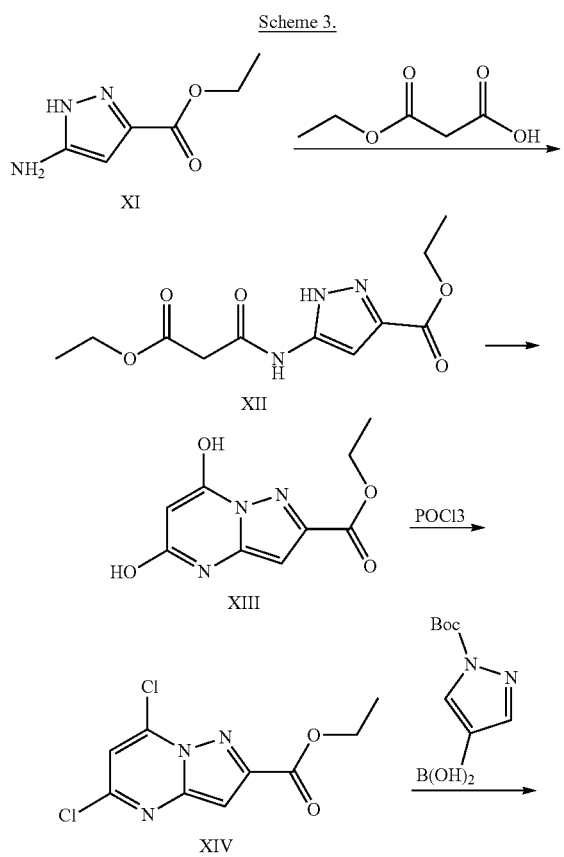

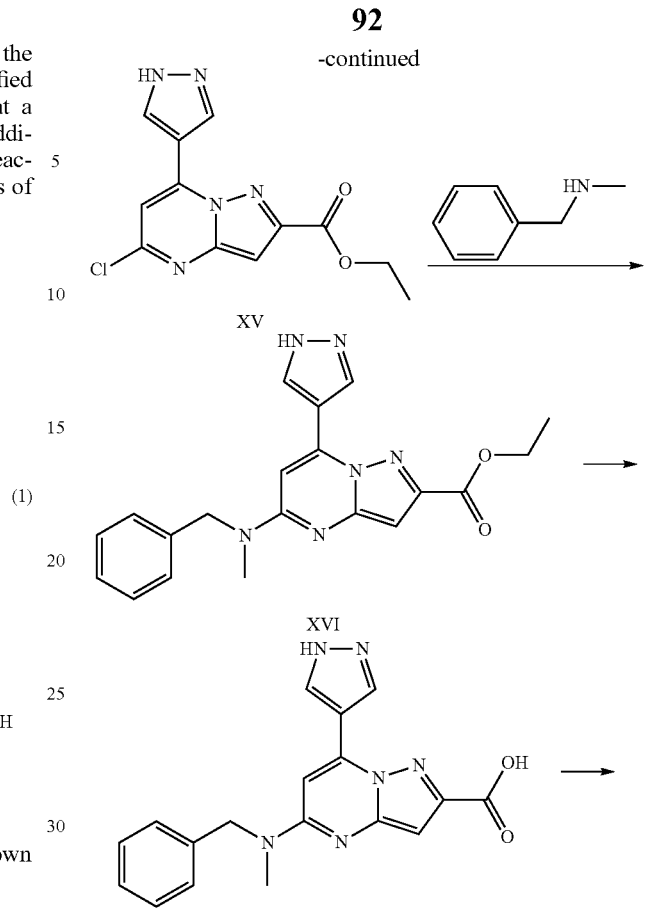

Step 1: ethyl 5-(3-ethoxy-3-oxopropanamido)-1H-pyrazole-3-carboxylate (XII)

A solution of ethyl 5-amino-1H-pyrazole-3-carboxylate (10 g, 64.40 mmol), 3-ethoxy-3-oxopropanoic acid (8.9 g, 67.74 mmol), DCC (17.3 g, 83.85 mmol), pyridine (15.3 g, 0.02 mmol) and DMAP (800 mg, 6.42 mmol) in DCM (100 mL) was stirred at room temperature overnight. The reaction mixture was filtered and the filtrate was concentrated under reduced pressure. The residue was purified by column chromatography on silica gel (DCM:MeOH, 20/1) to give the title product (10.5 g, 60.7%) as a yellow white. LCMS (Method A): $R_t$=0.51 min; $[M+H]^+$=270.1

Step 2: ethyl 5,7-dihydroxypyrazolo[1,5-a]pyrimidine-2-carboxylate (XIII)

A mixture of ethyl 5-(3-ethoxy-3-oxopropanamido)-1H-pyrazole-3-carboxylate (10.5 g, 39.02 mmol) and DMAP (14.3 g, 117.2 mmol) in ethanol (110 mL) and H$_2$O (110 mL) was stirred at 80° C. overnight. The mixture was concentrated under reduced pressure and the residue was partitioned between EtOAc and H2O (200 mL, 1/1). The organics were dried over Na2SO4 and concentrated under reduced pressure to give the title product (11.3 g, 70%) as a white solid. LCMS (Method A): R$_t$=0.69 min; [M+H]$^+$=224.2

Step 3: ethyl 5,7-dichloropyrazolo[1,5-a]pyrimidine-2-carboxylate (XIV)

A solution of ethyl 5,7-dihydroxypyrazolo[1,5-a]pyrimidine-2-carboxylate (11.3 g, 50.72 mmol) in phosphorus oxychloride (113 mL) was stirred at 110° C. overnight. The mixture was concentrated under reduced pressure to give a residue that was poured into ice-water and extracted with Et$_2$O (3×300 mL). The combined organics were washed with brine (100 mL), dried (Na$_2$SO$_4$), filtered and concentrated under reduced pressure. The residue was purified by column chromatography on silica gel (PE:EtOAc, 5:1) to give the title product (4.6 g, 35%) as a white solid. LCMS (Method A): R$_t$=1.41 min; [M+H]$^+$=261.0.

Step 4: ethyl 5-chloro-7-(1H-pyrazol-4-yl)pyrazolo[1,5-a]pyrimidine-2-carboxylate (XV)

A mixture of ethyl 5,7-dichloropyrazolo[1,5-a]pyrimidine-2-carboxylate (500 mg, 1.92 mmol), 1-Boc-pyrazole-4-boronic acid pinacol ester (408 mg, 1.92 mmol), Na$_2$CO$_3$ (0.384 g, 3.85 mmol) and Pd(dppf)$_2$Cl$_2$ (140.6 mg, 3.85 mmol) in degassed 1,4-dioxane (35 mL) and H$_2$O (7 mL) was stirred at 80° C. overnight under N$_2$. The mixture was poured into water and extracted with EtOAc (100 mL×3). The combined organics were washed with water and brine, dried over Na$_2$SO$_4$, filtered and concentrated under reduced pressure. The residue was purified by column chromatography on silica gel (DCM:MeOH, 80:1) to give the title product (137 mg, 25%) as a yellow solid. LCMS (Method A): R$_t$=2.34 min; [M+H]$^+$=292.0

Step 5: ethyl 5-(benzyl(methyl)amino)-7-(1H-pyrazol-4-yl)pyrazolo[1,5-a]pyrimidine-2-carboxylate (XVI)

A mixture of ethyl 5-chloro-7-(1H-pyrazol-4-yl)pyrazolo[1,5-a]pyrimidine-2-carboxylate (380 mg, 1.31 mmol), N-methyl-1-phenylmethanamine (316 mg, 2.61 mmol) and TEA (264 mg, 2.61 mmol) in DMF (15 mL) was stirred at 80° C. overnight. The mixture was diluted with water and the precipitate was filtered under reduced pressure, and purified by silica gel column chromatography (DCM:MeOH, 80:1) to give the desired product (400 mg, 81%) as a yellow solid. LCMS: (Method A), R$_t$=2.45 min, [M+H]$^+$=377.1.

Step 6: 5-(benzyl(methyl)amino)-7-(1H-pyrazol-4-yl)pyrazolo[1,5-a]pyrimidine-2-carboxylic acid (XVII)

To a solution of ethyl 5-(benzyl(methyl)amino)-7-(1H-pyrazol-4-yl)pyrazolo[1,5-a]pyrimidine-2-carboxylate (400 mg, 1.06 mmol) in THF (8 mL) and MeOH (8 mL) at 0° C. was slowly added an aqueous KOH solution(1M, 4 mL). The reaction mixture was stirred at 90° C. overnight. The mixture was concentrated under reduced pressure and the residue was partitioned between water (10 mL) and Et2O (10 mL). The organics were discarded and the aqueous were acidified to pH 2 with an aqueous HCl solution (1M). The aqueous phase was extracted with CHCl$_3$ (100 mL×3) and the combined organic extracts were dried over Na$_2$SO$_4$ and concentrated under reduced pressure to afford the desired product (340 mg, 89%) as a yellow solid. LCMS: (Method A), R$_t$=2.22 min, [M+H]$^+$=349.1.

Step 7: 5-(benzyl(methyl)amino)-N-(3-hydroxyphenyl)-7-(1H-pyrazol-4-yl)pyrazolo[1,5-a]pyrimidine-2-carboxamide (XVIII)

A mixture of 5-(benzyl(methyl)amino)-7-(1H-pyrazol-4-yl)pyrazolo[1,5-a]pyrimidine-2-carboxylic acid (100 mg, 0.29 mmol), 3-aminophenol (34.5 mg, 0.32 mmol), HATU (142 mg, 0.37 mmol) and DIEA (931 mg, 9.20 mmol) in DMF (4 mL) was stirred at room temperature overnight. The mixture was diluted with water and the solids were filtered under reduced pressure and purified by silica gel column chromatography (DCM:MeOH/, 30:1) to give the desired product (8 mg, 6.3%) as a yellow solid. LCMS: (Method A), R$_t$=2.28 min, [M+H]$^+$=440.2. $^1$HNMR (400 MHz, DMSO-d$_6$) δ 13.51 (s, 1H), 10.02 (s, 1H), 9.45 (s, 1H), 9.34 (s, 1H), 8.70 (d, J=2.8 Hz, 1H), 7.37-7.14 (m, 8H), 6.53 (s, 2H), 4.95 (s, 2H), 3.60 (s, 1H), 3.19 (s, 3H).

The following compounds were similarly prepared from the appropriate starting material 1 (SM1) in step 7 according to the method described for the synthesis of compound 1.

Example 2—5-(benzyl(methyl)amino)-7-(1H-pyrazol-4-yl)pyrazolo[1,5-a]pyrimidine-2-carboxamide (2)

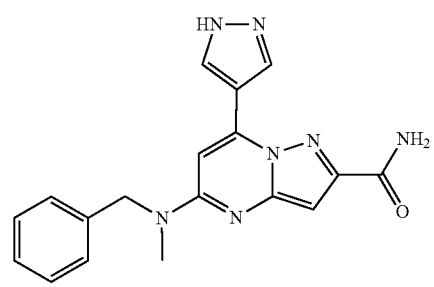

Starting material 1 used in step 7 of synthesis-ammonia, $^1$HNMR (400 MHz, DMSO-d$_6$) δ 13.47 (s, 1H), 9.36-9.22 (m, 1H), 8.81-8.58 (m, 1H), 8.05 (s, 1H), 7.45 (s, 1H), 7.36-7.24 (m, 5H), 7.14 (s, 1H), 6.38 (s, 1H), 4.94 (s, 2H), 3.17 (s, 3H). LCMS (Method A): R$_t$=1.91 min; [M+H]$^+$=348.0.

Example 3—N-benzyl-5-(benzyl(methyl)amino)-7-(1H-pyrazol-4-yl)pyrazolo[1,5-a]pyrimidine-2-carboxamide (3)

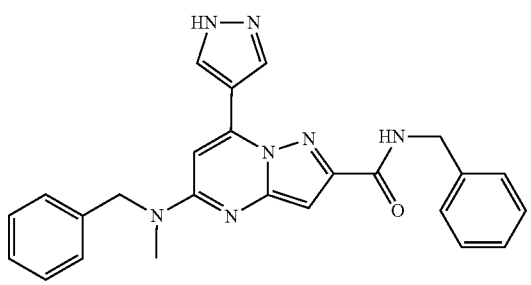

(3)

Starting material 1 used in step 7 of synthesis-benzylamine, $^1$HNMR (400 MHz, DMSO-d$_6$) δ 13.47 (s, 1H), 9.27 (s, 1H), 9.12 (s, 1H), 8.72 (s, 1H), 7.37-7.25 (m, 10H), 7.15 (s, 1H), 6.42 (s, 1H), 4.93 (s, 2H), 4.53 (d, J=6.4 Hz, 2H), 3.17 (s, 3H). LCMS (Method A): R$_t$=2.34 min; [M+H]$^+$=438.2;

Example 4—5-(benzyl(methyl)amino)-N-(4-hydroxyphenyl)-7-(1H-pyrazol-4-yl)pyrazolo[1,5-a]pyrimidine-2-carboxamide (4)

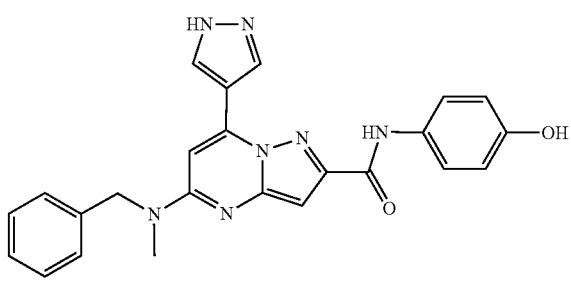

(4)

Starting material 1 used in step 7 of synthesis-4-aminophenol, $^1$HNMR (400 MHz, DMSO-d$_6$) δ 13.49 (s, 1H), 9.97 (s, 1H), 9.34 (s, 1H), 9.30 (s, 1H), 8.71 (s, 1H), 7.56 (d, J=8.9 Hz, 2H), 7.37-7.24 (m, 5H), 7.16 (s, 1H), 6.77 (d, J=8.8 Hz, 2H), 6.50 (s, 1H), 4.94 (s, 2H), 3.19 (s, 3H). LCMS (Method A):R$_t$=2.54 min; [M+H]$^+$=440.0.

Example 5—5-(benzyl(methyl)amino)-N-(3-methoxyphenyl)-7-(1H-pyrazol-4-yl)pyrazolo[1,5-a]pyrimidine-2-carboxamide (5)

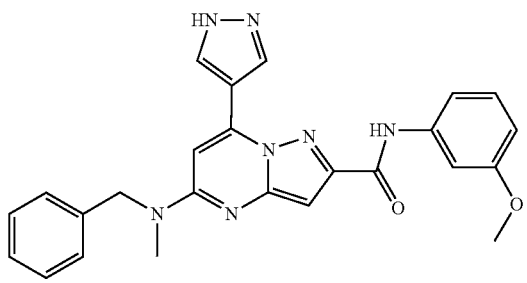

(5)

Starting material 1 used in step 7 of synthesis-3-methoxyaniline; $^1$HNMR (400 MHz, DMSO-d$_6$) δ 13.53 (s, 1H), 10.15 (s, 1H), 9.35 (s, 1H), 8.72 (s, 1H), 7.54 (t, J=2.4 Hz, 1H), 7.43 (s, 1H), 7.38-7.26 (m, 6H), 7.19 (s, 1H), 6.74 (s, 1H), 6.55 (s, 1H), 4.95 (s, 2H), 3.78 (s, 3H), 3.19 (s, 3H). LCMS (Method A):R$_t$=2.45 min; [M+H]$^+$=454.1.

Example 6—5-(benzyl(methyl)amino)-7-(1H-pyrazol-4-yl)-N-(pyridin-3-yl)pyrazolo[1,5-a]pyrimidine-2-carboxamide (6)

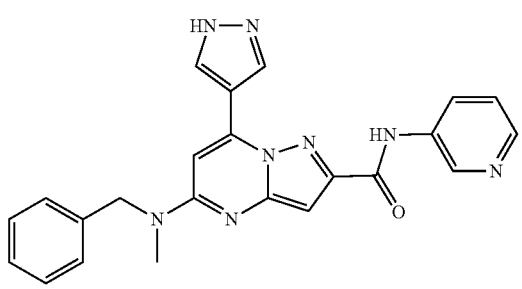

(6)

A Starting material 1 used in step 7 of synthesis-pyridin-3-amine; $^1$HNMR (400 MHz, DMSO-d$_6$) δ 13.53 (d, J=8.0 Hz, 1H), 10.40 (s, 1H), 9.28 (d, J=3.6 Hz, 1H), 9.02 (d, J=2.4 Hz, 1H), 8.79 (d, J=1.6 Hz, 1H), 8.37 (dd, J=3.6, 1.1 Hz, 1H), 8.29-8.24 (m, 1H), 7.47 (dd, J=8.4, 4.8 Hz, 1H), 7.38-7.24 (m, 5H), 7.20 (s, 1H), 6.57 (s, 1H), 4.95 (s, 2H), 3.20 (s, 3H).LCMS (Method A):R$_t$=2.41 min; [M+H]$^+$=425.0.

Example 7—5-(benzyl(methyl)amino)-7-(1H-pyrazol-4-yl)-N-(pyridin-4-yl)pyrazolo[1,5-a]pyrimidine-2-carboxamide (7)

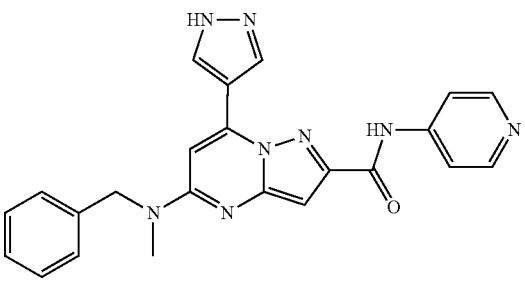

(7)

Starting material 1 used in step 7 of synthesis-pyridin-4-amine; $^1$HNMR (400 MHz, DMSO-d$_6$) δ 13.62-13.44 (m, 1H), 10.57 (s, 1H), 9.31 (s, 1H), 8.73 (s, 1H), 8.54 (d, J=6.4 Hz, 2H), 7.93 (d, J=6.4 Hz, 2H), 7.38-7.25 (m, 5H), 7.21 (s, 1H), 6.60 (s, 1H), 4.95 (s, 2H), 3.20 (s, 3H). LCMS (Method A):R$_t$=2.31 min; [M+H]$^+$=425.2;

Example 8—5-(benzyl(methyl)amino)-N-(2-methoxypyridin-4-yl)-7-(1H-pyrazol-4-yl)pyrazolo[1,5-a]pyrimidine-2-carboxamide (8)

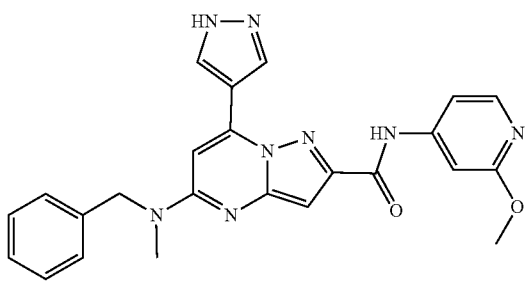
(8)

Starting material 1 used in step 7 of synthesis-2-methoxypyridin-4-amine; ¹HNMR (400 MHz, DMSO-d₆) δ 13.54 (s, 1H), 10.44 (s, 1H), 9.30 (s, 1H), 8.73 (s, 1H), 8.11 (d, J=6.0 Hz, 1H), 7.51-7.16 (m, 8H), 6.58 (s, 1H), 4.95 (s, 2H), 3.86 (s, 3H), 3.20 (s, 3H). LCMS (Method A): $R_t$=2.90 min; [M+H]⁺=455.1.

Example 9—5-(benzyl(methyl)amino)-N-(3,5-dimethoxyphenyl)-7-(1H-pyrazol-4-yl)pyrazolo[1,5-a]pyrimidine-2-carboxamide (9)

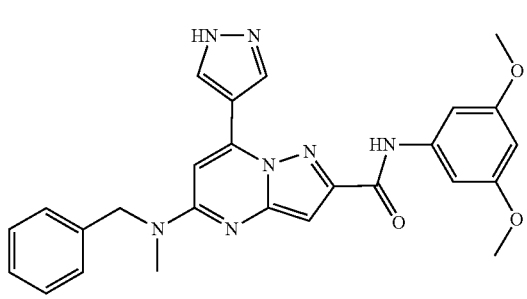
(9)

Starting material 1 used in step 7 of synthesis-3,5-dimethoxyaniline; ¹HNMR (400 MHz, DMSO-d₆) δ 13.51 (s, 1H), 10.07 (s, 1H), 9.33 (s, 1H), 8.70 (s, 1H), 7.37-7.25 (m, 5H), 7.17 (d, J=3.6 Hz, 3H), 6.55 (s, 1H), 6.30 (s, 1H), 4.95 (s, 2H), 3.77 (s, 6H), 3.20 (s, 3H). LCMS (Method C): $R_t$=3.09 min; [M+H]⁺=484.2.

Example 10—5-(benzyl(methyl)amino)-N-(3,5-dimethylisoxazol-4-yl)-7-(1H-pyrazol-4-yl)pyrazolo[1,5-a]pyrimidine-2-carboxamide (10)

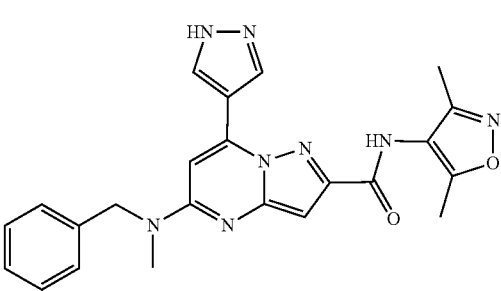
(10)

Starting material 1 used in step 7 of synthesis-3,5-dimethylisoxazol-4-amine; ¹HNMR (400 MHz, DMSO-d₆) δ 13.51 (s, 1H), 9.81 (s, 1H), 9.33 (s, 1H), 8.70 (s, 1H), 7.37-7.25 (m, 5H), 7.20 (s, 1H), 6.51 (s, 1H), 4.95 (s, 2H), 3.19 (s, 3H), 2.34 (s, 3H), 2.17 (s, 3H). LCMS (Method C): $R_t$=3.68 min; [M+H]⁺=442.9.

Example 11—5-(benzyl(methyl)amino)-N,7-di(1H-pyrazol-4-yl)pyrazolo[1,5-a]pyrimidine-2-carboxamide (11)

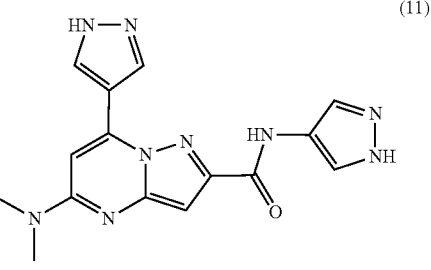
(11)

Starting material 1 used in step 7 of synthesis-1H-pyrazol-4-amine; ¹HNMR (400 MHz, DMSO-d₆) δ 13.51 (s, 1H), 12.64 (s, 1H), 10.38 (s, 1H), 9.34 (s, 1H), 8.74 (s, 1H), 7.92 (s, 2H), 7.37-7.25 (m, 5H), 7.17 (s, 1H), 6.50 (s, 1H), 4.95 (s, 2H), 3.19 (s, 3H). LCMS (Method C): $R_t$=1.35 min; [M+H]⁺=414.2

Example 12—5-(benzyl(methyl)amino)-N-(4-cyanophenyl)-7-(1H-pyrazol-4-yl)pyrazolo[1,5-a]pyrimidine-2-carboxamide (12)

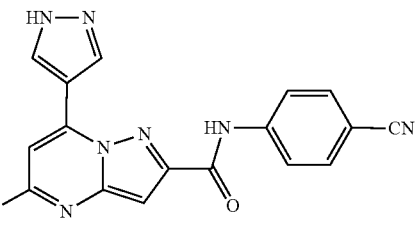
(12)

Starting material 1 used in step 7 of synthesis-4-aminobenzonitrile; ¹HNMR (400 MHz, DMSO-d₆) δ 13.53 (s, 1H), 10.55 (s, 1H), 9.31 (s, 1H), 8.72 (s, 1H), 8.08 (d, J=8.8 Hz, 2H), 7.86 (d, J=8.8 Hz, 2H), 7.40-7.24 (m, 5H), 7.20 (s, 1H), 6.59 (s, 1H), 4.95 (s, 2H), 3.20 (s, 3H). LCMS (Method A): $R_t$=2.46 min; [M+H]⁺=449.0.

Example 13—5-(benzyl(methyl)amino)-N-(3-cyanophenyl)-7-(1H-pyrazol-4-yl)pyrazolo[1,5-a]pyrimidine-2-carboxamide (13)

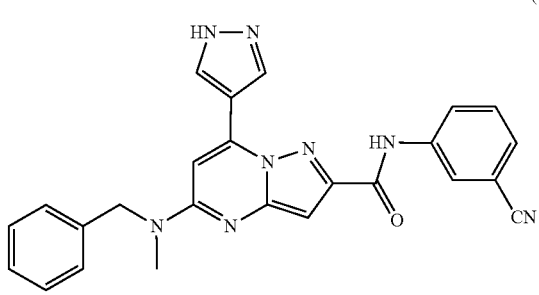

(13)

Starting material 1 used in step 7 of synthesis-3-aminobenzonitrile; $^1$HNMR (400 MHz, DMSO-d$_6$) δ 13.59 (s, 1H), 10.52 (s, 1H), 9.39 (s, 1H), 8.80 (s, 1H), 8.37 (s, 1H), 8.26-8.23 (m, 1H), 7.69 (t, J=6.4 Hz, 2H), 7.43-7.31 (m, 5H), 7.26 (s, 1H), 6.64 (s, 1H), 5.02 (s, 2H), 3.26 (s, 3H). LCMS (Method C): R$_t$=3.01 min; [M+H]$^+$=449.1

Example 14—5-(benzyl(methyl)amino)-N-(3-isopropoxyphenyl)-7-(1H-pyrazol-4-yl)pyrazolo[1,5-a]pyrimidine-2-carboxamide (18)

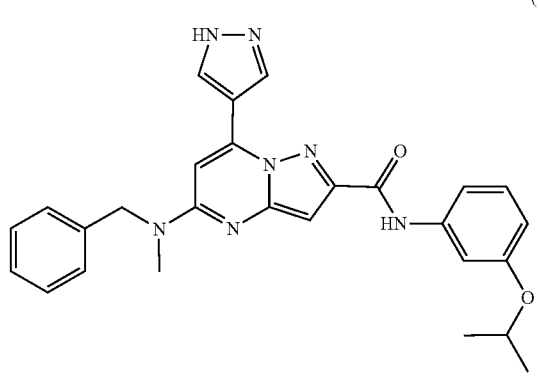

(18)

Starting material 1 used in step 7 of synthesis-3-isopropoxyaniline; $^1$HNMR (400 MHz, DMSO-d$_6$) δ 13.51 (s, 1H), 10.09 (s, 1H), 9.31 (s, 1H), 8.70 (s, 1H), 7.49 (t, J=2.4 Hz, 1H), 7.40-7.33 (m, 3H), 7.32-7.24 (m, 4H), 7.16 (s, 1H), 6.70 (d, J=8.0 Hz, 1H), 6.55 (s, 1H), 4.94 (s, 2H), 4.60 (s, 1H), 3.19 (s, 3H), 1.30 (d, J=6.0 Hz, 6H). LCMS (Method A): R$_t$=3.25 min; [M+H]$^+$=482.2

Example 15—5-(benzyl(methyl)amino)-N-(3-(difluoromethoxy)phenyl)-7-(1H-pyrazol-4-yl)pyrazolo[1,5-a]pyrimidine-2-carboxamide (19)

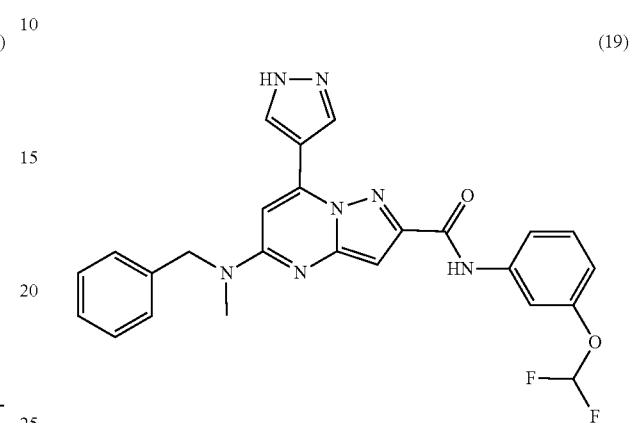

(19)

Starting material 1 used in step 7 of synthesis-3-(difluoromethoxy)aniline; A $^1$HNMR (400 MHz, DMSO-d$_6$) δ 13.53 (s, 1H), 10.32 (s, 1H), 9.32 (s, 1H), 8.71 (s, 1H), 7.79 (t, J=2.4 Hz, 1H), 7.75-7.70 (m, 1H), 7.46-7.41 (m, 1H), 7.38-7.33 (m, 2H), 7.32-7.26 (m, 3H), 7.24-7.04 (m, 2H), 6.96 (dd, J=8.0 Hz, 1H), 6.56 (s, 1H), 4.95 (s, 2H), 3.19 (s, 3H). LCMS (Method A): R$_t$=3.15 min; [M+H]$^+$=489.9

Example 16—5-(benzyl(methyl)amino)-N-(3-(dimethylamino)phenyl)-7-(1H-pyrazol-4-yl)pyrazolo[1,5-a]pyrimidine-2-carboxamide (20)

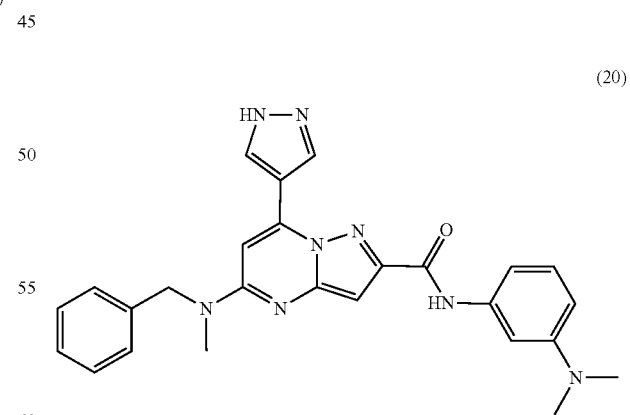

(20)

Starting material 1 used in step 7 of synthesis-N1,N1-dimethylbenzene-1,3-diamine; $^1$HNMR (400 MHz, DMSO-d$_6$) δ 9.97 (s, 1H), 9.03 (s, 1H), 8.42 (s, 1H), 7.38-7.25 (m, 6H), 7.19-7.16 (m, 3H), 6.54 (s, 1H), 4.95 (s, 2H), 3.19 (s, 3H), 2.94 (s, 6H). LCMS (Method A): R$_t$=3.84 min; [M+H]$^+$= 467.2

Example 17—5-(benzyl(methyl)amino)-N-(methylsulfonyl)-7-(1H-pyrazol-4-yl)pyrazolo[1,5-a]pyrimidine-2-carboxamide (21)

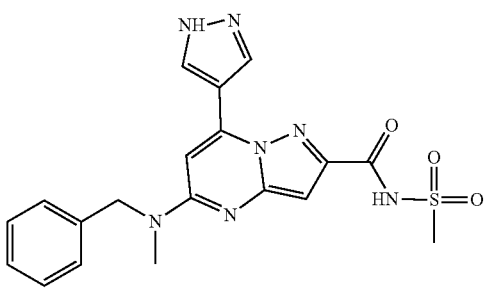

Starting material 1 used in step 7 of synthesis-methanesulfonamide; $^1$HNMR (400 MHz, DMSO-d$_6$) δ 9.97 (s, 1H), 9.59 (s, 1H), 8.51 (s, 1H), 7.37-7.26 (m, 5H), 6.79 (s, 1H), 6.66 (s, 1H), 4.89 (s, 2H), 3.47 (s, 3H), 3.24 (s, 4H). LCMS (Method A): R$_t$=3.58 min; [M+H]$^+$=425.1.

Example 18—5-(benzyl(methyl)amino)-N-(3-(4-methylpiperazin-1-yl)phenyl)-7-(1H-pyrazol-4-yl)pyrazolo[1,5-a]pyrimidine-2-carboxamide (22)

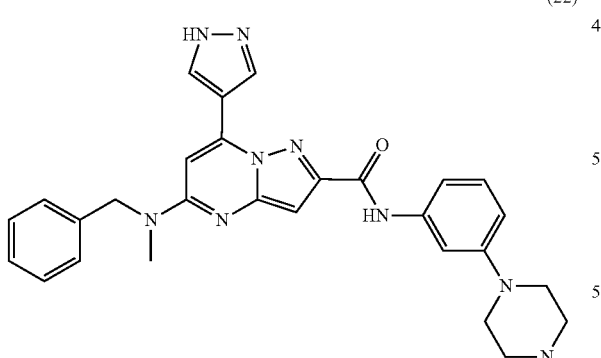

Starting material 1 used in step 7 of synthesis-3-(4-methylpiperazin-1-yl)aniline; $^1$HNMR (400 MHz, DMSO-d$_6$) δ 13.51 (s, 1H), 9.99 (s, 1H), 9.33 (s, 1H), 8.70 (s, 1H), 7.48 (s, 1H), 7.39-7.14 (m, 8H), 6.73 (d, J=8.2 Hz, 1H), 6.53 (s, 1H), 4.95 (s, 2H), 3.33 (s, 4H) 3.19 (s, 7H), 2.26 (s, 3H). LCMS (Method A): R$_t$=2.97 min; [M+H]$^+$=522.0.

Example 19—5-(benzyl(methyl)amino)-N-(4-chlorophenyl)-7-(1H-pyrazol-4-yl)pyrazolo[1,5-a]pyrimidine-2-carboxamide (29)

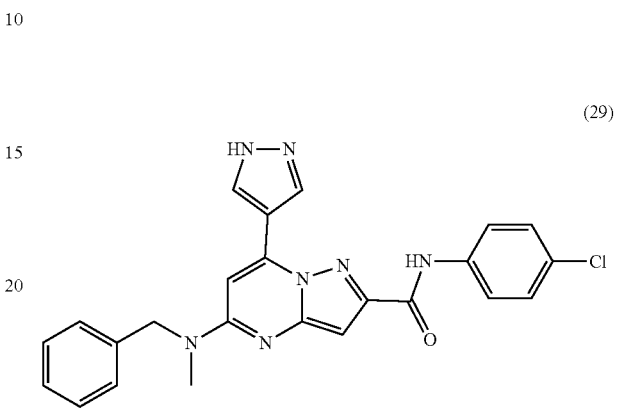

Starting material 1 used in step 7 of synthesis-4-chloroaniline; $^1$HNMR (400 MHz, DMSO-d$_6$) δ 13.54 (s, 1H), 10.29 (s, 1H), 9.33 (s, 1H), 8.72 (s, 1H), 7.88 (d, J=8.8 Hz, 2H), 7.45 (d, J=8.8 Hz, 2H), 7.37-7.25 (m, 5H), 7.19 (s, 1H), 6.55 (s, 1H), 4.96 (s, 2H), 3.20 (s, 3H). LCMS (Method A): R$_t$=3.27 min; [M+H]$^+$=458.0.

Example 20—5-(benzyl(methyl)amino)-N-(3-chlorophenyl)-7-(1H-pyrazol-4-yl)pyrazolo[1,5-a]pyrimidine-2-carboxamide (30)

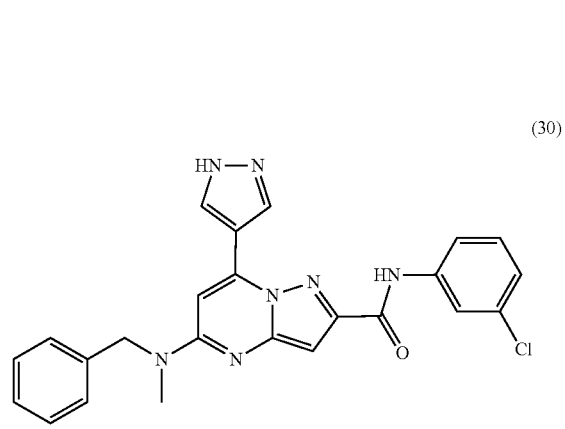 [SMILES: CN(Cc1ccccc1)c1cc(-c2cn[nH]c2)n2nc(C(=O)Nc3cccc(Cl)c3)cc2n1]

Starting material 1 used in step 7 of synthesis-3-chloroaniline; $^1$HNMR (400 MHz, DMSO-d$_6$) δ 10.32 (s, 1H), 9.05 (s, 1H), 8.01 (s, 1H), 7.84 (d, J=8.0 Hz, 1H), 7.45-7.20 (m, 8H), 6.56 (s, 1H), 4.96 (s, 2H), 3.20 (s, 3H). LCMS (Method A): R$_t$=4.29 min; [M+H]$^+$=458.1.

Example 21—5-(benzyl(methyl)amino)-N-(2-chlorophenyl)-7-(1H-pyrazol-4-yl)pyrazolo[1,5-a]pyrimidine-2-carboxamide (31)

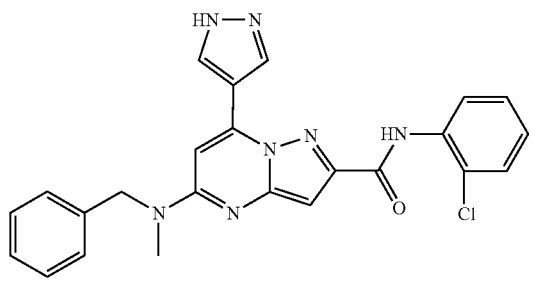

(31)

Starting material 1 used in step 7 of synthesis-2-chloroaniline; $^1$HNMR (400 MHz, DMSO-d$_6$) δ 13.56 (s, 1H), 9.98 (s, 1H), 9.18 (s, 1H), 8.70 (s, 1H), 8.10 (d, J=8.0 Hz, 1H), 7.62 (dd, J=6.8 Hz, 1.2 Hz, 1H), 7.44-7.22 (m, 8H), 6.56 (s, 1H), 4.96 (s, 2H), 3.20 (s, 3H). LCMS (Method A): R$_t$=4.39 min; [M+H]$^+$=458.1

Example 22—5-(benzyl(methyl)amino)-7-(1H-pyrazol-4-yl)-N-(4-(trifluoromethyl)phenyl)pyrazolo[1,5-a]pyrimidine-2-carboxamide (32)

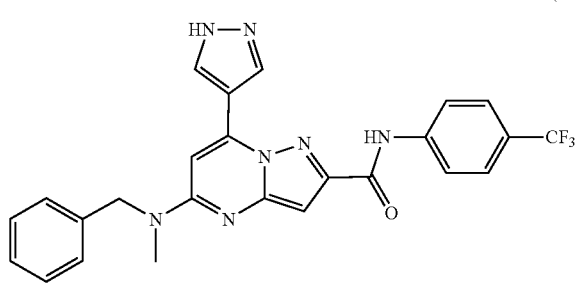

(32)

Starting material 1 used in step 7 of synthesis-4-(trifluoromethyl)aniline; $^1$HNMR (400 MHz, DMSO-d$_6$) δ 13.53 (s, 1H), 10.49 (s, 1H), 9.34 (s, 1H), 8.73 (s, 1H), 8.10 (d, J=8.4 Hz, 2H), 7.77 (d, J=8.8 Hz, 2H), 7.40-7.24 (m, 5H), 7.20 (s, 1H), 6.59 (s, 1H), 4.96 (s, 2H), 3.20 (s, 3H). LCMS (Method A): R$_t$=3.35 min; [M+H]$^+$=492.1

Example 23—5-(benzyl(methyl)amino)-7-(1H-pyrazol-4-yl)-N-(3-(trifluoromethyl)phenyl)pyrazolo[1,5-a]pyrimidine-2-carboxamide (33)

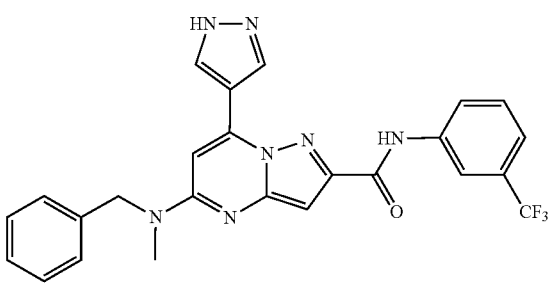

(33)

Starting material 1 used in step 7 of synthesis-3-(trifluoromethyl)aniline; $^1$HNMR (400 MHz, DMSO-d$_6$) δ 13.53 (s, 1H), 10.47 (s, 1H), 9.35 (s, 1H), 8.73 (s, 1H), 8.30 (s, 1H), 8.18 (d, J=8.4 Hz, 1H), 7.64 (t, J=8.0 Hz, 1H), 7.49 (d, J=7.8 Hz, 1H), 7.39-7.23 (m, 5H), 7.20 (s, 1H), 6.58 (s, 1H), 4.95 (s, 2H), 3.20 (s, 3H). LCMS (Method A): R$_t$=3.34 min; [M+H]$^+$=492.13.

Example 24—5-(benzyl(methyl)amino)-7-(1H-pyrazol-4-yl)-N-(2-(trifluoromethyl)phenyl)pyrazolo[1,5-a]pyrimidine-2-carboxamide (34)

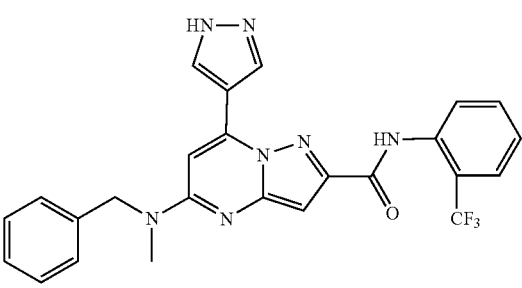

(34)

Starting material 1 used in step 7 of synthesis-2-(trifluoromethyl)aniline; $^1$HNMR (400 MHz, DMSO-d$_6$) δ 13.57 (s, 1H), 9.91 (s, 1H), 9.15 (s, 1H), 8.68 (s, 1H), 8.02 (d, J=8.0 Hz, 1H), 7.85-7.74 (m, 2H), 7.49 (t, J=7.6 Hz, 1H), 7.38-7.24 (m, 5H), 7.22 (s, 1H), 6.55 (s, 1H), 4.96 (s, 2H), 3.19 (s, 3H). LCMS (Method A): R$_t$=4.44 min; [M+H]$^+$=492.2;

Example 25—5-(benzyl(methyl)amino)-N-(4-fluorophenyl)-7-(1H-pyrazol-4-yl)pyrazolo[1,5-a]pyrimidine-2-carboxamide (35)

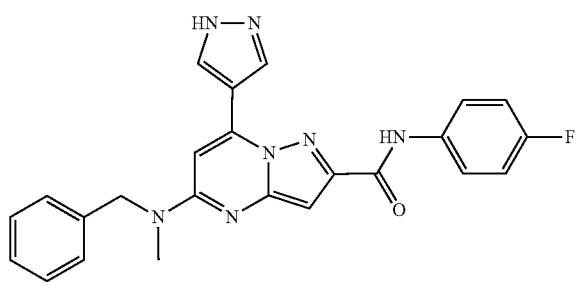

(35)

Starting material 1 used in step 7 of synthesis-4-fluoroaniline; ¹HNMR (400 MHz, DMSO-d₆) δ 13.50 (s, 1H), 10.28 (s, 1H), 9.33 (s, 1H), 8.72 (s, 1H), 7.84 (dd, J=5.2 Hz, 2.0 Hz, 2H), 7.37-7.18 (m, 8H), 6.57 (s, 1H), 4.95 (s, 2H), 3.19 (s, 3H). LCMS (Method C): $R_t$=3.05 min; [M+H]⁺=488.1

Example 26—5-(benzyl(methyl)amino)-N-(3-fluorophenyl)-7-(1H-pyrazol-4-yl)pyrazolo[1,5-a]pyrimidine-2-carboxamide (36)

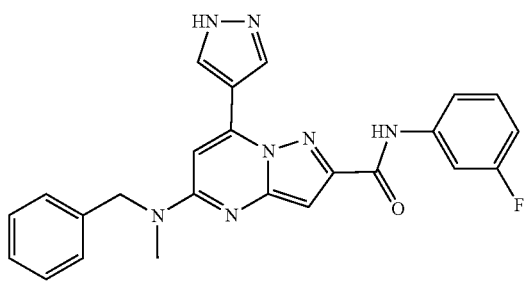

(36)

Starting material 1 used in step 7 of synthesis-3-fluoroaniline; ¹HNMR (400 MHz, DMSO-d₆) δ 13.52 (s, 1H), 10.33 (s, 1H), 9.32 (s, 1H), 8.72 (s, 1H), 7.81 (d, J=11.6 Hz, 1H), 7.67 (d, J=8.4 Hz, 1H), 7.47-7.24 (m, 6H), 7.19 (s, 1H), 6.97 (td, J=8.6 Hz, 2.4 Hz, 1H), 6.56 (s, 1H), 4.95 (s, 2H), 3.19 (s, 3H). LCMS (Method A): $R_t$=3.12 min; [M+H]⁺=442.03.

Example 27—5-(benzyl(methyl)amino)-N-(2-fluorophenyl)-7-(1H-pyrazol-4-yl)pyrazolo[1,5-a]pyrimidine-2-carboxamide (37)

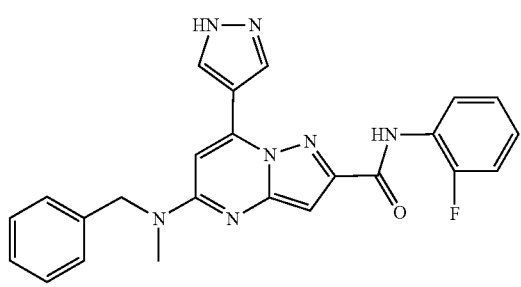

(37)

Starting material 1 used in step 7 of synthesis-2-fluoroaniline; ¹HNMR (400 MHz, DMSO-d₆) δ 13.52 (s, 1H), 10.00 (s, 1H), 9.28 (s, 1H), 8.72 (s, 1H), 7.78 (td, J=7.8, 2.1 Hz, 1H), 7.39-7.22 (m, 8H), 7.19 (s, 1H), 6.53 (s, 1H), 4.95 (s, 2H), 3.19 (s, 3H). LCMS (Method A): $R_t$=3.10 min; [M+H]⁺=442.09.

The following compounds were similarly prepared from the appropriate starting material in step 5 and the appropriate starting material 2 in step 7 according to the method described for the synthesis of compound 1 in scheme 3 above.

Example 28—(S)—N-(3-methoxyphenyl)-5-(methyl (1-phenylethyl)amino)-7-(1H-pyrazol-4-yl)pyrazolo[1,5-a]pyrimidine-2-carboxamide (14)

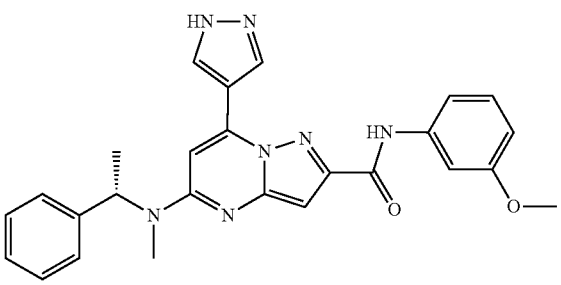

(14)

Starting material used in step 5 (S)—N-methyl-1-phenylethan-1-amine; Starting material used in step 7 3-methoxyaniline; ¹HNMR (400 MHz, DMSO-d₆) δ 13.52 (s, 1H), 10.14 (s, 1H), 9.35 (s, 1H), 8.75 (s, 1H), 7.54 (d, J=2.4 Hz, 1H), 7.45-7.27 (m, 7H), 7.19 (s, 1H), 6.73 (dd, J=8.2 Hz, 2.0 Hz, 1H), 6.56 (s, 1H), 6.27-6.11 (m, 1H), 3.79 (s, 3H), 2.90 (s, 3H), 1.60 (d, J=6.8 Hz, 3H). LCMS (Method A): $R_t$=2.53 min; [M+H]⁺=468.0

Example 29 (S)—N-(3-hydroxyphenyl)-5-(methyl (1-phenylethyl)amino)-7-(1H-pyrazol-4-yl)pyrazolo [1,5-a]pyrimidine-2-carboxamide (15)

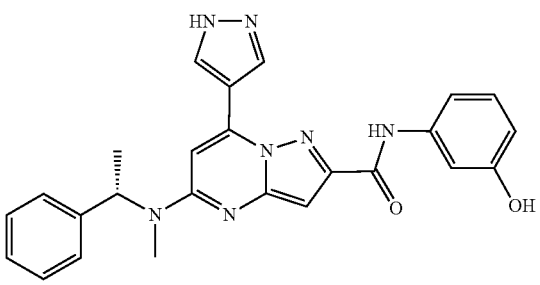

(15)

Starting material used in step 5 S)—N-methyl-1-phenylethan-1-amine; starting material used in step 7 3-aminophenol; ¹HNMR (400 MHz, DMSO-d₆) δ 13.51 (s, 1H), 10.04 (s, 1H), 9.40 (d, J=16 Hz, 2H), 8.74 (s, 1H), 7.40-7.14 (m, 9H), 6.54 (s, 2H), 6.18 (dd, J=2.8 Hz, 1.2 Hz, 1H), 2.89 (s, 3H), 1.60 (d, J=6.8 Hz, 3H). LCMS (Method A): $R_t$=2.34 min; [M+H]⁺=454.0.

Example 30—(S)-5-(methyl(1-phenylethyl)amino)-N-phenyl-7-(1H-pyrazol-4-yl)pyrazolo[1,5-a]pyrimidine-2-carboxamide (16)

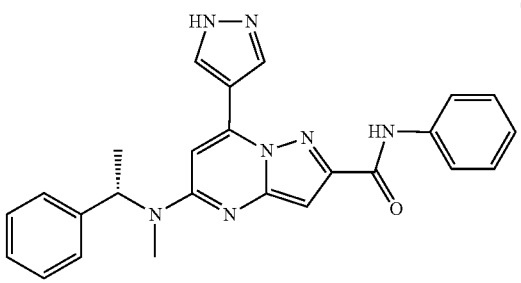
(16)

Starting material used in step 5 S)—N-methyl-1-phenylethan-1-amine; Starting material used in step 7 aniline; $^1$HNMR (400 MHz, DMSO-$d_6$) δ 13.51 (s, 1H), 10.17 (s, 1H), 9.35 (s, 1H), 8.75 (s, 1H), 7.84 (d, J=7.8 Hz, 2H), 7.52-7.07 (m, 9H), 6.55 (s, 1H), 6.19 (s, 1H), 2.89 (s, 3H), 1.60 (d, J=6.4 Hz, 3H). LCMS (Method A): $R_t$=3.15 min; [M+H]$^+$=438.0.

Example 31—(S)-5-(methyl(1-phenylethyl)amino)-7-(1H-pyrazol-4-yl)pyrazolo[1,5-a]pyrimidine-2-carboxamide (17)

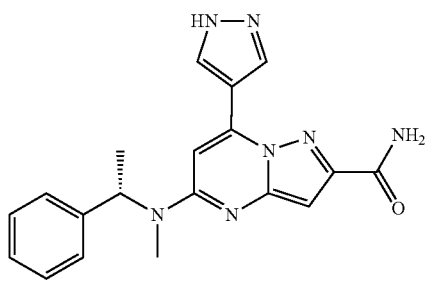
(17)

Starting material used in step 5 (S)—N-methyl-1-phenylethan-1-amine; Starting material used in step 7 ammonia; $^1$HNMR (400 MHz, DMSO-$d_6$) δ 13.46 (s, 1H), 9.30 (d, J=1.6 Hz, 1H), 8.70 (d, J=2.8 Hz, 1H), 8.04 (s, 1H), 7.51-7.14 (m, 7H), 6.39 (s, 1H), 6.30-6.06 (m, 1H), 2.87 (s, 3H), 1.58 (d, J=6.8 Hz, 3H). LCMS (Method A): $R_t$=2.09 min; [M+H]$^+$=362.0.

Example 32—5-(isoindolin-2-yl)-N-phenyl-7-(1H-pyrazol-4-yl)pyrazolo[1,5-a]pyrimidine-2-carboxamide (23)

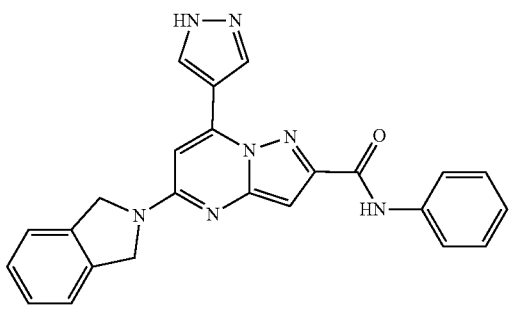
(23)

Starting material used in step 5 isoindoline; Starting material used in step 7 aniline; $^1$HNMR (400 MHz, DMSO-$d_6$) δ 13.51 (s, 1H), 10.19 (s, 1H), 9.38 (s, 1H), 8.78 (s, 1H), 7.48 (d, J=7.6 Hz, 2H), 7.45-7.35 (m, 6H), 7.15 (d, J=7.2 Hz, 1H), 7.09 (s, 1H), 6.60 (s, 1H), 4.97 (s, 4H). LCMS (Method C): $R_t$=3.01 min; [M+H]$^+$=422.1.

Example 33—N-(3-hydroxyphenyl)-5-(isoindolin-2-yl)-7-(1H-pyrazol-4-yl)pyrazolo[1,5-a]pyrimidine-2-carboxamide (24)

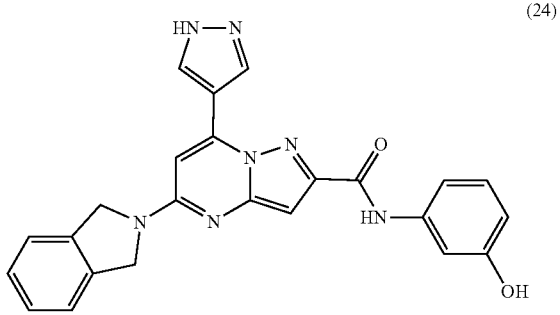 [SMILES: O=C(Nc1cccc(O)c1)c1cc2nc(N3Cc4ccccc4C3)cc(-c3cn[nH]c3)n2n1]
(24)

Starting material used in step 5 isoindoline, starting material used in step 7 3-aminophenol; $^1$HNMR (400 MHz, DMSO-$d_6$) δ 13.51 (s, 1H), 10.19 (s, 1H), 9.45 (s, 1H), 9.08 (s, 2H), 7.45 (s, 2H), 7.38 (t, J=2.8 Hz, 3H), 7.23 (s, 1H), 7.15 (d, J=7.2 Hz, 1H), 7.09 (s, 1H), 6.57 (s, 2H), 4.97 (s, 4H). LCMS (Method A): $R_t$=3.66 min; [M+H]$^+$=438.1.

Example 34—5-(isoindolin-2-yl)-N-(3-methoxyphenyl)-7-(1H-pyrazol-4-yl)pyrazolo[1,5-a]pyrimidine-2-carboxamide (25)

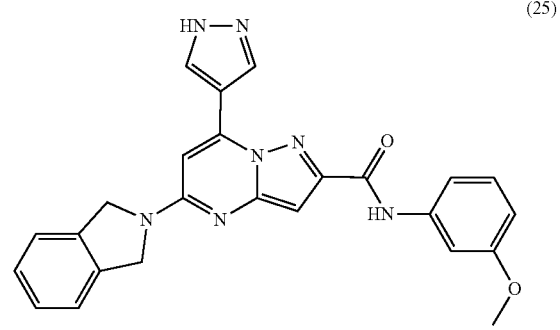 [SMILES: COc1cccc(NC(=O)c2cc3nc(N4Cc5ccccc5C4)cc(-c4cn[nH]c4)n3n2)c1]
(25)

Starting material used in step 5 isoindoline, starting material used in step 7 3-methoxyaniline; $^1$HNMR (400 MHz, DMSO-$d_6$) δ 13.53 (s, 1H), 10.15 (s, 1H), 9.38 (s, 1H), 8.77 (s, 1H), 7.54-7.36 (m, 6H), 7.30 (t, J=7.2 Hz, 1H), 7.09 (s, 1H), 6.73 (d, J=7.6 Hz, 1H), 6.60 (s, 1H), 4.97 (s, 4H), 3.97 (s, 3H). LCMS (Method C): $R_t$=3.01 min; [M+H]$^+$= 452.1

Example 35—5-(isoindolin-2-yl)-7-(1H-pyrazol-4-yl)-N-(3-(trifluoromethoxy)phenyl)pyrazolo[1,5-a]pyrimidine-2-carboxamide (26)

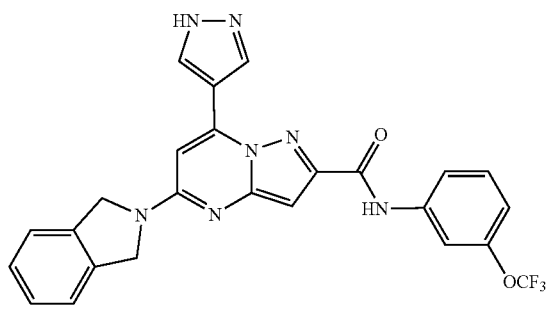

(26)

Starting material used in step 5 isoindoline; Starting material used in step 7 3-trifluoromethoxyaniline; $^1$HNMR (400 MHz, DMSO-$d_6$) δ 13.55 (s, 1H), 10.45 (s, 1H), 9.37 (s, 1H), 8.79 (d, J=7.8 Hz, 1H), 8.01 (s, 1H), 7.93-7.86 (m, 1H), 7.56-7.33 (m, 5H), 7.17-7.08 (m, 2H), 6.63 (s, 1H), 4.97 (s, 4H). LCMS (Method A): $R_t$=3.37 min; [M+H]$^+$= 506.0.

Example 36—N-(3-ethoxyphenyl)-5-(isoindolin-2-yl)-7-(1H-pyrazol-4-yl)pyrazolo[1,5-a]pyrimidine-2-carboxamide (27)

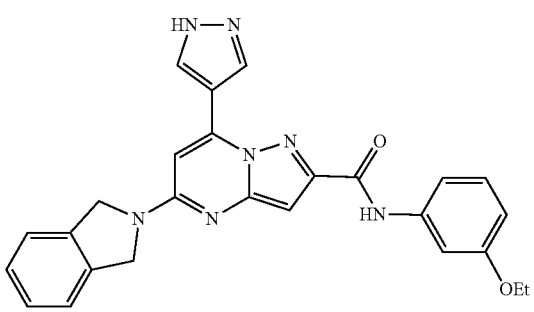

(27)

Starting material used in step 5 isoindoline; Starting material used in step 7 3-ethoxyaniline; $^1$HNMR (400 MHz, DMSO-$d_6$) δ 13.54 (s, 1H), 10.14 (s, 1H), 9.38 (s, 1H), 8.77 (s, 1H), 7.56-7.23 (m, 7H), 7.10 (s, 1H), 6.71 (d, J=8.4 Hz, 1H), 6.61 (s, 1H), 4.98 (d, J=1.6 Hz, 4H), 4.05 (d, J=6.8 Hz, 2H), 1.37 (s, 3H). LCMS (Method A): $R_t$=3.17 min; [M+H]$^+$= 466.11.

Example 37—5-(isoindolin-2-yl)-N-(3-isopropoxyphenyl)-7-(1H-pyrazol-4-yl)pyrazolo[1,5-a]pyrimidine-2-carboxamide (28)

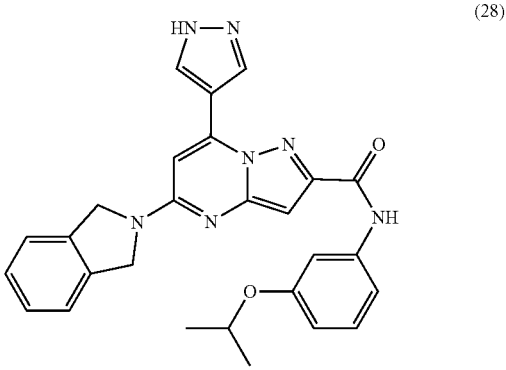 [SMILES: CC(C)Oc1cccc(NC(=O)c2cc3nc(N4Cc5ccccc5C4)cc(-c4cn[nH]c4)n3n2)c1]

(28)

Starting material used in step 5 isoindoline; starting material used in step 7 3-isopropoxyaniline; $^1$HNMR (400 MHz, DMSO-$d_6$) δ 13.54 (s, 1H), 10.12 (s, 1H), 9.37 (s, 1H), 8.77 (s, 1H), 7.53-7.35 (m, 6H), 7.27 (t, J=8.2 Hz, 1H), 7.10 (s, 1H), 6.70 (dd, J=8.2, 1.9 Hz, 1H), 6.61 (s, 1H), 4.98 (s, 4H), 4.66-4.56 (m, 1H), 1.31 (d, J=6.0 Hz, 6H). LCMS (Method A): $R_t$=3.25 min; [M+H]$^+$=480.11.

Example 38—N-(4-chlorophenyl)-5-((4-methoxybenzyl)(methyl)amino)-7-(1H-pyrazol-4-yl)pyrazolo[1,5-a]pyrimidine-2-carboxamide (38)

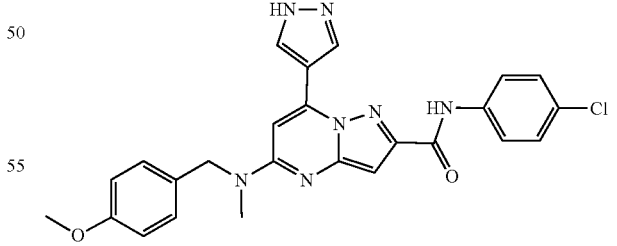

(38)

Starting material used in step 5—1-(4-methoxyphenyl)-N-methylmethanamine; starting material used in step 7 4-chloroaniline; $^1$HNMR (400 MHz, DMSO-$d_6$) δ 13.50 (s, 1H), 10.28 (s, 1H), 9.32 (s, 1H), 8.71 (s, 1H), 7.88 (d, J=8.8 Hz, 2H), 7.45 (d, J=8.8 Hz, 2H), 7.26 (s, 1H), 7.24 (s, 1H), 7.17 (s, 1H), 6.91 (s, 1H), 6.89 (s, 1H), 6.54 (s, 1H), 4.86 (s, 2H), 3.72 (s, 3H), 3.16 (s, 3H). LCMS (Method A): $R_t$=4.22 min; [M+H]$^+$=488.1.

Example 39—N-(4-chlorophenyl)-5-((3-methoxybenzyl)(methyl)amino)-7-(1H-pyrazol-4-yl)pyrazolo[1,5-a]pyrimidine-2-carboxamide (39)

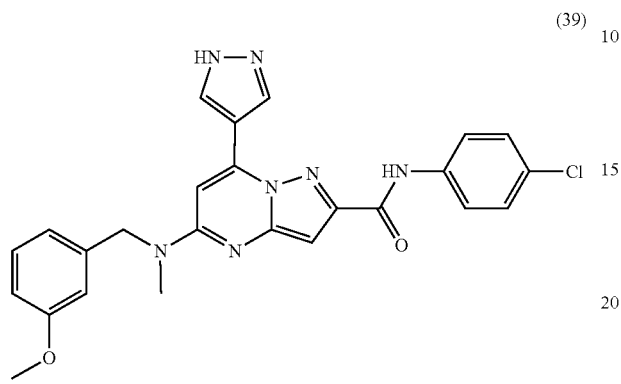

Starting material used in step 5 1-(3-methoxyphenyl)-N-methylmethanamine; starting material used in step 7 4-chloroaniline; $^1$HNMR (400 MHz, DMSO-$d_6$) δ 10.29 (s, 1H), 9.02 (s, 1H), 8.71 (s, 1H), 7.88 (d, J=7.2 Hz, 2H), 7.45 (d, J=8.8 Hz, 2H), 7.26 (t, J=7.6 Hz, 1H), 7.17 (s, 1H), 6.91 (t, J=7.2 Hz, 3H), 6.55 (s, 1H), 5.77 (s, 1H), 4.91 (s, 2H), 3.72 (s, 3H), 3.16 (s, 3H). LCMS (Method A): $R_t$=3.47 min; [M+H]$^+$=488.2.

Example 40 N-(4-chlorophenyl)-5-((2-methoxybenzyl)(methyl)amino)-7-(1H-pyrazol-4-yl)pyrazolo[1,5-a]pyrimidine-2-carboxamide (40)

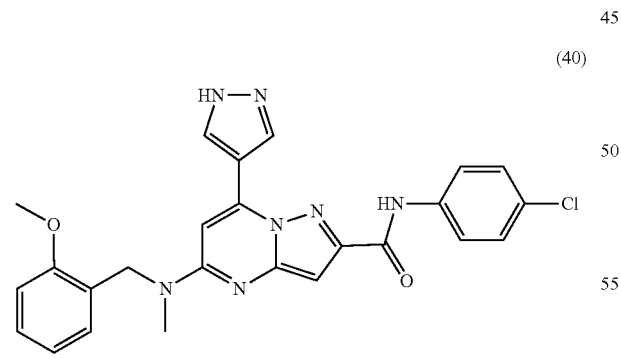

Starting material used in step 5 1-(2-methoxyphenyl)-N-methylmethanamine; starting material used in step 7 4-chloroaniline; $^1$HNMR (400 MHz, DMSO-$d_6$) δ 13.50 (s, 1H), 10.28 (s, 1H), 9.32 (s, 1H), 8.71 (s, 1H), 7.88 (d, J=7.2 Hz, 2H), 7.44 (d, J=8.8 Hz, 2H), 7.25 (t, J=6.4 Hz, 1H), 7.17 (s, 1H), 7.05 (d, J=8.0 Hz, 2H), 6.89 (t, J=6.8 Hz, 1H), 6.52 (s, 1H), 4.86 (s, 2H), 3.72 (s, 3H), 3.16 (s, 3H). LCMS (Method A): $R_t$=4.26 min; [M+H]$^+$=488.2.

Example 41—N-(4-chlorophenyl)-5-(methyl(4-(trifluoromethyl)benzyl)amino)-7-(1H-pyrazol-4-yl)pyrazolo[1,5-a]pyrimidine-2-carboxamide (41)

Starting material used in step 5—1-(4-trifluoromethoxyphenyl)-N-methylmethanamine; starting material used in step 7 4-chloroaniline; $^1$HNMR (400 MHz, DMSO-$d_6$) δ 13.53 (s, 1H), 10.30 (s, 1H), 9.34 (s, 1H), 8.73 (s, 1H), 7.88 (d, J=8.8 Hz, 2H), 7.71 (d, J=8.0 Hz, 2H), 7.48 (dd, J=16.0 Hz, 8.0 Hz, 4H), 7.19 (s, 1H), 6.55 (s, 1H), 5.04 (s, 2H), 3.23 (s, 3H). LCMS (Method C): $R_t$=3.46 min; [M+H]$^+$=525.9.

Example 42—N-(4-chlorophenyl)-5-(methyl(3-(trifluoromethyl)benzyl)amino)-7-(1H-pyrazol-4-yl)pyrazolo[1,5-a]pyrimidine-2-carboxamide (42)

Starting material used in step 5 1-(3-trifluoromethoxyphenyl)-N-methylmethanamine; starting material used in step 7 4-chloroaniline; $^1$HNMR (400 MHz, DMSO-$d_6$) δ 13.52 (s, 1H), 10.30 (s, 1H), 9.33 (s, 1H), 8.73 (s, 1H), 7.88 (d, J=8.8 Hz, 2H), 7.69 (s, 1H), 7.71-7.63 (m, 1H), 7.59 (d, J=5.2 Hz, 2H), 7.45 (dd, J=8.80 Hz, 2.8 Hz, 2H), 7.19 (s, 1H), 6.55 (s, 1H), 5.04 (s, 2H), 3.23 (s, 3H). LCMS (Method A): $R_t$=4.45 min; [M+H]$^+$=526.1.

Example 43 N-(4-chlorophenyl)-5-(methyl(2-(trifluoromethyl)benzyl)amino)-7-(1H-pyrazol-4-yl)pyrazolo[1,5-a]pyrimidine-2-carboxamide (43)

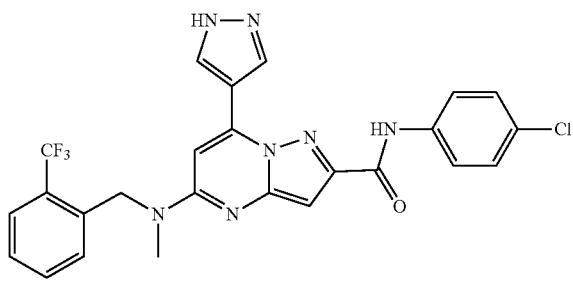

(43)

Starting material used in step 5—1-(2-trifluoromethoxyphenyl)-N-methylmethanamine; starting material used in step 7 4-chloroaniline; ¹HNMR (400 MHz, DMSO-d$_6$) δ 13.53 (s, 1H), 10.29 (s, 1H), 9.34 (s, 1H), 8.73 (s, 1H), 7.91-7.77 (m, 3H), 7.62 (t, J=7.6 Hz, 1H), 7.53-7.41 (m, 3H), 7.33-7.17 (m, 2H), 6.53 (s, 1H), 5.11 (s, 2H), 3.24 (s, 3H). LCMS (Method A): R$_t$=4.62 min; [M+H]$^+$=526.1.

Example 44—5-((4-chlorobenzyl)(methyl)amino)-N-(4-chlorophenyl)-7-(1H-pyrazol-4-yl)pyrazolo[1,5-a]pyrimidine-2-carboxamide (44)

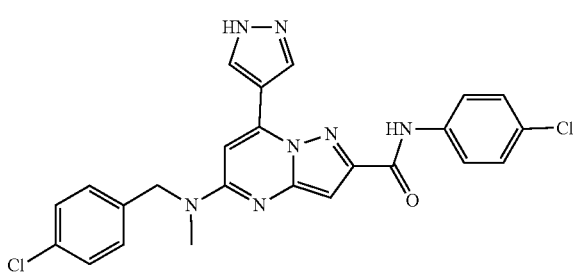

(44)

Starting material used in step 5—1-(4-chlorophenyl)-N-methylmethanamine; starting material used in step 7 4-chloroaniline; ¹HNMR (400 MHz, DMSO-d$_6$) δ 13.52 (s, 1H), 10.30 (s, 1H), 9.33 (s, 1H), 8.72 (s, 1H), 7.88 (d, J=8.9 Hz, 2H), 7.47-7.38 (m, 4H), 7.33 (d, J=8.5 Hz, 2H), 7.17 (s, 1H), 6.55 (s, 1H), 4.93 (s, 2H), 3.19 (s, 3H). LCMS (Method A): R$_t$=4.39 min; [M+H]+=492.1.

Example 45—5-((3-chlorobenzyl)(methyl)amino)-N-(4-chlorophenyl)-7-(1H-pyrazol-4-yl)pyrazolo[1,5-a]pyrimidine-2-carboxamide (45)

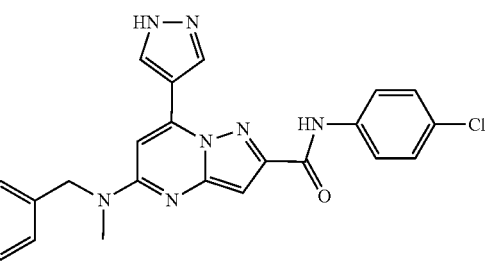

(45)

Starting material used in step 5—1-(3-chlorophenyl)-N-methylmethanamine; starting material used in step 7 -4-chloroaniline; ¹HNMR (400 MHz, DMSO-d$_6$) δ 13.53 (s, 1H), 10.30 (s, 1H), 9.33 (s, 1H), 8.73 (s, 1H), 7.88 (d, J=8.9 Hz, 2H), 7.45 (d, J=8.8 Hz, 2H), 7.41-7.31 (m, 3H), 7.26 (d, J=7.4 Hz, 1H), 7.17 (s, 1H), 6.56 (s, 1H), 4.95 (s, 2H), 3.21 (s, 3H). LCMS (Method A): R$_t$=3.36 min; [M+H]$^+$=492.02.

Example 46—5-((2-chlorobenzyl)(methyl)amino)-N-(4-chlorophenyl)-7-(1H-pyrazol-4-yl)pyrazolo[1,5-a]pyrimidine-2-carboxamide (46)

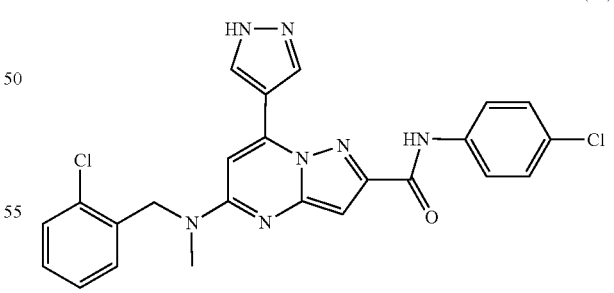

(46)

Starting material used in step 5 -1-(2-chlorophenyl)-N-methylmethanamine; starting material used in step 7 -4-chloroaniline; ¹HNMR (400 MHz, DMSO-d$_6$) δ 13.52 (s, 1H), 10.30 (s, 1H), 9.33 (s, 1H), 8.74 (s, 1H), 7.88 (d, J=4.4 Hz, 2H), 7.51 (d, J=6.0 Hz, 1H), 7.44 (d, J=8.8 Hz, 2H), 7.31 (t, J=2.8 Hz, 2H), 7.19-7.16 (m, 2H), 6.54 (s, 1H), 5.00 (s, 2H), 3.24 (s, 3H). LCMS (Method A): R$_t$=4.54 min; [M+H]$^+$= 429.1.

Example 47—5-(isoindolin-2-yl)-N-(3-morpholinophenyl)-7-(1H-pyrazol-4-yl)pyrazolo[1,5-a]pyrimidine-2-carboxamide (47)

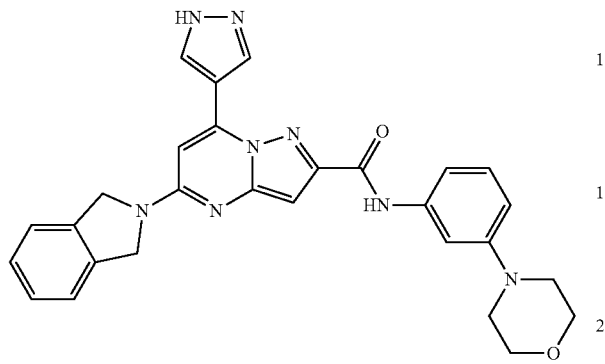

(47)

Starting material used in step 5—isoindoline; starting material used in step 7 -3-morpholinoaniline; $^1$HNMR (400 MHz, DMSO-d$_6$) δ 13.52 (s, 1H), 10.05 (s, 1H), 9.37 (s, 1H), 8.74 (s, 1H), 7.48 (d, J=2.0 Hz, 1H), 7.39-7.34 (m, 3H), 7.23 (t, J=8.0 Hz, 1H), 7.09 (s, 1H), 6.75 (dd, J=6.0 Hz, 2.0 Hz, 1H), 6.60 (s, 1H), 4.97 (s, 4H), 3.77 (t, J=5.2 Hz, 4H), 3.13 (t, J=4.8 Hz, 4H). LCMS (Method A): R$_t$=3.91 min; [M+H]$^+$=507.2.

Example 48—5-(isoindolin-2-yl)-N-(3-(4-methylpiperazin-1-yl)phenyl)-7-(1H-pyrazol-4-yl)pyrazolo[1,5-a]pyrimidine-2-carboxamide (48)

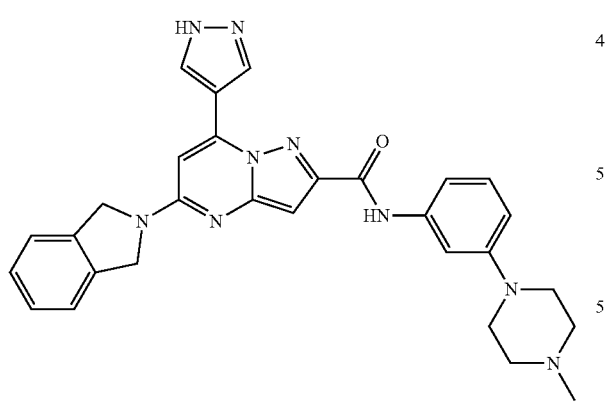

(48)

Starting material used in step 5-isoindoline; starting material used in step 7 -3-(4-methylpiperazin-1-yl)aniline; $^1$HNMR (400 MHz, DMSO-d$_6$) δ 13.54 (s, 1H), 10.05 (s, 1H), 9.36 (d, J=1.6 Hz, 1H), 8.78 (d, J=1.6 Hz, 1H), 7.54-7.20 (m, 7H), 7.09 (s, 1H), 6.83-6.72 (m, 1H), 6.60 (s, 1H), 4.97 (s, 4H), 3.26 (s, 8H), 2.82 (s, 3H). LCMS (Method A): R$_t$=3.09 min; [M+H]$^+$=520.16

Example 49—N-(3-(4-acetylpiperazin-1-yl)phenyl)-5-(isoindolin-2-yl)-7-(1H-pyrazol-4-yl)pyrazolo[1,5-a]pyrimidine-2-carboxamide (49)

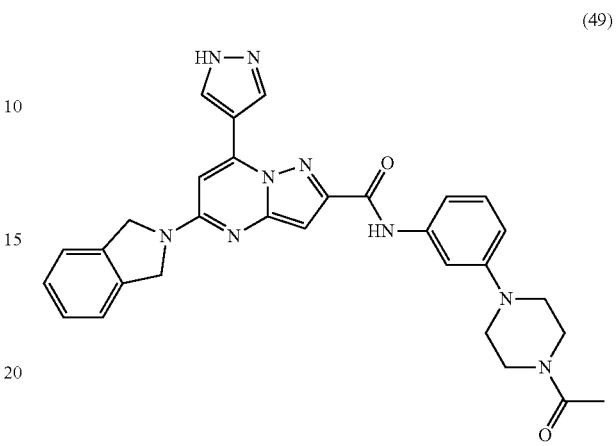

(49)

Starting material used in step 5—isoindoline, starting material used in step 7 -1-(4-(3-aminophenyl)piperazin-1-yl)ethan-1-one; $^1$HNMR (400 MHz, DMSO-d$_6$) δ 13.54 (s, 1H), 10.05 (s, 1H), 9.36 (s, 1H), 8.78 (s, 1H), 7.51 (s, 1H), 7.45 (s, 2H), 7.37-7.33 (m, 3H), 7.09 (s, 1H), 6.76 (d, J=8.0 Hz, 1H), 6.60 (s, 1H), 4.97 (s, 4H), 3.61 (s, 4H), 3.19 (s, 2H), 3.12 (s, 2H), 2.06 (s, 3H). LCMS (Method A): R$_t$=3.69 min; [M+H]$^+$=548.2;

Example 50—N-(3-cyclobutoxyphenyl)-5-(isoindolin-2-yl)-7-(1H-pyrazol-4-yl)pyrazolo[1,5-a]pyrimidine-2-carboxamide (50)

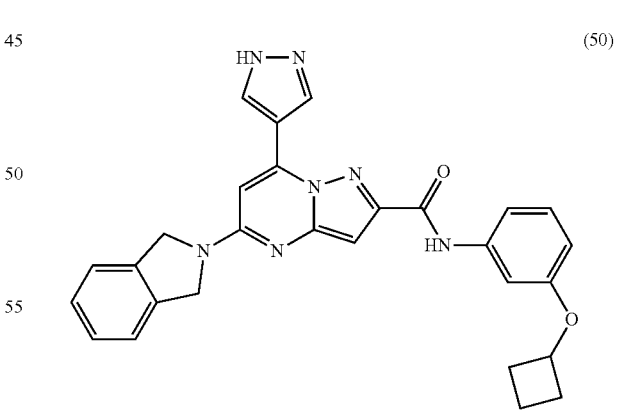

(50)

Starting material used in step 5—isoindoline, starting material used in step 7 -3-cyclobutoxyaniline; $^1$HNMR (400 MHz, DMSO-d$_6$) δ 13.54 (s, 1H), 10.14 (s, 1H), 9.37 (d, J=2.8 Hz, 1H), 8.77 (s, 1H), 7.57-7.21 (m, 8H), 7.09 (s, 1H), 6.62 (d, J=11.2 Hz, 2H), 4.98 (d, J=2.8 Hz, 4H), 4.80-4.56 (m, 1H), 2.51 (s, 1H), 2.15-2.01 (m, 2H), 1.86-1.61 (m, 2H). LCMS (Method A): R$_t$=4.47 min; [M+H]$^+$=492.2;

Example 51—N-(3,5-dimethoxyphenyl)-5-(isoindolin-2-yl)-7-(1H-pyrazol-4-yl)pyrazolo[1,5-a]pyrimidine-2-carboxamide (51)

Example 53—N-(4-chloro-3-methoxyphenyl)-5-(isoindolin-2-yl)-7-(1H-pyrazol-4-yl)pyrazolo[1,5-a]pyrimidine-2-carboxamide (53)

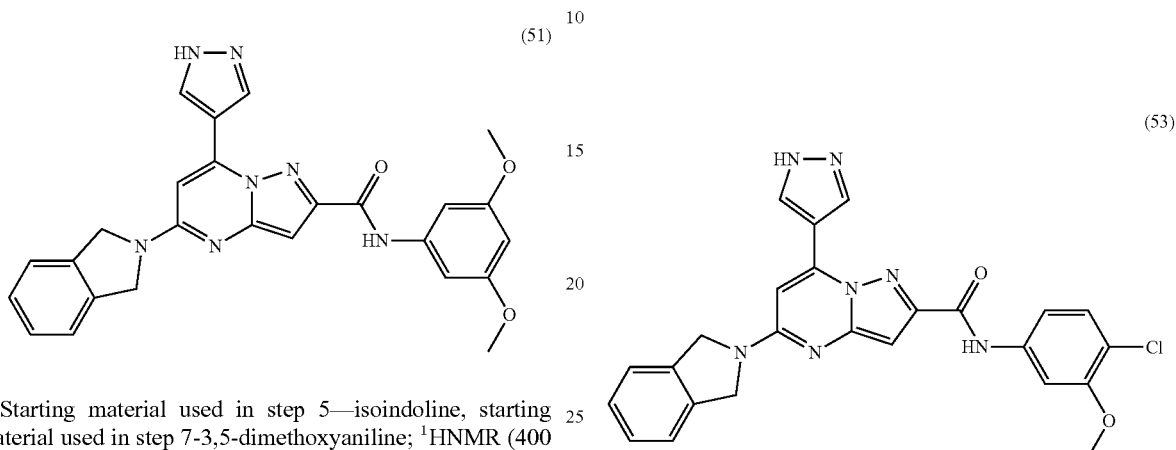

(51)

(53)

Starting material used in step 5—isoindoline, starting material used in step 7-3,5-dimethoxyaniline; ¹HNMR (400 MHz, DMSO-d₆) δ 13.53 (s, 1H), 10.05 (s, 1H), 9.35 (s, 1H), 8.80 (s, 1H), 7.44 (d, J=2.8 Hz, 2H), 7.37-7.35 (m, 2H), 7.16 (d, J=2.0 Hz, 2H), 7.09 (s, 1H), 6.60 (s, 1H), 6.31 (s, 1H), 4.97 (s, 4H), 3.77 (s, 6H). LCMS (Method A): R$_t$=4.10 min; [M+H]⁺=482.2.

Example 52—N-(3-chloro-5-methoxyphenyl)-5-(isoindolin-2-yl)-7-(1H-pyrazol-4-yl)pyrazolo[1,5-a]pyrimidine-2-carboxamide (52)

Starting material used in step 5—isoindoline; starting material used in step 7—4-chloro-3-methoxyaniline; ¹HNMR (400 MHz, DMSO-d₆) δ 13.56 (s, 1H), 10.30 (s, 1H), 9.37 (s, 1H), 9.00-8.59 (m, 1H), 7.79 (d, J=2.0 Hz, 1H), 7.57-7.32 (m, 6H), 7.10 (s, 1H), 6.62 (s, 1H), 4.97 (d, J=1.6 Hz, 4H), 3.89 (s, 3H). LCMS (Method A): R$_t$=4.27 min; [M+H]=486.1

Example 54—5-(isoindolin-2-yl)-N-(4-methoxyphenyl)-7-(1H-pyrazol-4-yl)pyrazolo[1,5-a]pyrimidine-2-carboxamide (54)

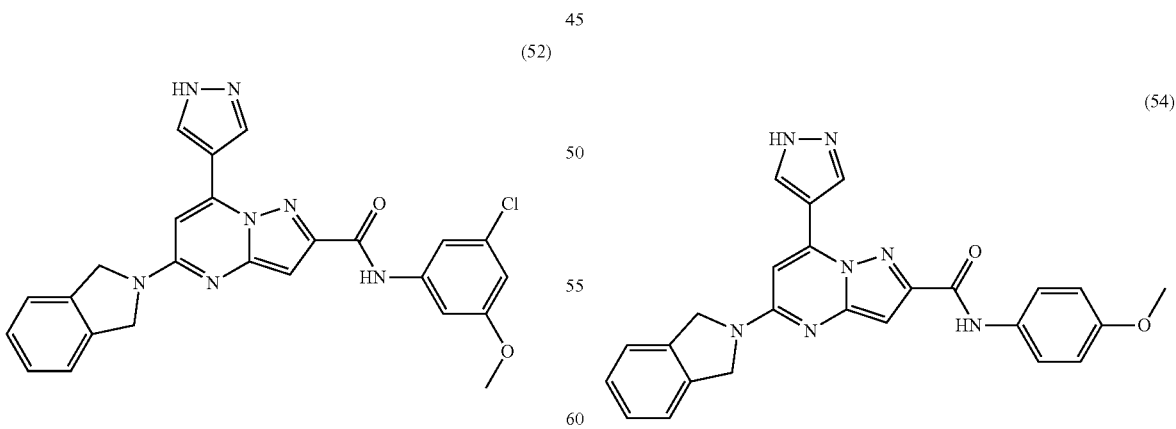

(52)

(54)

Starting material used in step 5—isoindoline, Sstarting material used in step 7—3-chloro-5-methoxyaniline; ¹HNMR (400 MHz, DMSO-d₆) δ 13.53 (s, 1H), 10.29 (s, 1H), 9.35 (s, 1H), 8.80 (s, 1H), 7.61 (s, 1H), 7.55 (s, 1H), 7.45 (s, 2H), 7.37 (d, J=2.8 Hz, 2H), 7.11 (s, 1H), 6.82 (s, 1H), 6.62 (s, 1H), 4.97 (s, 4H), 3.81 (s, 3H). LCMS (Method A): R$_t$=4.49 min; [M+H]⁺=486.1.

Starting material used in step 5—isoindoline; starting material used in step 7—4-methoxyaniline; ¹HNMR (400 MHz, DMSO-d₆) δ 13.53 (s, 1H), 10.09 (s, 1H), 9.37 (s, 1H), 8.77 (s, 1H), 7.71 (s, 2H), 7.41 (d, J=8.0 Hz, 4H), 7.08 (s, 1H), 6.97 (s, 2H), 6.58 (s, 1H), 4.97 (s, 4H), 3.71 (s, 3H). LCMS (Method A): R$_t$=3.93 min; [M+H]⁺=452.2.

Example 55—N-(4-ethoxyphenyl)-5-(isoindolin-2-yl)-7-(1H-pyrazol-4-yl)pyrazolo[1,5-a]pyrimidine-2-carboxamide (55)

Example 57—5-(5-chloroisoindolin-2-yl)-N-(3-methoxyphenyl)-7-(1H-pyrazol-4-yl)pyrazolo[1,5-a]pyrimidine-2-carboxamide (61)

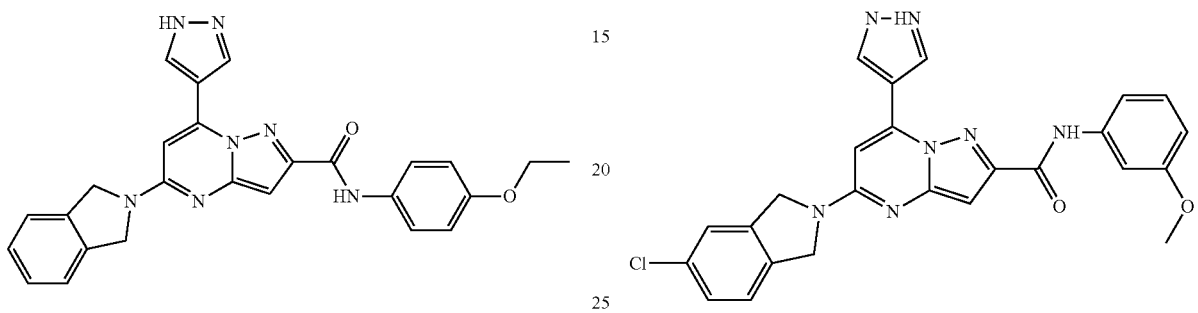

Starting material used in step 5—isoindoline, starting material used in step 7—4-ethoxyaniline, $^1$HNMR (400 MHz, DMSO-$d_6$) δ 13.52 (s, 1H), 10.09 (s, 1H), 9.38 (s, 1H), 8.77 (s, 1H), 7.70 (d, J=8.8 Hz, 2H), 7.53-7.32 (m, 4H), 7.08 (s, 1H), 6.95 (d, J=8.8 Hz, 2H), 6.57 (s, 1H), 4.97 (s, 4H), 4.03 (q, J=6.4 Hz, 2H), 1.34 (t, J=6.0 Hz, 3H). LCMS (Method A): $R_t$=3.18 min; [M+H]$^+$=466.04.

Starting material used in step 5—5-chloroisoindoline, starting material used in step 7—4-methoxyaniline; $^1$HNMR (400 MHz, DMSO-$d_6$) δ 13.55 (s, 1H), 10.16 (s, 1H), 9.37 (s, 1H), 8.75 (s, 1H), 7.50 (d, J=3.2 Hz, 5H), 7.30 (s, 1H), 7.07 (s, 1H), 6.75 (s, 1H), 6.60 (s, 1H), 4.97 (s, 4H), 3.79 (s, 3H). LCMS (Method A): $R_t$=4.37 min; [M+H]$^+$=466.1;

Example 56—5-(isoindolin-2-yl)-N-(4-isopropoxyphenyl)-7-(1H-pyrazol-4-yl)pyrazolo[1,5-a]pyrimidine-2-carboxamide (56)

Example 58—5-(5-chloroisoindolin-2-yl)-N-(3-hydroxyphenyl)-7-(1H-pyrazol-4-yl)pyrazolo[1,5-a]pyrimidine-2-carboxamide (62)

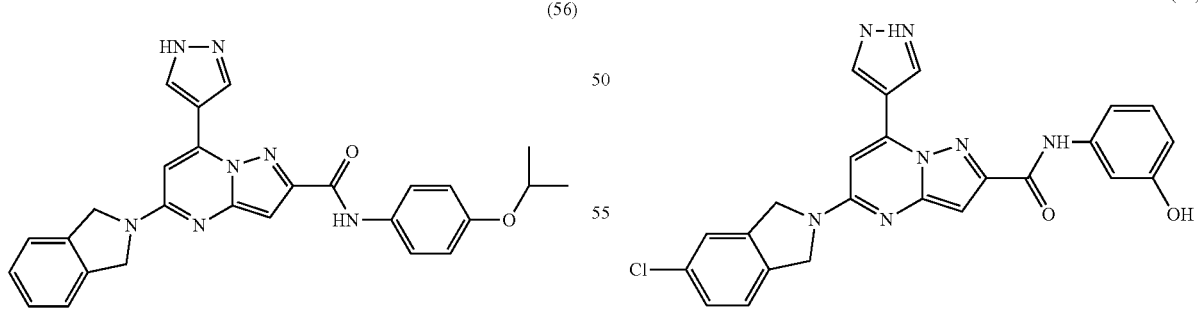

Starting material used in step 5—isoindoline, starting material used in step 7—4-isopropoxyaniline, $^1$HNMR (400 MHz, DMSO-$d_6$) δ 13.55 (s, 1H), 10.09 (s, 1H), 9.35 (s, 1H), 8.77 (s, 1H), 7.66 (d, J=8.8 Hz, 2H), 7.44 (d, J=3.2 Hz, 2H), 7.37-7.35 (m, 2H), 7.07 (s, 1H), 6.95 (d, J=8.8 Hz, 2H), 6.57 (s, 1H), 4.97 (s, 4H), 4.62-4.55 (m, 1H), 1.27 (t, J=6.0 Hz, 3H). LCMS (Method A): $R_t$=42.2 min; [M+H]$^+$=480.2.

Starting material used in step 5—5-chloroisoindoline, starting material used in step 7-4-aminophenol, $^1$HNMR (400 MHz, DMSO-$d_6$) δ 13.49 (s, 1H), 10.04 (s, 1H), 9.43 (s, 1H), 8.74 (s, 1H), 7.53 (s, 1H), 7.47 (d, J=8.0 Hz, 1H), 7.42-7.38 (m, 3H), 7.22 (d, J=7.6 Hz, 1H), 7.15 (t, J=8.0 Hz, 1H), 7.06 (s, 1H), 6.59 (s, 1H), 4.55 (d, J=8.0 Hz, 1H), 4.95 (s, 4H). LCMS (Method A): $R_t$=3.90 min; [M+H]$^+$=472.1.

Example 59—5-(5-fluoroisoindolin-2-yl)-N-(3-methoxyphenyl)-7-(1H-pyrazol-4-yl)pyrazolo[1,5-a]pyrimidine-2-carboxamide (63)

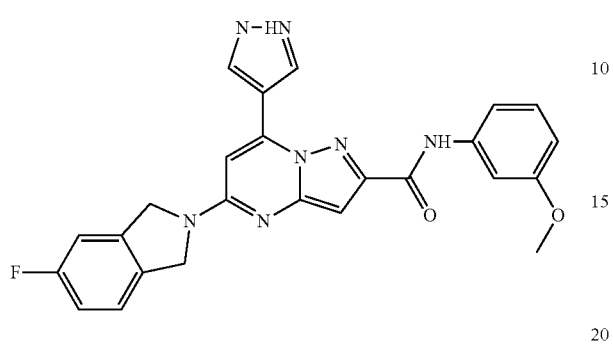

(63)

Starting material used in step 5—5-fluoroisoindoline, starting material used in step 7-4-methoxyaniline; ¹HNMR (400 MHz, DMSO-d$_6$) δ 13.54 (s, 1H), 10.16 (s, 1H), 9.37 (s, 1H), 8.76 (s, 1H), 7.65-7.00 (m, 7H), 6.83-6.47 (m, 2H), 5.20-4.73 (m, 4H), 3.79 (s, 3H). LCMS (Method A): R$_t$=4.10 min; [M+H]$^+$=470.1.

Example 60—5-(5-fluoroisoindolin-2-yl)-N-(3-hydroxyphenyl)-7-(1H-pyrazol-4-yl)pyrazolo[1,5-a]pyrimidine-2-carboxamide (64)

(64)

Starting material used in step 5—5-fluoroisoindoline, starting material used in step 7-4-aminophenol, ¹HNMR (400 MHz, DMSO-d$_6$) δ 13.53 (s, 1H), 10.06 (s, 1H), 9.53-9.29 (m, 2H), 8.75 (s, 1H), 7.49-7.43 (m, 1H), 7.38 (s, 1H), 7.32-7.12 (m, 4H), 7.06 (s, 1H), 6.65-6.50 (m, 2H), 4.94 (dd, J=2.0 Hz, 1.2 Hz, 4H). LCMS (Method A): R$_t$=3.93 min; [M+H]$^+$=456.1.

The following compounds were similarly prepared from the appropriate starting material in step 4, the appropriate starting material instep 5 and the appropriate starting material in step 7 according to the method described for the synthesis of compound 1.

Example 61—5-(isoindolin-2-yl)-N-(3-methoxyphenyl)-7-(1-methyl-1H-pyrazol-4-yl)pyrazolo[1,5-a]pyrimidine-2-carboxamide (57)

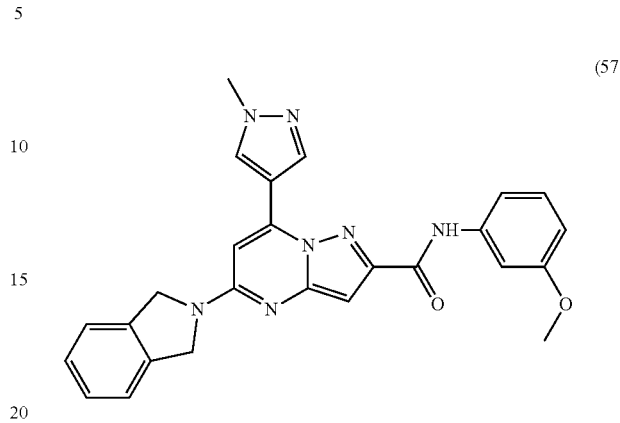

(57)

Starting material used in step 4—1-methyl-4-(4,4,5,5-tetramethyl-1,3,2-dioxaborolan-2-yl)-1H-pyrazole; starting material used in step 5—isoindoline. starting material used in step 7-4-methoxyaniline, ¹HNMR (400 MHz, DMSO-d$_6$) δ 10.05 (s, 1H), 9.31 (s, 1H), 8.77 (s, 1H), 7.57 (t, J=2.0 Hz, 1H), 7.34 (t, J=8.8 Hz, 2H), 7.37-7.35 (m, 2H), 7.30 (t, J=8.4 Hz, 1H), 7.07 (s, 1H), 6.73 (dd, J=6.0 Hz, 2.0 Hz, 1H), 6.60 (s, 1H), 4.97 (s, 4H), 4.00 (s, 3H), 3.79 (s, 3H). LCMS (Method A): R$_t$=4.23 min; [M+H]$^+$=466.2.

Example 62—N-(3-hydroxyphenyl)-5-(isoindolin-2-yl)-7-(1-methyl-1H-pyrazol-4-yl)pyrazolo[1,5-a]pyrimidine-2-carboxamide (58)

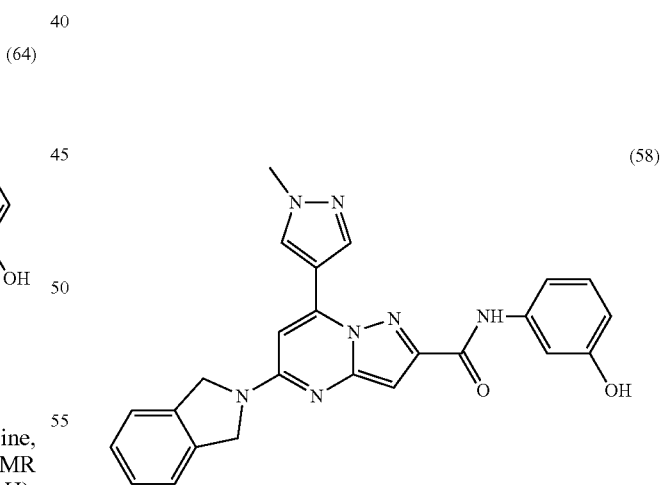

(58)

Starting material used in step 4—1-methyl-4-(4,4,5,5-tetramethyl-1,3,2-dioxaborolan-2-yl)-1H-pyrazole, starting material used in step 5—isoindoline, starting material used in step 7-4-aminophenol; ¹HNMR (400 MHz, DMSO-d$_6$) δ 9.95 (s, 1H), 9.46 (s, 1H), 9.31 (s, 1H), 8.70 (s, 1H), 7.44-7.36 (m, 5H), 7.24 (t, J=7.6 Hz, 1H), 7.16 (t, J=8.0 Hz, 1H), 7.07 (s, 1H), 6.75 (t, J=8.0 Hz, 2H), 4.97 (s, 4H), 4.03 (s, 3H). LCMS (Method A): R$_t$=3.81 min; [M+H]$^+$=452.1.

Example 63—5-(isoindolin-2-yl)-N-(3-methoxyphenyl)-7-(1,3,5-trimethyl-1H-pyrazol-4-yl)pyrazolo[1,5-a]pyrimidine-2-carboxamide (59)

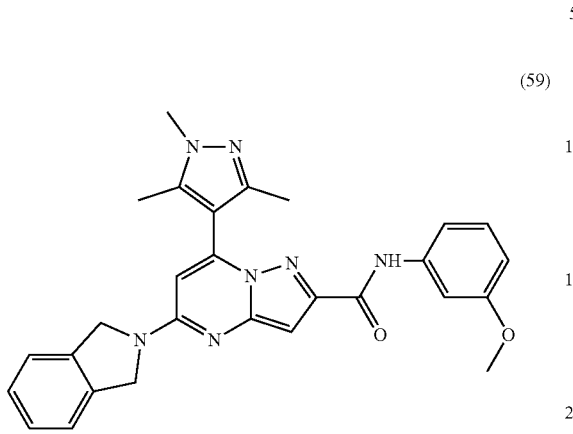
(59)

Starting material used in step 4-1,3,5-trimethyl-4-(4,4,5,5-tetramethyl-1,3,2-dioxaborolan-2-yl)-1H-pyrazole, starting material used in step 5—isoindoline, tarting material used in step 7—4-methoxyaniline; ¹HNMR (400 MHz, DMSO-d₆) δ 9.85 (s, 1H), 7.62-7.18 (m, 7H), 6.78-6.46 (m, 3H), 4.94 (s, 4H), 3.78 (d, J=8.8 Hz, 6H), 2.25 (d, J=6.4 Hz, 6H). LCMS (Method A): R$_t$=4.20 min; [M+H]⁺=494.2.

Example 64—N-(3-hydroxyphenyl)-5-(isoindolin-2-yl)-7-(1,3,5-trimethyl-1H-pyrazol-4-yl)pyrazolo[1,5-a]pyrimidine-2-carboxamide (60)

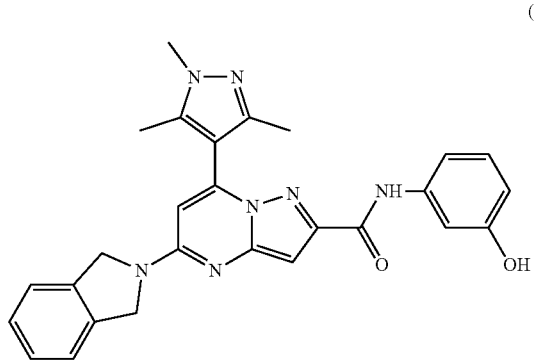
(60)

Starting material used in step 4-1,3,5-trimethyl-4-(4,4,5,5-tetramethyl-1,3,2-dioxaborolan-2-yl)-1H-pyrazole, starting material used in step 5—isoindoline, starting material used in step 7—4-aminophenol, ¹HNMR (400 MHz, DMSO-d₆) δ 9.68 (s, 1H), 9.41 (s, 1H), 7.49-7.31 (m, 5H), 7.18-7.07 (m, 2H), 6.61 (s, 1H), 6.55-6.48 (m, 2H), 4.93 (s, 4H), 3.80 (s, 3H), 2.29 (s, 3H), 2.20 (s, 3H). LCMS (Method A): R$_t$=3.81 min; [M+H]⁺=480.2.

Example 65—5-(isoindolin-2-yl)-N-(3-methoxyphenyl)-3-methyl-7-(1H-pyrazol-4-yl)pyrazolo[1,5-a]pyrimidine-2-carboxamide

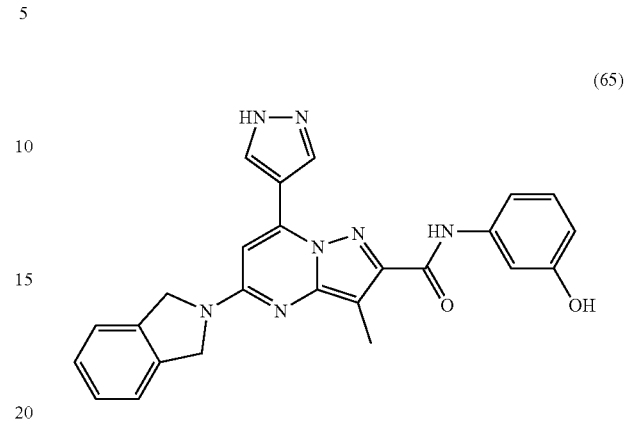
(65)

Compound 65 was made using the procedure outlined in scheme 4.

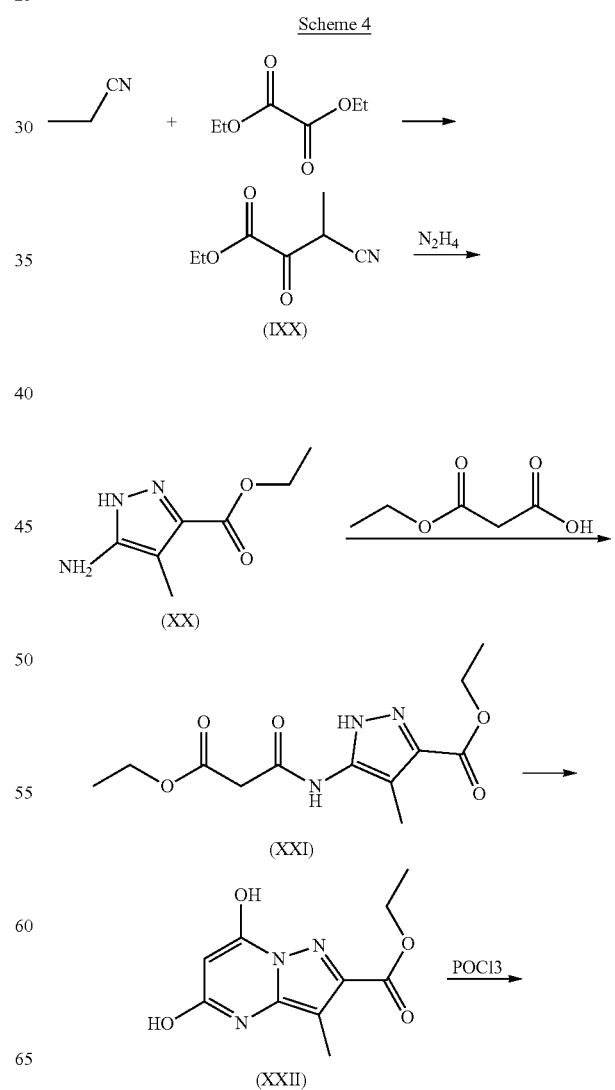

-continued

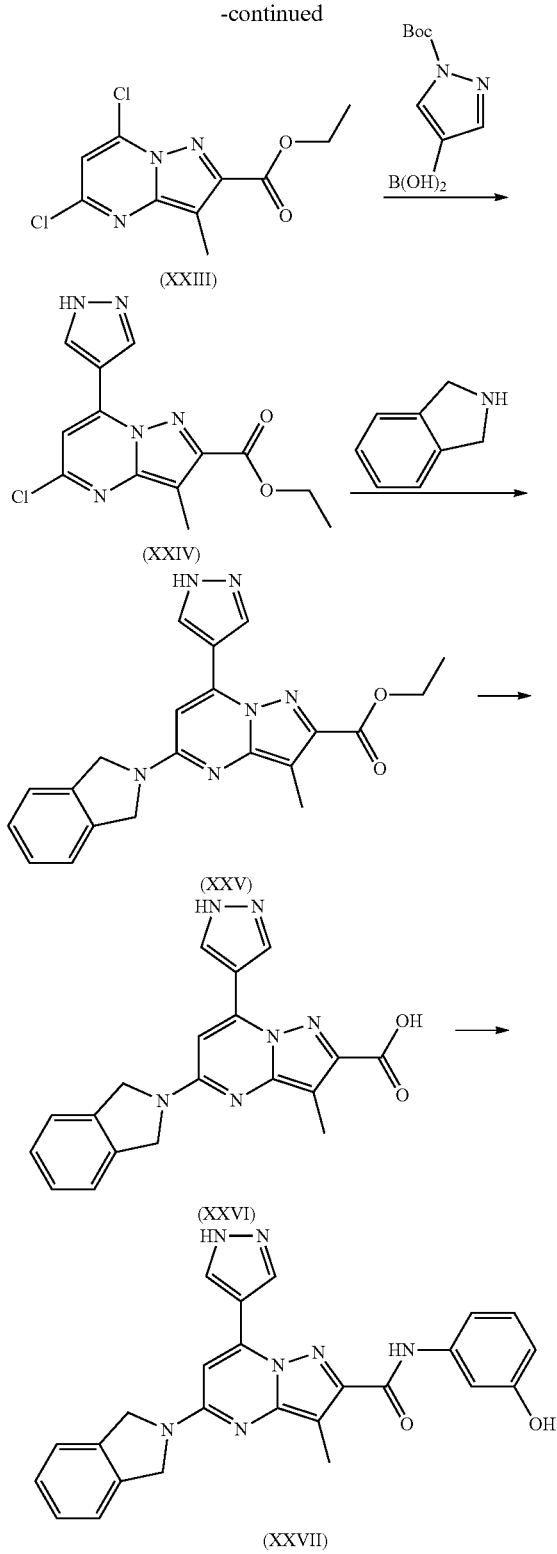

Step 1: ethyl 3-cyano-2-oxobutanoate (IXX)

To a solution of lithium bis(trimethylsilyl)amide (1.0 M in THF, 13.7 mL, 13.71 mmol) in THF (15 mL) under N₂ cooled to −78° C. was added propiononitrile (0.90 g, 16.42 mmol) dropwise over 5 minutes, and the mixture was stirred at −78° C. for 1 hour. Diethyl oxalate (2.01 g, 13.72 mmol) was added dropwise over 5 minutes and the reaction mixture was stirred at-78° C. for 45 minutes and then 0° C. for 1 hour. H₂O (100 mL) was added the organic phase was removed with Et₂O (100 mL). The aqueous phase was adjusted to pH 5 with aqueous HCl (6M) and extracted with Et₂O (3×100 mL). The combined organics were washed with brine (300 mL), dried over Na₂SO₄, filtered and concentrated under reduced pressure to afford the desired product (7.5 g, 89%) as a yellow oil. LCMS (Method A): R$_f$=2.36 min; [M+H]⁺=157.1

Step 2: ethyl 5-amino-4-methyl-1H-pyrazole-3-carboxylate (XX)

A mixture of ethyl 3-cyano-2-oxobutanoate (8.8 g, 44.00 mmol) and hydrazine hydrate (4.47 g, 89.20 mmol) in AcOH (10 mL) and toluene (100 mL) was stirred at 110° C. overnight. The mixture was concentrated under reduced pressure and the reside was purified by column chromatography on silica gel (DCM:MeOH, 100/1) to give the title product (3.6 g, 38%) as a yellow oil. LCMS (Method A): R$_f$=2.54 min; [M+H]⁺=170.2

Step 3: ethyl 5-(3-ethoxy-3-oxopropanamido)-4-methyl-1H-pyrazole-3-carboxylate (XXI)

A mixture of ethyl 5-amino-4-methyl-1H-pyrazole-3-carboxylate (1.0 g, 5.92 mmol), 3-ethoxy-3-oxopropanoic acid (0.82 g, 6.22 mmol), DCC (1.59 g, 7.71 mmol), pyridine (1.40 g, 17.76 mmol) and DMAP (72 mg, 0.59 mmol) in DCM (15 mL) was stirred at room temperature overnight. The mixture was filtered, rinsed with DCM (2×10 mL) and the combined filtrates were concentrated under reduced pressure. The residue was purified by column chromatography on silica gel (DCM:MeOH, 100:1) to give the title product (1.46 g, 87%) as a yellow oil. LCMS (Method A): R$_f$=2.91 min; [M+H]⁺=284.1

Step 4: ethyl 5,7-dihydroxy-3-methylpyrazolo[1,5-a]pyrimidine-2-carboxylate (XXII)

A mixture of ethyl 5-(3-ethoxy-3-oxopropanamido)-4-methyl-1H-pyrazole-3-carboxylate (1.46 g, 5.16 mmol) and DMAP (1.89 g, 15.48 mmol) in ethanol (15 mL) and H₂O (15 mL) was stirred at 80° C. overnight. The mixture was concentrated under reduced pressure and the residue was partitioned between EtOAc (50 mL) and H₂O (50 mL). The organics were dried over Na2SO4 and concentrated under reduced pressure to give the title product (1.6 g, 100%) as a white solid. LCMS (Method A): R$_f$=4.00 min; [M+H]⁺=238.1

Step 5: ethyl 5,7-dichloro-3-methylpyrazolo[1,5-a]pyrimidine-2-carboxylate (XXIII)

A mixture of ethyl 5,7-dihydroxy-3-methylpyrazolo[1,5-a]pyrimidine-2-carboxylate (2.3 g, 9.71 mmol) in phosphorus oxychloride (25 mL) was stirred at 110° C. overnight. The mixture was concentrated under reduced pressure, and the residue was poured into ice-water and extracted with Et₂O (3×300 mL). The combined organics were washed with brine (100 mL), dried (Na₂SO₄), filtered and concentrated under reduced pressure. The residue was purified by column chromatography on silica gel (PE:EtOAc, 10:1) to give the title product (1.6 g, 60.4%) as a yellow oil. LCMS (Method A): $R_t$=2.93 min; [M+H]$^+$=274.0.

Step 6: ethyl 5-chloro-3-methyl-7-(1H-pyrazol-4-yl)pyrazolo[1,5-a]pyrimidine-2-carboxylate (XXIV)

A mixture of ethyl 5,7-dichloro-3-methylpyrazolo[1,5-a]pyrimidine-2-carboxylate (3 g, 11.15 mmol), 1-Boc-pyrazole-4-boronic acid pinacol ester (2.3 g, 11.15 mmol), Na$_2$CO$_3$ (2.3 g, 22.30 mmol) and Pd(dppf)$_2$Cl$_2$ (0.80 g, 1.11 mmol) in degassed 1,4-dioxane (50 mL) and H$_2$O (10 mL) was stirred at 80° C. overnight under N$_2$. The mixture was poured into water and extracted with EtOAc (100 mL×3). The combined organics were washed with water and brine, dried over Na$_2$SO$_4$, filtered and concentrated under reduced pressure. The residue was purified by column chromatography on silica gel (DCM:MeOH, 100:1) to give the title product (1.5 g, 45%) as a yellow solid. LCMS (Method A): $R_t$=3.75 min; [M+H]$^+$=306.1

Step 7: ethyl 5-(isoindolin-2-yl)-3-methyl-7-(1H-pyrazol-4-yl)pyrazolo [1,5-a]pyrimidine-2-carboxylate (XXV)

A mixture of ethyl 5-chloro-3-methyl-7-(1H-pyrazol-4-yl)pyrazolo [1,5-a]pyrimidine-2-carboxylate (1.5 g, 4.91 mmol), isoindoline (1.5 g, 9.86 mmol) and triethylamine (2.0 g, 19.61 mmol) in DMF (20 mL) was stirred at 80° C. overnight. The mixture was diluted with water and the solids were filtered under reduced pressure. The solids were purified by silica gel column chromatography (DCM:MeOH, 90:10) to give the desired product (1 g, 53%) as a yellow solid. LCMS: (Method A), $R_t$=4.97 min, [M+H]$^+$=389.2

Step 8: 5-(isoindolin-2-yl)-3-methyl-7-(1H-pyrazol-4-yl)pyrazolo[1,5-a]pyrimidine-2-carboxylic acid (XXVI)

To a solution of ethyl 5-(isoindolin-2-yl)-3-methyl-7-(1H-pyrazol-4-yl)pyrazolo[1,5-a]pyrimidine-2-carboxylate (1 g, 2.62 mmol) in THF (12 mL) and MeOH (12 mL) at 0° C. was slowly added an aqueous solution of KOH (1M, 6 mL). The reaction mixture was stirred at 90° C. overnight. The mixture was concentrated under reduced pressure and the residue was partitonned between H2O and Et2O (50 mL, 1/1). The organics were discarded and the aqueous were acidified to pH 2 with an aqueous HCL solution (2M). The aqueous phase was extracted with CHCl$_3$ (100 mL×3) and the combined organics were dried over Na$_2$SO$_4$ and concentrated under reduced pressure to afford the desired product (860 mg, 93%) as a yellow solid. LCMS: (Method A), $R_t$=4.22 min. [M+H]$^+$=361.1

Step 9: 5-(isoindolin-2-yl)-N-(3-methoxyphenyl)-3-methyl-7-(1H-pyrazol-4-yl)pyrazolo[1,5-a]pyrimidine-2-carboxamide (XXVII) (Compound 65

A mixture of 5-(isoindolin-2-yl)-3-methyl-7-(1H-pyrazol-4-yl)pyrazolo[1,5-a]pyrimidine-2-carboxylic acid (200 mg, 0.56 mmol), 3-aminophenol (68 mg, 0.62 mmol), HATU (319 mg, 0.84 mmol) and DIEA (142 mg, 1.12 mmol) in DMF (2 mL) was stirred at room temperature overnight. The mixture was diluted with water and the solids were filtered under reduced pressure. The filtered cake was dried and purified by silica gel column chromatography (DCM:MeOH 90:10) to give the title product (58 mg, 23%) as a yellow solid. LCMS: (Method A), $R_t$=4.10 min, [M+H]$^+$=452.1.

$^1$HNMR (400 MHz, DMSO-d$_6$) δ 13.47 (s, 1H), 9.99 (s, 1H), 9.41 (s, 1H), 8.97 (s, 1H), 7.46-7.35 (m, 6H), 7.22 (t, J=8.0 Hz, 1H), 7.14 (t, J=8.0 Hz, 1H), 7.06 (s, 1H), 6.53 (d, J=6.0 Hz, 1H), 4.96 (s, 4H), 2.42 (s, 3H).

Example 66—5-(isoindolin-2-yl)-N-(3-methoxyphenyl)-3-methyl-7-(1H-pyrazol-4-yl)pyrazolo[1,5-a]pyrimidine-2-carboxamide (66)

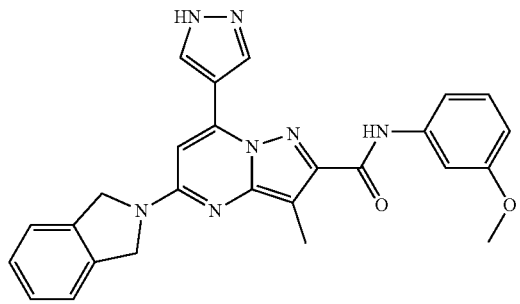

(66)

Starting material used in step 7—isoindoline, starting material used in step 9—3-methoxyaniline, $^1$HNMR (400 MHz, DMSO-d$_6$) δ 13.51 (s, 1H), 10.0 (s, 1H), 9.36 (s, 1H), 8.74 (s, 1H), 7.55 (s, 1H), 7.45-7.35 (m, 5H), 7.28 (t, J=8.0 Hz, 1H), 7.06 (s, 1H), 6.72 (d, J=6.0 Hz, 1H), 4.96 (s, 4H), 3.79 (s, 3H), 2.42 (s, 3H). LCMS: (Method A), $R_t$=4.61 min. [M+H]$^+$=465.2.

Example 67—5-(isoindolin-2-yl)-3-methyl-7-(1H-pyrazol-4-yl)-N-(3-(trifluoromethoxy)phenyl)pyrazolo[1,5-a]pyrimidine-2-carboxamide (67)

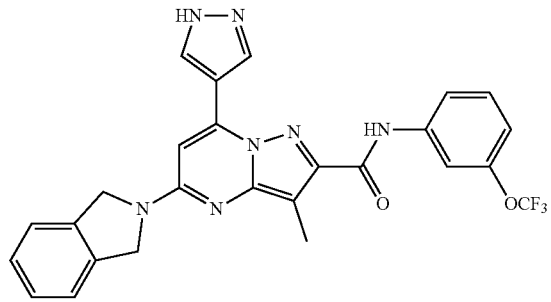

(67)

Starting material used in step 7—isoindoline, starting material used in step 9—3-(trifluoromethoxy)aniline, $^1$HNMR (400 MHz, DMSO-d$_6$) δ 13.51 (s, 1H), 10.40 (s, 1H), 9.36 (s, 1H), 8.74 (s, 1H), 8.01 (s, 1H), 7.88 (t, J=7.6 Hz, 1H), 7.53-7.46 (m, 3H), 7.37-7.35 (m, 2H), 7.11 (t, J=7.6 Hz, 2H), 4.78 (s, 4H), 2.42 (s, 3H). LCMS: (Method A), $R_t$=3.54 min, [M+H]$^+$=520.1.

Example 68—5-(benzyl(methyl)amino)-N-(3-hydroxyphenyl)-3-methyl-7-(1H-pyrazol-4-yl)pyrazolo[1,5-a]pyrimidine-2-carboxamide (68)

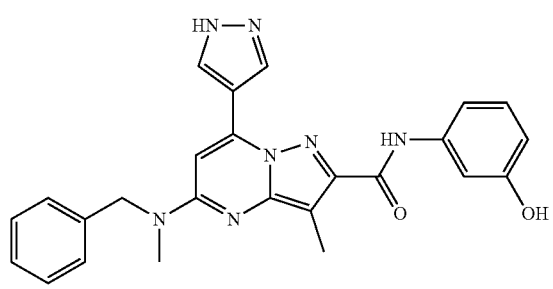

(68)

Starting material used in step 7—N-methyl-1-phenylmethanamine, starting material used in step 9—3-aminophenol, $^{1}$HNMR (400 MHz, DMSO-d$_6$) δ 13.46 (s, 1H), 9.97 (s, 1H), 9.40 (s, 1H), 9.30 (s, 1H), 8.68 (s, 1H), 7.41 (s, 1H), 7.34 (s, 4H), 7.27 (s, 1H), 7.21 (d, J=8.0 Hz, 1H), 7.13 (t, J=7.6 Hz, 2H), 6.52 (d, J=7.6 Hz, 1H), 4.96 (s, 2H), 3.21 (s, 3H), 2.37 (s, 3H). LCMS: (Method A), R$_t$=4.13 min. [M+H]$^+$=454.2.

Example 69—5-(benzyl(methyl)amino)-N-(3-methoxyphenyl)-3-methyl-7-(1H-pyrazol-4-yl)pyrazolo[1,5-a]pyrimidine-2-carboxamide (69)

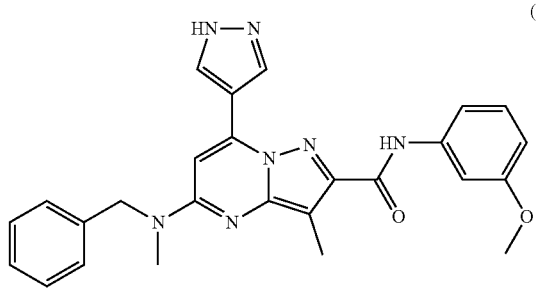

(69)

Starting material used in step 7—N-methyl-1-phenylmethanamine, starting material used in step 9—3-methoxyaniline, $^{1}$HNMR (400 MHz, DMSO-d$_6$) δ 13.46 (s, 1H), 10.06 (s, 1H), 9.32 (s, 1H), 8.69 (s, 1H), 7.54 (t, J=2.4 Hz, 1H), 7.43 (d, J=8.0 Hz, 4H), 7.35 (t, J=3.2 Hz, 4H), 7.28 (t, J=8.0 Hz, 2H), 7.15 (s, 1H), 6.71 (d, J=6.0 Hz, 1H), 4.96 (s, 2H), 3.78 (s, 3H), 3.21 (s, 3H), 2.37 (s, 3H). LCMS: (Method A), R$_t$=4.62 min, [M+H]$^+$=468.2.

Example 70—5-(benzyl(methyl)amino)-3-methyl-7-(1H-pyrazol-4-yl)-N-(3-(trifluoromethoxy)phenyl)pyrazolo[1,5-a]pyrimidine-2-carboxamide (70)

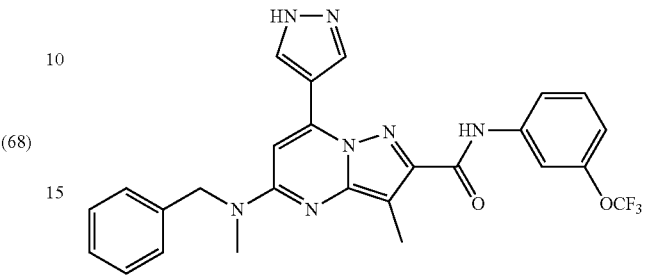

(70)

Starting material used in step 7—N-methyl-1-phenylmethanamine, starting material used in step 9—3-(trifluoromethoxy)aniline, $^{1}$HNMR (400 MHz, DMSO-d$_6$) δ 13.46 (s, 1H), 10.36 (s, 1H), 9.32 (s, 1H), 8.70 (s, 1H), 8.01 (s, 1H), 7.88 (d, J=8.0 Hz, 1H), 7.51 (t, J=7.6 Hz, 1H), 7.43 (s, 4H), 7.27 (d, J=3.2 Hz, 1H), 7.16 (s, 1H), 7.11 (d, J=8.0 Hz, 1H), 4.96 (s, 2H), 3.21 (s, 3H), 2.37 (s, 3H). LCMS: (Method A), R$_t$=3.2 min. [M+H]$^+$=521.2.

Example 71—N-(3-hydroxyphenyl)-5-(isoindolin-2-yl)-3-isopropyl-7-(1H-pyrazol-4-yl)pyrazolo[1,5-a]pyrimidine-2-carboxamide (71)

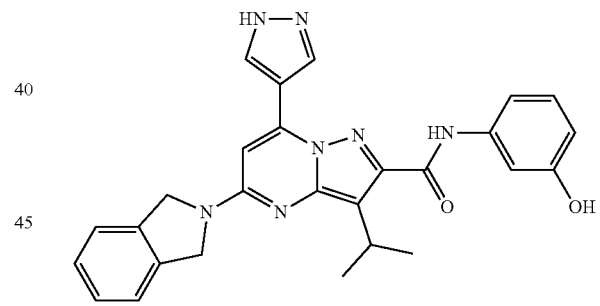

(71)

Compound 71 was made using the procedure outlined in scheme 5.

Scheme 5

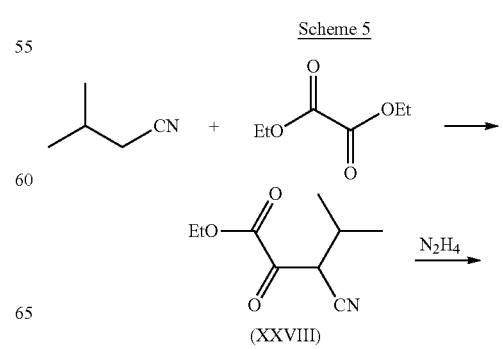

(XXVIII)

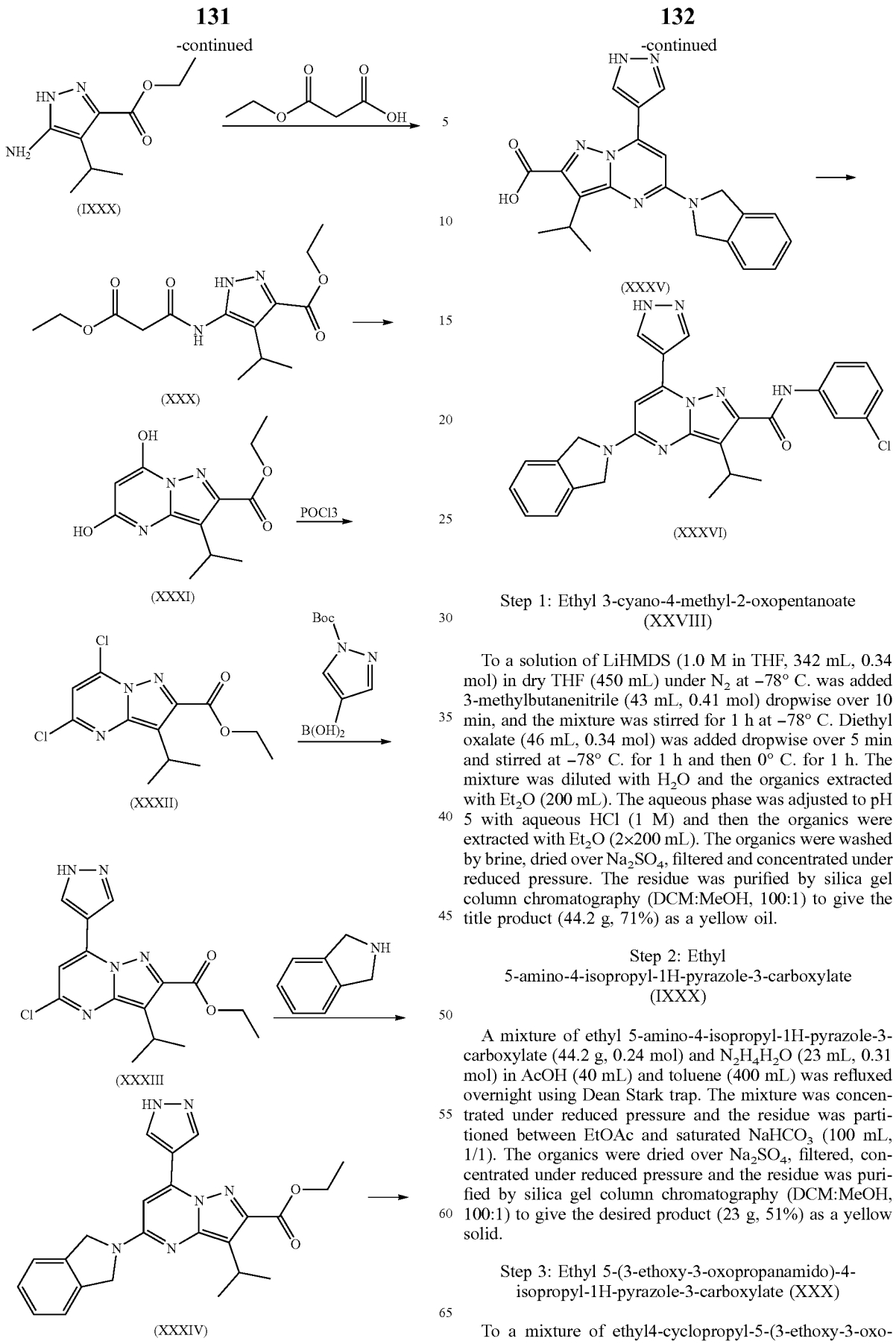

Step 1: Ethyl 3-cyano-4-methyl-2-oxopentanoate (XXVIII)

To a solution of LiHMDS (1.0 M in THF, 342 mL, 0.34 mol) in dry THF (450 mL) under $N_2$ at −78° C. was added 3-methylbutanenitrile (43 mL, 0.41 mol) dropwise over 10 min, and the mixture was stirred for 1 h at −78° C. Diethyl oxalate (46 mL, 0.34 mol) was added dropwise over 5 min and stirred at −78° C. for 1 h and then 0° C. for 1 h. The mixture was diluted with $H_2O$ and the organics extracted with $Et_2O$ (200 mL). The aqueous phase was adjusted to pH 5 with aqueous HCl (1 M) and then the organics were extracted with $Et_2O$ (2×200 mL). The organics were washed by brine, dried over $Na_2SO_4$, filtered and concentrated under reduced pressure. The residue was purified by silica gel column chromatography (DCM:MeOH, 100:1) to give the title product (44.2 g, 71%) as a yellow oil.

Step 2: Ethyl 5-amino-4-isopropyl-1H-pyrazole-3-carboxylate (IXXX)

A mixture of ethyl 5-amino-4-isopropyl-1H-pyrazole-3-carboxylate (44.2 g, 0.24 mol) and $N_2H_4H_2O$ (23 mL, 0.31 mol) in AcOH (40 mL) and toluene (400 mL) was refluxed overnight using Dean Stark trap. The mixture was concentrated under reduced pressure and the residue was partitioned between EtOAc and saturated $NaHCO_3$ (100 mL, 1/1). The organics were dried over $Na_2SO_4$, filtered, concentrated under reduced pressure and the residue was purified by silica gel column chromatography (DCM:MeOH, 100:1) to give the desired product (23 g, 51%) as a yellow solid.

Step 3: Ethyl 5-(3-ethoxy-3-oxopropanamido)-4-isopropyl-1H-pyrazole-3-carboxylate (XXX)

To a mixture of ethyl4-cyclopropyl-5-(3-ethoxy-3-oxopropanamido)-1H-pyrazole-3-carboxylate (20 g, 0.16 mol), DCC (30.7 g, 0.15 mol), pyridine (27.2 g, 0.34 mol) and DMAP (1.4 g, 0.01 mol) in anhydrous DCM (220 mL) was added 3-ethoxy-3-oxopropanoic acid (15.8 g, 0.12 mol) dropwise over 10 min at 0° C. The reaction mixture was stirred at RT overnight. The solids were removed by filtration and washed with DCM. The combined organics were concentrated under reduced pressure and the residue was purified by silica gel column chromatography (DCM: MeOH, 100:1) to give the desired product (35.6 g, 99.7%) as a yellow oil. LCMS: (Agilent 5 min), $R_1$=1.83 min, $[M+H]^+$=311.8.

Step 4: ethyl 5,7-dihydroxy-3-isopropylpyrazolo[1,5-a]pyrimidine-2-carboxylate (XXXI)

A mixture of ethyl 4-cyclopropyl-5-(3-ethoxy-3-oxopropanamido)-1H-pyrazole-3-carboxylate (1.5 g, 4.79 mmol) and DMAP (1.8 g, 14.4 mmol) in ethanol (15 mL) and $H_2O$ (15 mL) was stirred at 80° C. overnight. The mixture was concentrated under reduced pressure and the residue was partitioned between EtOAc (200 mL) and water (50 mL). The organics were washed with brine, dried and concentrated under reduced pressure to give the title product (1.0 g, 78%) as a white solid. LCMS: (Agilent 5 min), $R_t$=0.91 min, $[M+H]^+$=266.0

Step 5: ethyl 5, 7-dichloro-3-isopropylpyrazolo[1,5-a]pyrimidine-2-carboxylate (XXXII)

A solution of ethyl 5, 7-dihydroxy-3-isopropylpyrazolo[1,5-a] pyrimidine-2-carboxylate (1.0 g, 3.76 mol) in phosphorus oxychloride (15 mL) was stirred at 110° C. overnight. The mixture was concentrated under reduced pressure and the residue was poured into ice-water, extracted with DCM (3×20 mL), and the combined organics were washed with brine (100 mL), dried over $Na_2SO_4$, filtered, and concentrated under reduced pressure. The residue was purified by silica gel column chromatography (PE:EtOAc, 10:1) to give the desired product (700 mg, 62%) as a white solid. LCMS: (Agilent 5 min), $R_t$=4.54 min, $[M+H]^+$=302.0

Step 6: ethyl 5-chloro-3-isopropyl-7-(1H-pyrazol-4-yl)pyrazolo[1,5-a]pyrimidine-2-carboxylate (XXXIII)

A mixture of ethyl 5, 7-dichloro-3-isopropylpyrazolo[1,5-a]pyrimidine-2-carboxylate (1.0 g, 3.32 mmol), (1-(tert-butoxycarbonyl)-1H-pyrazol-4-yl)boronic acid (704 mg, 3.32 mmol), $Na_2CO_3$ (704 mg, 6.64 mmol) and $Pd(dppf)_2Cl_2$ (243 mg, 0.39 mmol) in degassed 1,4-dioxane (40 mL) and $H_2O$ (8 mL) was stirred under $N_2$ atmosphere at 80° C. overnight. The mixture was poured into water and extracted with DCM (20 mL×3). The organics were washed with water and brine, dried over $Na_2SO_4$, filtered and concentrated under reduced pressure. The reside was purified by silica gel column chromatography (DCM:MeOH, 100:1) to give the desired product (525 mg, 61%) as a yellow solid. LCMS (Method A), $R_t$=4.20 min; $[M+H]^+$=334.1.

Step 7: ethyl 5-(isoindolin-2-yl)-3-isopropyl-7-(1H-pyrazol-4-yl)pyrazolo[1,5-a]pyrimidine-2-carboxylate (XXXIV)

A mixture of ethyl 5-chloro-3-isopropyl-7-(1H-pyrazol-4-yl)pyrazolo[1,5-a]pyrimidine-2-carboxylate (800 mg, 2.40 mmol), isoindoline hydrochloride (747 mg, 4.80 mmol) and triethylamine (968 mg, 9.58 mmol) in DMF (10 mL) was stirred at 80° C. overnight. The mixture was diluted with $H_2O$ and filtered to give a crude product. The crude product was purified by silica gel column (DCM/MeOH=75/1) to give the desired product (862 mg, 86%) as a yellow solid. LCMS: (Method A), $R_t$=3.70 min. $[M+H]^+$=417.1.

Step 8: 5-(isoindolin-2-yl)-3-isopropyl-7-(1H-pyrazol-4-yl)pyrazolo[1,5-a]pyrimidine-2-carboxylic acid (XXXV)

A mixture of ethyl 5-chloro-3-isopropyl-7-(1H-pyrazol-4-yl)pyrazolo[1,5-a]pyrimidine-2-carboxylate (862 mg, 2.1 mmol) and KOH (2N, 10 mL, 20.0 mmol) in THF (20 mL) and MeOH (20 mL) was stirred at 80° C. for 3 h. The mixture was concentrated in vacuo and then poured into $H_2O$, the aqueous phase was adjusted to pH 3~4 with HCl, filtered and dried to give the desired product (750 mg, 93%) as a yellow solid. LCMS: (Method A), $R_t$=3.20 min, $[M+H]^+$=389.1

Step 9: N-(3-hydroxyphenyl)-5-(isoindolin-2-yl)-3-isopropyl-7-(1H-pyrazol-4-yl)pyrazolo[1,5-a]pyrimidine-2-carboxamide (XXXVI)

A mixture of ethyl 5-chloro-3-isopropyl-7-(1H-pyrazol-4-yl)pyrazolo[1,5-a]pyrimidine-2-carboxylate (200 mg, 0.52 mmol), 3-aminophenol (62 mg, 0.57 mmol), HATU (294 mg, 0.77 mmol) and DIEA (134 mg, 1.04 mmol) in DMF (5 mL) was stirred at RT overnight. The mixture was diluted with $H_2O$ and the residue was filtered, and then purified by silica gel column chromatography (DCM: MeOH, 100:0 to 98:2) to give the title product (142 mg, 58%) as a yellow solid. $^1$HNMR (400 MHz, DMSO-$d_6$) δ 13.48 (s, 1H), 10.05 (s, 1H), 9.40 (s, 1H), 9.27 (s, 1H), 8.71 (s, 1H), 7.47-7.35 (m, 5H), 7.22 (d, J=8.4 Hz, 1H), 7.14 (t, J=8 Hz, 1H), 7.04 (s, 1H), 6.53 (d, J=1.6 Hz, 1H), 4.97 (s, 4H), 3.83-3.76 (m, 1H), 1.46 (d, J=7.2 Hz, 6H). LCMS: (Method A), $R_t$=4.61 min, $[M+H]^+$=480.2.

The following compounds were similarly prepared using appropriate starting materials in step 7 and step 9 of scheme 5 according to the method described for the synthesis of compound 71.

Example 72—5-(isoindolin-2-yl)-3-isopropyl-N-(3-methoxyphenyl)-7-(1H-pyrazol-4-yl)pyrazolo[1,5-a]pyrimidine-2-carboxamide (72)

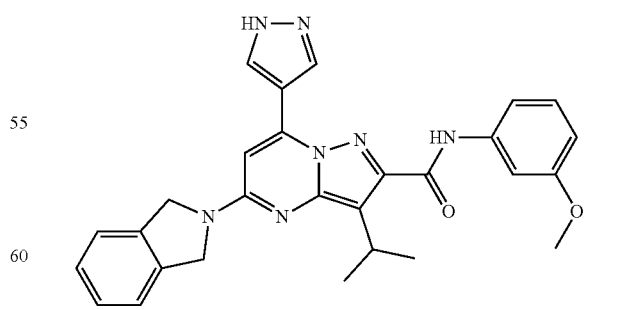

(72)

Starting material used in step 7—isoindoline, starting material used in step 9—3-methoxyaniline, $^1$HNMR (400 MHz, DMSO-$d_6$) δ 13.50 (s, 1H), 10.45 (s, 1H), 9.48-9.11 (m, 1H), 8.94-8.53 (m, 1H), 8.02 (s, 1H), 7.87 (d, J=8.0 Hz, 1H), 7.56-7.42 (m, 3H), 7.36 (dd, J=5.6 Hz, 3.2 Hz, 2H), 7.16-7.04 (m, 2H), 4.98 (s, 4H), 3.88-3.74 (m, 1H), 1.47 (d, J=7.2 Hz, 6H). LCMS: (Method A), $R_t$=4.16 min, [M+H]$^+$=548.1

Example 73—5-(isoindolin-2-yl)-3-isopropyl-7-(1H-pyrazol-4-yl)-N-(3-(trifluoromethoxy)phenyl)pyrazolo[1,5-a]pyrimidine-2-carboxamide (73)

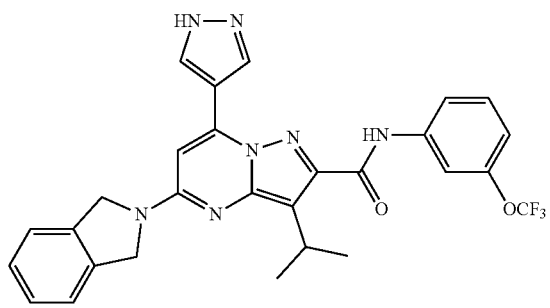

(73)

Starting material used in step 7—isoindoline, starting material used in step 9—3-(trifluoromethoxy)aniline, $^1$HNMR (400 MHz, DMSO-d$_6$) δ 13.50 (s, 1H), 10.45 (s, 1H), 9.48-9.11 (m, 1H), 8.94-8.53 (m, 1H), 8.02 (s, 1H), 7.87 (d, J=8.0 Hz, 1H), 7.56-7.42 (m, 3H), 7.36 (dd, J=5.6 Hz, 3.2 Hz, 2H), 7.16-7.04 (m, 2H), 4.98 (s, 4H), 3.88-3.74 (m, 1H), 1.47 (d, J=7.2 Hz, 6H). LCMS: (Method A), $R_t$=4.16 min, [M+H]$^+$=548.1

Example 74—5-(benzyl(methyl)amino)-N-(3-hydroxyphenyl)-3-isopropyl-7-(1H-pyrazol-4-yl)pyrazolo[1,5-a]pyrimidine-2-carboxamide (74)

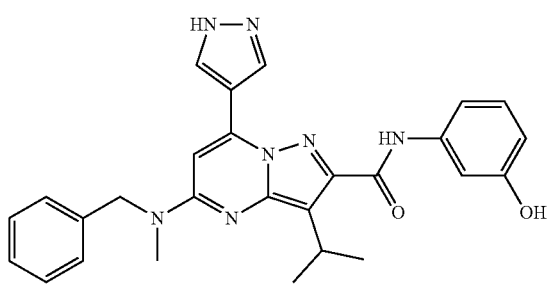

(74)

Starting material used in step 7—N-methyl-1-phenylmethanamine, starting material used in step 9—3-aminophenol, $^1$HNMR (400 MHz, DMSO-d$_6$) δ 13.45 (s, 1H), 10.0 (s, 1H), 9.40 (s, 1H), 9.22 (s, 1H), 8.65 (s, 1H), 7.42-7.10 (m, 9H), 6.53 (dd, J=8.0 Hz, 1.3 Hz, 1H), 4.93 (s, 2H), 3.81-3.65 (m, 1H), 3.20 (s, 3H), 1.37 (d, J=7.2 Hz, 6H). LCMS (Method A): $R_t$=4.45 min, [M+H]$^+$=482.2.

Example 75—5-(benzyl(methyl)amino)-3-isopropyl-N-(3-methoxyphenyl)-7-(1H-pyrazol-4-yl)pyrazolo[1,5-a]pyrimidine-2-carboxamide (75)

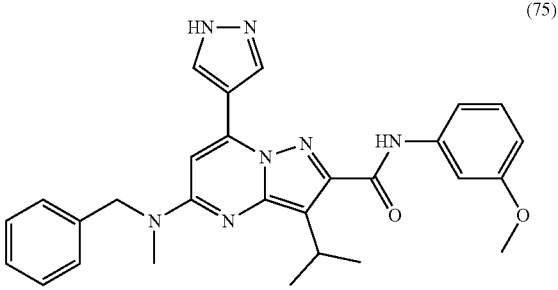 [SMILES: COc1cccc(NC(=O)c2nn3c(-c4cn[nH]c4)cc(N(C)Cc4ccccc4)nc3c2C(C)C)c1]

(75)

Starting material used in step 7—N-methyl-1-phenylmethanamine, starting material used in step 9—3-methoxyaniline, $^1$HNMR (400 MHz, DMSO-d$_6$) δ 13.45 (s, 1H), 10.10 (s, 1H), 9.23 (s, 1H), 8.66 (s, 1H), 7.54 (s, 1H), 7.43-7.39 (m, 1H), 7.34 (d, J=4.4 Hz, 4H), 7.27 (t, J=8.0 Hz, 2H), 7.13 (s, 1H), 6.70 (dd, J=8.0 Hz, 2.0 Hz, 1H), 4.93 (s, 2H), 3.78 (s, 4H), 3.21 (s, 3H), 1.37 (d, J=7.2 Hz, 6H). LCMS (Method A): $R_t$=3.26 min, [M+H]$^+$=496.2

Example 76—5-(benzyl(methyl)amino)-3-isopropyl-7-(1H-pyrazol-4-yl)-N-(3-(trifluoromethoxy)phenyl)pyrazolo[1,5-a]pyrimidine-2-carboxamide (76)

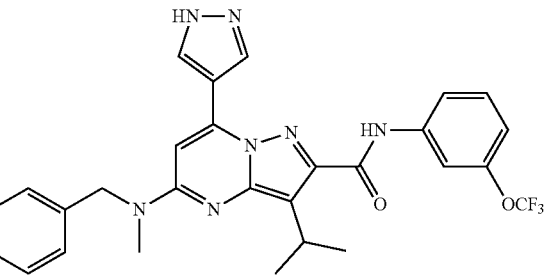

(76)

Starting material used in step 7—N-methyl-1-phenylmethanamine, starting material used in step 9 -3-(trifluoromethoxy)aniline, $^1$HNMR (400 MHz, DMSO-d$_6$) δ 13.48 (s, 1H), 10.36 (s, 1H), 9.24 (s, 1H), 8.68 (s, 1H), 8.0 (s, 1H), 7.85 (d, J=8.0 Hz, 1H), 7.50 (t, J=7.6 Hz, 1H), 7.34 (s, 4H), 7.27 (d, J=4.0 Hz, 1H), 7.12 (t, J=8.0 Hz, 2H), 4.93 (s, 2H), 3.78 (s, 1H), 3.21 (s, 3H), 1.37 (d, J=6.4 Hz, 6H). LCMS (Method A): $R_t$=3.96 min. [M+H]$^+$=550.1

Example 77—5-(5-fluoroisoindolin-2-yl)-3-isopropyl-N-(3-methoxyphenyl)-7-(1H-pyrazol-4-yl)pyrazolo[1,5-a]pyrimidine-2-carboxamide (77)

(77)

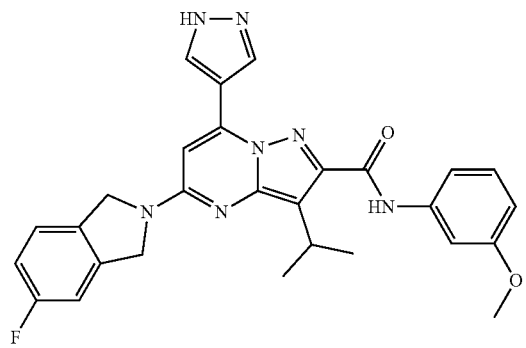

Starting material used in step 7—5-fluoroisoindoline, starting material used in step 9-3-methoxyaniline, $^1$HNMR (400 MHz, DMSO-d$_6$) δ 13.50 (s, 1H), 10.15 (s, 1H), 9.28 (s, 1H), 8.71 (s, 1H), 7.58-7.48 (m, 2H), 7.44-7.31 (m, 2H), 7.28 (t, J=8.8 Hz, 1H), 7.19 (t, J=8.0 Hz, 1H), 7.04 (s, 1H), 6.71 (d, J=6.4 Hz, 1H), 4.95 (d, J=12.0 Hz, 4H), 3.79 (s, 4H), 1.46 (d, J=7.2 Hz, 6H). LCMS (Method A): R$_t$=3.53 min, [M+H]$^+$=512.2.

Example 78—N-(3-acetamidophenyl)-5-(5-fluoroisoindolin-2-yl)-3-isopropyl-7-(1H-pyrazol-4-yl)pyrazolo[1,5-a]pyrimidine-2-carboxamide (78)

(78)

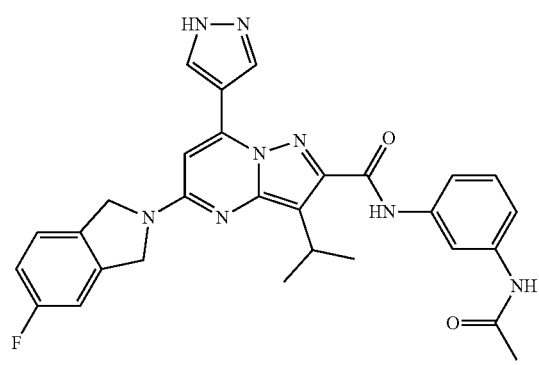

Starting material used in step 7—5-fluoroisoindoline, starting material used in step 9—N-(3-aminophenyl) acetamide, $^1$HNMR (400 MHz, DMSO-d$_6$) δ 10.17 (s, 1H), 9.99 (s, 1H), 9.02 (s, 2H), 8.13 (s, 1H), 7.67-6.98 (m, 7H), 4.93 (s, 4H), 3.80 (s, 1H), 3.21 (s, 3H), 1.46 (s, 6H). LCMS (Method A): R$_t$=4.42 min, [M+H]$^+$=539.2.

Example 79—N-(3-(4-acetylpiperazin-1-yl)phenyl)-5-(5-fluoroisoindolin-2-yl)-3-isopropyl-7-(1H-pyrazol-4-yl)pyrazolo[1,5-a]pyrimidine-2-carboxamide (79)

(79)

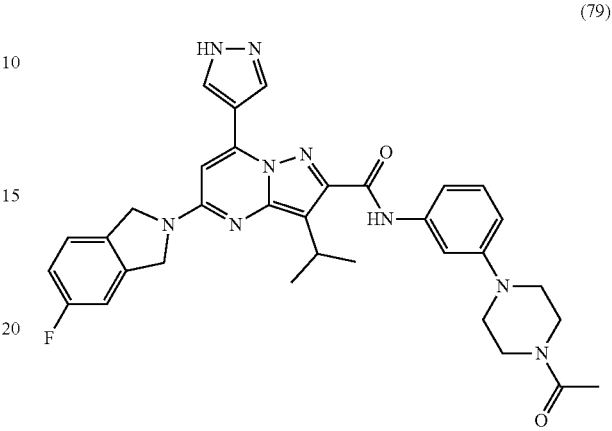

Starting material used in step 7—5-fluoroisoindoline, Starting material used in step 9 1-(4-(3-aminophenyl)piperazin-1-yl)ethan-1-one; $^1$HNMR (400 MHz, DMSO-d$_6$) δ 13.50 (s, 1H), 10.03 (s, 1H), 9.28 (s, 1H), 8.71 (s, 1H), 7.58-7.16 (m, 6H), 7.02 (s, 1H), 6.75 (d, J=1.6 Hz, 1H), 4.93 (s, 4H), 3.85-3.78 (m, 1H), 3.61 (s, 4H), 3.18-3.11 (m, 4H), 2.06 (s, 3H), 1.46 (d, J=7.2 Hz, 6H). LCMS (Method A): R$_t$=4.54 min, [M+H]$^+$=608.3

Example 80—N-(4-(4-acetylpiperazin-1-yl)phenyl)-5-(5-fluoroisoindolin-2-yl)-3-isopropyl-7-(1H-pyrazol-4-yl)pyrazolo[1,5-a]pyrimidine-2-carboxamide (80)

(80)

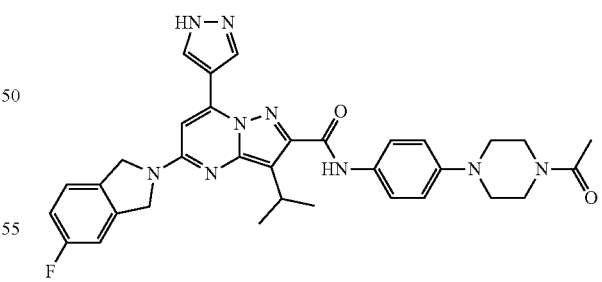

Starting material used in step 7—5-fluoroisoindoline, starting material used in step 9-1-(4-(4-aminophenyl)piperazin-1-yl)ethan-1-one, $^1$HNMR (400 MHz, DMSO-d$_6$) δ 13.49 (s, 1H), 10.0 (s, 1H), 9.28 (s, 1H), 8.70 (s, 1H), 7.68 (d, J=6.8 Hz, 1H), 7.49 (s, 1H), 7.35 (s, 1H), 7.19 (t, J=6.8 Hz, 1H), 6.99 (t, J=6.4 Hz, 3H), 4.94 (t, J=11.2 Hz, 4H), 3.83-3.79 (m, 1H), 3.61 (s, 4H), 3.14 (s, 2H), 3.08 (s, 2H), 2.05 (s, 3H), 1.46 (d, J=7.2 Hz, 6H). LCMS (Method A): R$_t$=4.44 min, [M+H]$^+$=608.3

Example 81—5-(5-chloroisoindolin-2-yl)-3-isopropyl-N-(3-methoxyphenyl)-7-(1H-pyrazol-4-yl)pyrazolo[1,5-a]pyrimidine-2-carboxamide (81)

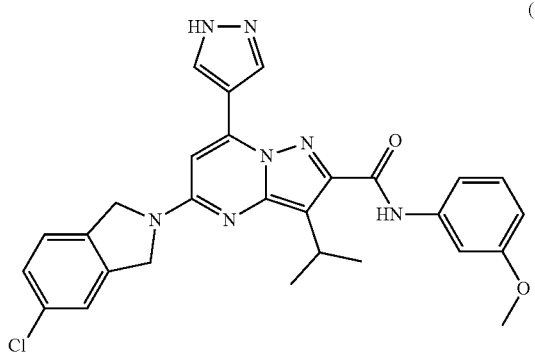

Starting material used in step 7—5-chloroisoindoline, starting material used in step 9—3-methoxyaniline, ¹HNMR (400 MHz, DMSO-d₆) δ 13.49 (s, 1H), 10.0 (s, 1H), 9.28 (s, 1H), 8.70 (s, 1H), 7.54 (s, 3H), 7.42 (s, 2H), 7.27 (t, J=8.0 Hz, 1H), 7.03 (s, 1H), 6.71 (d, J=6.4 Hz, 1H), 4.94 (s, 4H), 3.78 (s, 4H), 1.46 (d, J=7.2 Hz, 6H), LCMS (Method A): R$_t$=3.86 min, [M+H]$^+$=528.2.

Example 82—N-(3-acetamidophenyl)-5-(5-chloroisoindolin-2-yl)-3-isopropyl-7-(1H-pyrazol-4-yl)pyrazolo[1,5-a]pyrimidine-2-carboxamide (82)

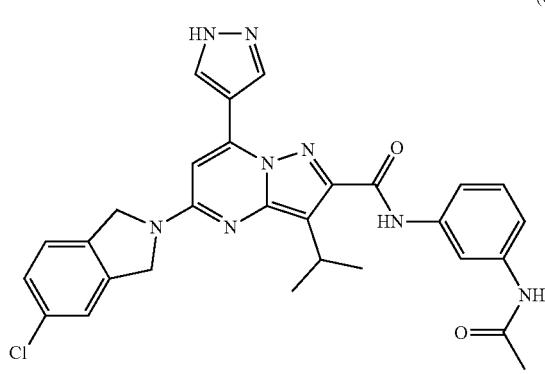

Starting material used in step 7—5-chloroisoindoline, starting material used in step 9—N-(3-aminophenyl) acetamide, ¹HNMR (400 MHz, DMSO-d₆) δ 13.47 (s, 1H), 10.17 (s, 1H), 9.99 (s, 1H), 8.73 (s, 1H), 8.13 (s, 1H), 7.66-7.36 (m, 5H), 7.27 (t, J=4.8 Hz, 1H), 7.03 (s, 1H), 4.94 (s, 4H), 3.80 (t, J=7.2 Hz, 1H), 2.06 (s, 3H), 1.46 (d, J=7.2 Hz, 6H). LCMS (Method A): R$_t$=4.72 min, [M+H]$^+$=555.2

Example 83—N-(3-(4-acetylpiperazin-1-yl)phenyl)-5-(5-chloroisoindolin-2-yl)-3-isopropyl-7-(1H-pyrazol-4-yl)pyrazolo[1,5-a]pyrimidine-2-carboxamide (83)

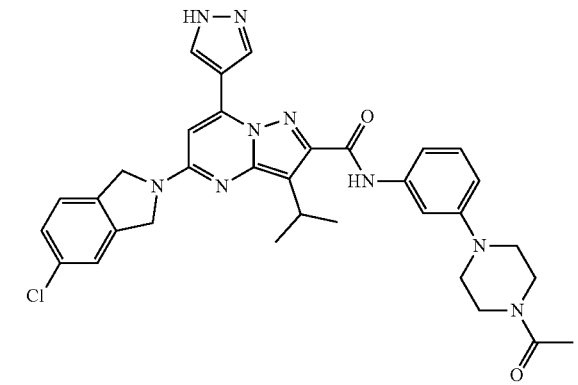

Starting material used in step 7—5-chloroisoindoline, starting material used in step 9—1-(4-(3-aminophenyl)piperazin-1-yl)ethan-1-one, ¹HNMR (400 MHz, DMSO-d₆) δ 13.47 (s, 1H), 10.03 (s, 1H), 9.27 (s, 1H), 8.70 (s, 1H), 7.55-7.16 (m, 6H), 7.02 (s, 1H), 6.75 (d, J=6.4 Hz, 1H), 4.95 (s, 4H), 3.83-3.78 (m, 1H), 3.61 (s, 4H), 3.18 (d, J=2.4 Hz, 4H), 2.06 (d, J=7.6 Hz, 3H), 1.46 (d, J=6.8 Hz, 6H). LCMS (Method A): R$_t$=4.81 min, [M+H]$^+$=623.2.

Example 84—N-(4-(4-acetylpiperazin-1-yl)phenyl)-5-(5-chloroisoindolin-2-yl)-3-isopropyl-7-(1H-pyrazol-4-yl)pyrazolo[1,5-a]pyrimidine-2-carboxamide (84)

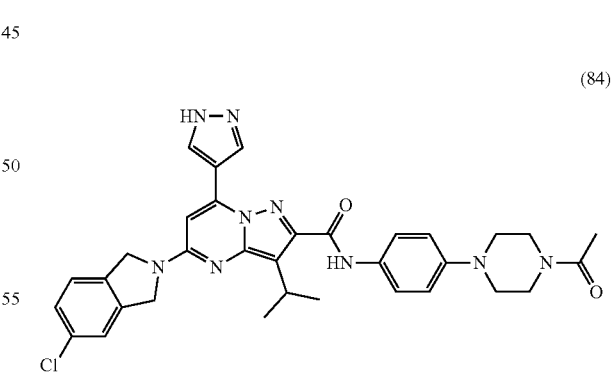

Starting material used in step 7—5-chloroisoindoline, starting material used in step 9—1-(4-(4-aminophenyl)piperazin-1-yl)ethan-1-one, ¹HNMR (400 MHz, DMSO-d₆) δ 13.47 (s, 1H), 10.03 (s, 1H), 9.27 (s, 1H), 8.70 (s, 1H), 7.70-7.40 (m, 5H), 7.0 (t, J=7.2 Hz, 3H), 4.95 (s, 4H), 3.82 (t, J=6.8 Hz, 1H), 3.59 (d, J=4.0 Hz, 4H) 3.14 (s, 2H), 3.07 (s, 2H), 2.06 (d, J=7.6 Hz, 3H), 1.46 (d, J=6.8 Hz, 6H). LCMS (Method A): R$_t$=4.62 min, [M+H]$^+$=624.2.

Example 85—5-(5-fluoroisoindolin-2-yl)-N-(3-hydroxyphenyl)-3-isopropyl-7-(1H-pyrazol-4-yl)pyrazolo[1,5-a]pyrimidine-2-carboxamide (99)

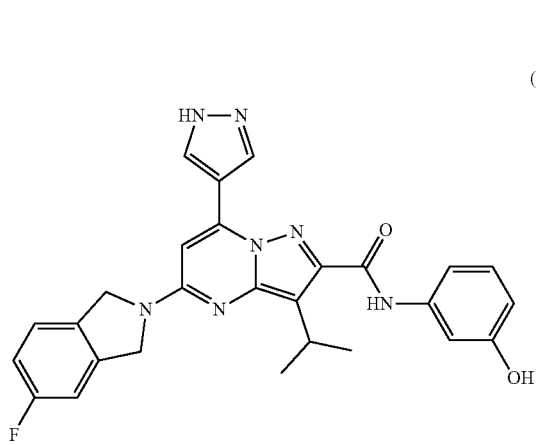

(99)

Starting material used in step 7—5-fluoroisoindoline, starting material used in step 9-3-aminophenol, ¹HNMR (400 MHz, DMSO-d$_6$) δ 13.49 (s, 1H), 10.05 (s, 1H), 9.41 (s, 1H), 9.27 (s, 1H), 8.70 (s, 1H), 7.42 (s, 1H), 7.23-7.12 (m, 4H), 7.03 (s, 1H), 6.54 (d, J=9.2 Hz, 1H), 4.95 (d, J=11.6 Hz, 4H), 3.83-3.76 (m, 1H), 3.21-3.17 (m, 1H), 1.46 (d, J=7.0 Hz, 6H). LCMS: (Method A), R$_t$=4.66 min, [M+H]$^+$=498.2

Example 86—5-(5-chloroisoindolin-2-yl)-N-(3-hydroxyphenyl)-3-isopropyl-7-(1H-pyrazol-4-yl)pyrazolo[1,5-a]pyrimidine-2-carboxamide (100)

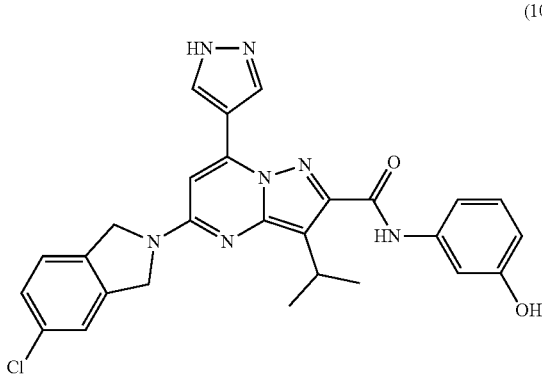

(100)

Starting material used in step 7—5-chloroisoindoline, starting material used in step 9—3-aminophenol. ¹HNMR (400 M Hz, DMSO-d$_6$) δ 13.48 (s, 1H), 10.04 (s, 1H), 9.39 (s,1H), 9.26 (s,1H), 8.70 (s,1H), 7.57-7.40 (m, 4H), 7.22 (d, J=8.4 Hz, 1H), 7.14 (t, J=8.0 Hz, 1H), 7.02 (s, 1H), 6.54 (d, J=6.5 Hz, 1H), 4.96 (s, 4H), 3.83-3.76 (m, 1H), 1.46 (d, J=6.8 Hz, 6H). LCMS (Method A): R$_t$=4.69 min; [MH]+=514.2.

Example 87—5-(5-fluoroisoindolin-2-yl)-3-isopropyl-N-(3-morpholinophenyl)-7-(1H-pyrazol-4-yl)pyrazolo[1,5-a]pyrimidine-2-carboxamide (101)

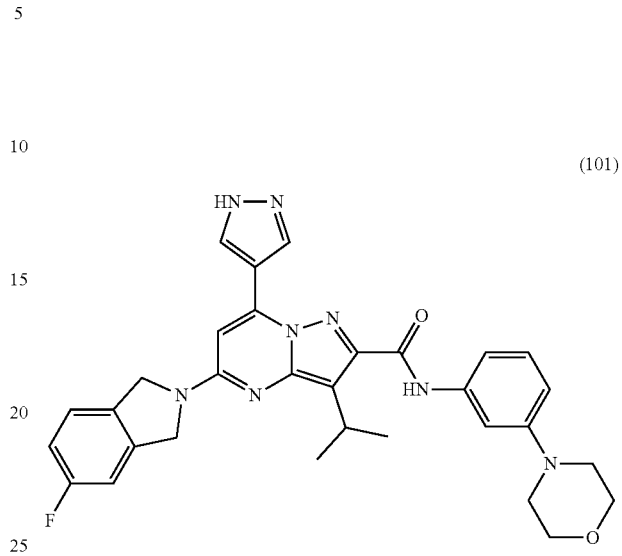

(101)

Starting material used in step 7—5-fluoroisoindoline, starting material used in step 9-3-morpholinoaniline, ¹HNMR (400 MHz, DMSO-d$_6$) δ 13.49 (s, 1H), 10.01 (s, 1H), 9.27 (s, 1H), 8.69 (s, 1H), 7.55-7.29 (m, 4H), 7.23-7.16 (m, 2H), 7.02 (s, 1H), 6.73 (d, J=1.6 Hz, 1H), 4.94 (d, J=11.6 Hz, 4H), 3.85-3.76 (m, 5H), 3.1-3.11 (m, 4H), 1.45 (d, J=7.0 Hz, 6H). LCMS: (Method A), R$_t$=3.42 min, [M+H]$^+$=567.2.

Example 88—5-(5-fluoroisoindolin-2-yl)-3-isopropyl-N-(4-(2-methoxyethoxy)phenyl)-7-(1H-pyrazol-4-yl)pyrazolo[1,5-a]pyrimidine-2-carboxamide (102)

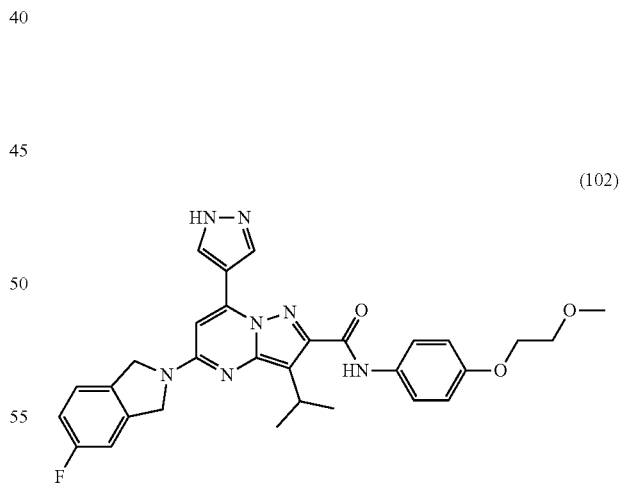

(102)

Starting material used in step 7—5-fluoroisoindoline, starting material used in step 9-4-(2-methoxyethoxy)aniline, ¹HNMR (400 MHz, DMSO-d$_6$) δ 13.48 (s, 1H), 10.06 (s, 1H), 9.29 (s, 1H), 8.70 (s, 1H), 7.71 (d, J=8.8 Hz, 2H), 7.49-7.16 (m, 3H), 7.02 (s, 1H), 6.96 (d, J=9.2 Hz, 2H), 4.94 (d, J=12.0 Hz, 4H), 4.10 (t, J=4.8 Hz, 2H), 3.85-3.78 (m, 1H), 3.67 (t, J=4.4 Hz, 2H), 3.33 (s, 3H), 1.45 (d, J=7.0 Hz, 6H). LCMS: (Method A), R$_t$=4.81 min, [M+H]$^+$=556.2.

Example 89—5-(5-fluoroisoindolin-2-yl)-3-isopropyl-N-(2-oxo-1,2,3,4-tetrahydroquinolin-7-yl)-7-(1H-pyrazol-4-yl)pyrazolo[1,5-a]pyrimidine-2-carboxamide (103)

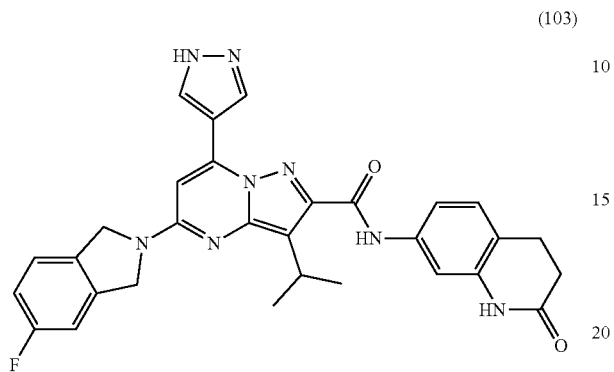

(103)

Starting material used in step 7—5-fluoroisoindoline, starting material used in step 9-7-amino-3,4-dihydroquinolin-2(1H)-one, $^1$HNMR (400 MHz, DMSO-$d_6$) δ 13.49 (s, 1H), 10.14 (d, J=14.8 Hz, 2H), 9.27 (s, 1H), 8.71 (s, 1H), 7.57-7.35 (m, 3H), 7.25-7.14 (m, 3H), 7.02 (s, 1H), 4.95 (d, J=11.6 Hz, 4H), 3.84-3.77 (m, 1H), 2.85 (t, J=7.2 Hz, 2H), 2.47-2.44 (m, 2H), 1.45 (d, J=6.8 Hz, 6H). LCMS: (Method A), $R_t$=4.71 min, [M+H]$^+$=551.2

Example 90—5-(5-fluoroisoindolin-2-yl)-N-(1H-indazol-6-yl)-3-isopropyl-7-(1H-pyrazol-4-yl)pyrazolo[1,5-a]pyrimidine-2-carboxamide (104)

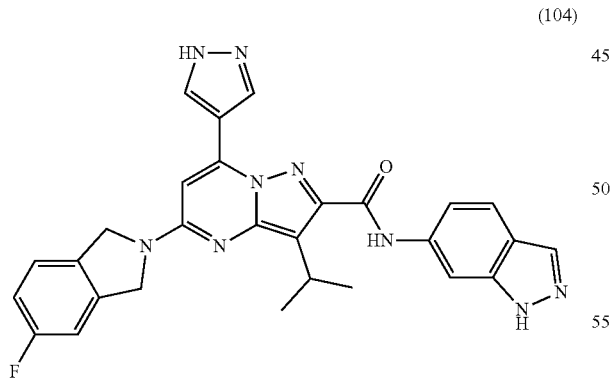

(104)

Starting material used in step 7—5-fluoroisoindoline, starting material used in step 9-1H-indazol-6-amine, $^1$HNMR (400 MHz, DMSO-$d_6$) δ 13.50 (s, 1H), 12.98 (s, 1H), 10.30 (s, 1H), 9.31 (s, 1H), 8.72 (s, 1H), 8.30 (s, 1H), 8.02 (s, 1H), 7.73 (d, J=8.8 Hz, 1H), 7.54-7.32 (m, 3H), 7.20 (t, J=8.8 Hz, 1H), 7.04 (s, 1H), 4.96 (d, J=11.6 Hz, 4H), 3.86-3.79 (s, 1H), 1.48 (d, J=7.0 Hz, 6H). LCMS: (Method A), $R_t$=4.66 min, [M+H]$^+$=522.2

Example 91—5-(5-fluoroisoindolin-2-yl)-3-isopropyl-N-(3 (methylsulfon amido) phenyl)-7-(1H-pyrazol-4-yl)pyrazolo[1,5-a]pyrimidine-2-carboxamide (105)

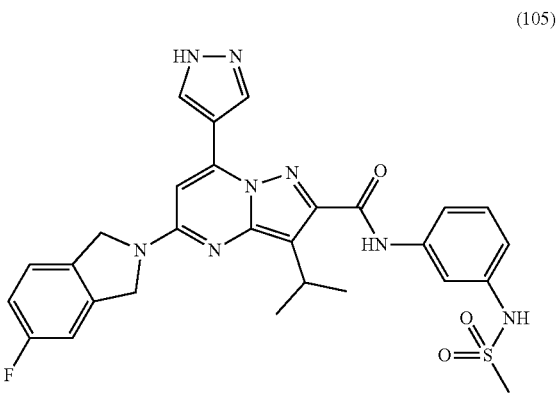 [SMILES: CC(C)c1c(C(=O)Nc2cccc(NS(C)(=O)=O)c2)nn2c(-c3cn[nH]c3)cc(N3Cc4ccc(F)cc4C3)nc12]

(105)

Starting material used in step 7—5-fluoroisoindoline, starting material used in step 9—N-(3-aminophenyl) methanesulfonamide, $^1$HNMR (400 MHz, DMSO-$d_6$) δ 13.50 (s, 1H), 10.25 (s, 1H), 9.76 (s, 1H), 9.27 (s, 1H), 8.71 (s, 1H), 7.84 (s, 1H), 7.52 (d, J=8.4 Hz, 2H), 7.32 (t, J=8.0 Hz, 2H), 7.19 (t, J=10.8 Hz, 1H), 7.04-6.96 (m, 2H), 4.95 (d, J=11.6 Hz, 4H), 3.83-3.75 (m, 1H), 3.03 (s, 3H), 1.46 (d, J=7.2 Hz, 6H). LCMS: (Method A), $R_t$=4.64 min, [M+H]$^+$=575.2

Example 92—5-(5-fluoroisoindolin-2-yl)-3-isopropyl-N-(4-morpholinophenyl)-7-(1H-pyrazol-4-yl)pyrazolo[1,5-a]pyrimidine-2-carboxamide (106)

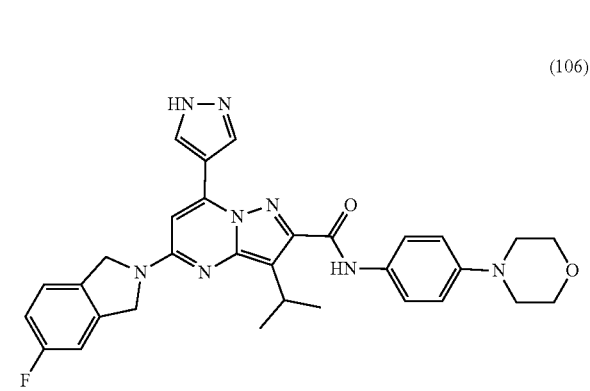 [SMILES: CC(C)c1c(C(=O)Nc2ccc(N3CCOCC3)cc2)nn2c(-c3cn[nH]c3)cc(N3Cc4ccc(F)cc4C3)nc12]

(106)

Starting material used in step 7—5-fluoroisoindoline, Starting material used in step 9—4-morpholinoaniline, $^1$HNMR (400 MHz, DMSO-$d_6$) δ 13.48 (s, 1H), 9.99 (s, 1H), 9.28 (s, 1H), 8.70 (s, 1H), 7.69-7.40 (m, 5H), 7.01 (s, 1H), 6.96 (d, J=8.4 Hz, 2H), 4.94 (s, 4H), 4.10 (q, J=5.2 Hz, 1H), 3.84-3.76 (m, 5H), 3.17 (d, J=5.6 Hz, 2H), 3.09 (s, 4H), 1.45 (d, J=7.2 Hz, 6H). LCMS: (Method A), $R_t$=3.11 min, [M+H$^+$=567.2.

Example 93—5-(5-chloroisoindolin-2-yl)-3-isopropyl-N-(4-morpholinophenyl)-7-(1H-pyrazol-4-yl)pyrazolo[1,5-a]pyrimidine-2-carboxamide (107)

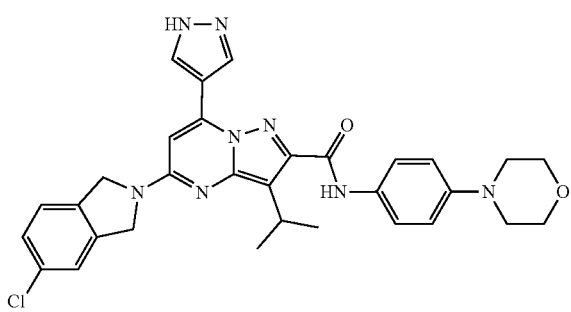
(107)

Starting material used in step 7—5-chloroisoindoline, Starting material used in step 9—4-morpholinoaniline, $^1$HNMR (400 MHz, DMSO-d$_6$) δ 13.48 (s, 1H), 9.99 (s, 1H), 9.28 (s, 1H), 8.70 (s, 1H), 7.69-7.40 (m, 5H), 7.01 (s, 1H), 6.96 (d, J=8.4 Hz, 2H), 4.94 (s, 4H), 4.10 (q, J=5.2 Hz, 1H), 3.84-3.76 (m, 5H), 3.17 (d, J=5.6 Hz, 2H), 3.09 (s, 4H), 1.45 (d, J=7.2 Hz, 6H). LCMS: (Method A), R$_t$=2.67 min, [M+H]$^+$=583.1

Example 94—5-(5-chloroisoindolin-2-yl)-3-isopropyl-N-(3-morpholinophenyl)-7-(1H-pyrazol-4-yl)pyrazolo[1,5-a]pyrimidine-2-carboxamide (108)

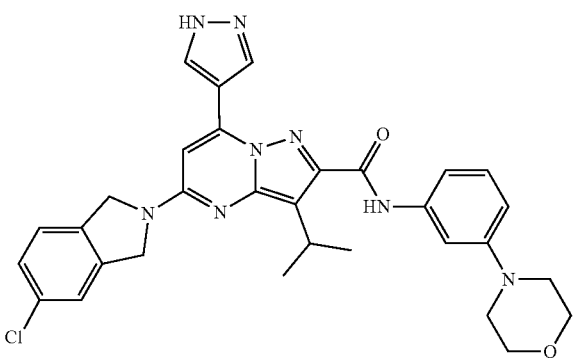
(108)

Starting material used in step 7—5-chloroisoindoline, Starting material used in step 9—3-morpholinoaniline, $^1$HNMR (400 MHz, DMSO-d$_6$) δ 13.49 (s, 1H), 10.02 (s, 1H), 9.27 (s, 1H), 8.70 (s, 1H), 7.53-7.03 (m, 8H), 6.74 (s, 1H), 4.95 (s, 4H), 3.77 (s, 4H), 3.12 (m, 4H), 1.45 (d, J=6.0 Hz, 6H). LCMS: (Method A), R$_t$=2.96 min. [M+H]$^+$=583.2.

Example 95—5-(5-chloroisoindolin-2-yl)-3-isopropyl-N-(4-(2-methoxyethoxy)phenyl)-7-(1H-pyrazol-4-yl)pyrazolo[1,5-a]pyrimidine-2-carboxamide (109)

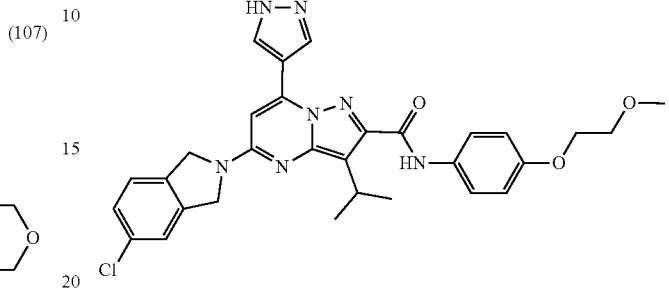
(109)

Starting material used in step 7—5-chloroisoindoline, Starting material used in step 9—4-(2-methoxyethoxy)aniline, $^1$HNMR (400 MHz, DMSO-d$_6$) δ 13.48 (s, 1H), 10.06 (s, 1H), 9.29 (s, 1H), 8.70 (s, 1H), 7.71 (d, J=8.8 Hz, 2H), 7.59-7.40 (m, 3H), 7.02-6.95 (m, 3H), 4.95 (s, 4H), 4.10 (s, 2H), 3.84-3.78 (m, 1H), 3.67 (s, 2H), 3.33 (s, 3H), 1.45 (d, J=6.8 Hz, 6H). LCMS: (Method A), R$_t$=3.59 min, [M+H]$^+$=572.2.

Example 96—5-(5-chloroisoindolin-2-yl)-3-isopropyl-7-(1H-pyrazol-4-yl)-N-(3-((tetrahydro-2H-pyran-4-yl)oxy)phenyl)pyrazolo[1,5-a]pyrimidine-2-carboxamide (117)

(117)

Starting material used in step 7—5-chloroisoindoline, Starting material used in step 9—3-((tetrahydro-2H-pyran-4-yl)oxy)aniline, $^1$HNMR (400 MHz, DMSO-d$_6$) δ 13.49 (s, 1H), 10.12 (s, 1H), 9.26 (s, 1H), 8.70 (s, 1H), 7.53-7.40 (m, 5H), 7.26 (t, J=8.0 Hz, 1H), 7.03 (s, 1H), 6.76 (d, J=8.2 Hz, 1H), 4.95 (s, 4H), 4.59-4.53 (m, 1H), 3.90-3.76 (m, 3H), 3.54-3.48 (m, 2H), 2.02-1.98 (m, 2H), 1.66-1.57 (m, 2H), 1.45 (d, J=7.0 Hz, 6H). LCMS: (Method A), R$_t$=2.70 min, [M+H]$^+$=598.4

Example 97—5-(5-chloroisoindolin-2-yl)-N-(2-fluoro-3-methoxyphenyl)-3-isopropyl-7-(1H-pyrazol-4-yl)pyrazolo[1,5-a]pyrimidine-2-carboxamide (118)

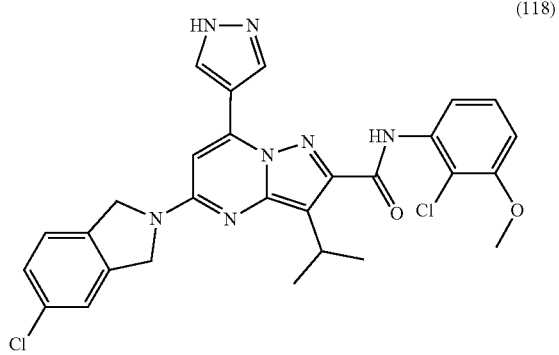 [SMILES: COc1cccc(NC(=O)c2nn3c(-c4cn[nH]c4)cc(N4Cc5ccc(Cl)cc5C4)nc3c2C(C)C)c1Cl]

Starting material used in step 7—5-chloroisoindoline, starting material used in step 9—2-fluoro-3-methoxyaniline, $^1$HNMR (400 MHz, DMSO-d$_6$) δ 13.53 (s, 1H), 9.87 (s, 1H), 9.21 (s, 1H), 8.70 (s, 1H), 7.57-7.39 (m, 4H), 7.19-7.14 (m, 1H), 7.06-7.02 (m, 2H), 4.94 (s, 4H), 3.92-3.85 (m, 4H), 1.45 (d, J=7.0 Hz, 6H). LCMS: (Method A), R$_t$=2.94 min, [M+H]$^+$=546.4

Example 98—5-(5-chloroisoindolin-2-yl)-3-isopropyl-7-(1H-pyrazol-4-yl)-N-(4-((tetrahydro-2H-pyran-4-yl)oxy)phenyl)pyrazolo[1,5-a]pyrimidine-2-carboxamide (119)

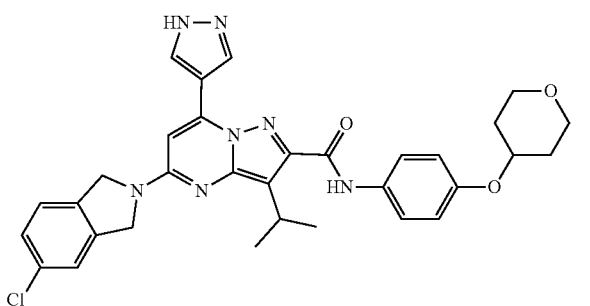

Starting material used in step 7—5-chloroisoindoline, starting material used in step 9—4-((tetrahydro-2H-pyran-4-yl)oxy)aniline, $^1$HNMR (400 MHz, DMSO-d$_6$) δ 13.48 (s, 1H), 10.06 (s, 1H), 9.28 (s, 1H), 8.70 (s, 1H), 7.73-7.40 (m, 5H), 7.02-6.98 (m, 3H), 4.95 (s, 4H), 4.55-4.58 (m, 1H), 3.89-3.78 (m, 3H), 3.52-3.46 (m, 2H), 1.97 (s, 2H), 1.63-1.55 (m, 2H), 1.45 (d, J=7.0 Hz, 6H). LCMS: (Method A), R$_t$=2.74 min, [M+H]$^+$=598.2

Example 99—5-(5-chloroisoindolin-2-yl)-N-(2-fluoro-5-methoxyphenyl)-3-isopropyl-7-(1H-pyrazol-4-yl)pyrazolo[1,5-a]pyrimidine-2-carboxamide (120)

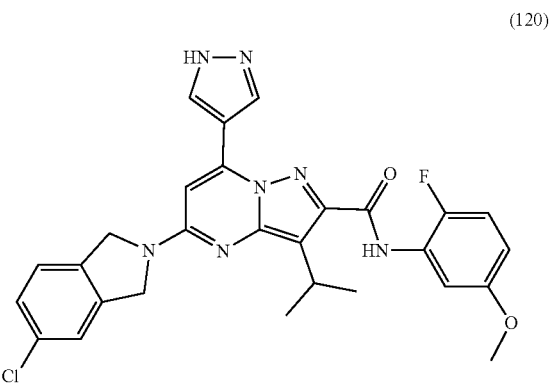 [SMILES: COc1ccc(F)c(NC(=O)c2nn3c(-c4cn[nH]c4)cc(N4Cc5ccc(Cl)cc5C4)nc3c2C(C)C)c1]

Starting material used in step 7—5-chloroisoindoline, starting material used in step 9-2-fluoro-5-methoxyaniline, $^1$HNMR (400 MHz, DMSO-d$_6$) δ 13.52 (s, 1H), 9.83 (s, 1H), 9.18 (s, 1H), 8.69 (s, 1H), 7.59-7.39 (m, 4H), 7.28-7.23 (m, 1H), 7.05 (s, 1H), 6.81-6.77 (m, 1H), 4.95 (s, 4H), 3.94-3.87 (m, 1H), 3.78 (s, 3H), 1.45 (d, J=7.0 Hz, 6H). LCMS: (Method A), R$_t$=4.14 min, [M+H]$^+$=545.2

Example 100—5-(5-fluoroisoindolin-2-yl)-3-isopropyl-7-(1H-pyrazol-4-yl)-N-(3-((tetrahydro-2H-pyran-4-yl)oxy)phenyl)pyrazolo[1,5-a]pyrimidine-2-carboxamide (121)

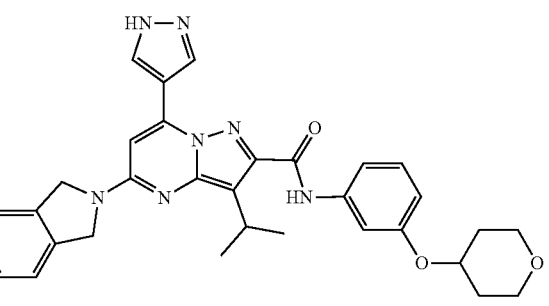

Starting material used in step 7—5-fluoroisoindoline, starting material used in step 9-3-((tetrahydro-2H-pyran-4-yl)oxy)aniline, $^1$HNMR (400 MHz, DMSO-d$_6$) δ 10.12 (s, 1H), 9.00 (s, 2H), 7.53-7.16 (m, 6H), 7.03 (s, 1H), 6.76 (dd, J=8.2 Hz, 2.0 Hz, 1H), 4.95 (d, J=11.6 Hz, 4H), 4.59-4.52 (m, 1H), 3.90-3.76 (m, 3H), 3.54-3.48 (m, 2H), 2.06-1.93 (m, 2H), 1.68-1.55 (m, 2H), 1.45 (d, J=7.0 Hz, 6H). LCMS: (Method A), R$_t$=2.43 min. [M+H]$^+$=582.2.

Example 101—N-(2-fluoro-3-methoxyphenyl)-5-(5-fluoroisoindolin-2-yl)-3-isopropyl-7-(1H-pyrazol-4-yl)pyrazolo[1,5-a]pyrimidine-2-carboxamide (122)

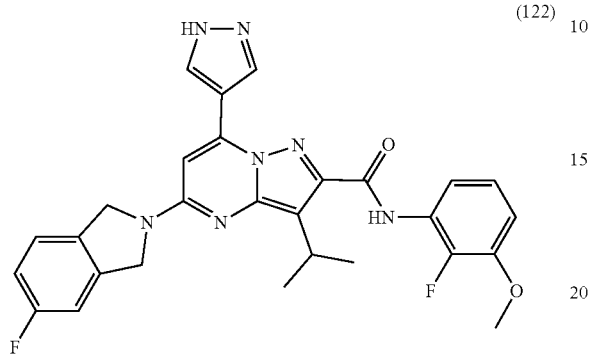

Starting material used in step 7—5-fluoroisoindoline, starting material used in step 9-2-fluoro-3-methoxyaniline, ¹HNMR (400 MHz, DMSO-d₆) δ 13.52 (s, 1H), 9.88 (s, 1H), 9.23 (s, 1H), 8.71 (s, 1H), 7.12-7.05 (m, 7H), 4.95 (s, 3H), 3.89 (s, 4H), 2.69 (s, 1H), 1.45 (d, J=7.0 Hz, 6H). LCMS: (Method A), $R_t$=2.88 min, [M+H]⁺=530.1

Example 102—5-(5-fluoroisoindolin-2-yl)-3-isopropyl-7-(1H-pyrazol-4-yl)-N-(4-((tetrahydro-2H-pyran-4-yl)oxy)phenyl)pyrazolo[1,5-a]pyrimidine-2-carboxamide (123)

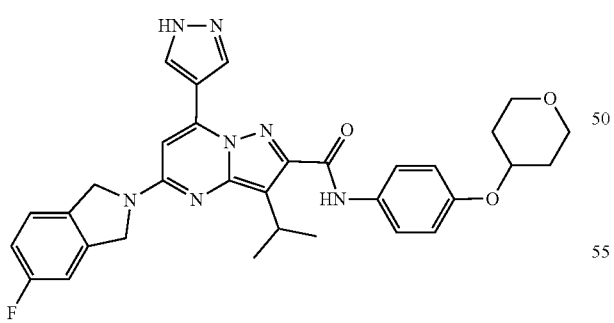

Starting material used in step 7—5-fluoroisoindoline, starting material used in step 9-4-((tetrahydro-2H-pyran-4-yl)oxy)aniline, ¹HNMR (400 MHz, DMSO-d₆) δ 13.49 (s, 1H), 10.06 (s, 1H), 9.28 (s, 1H), 8.71 (s, 1H), 7.71 (d, J=8.2 Hz, 2H), 7.43 (m, 3H), 7.01 (t, J=13.2 Hz, 3H), 4.95 (d, J=10.8 Hz, 4H), 4.55 (s, 1H), 3.94-3.76 (m, 3H), 3.53-3.46 (m, 2H), 1.98 (d, J=8.8 Hz, 2H), 1.58 (s, 2H), 1.45 (d, J=6.6 Hz, 6H). LCMS: (Method A), $R_t$=2.23 min. [M+H]⁺=582.2

Example 103—N-(2-fluoro-5-methoxyphenyl)-5-(5-fluoroisoindolin-2-yl)-3-isopropyl-7-(1H-pyrazol-4-yl)pyrazolo[1,5-a]pyrimidine-2-carboxamide (124)

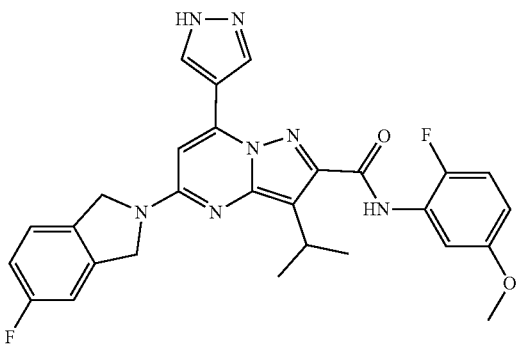

Starting material used in step 7—5-fluoroisoindoline, starting material used in step 9-2-fluoro-5-methoxyaniline, ¹HNMR (400 MHz, DMSO-d₆) δ 13.56 (s, 1H), 9.84 (s, 1H), 7.68-6.98 (m, 7H), 6.78 (s, 1H), 4.95 (s, 4H), 3.78 (s, 5H), 1.46 (s, 6H). LCMS: (Method A), $R_t$=2.83 min, [M+H]⁺=530.2

Example 104—5-(4-fluoroisoindolin-2-yl)-3-isopropyl-N-(3-methoxyphenyl)-7-(1H-pyrazol-4-yl)pyrazolo[1,5-a]pyrimidine-2-carboxamide (125)

Starting material used in step 7—4-fluoroisoindoline, starting material used in step 9-3-methoxyaniline, ¹HNMR (400 MHz, DMSO-d₆) δ 13.49 (s, 1H), 10.15 (s, 1H), 9.28 (s, 1H), 8.74 (s, 1H), 7.55 (s, 1H), 7.44-7.26 (m, 4H), 7.19 (t, J=9.2 Hz, 1H), 7.09 (s, 1H), 6.71 (dd, J=6.4 Hz, 2.0 Hz, 1H), 5.01 (s, 4H), 3.86-3.79 (m, 1H), 3.78 (s, 3H), 1.46 (d, J=7.2 Hz, 6H). LCMS: (Method A), $R_t$=2.46 min. [M+H]⁺=512.2.

Example 105—5-(4-chloroisoindolin-2-yl)-3-isopropyl-N-(3-methoxyphenyl)-7-(1H-pyrazol-4-yl)pyrazolo[1,5-a]pyrimidine-2-carboxamide (126)

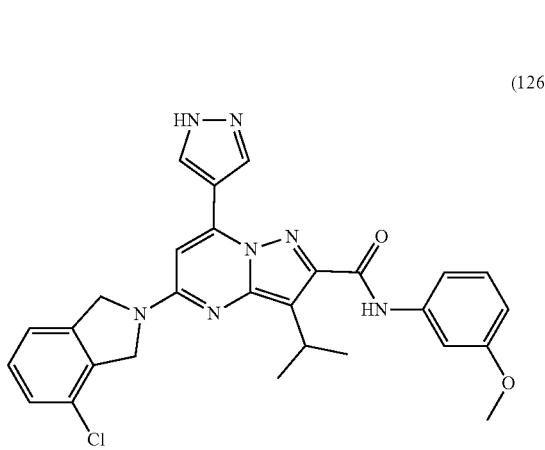

(126)

Starting material used in step 7—4-chloroisoindoline, starting material used in step 9—3-methoxyaniline, $^1$HNMR (400 MHz, DMSO-$d_6$) δ 13.49 (s, 1H), 10.15 (s, 1H), 9.28 (s, 1H), 8.74 (s, 1H), 7.55-7.38 (m, 5H), 7.27 (s, 1H), 7.09 (s, 1H), 6.71 (dd, J=8.2 Hz, 2.0 Hz, 1H), 5.04 (d, J=0.8 Hz, 4H), 3.78 (s, 4H), 1.46 (d, J=7.0 Hz, 6H). LCMS: (Method A), $R_t$=2.94 min, [M+H]+=528.0.

Example 106—5-(5-fluoroisoindolin-2-yl)-3-isopropyl-N-(2-methoxypyridin-4-yl)-7-(1H-pyrazol-4-yl)pyrazolo[1,5-a]pyrimidine-2-carboxamide (127)

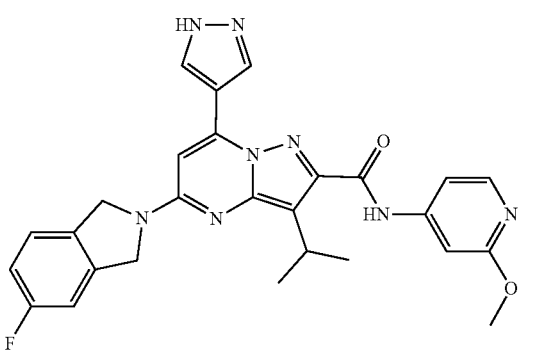

(127)

Starting material used in step 7—4-fluoroisoindoline, starting material used in step 9-2-methoxypyridin-4-amine, $^1$HNMR (400 MHz, DMSO-$d_6$) δ 13.51 (s, 1H), 10.46 (s, 1H), 9.26 (s, 1H), 8.69 (s, 1H), 8.10 (d, J=6.0 Hz, 1H), 7.52-7.36 (m, 4H), 7.19 (d, J=7.6 Hz, 1H), 7.05 (s, 1H), 4.95 (d, J=11.6 Hz, 4H), 3.86 (s, 3H), 3.82-3.74 (m, 1H), 1.46 (d, J=7.0 Hz, 6H). LCMS: (Method A), $R_t$=3.28 min, [M+H]+=513.2.

Example 107—3-cyclopropyl-5-(isoindolin-2-yl)-N-(3-methoxyphenyl)-7-(1H-pyrazol-4-yl)pyrazolo[1,5-a]pyrimidine-2-carboxamide (93)

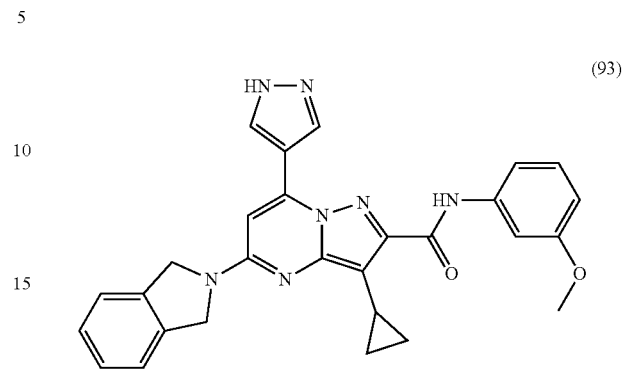

(93)

Compound 93 was made using the procedure outlined in scheme 6.

Scheme 6

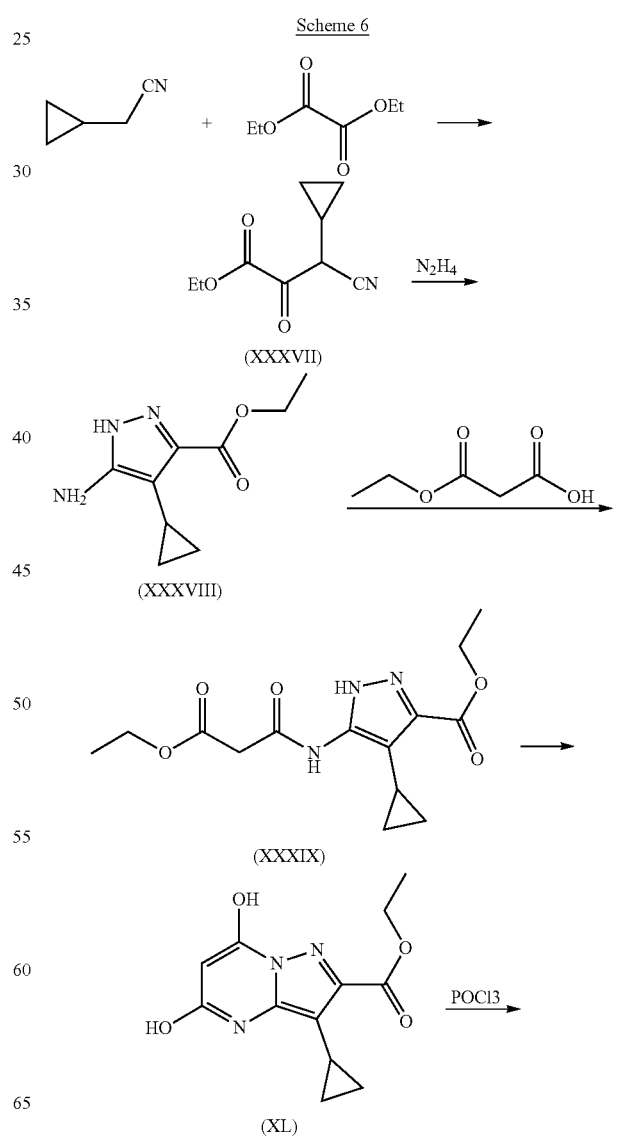

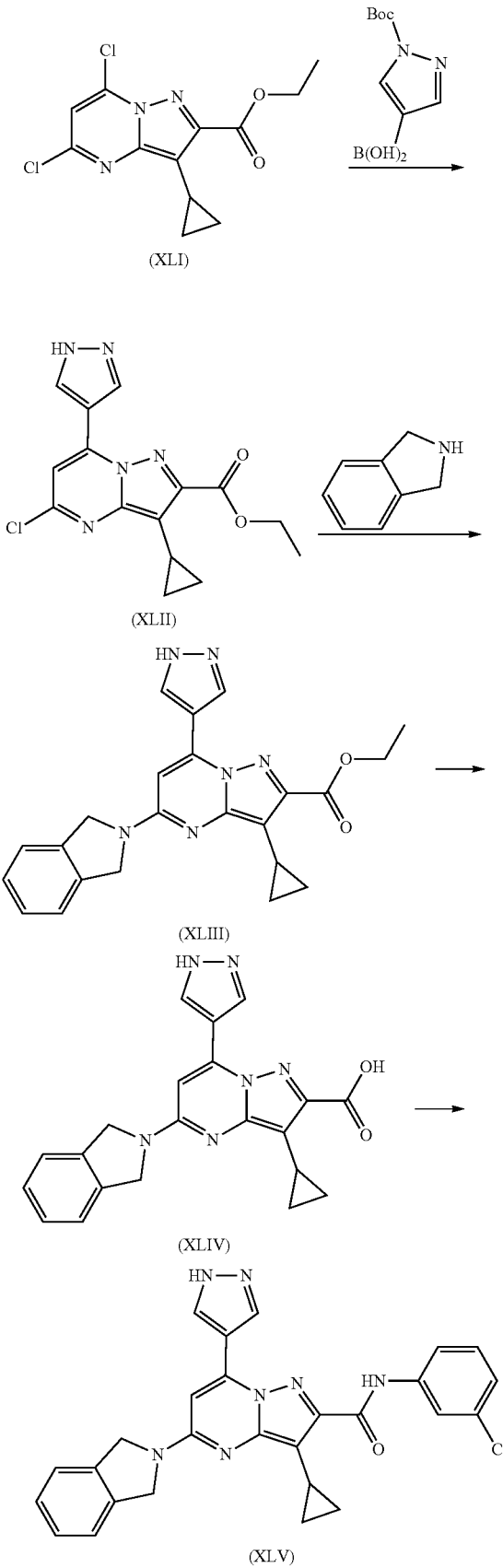

Step 1: ethyl 3-cyano-3-cyclopropyl-2-oxopropanoate (XXXVII)

To a solution of LiHMDS (1.0 M in THF, 240 mL, 0.24 mol) in dry THF (450 mL) under $N_2$ at −78° C. was added 2-cyclopropylacetonitrile (29 mL, 0.28 mol) dropwise over 10 min, and the mixture was stirred for 1 h at −78° C. Diethyl oxalate (33 mL, 0.24 mol) was added dropwise over 5 min and stirred at −78° C. for 1 h and then 0° C. for 1 h. The mixture was diluted with $H_2O$ and the organics extracted with $Et_2O$ (200 mL). The aqueous phase was adjusted to pH 5 with aqueous HCl (1 M) and then the organics were extracted with $Et_2O$ (2×200 mL). The organics were washed by brine, dried over $Na_2SO_4$, filtered and concentrated under reduced pressure. The residue was purified by silica gel column chromatography (DCM:MeOH, 100:1) to give the title product (28 g, 65%) as a yellow oil. LCMS: (Method A), $R_t$=3.02 min, $[M+H]^+$=182.1.

Step 2: ethyl 5-amino-4-cyclopropyl-1H-pyrazole-3-carboxylate (XXXVIII)

A mixture of ethyl 3-cyano-3-cyclopropyl-2-oxopropanoate (28.0 g, 0.15 mol) and $N_2H_4H_2O$ (15.5 g, 0.31 mol) in a mixture AcOH (40 mL) and toluene (400 mL) was refluxed overnight using a Dean Stark trap. The reaction mixture was concentrated under reduced pressure, and the residue was partitioned between EtOAc and an aqueous saturated solution of $NaHCO_3$. The organic layer was dried over $Na_2SO_4$, filtered, concentrated under reduced pressure and purified by silica gel column chromatography (DCM:MeOH, 100:1) to give the desired product (18 g, 60%) as a yellow solid. LCMS: (Method A), $R_t$=3.80 min, $[M+H]^+$=196.1

Step 3: ethyl 4-cyclopropyl-5-(3-ethoxy-3-oxopropanamido)-1H-pyrazole-3-carboxylate(XXXIX)

A mixture of ethyl 5-amino-4-cyclopropyl-1H-pyrazole-3-carboxylate (18 g, 0.09 mol), DCC (24.6 g, 0.11 mol), pyridine (21.8 g, 0.28 mol) and DMAP (1.1 g, 0.01 mol) in anhydrous DCM (300 mL) was added 3-ethoxy-3-oxopropanoic acid (12.8 g, 0.10 mol) dropwise at 0° C. The reaction mixture was stirred at RT overnight. The solids were removed by filtration and washed with DCM. The combined organics were concentrated under reduced pressure and the residue was purified by silica gel column chromatography (DCM:MeOH, 70:1) to give the desired product (20 g, 71%) as a yellow solid. LCMS: (Agilent 5 min), $R_1$=4.17 min, $[M+H]^+$=543.2.

Step 4: ethyl 3-cyclopropyl-5,7-dihydroxypyrazolo[1,5-a]pyrimidine-2-carboxylate (XL)

A mixture of ethyl 4-cyclopropyl-5-(3-ethoxy-3-oxopropanamido)-1H-pyrazole-3-carboxylate (20 g, 64.70 mmol) and DMAP (23.7 g, 0.194 mmol) in ethanol (200 mL) and $H_2O$ (200 mL) was stirred at 80° C. overnight. The mixture was concentrated under reduced pressure and the residue was partitioned between EtOAc (200 mL) and water (200 mL). The organics were washed with brine, dried and concentrated under reduced pressure to give the title product (17 g, 100%) as a yellow solid. LCMS: (Agilent 5 min), $R_t$=2.60 min, $[M+H]^+$=264.1.

Step 5: ethyl 5,7-dichloro-3-cyclopropylpyrazolo[1,5-a]pyrimidine-2-carboxylate (XLI)

A solution of ethyl 3-cyclopropyl-5,7-dihydroxypyrazolo[1,5-a]pyrimidine-2-carboxylate (17.0 g, 0.06 mol) in phosphorus oxychloride (400 mL) was stirred at 110° C. overnight. The mixture was concentrated under reduced pressure and the residue was poured into ice-water, extracted with DCM (3×300 mL), and the combined organics were washed with brine (100 mL), dried over $Na_2SO_4$, filtered, and concentrated under reduced pressure. The residue was purified by silica gel column chromatography (PE:EtOAc, 10:1) to give the desired product (11 g, 57%) as a yellow solid. LCMS: (Agilent 5 min), $R_t$=4.27 min, [M+H]$^+$=300.0.

Step 6: ethyl 5-chloro-3-cyclopropyl-7-(1H-pyrazol-4-yl)pyrazolo[1,5-a]pyrimidine-2-carboxylate (XLII)

A mixture of ethyl 5,7-dichloro-3-cyclopropylpyrazolo[1,5-a]pyrimidine-2-carboxylate (2 g, 6.7 mmol), tert-butyl 4-(4,4,5,5-tetramethyl-1,3,2-dioxaborolan-2-yl)-1H-pyrazole-1-carboxylate (2 g, 6.7 mmol), $Na_2CO_3$ (1.4 g, 13.4 mmol) and Pd(dppf)$_2$Cl$_2$ (490 mg, 0.67 mmol) in degassed 1,4-dioxane (100 mL) and $H_2O$ (20 mL) was stirred under $N_2$ atmosphere at 80° C. overnight. The mixture was poured into water and extracted with DCM (100 mL×3). The organics were washed with water and brine, dried over $Na_2SO_4$, filtered and concentrated under reduced pressure. The reside was purified by silica gel column chromatography (DCM:MeOH, 100:1) to give the desired product (1.4 g, 61%) as a yellow solid. LCMS (Method A): $R_t$=4.05 min; [M+H]+=332.2.

Step 7: ethyl-3-cyclopropyl-5-(isoindolin-2-yl)-7-(1H-pyrazol-4-yl)pyrazolo[1,5-a]pyrimidine-2-carboxylate (XLIII)

A mixture of ethyl 5-chloro-3-cyclopropyl-7-(1H-pyrazol-4-yl)pyrazolo[1,5-a]pyrimidine-2-carboxylate (2 g, 6.04 mmol), isoindoline hydrochloride (1.9 g, 12.08 mmol) and triethylamine (2.4 g, 24.16 mmol) in DMF (30 mL) was stirred at 80° C. overnight. The mixture was diluted with $H_2O$ and filtered to give a crude product. The crude product was purified by silica gel column (DCM/MeOH=50/1) to give the desired product (2.4 g, 96%) as a yellow solid. LCMS: (Method A), $R_t$=4.66 min. [M+H]$^+$=465.2.

Step 8: 3-cyclopropyl-5-(isoindolin-2-yl)-7-(1H-pyrazol-4-yl)pyrazolo[1,5-a]pyrimidine-2-carboxylic acid (XLIV)

A mixture of ethyl 3-cyclopropyl-5-(isoindolin-2-yl)-7-(1H-pyrazol-4-yl)pyrazolo[1,5-a]pyrimidine-2-carboxylate (2.4 g, 5.8 mmol) and aqueous KOH (2M, 29 mL, 58.0 mmol) in THF (30 mL) and MeOH (30 mL) was stirred at 80° C. for 3 h. The mixture was concentrated in vacuo and then poured into $H_2O$. The aqueous phase was adjusted to pH 3~4 with HCl 2M and the precipitate formed was filtered and dried under reduced pressure to give the desired product (750 mg, 93%) as a yellow solid. LCMS: (Method A), $R_t$=3.39 min, [M+H]$^+$=387.1.

Step 9: 3-cyclopropyl-5-(isoindolin-2-yl)-N-(3-methoxyphenyl)-7-(1H-pyrazol-4-yl)pyrazolo[1,5-a]pyrimidine-2-carboxamide (XLV)

A mixture of 3-cyclopropyl-5-(isoindolin-2-yl)-7-(1H-pyrazol-4-yl)pyrazolo[1,5-a]pyrimidine-2-carboxylic acid (200 mg, 0.52 mmol), 3-methoxyaniline (70 mg, 0.57 mmol), HATU (296 mg, 0.78 mmol) and DIEA (134 mg, 1.04 mmol) in DMF (8 mL) was stirred at RT overnight. The mixture was diluted with $H_2O$ and the residue was filtered, and then purified by silica gel column chromatography (DCM:MeOH, 100:0 to 98:2) to give the title product (85 mg, 33%) as a yellow solid. $^1$HNMR (400 MHz, DMSO-d$_6$) δ 13.50 (s, 1H), 10.12 (s, 1H), 9.29 (s, 1H), 8.70 (s, 1H), 7.56-7.42 (m, 4H), 7.38-7.34 (m, 2H), 7.28 (t, J=16 Hz, 1H), 7.02 (s, 1H), 6.72 (d, J=6 Hz,1.6 Hz, 1H), 4.93 (s, 4H), 3.78 (s, 3H), 2.61-2.55 (m, 1H), 1.49-1.45 (m, 2H), 0.85-0.81 (m, 2H). LCMS: (Method A), $R_t$=3.19 min, [M+H]$^+$=492.2.

The following compounds were similarly prepared using appropriate starting materials in step 7 and step 9 of scheme 6 according to the method described for the synthesis of compound 93.

Example 108—3-cyclopropyl-N-(3-hydroxyphenyl)-5-(isoindolin-2-yl)-7-(1H-pyrazol-4-yl)pyrazolo[1,5-a]pyrimidine-2-carboxamide (94)

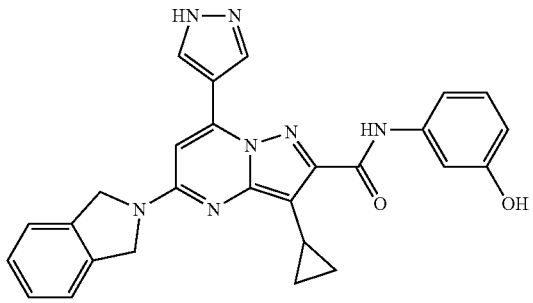

(94)

Starting material used in step 7—isoindoline, starting material used in step 9—3-aminophenol, $^1$HNMR (400 MHz, DMSO-d6) δ 13.49 (s, 1H), 10.02 (s, 1H), 9.41 (s, 1H), 9.28 (s, 1H), 8.70 (s, 1H), 7.46-7.35 (m, 5H), 7.23-7.12 (m, 2H), 7.02 (s, 1H), 6.53 (d, J=6.4 Hz, 1.6 Hz, 1H), 4.93 (s, 4H), 2.60-2.50 (m,1H), 1.47-1.45 (m, 2H), 0.84-0.82 (m, 2H). LCMS: (Method A), $R_t$=4.29 min, [M+H]$^+$=478.2

Example 109—N-(3-(4-acetylpiperazin-1-yl)phenyl)-3-cyclopropyl-5-(isoindolin-2-yl)-7-(1H-pyrazol-4-yl)pyrazolo[1,5-a]pyrimidine-2-carboxamide (95)

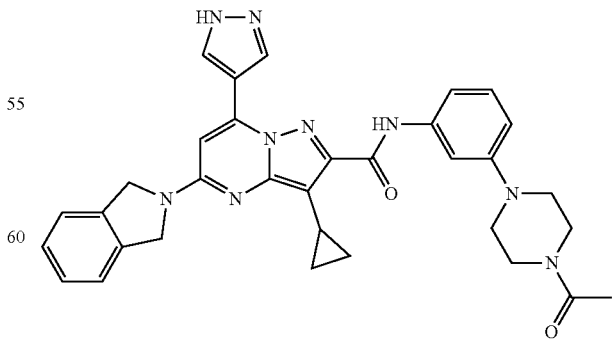

(95)

Starting material used in step 7—isoindoline, starting material used in step 9—1-(4-(3-aminophenyl)piperazin-1- yl)ethan-1-one; $^1$HNMR (400 MHz, DMSO-d$_6$) δ 13.50 (s, 1H), 10.01 (s, 1H), 9.28 (s, 1H), 8.70 (s, 1H), 7.55-7.31 (m, 6H), 7.23 (t, J=8 Hz, 1H), 7.03 (s, 1H), 6.75 (d, J=8 Hz, 1H) 4.94 (s, 4H), 3.61 (s, 4H), 3.20-3.11 (m, 4H), 2.63-2.56 (m, 1H), 2.06 (s, 3H), 1.49-1.46 (m, 2H), 0.85-0.81 (m, 2H). LCMS: (Method A), R$_t$=4.42 min, [M+H]$^+$=588.3.

Example 110—3-cyclopropyl-5-(isoindolin-2-yl)-N-(4-methoxyphenyl)-7-(1H-pyrazol-4-yl)pyrazolo[1,5-a]pyrimidine-2-carboxamide (96)

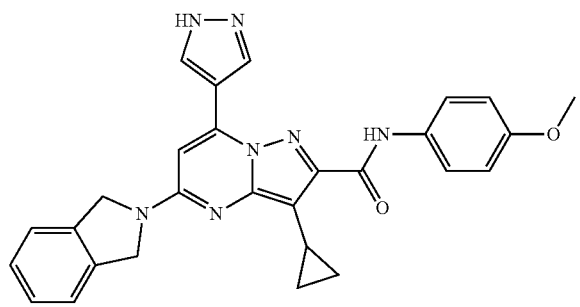

(96)

Starting material used in step 7—isoindoline, starting material used in step 9—4-methoxyaniline, $^1$HNMR (400 MHz, DMSO-d$_6$) δ 13.48 (s, 1H), 10.04 (s, 1H), 9.30 (s, 1H), 8.71 (s, 1H), 7.73 (d, J=8 Hz, 2H), 7.47 (s, 2H), 7.37-7.34 (m, 4H), 7.01 (s, 1H), 6.96 (d, J=8.8 Hz, 2H), 4.93 (s, 4H), 3.77 (s, 3H), 2.69-2.58 (m, 1H), 1.47 (d, J=3.2 Hz, 2H), 0.87-0.77 (m, 2H). LCMS: (Method A), R$_t$=4.56 min, [M+H]$^+$=492.2.

Example 111—N-(3-acetamidophenyl)-3-cyclopropyl-5-(isoindolin-2-yl)-7-(1H-pyrazol-4-yl)pyrazolo[1,5-a]pyrimidine-2-carboxamide (97)

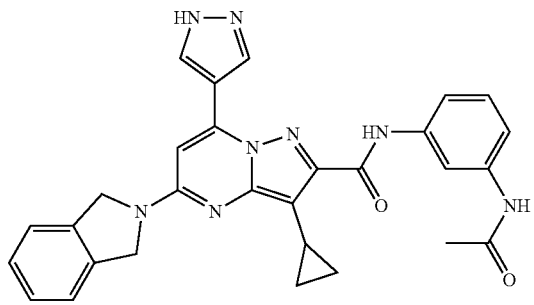

(97)

Starting material used in step 7—isoindoline, starting material used in step 9—N-(3-aminophenyl)acetamide, $^1$HNMR (400 MHz, DMSO-d$_6$) δ 13.49 (s, 1H), 10.15 (s, 1H), 9.99 (s, 1H), 9.30 (s, 1H), 8.71 (s, 1H), 8.13 (s, 1H), 7.47-7.35 (m, 6H), 7.27 (t, J=8.0 Hz, 1H), 7.02 (s, 1H), 4.94 (s, 4H), 2.61-2.54 (m, 1H), 2.06 (s, 3H), 1.46 (d, J=3.2 Hz, 2H), 0.84-0.81 (m, 2H). LCMS: (Method A), R$_t$=4.25 min, [M+H]$^+$=519.2.

Example 112—N-(3-chlorophenyl)-3-cyclopropyl-5-(isoindolin-2-yl)-7-(1H-pyrazol-4-yl)pyrazolo[1,5-a]pyrimidine-2-carboxamide (98)

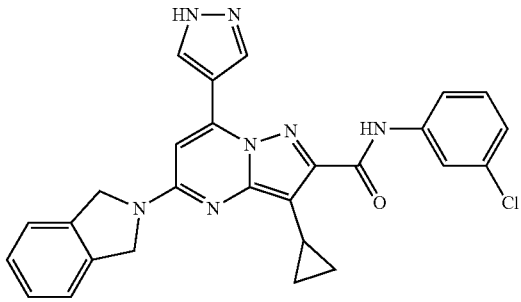

(98)

Starting material used in step 7—isoindoline, starting material used in step 9—3-chloroaniline, $^1$HNMR (400 MHz, DMSO-d$_6$) δ 13.50 (s, 1H), 10.30 (s, 1H), 9.30 (s, 1H), 8.71 (s, 1H), 8.03 (s, 1H), 7.83 (d, J=9.2 Hz, 1H), 7.47-7.33 (m, 5H), 7.19 (d, J=8.0 Hz, 1H), 7.03 (s, 1H), 4.93 (s, 4H), 2.61-2.54 (m, 1H), 1.49-1.45 (s, 2H), 0.86-0.81 (m, 2H). LCMS: (Method A), R$_t$=3.71 min. [M+H]$^+$=496.1

Example 113—3-(tert-butyl)-N-(3-hydroxyphenyl)-5-(isoindolin-2-yl)-7-(1H-pyrazol-4-yl)pyrazolo[1,5-a]pyrimidine-2-carboxamide (85)

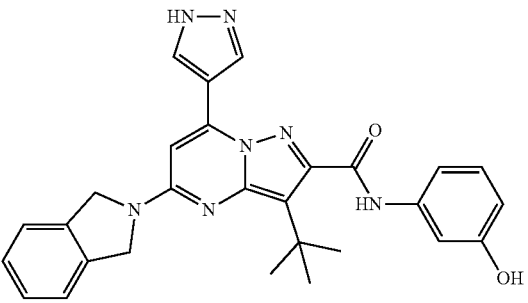

(85)

A Compound 85 was made using the procedure outlined in scheme 7.

Scheme 7

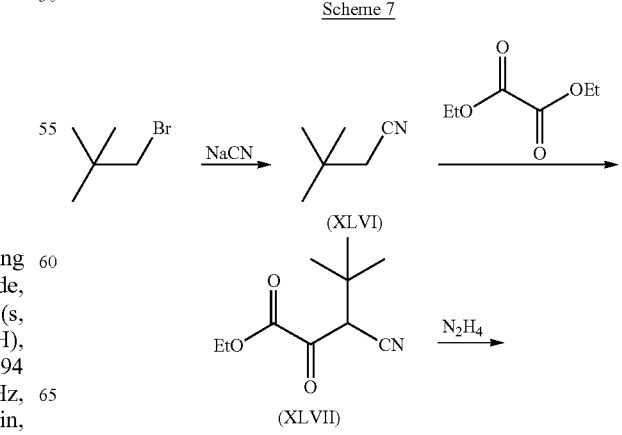

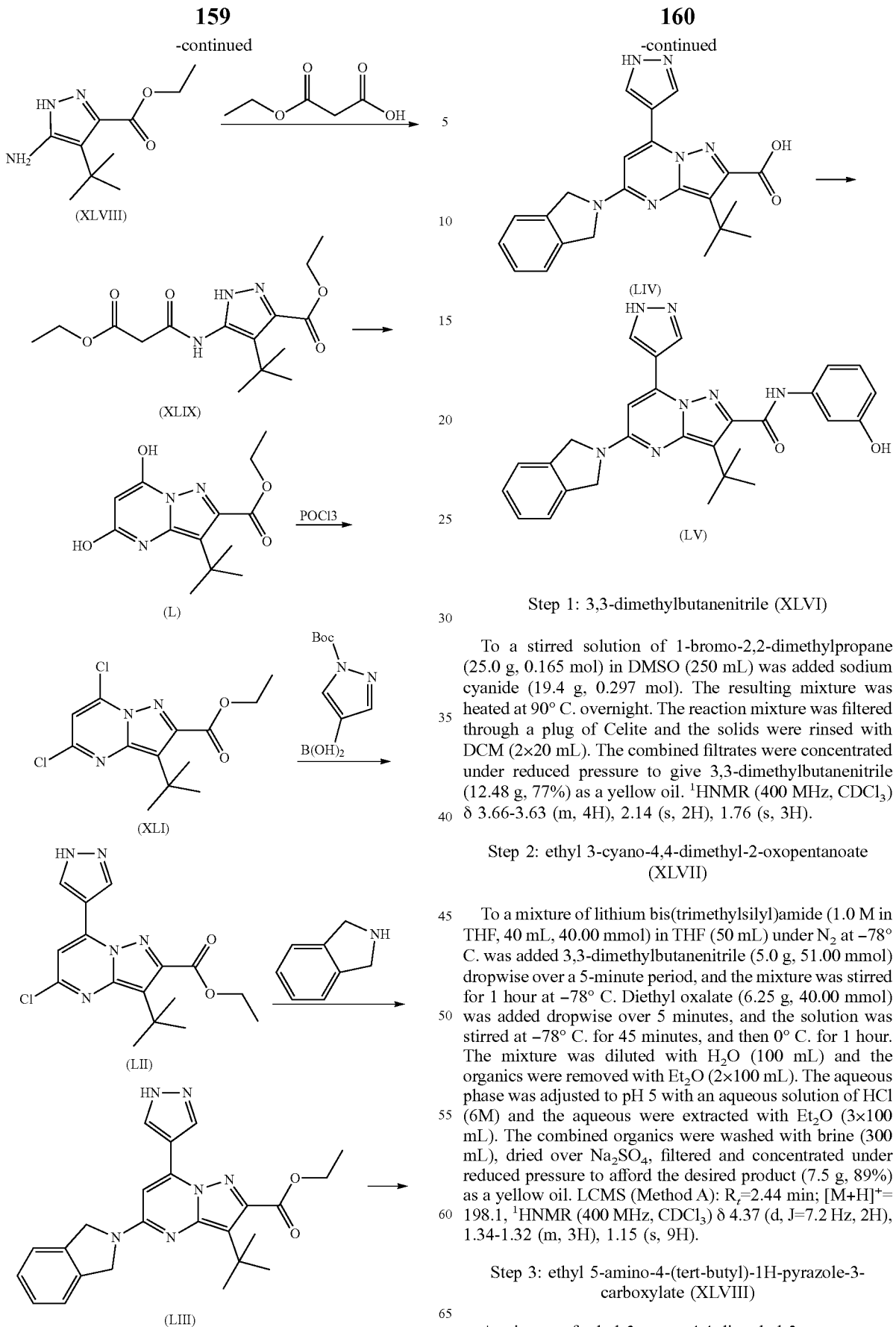

Step 1: 3,3-dimethylbutanenitrile (XLVI)

To a stirred solution of 1-bromo-2,2-dimethylpropane (25.0 g, 0.165 mol) in DMSO (250 mL) was added sodium cyanide (19.4 g, 0.297 mol). The resulting mixture was heated at 90° C. overnight. The reaction mixture was filtered through a plug of Celite and the solids were rinsed with DCM (2×20 mL). The combined filtrates were concentrated under reduced pressure to give 3,3-dimethylbutanenitrile (12.48 g, 77%) as a yellow oil. $^1$HNMR (400 MHz, CDCl$_3$) δ 3.66-3.63 (m, 4H), 2.14 (s, 2H), 1.76 (s, 3H).

Step 2: ethyl 3-cyano-4,4-dimethyl-2-oxopentanoate (XLVII)

To a mixture of lithium bis(trimethylsilyl)amide (1.0 M in THF, 40 mL, 40.00 mmol) in THF (50 mL) under N$_2$ at −78° C. was added 3,3-dimethylbutanenitrile (5.0 g, 51.00 mmol) dropwise over a 5-minute period, and the mixture was stirred for 1 hour at −78° C. Diethyl oxalate (6.25 g, 40.00 mmol) was added dropwise over 5 minutes, and the solution was stirred at −78° C. for 45 minutes, and then 0° C. for 1 hour. The mixture was diluted with H$_2$O (100 mL) and the organics were removed with Et$_2$O (2×100 mL). The aqueous phase was adjusted to pH 5 with an aqueous solution of HCl (6M) and the aqueous were extracted with Et$_2$O (3×100 mL). The combined organics were washed with brine (300 mL), dried over Na$_2$SO$_4$, filtered and concentrated under reduced pressure to afford the desired product (7.5 g, 89%) as a yellow oil. LCMS (Method A): R$_t$=2.44 min; [M+H]$^+$= 198.1, $^1$HNMR (400 MHz, CDCl$_3$) δ 4.37 (d, J=7.2 Hz, 2H), 1.34-1.32 (m, 3H), 1.15 (s, 9H).

Step 3: ethyl 5-amino-4-(tert-butyl)-1H-pyrazole-3-carboxylate (XLVIII)

A mixture of ethyl 3-cyano-4,4-dimethyl-2-oxopentanoate (8.8 g, 44.00 mmol) and hydrazine hydrate (4.47 g, 89.20 mmol) in AcOH (10 mL) and toluene (100 mL) was stirred at 110° C. overnight. The mixture was concentrated under reduced pressure and the residue was purified by chromatography on silica gel (DCM:MeOH, 100:1) to give the title product (3.6 g, 38%) as a yellow oil. LCMS (Method A): R$_t$=2.60 min; [M+H]$^+$=212.1, $^1$HNMR (400 MHz, CDCl$_3$) δ 4.30 (d, J=7.2 Hz, 2H), 1.40-1.29 (m, 12H).

Step 4: ethyl 4-(tert-butyl)-5-(3-ethoxy-3-oxopropanamido)-1H-pyrazole-3-carboxylate (XLIX)

A mixture of ethyl 5-amino-4-(tert-butyl)-1H-pyrazole-3-carboxylate (3.6 g, 17.00 mmol), 3-ethoxy-3-oxopropanoic acid (2.36 g, 17.00 mmol), DCC (4.57 g, 22.00 mmol), pyridine (4.04 g, 51.00 mmol) and DMAP (208 mg, 1.70 mmol) in DCM (36 mL) was stirred at room temperature overnight. The mixture was filtered and the filtrate was concentrated under reduced pressure and purified by column chromatography on silica gel (DCM:MeOH, 100:1) to give the title product (5.5 g, 95%) as a yellow oil. LCMS (Method A): R$_t$=3.28 min; [M+H]$^+$=326.1, $^1$HNMR (400 MHz, DMSO-d$_6$) δ 13.52 (s, 1H), 9.67 (s, 1H), 4.33-4.22 (m, 2H), 4.13-4.07 (m, 2H), 3.39 (d, J=12.0 Hz, 2H), 1.35-1.21 (m, 15H).

Step 5: ethyl 3-(tert-butyl)-5,7-dihydroxypyrazolo[1,5-a]pyrimidine-2-carboxylate (L)

A mixture of ethyl 4-(tert-butyl)-5-(3-ethoxy-3-oxopropanamido)-1H-pyrazole-3-carboxylate (5.5 g, 17.00 mmol) and DMAP (6.2 g, 51.00 mmol) in ethanol (112 mL) and H$_2$O (112 mL) was stirred at 80° C. overnight. The mixture was concentrated under reduced pressure and the residue was partitioned between EtOAc (100 mL) and H2O (100 mL). The organics were dried over Na2SO4 and concentrated under reduced pressure to give the title product (3.0 g, 64%) as a white solid. LCMS (Method A): R$_t$=2.83 min; [M+H]$^+$=280.1

Step 6: ethyl 3-(tert-butyl)-5,7-dichloropyrazolo[1,5-a]pyrimidine-2-carboxylate(LI)

A mixture of ethyl 3-(tert-butyl)-5,7-dihydroxypyrazolo[1,5-a]pyrimidine-2-carboxylate (4.0 g, 14.00 mmol) in phosphorus oxychloride (200 mL) was stirred at 110° C. overnight. The mixture was concentrated under reduced pressure and the residue was poured into ice-water and extracted with Et$_2$O (3×300 mL). The combined organics were washed with brine (100 mL), dried (Na$_2$SO$_4$), filtered and concentrated under reduced pressure. The residue was purified by column chromatography on silica gel (PE:EtOAc, 10/1) to give the title product (1.0 g, 22%) as a yellow oil. LCMS (Method A): R$_t$=3.49 min; [M+H]$^+$=316.9. $^1$HNMR (400 MHz, DMSO-d$_6$) δ 6.92 (s, 1H), 4.41 (q, J=6.8 Hz, 2H), 1.51 (s, 3H) 1.47 (s, 9H).

Step 7: ethyl 3-(tert-butyl)-5-chloro-7-(1H-pyrazol-4-yl)pyrazolo[1,5-a]pyrimidine-2-carboxylate (LII)

A mixture of ethyl 3-(tert-butyl)-5,7-dichloropyrazolo[1,5-a]pyrimidine-2-carboxylate (1.15 g, 3.60 mmol), 1-Boc-pyrazole-4-boronic acid pinacol ester (1.07 g, 3.60 mmol), Na$_2$CO$_3$ (0.774 g, 7.20 mmol) and Pd(dppf)$_2$Cl$_2$ (534 mg, 0.73 mmol) in degassed 1,4-dioxane (35 mL) and H$_2$O (7 mL) was stirred at 80° C. overnight under N$_2$. The mixture was poured into water and extracted with EtOAc (100 mL×3). The combined organics were washed with water and brine, dried over Na$_2$SO$_4$, filtered and concentrated under reduced pressure. The residue was purified by column chromatography on silica gel (DCM:MeOH, 100:1) to give the title product (600 mg, 61%) as a yellow solid. LCMS (Method A): R$_t$=4.36 min; [M+H]$^+$=348.1. $^1$HNMR (400 MHz, DMSO-d$_6$) δ 8.69 (s, 1H), 7.19 (s, 1H), 7.03 (s, 1H), 4.41 (q, J=7.2 Hz, 2H), 1.49 (s, 9H), 1.36 (t, J=7.2 Hz, 3H).

Step 8: ethyl 3-(tert-butyl)-5-(isoindolin-2-yl)-7-(1H-pyrazol-4-yl)pyrazolo[1,5-a]pyrimidine-2-carboxylate (LIII)

A mixture of ethyl 3-(tert-butyl)-5-chloro-7-(1H-pyrazol-4-yl)pyrazolo[1, 5-a]pyrimidine-2-carboxylate (800 mg, 2.30 mmol), isoindoline (714 mg, 4.36 mmol) and triethylamine (931 mg, 9.20 mmol) in DMF (20 mL) was stirred at 80° C. overnight. The mixture was diluted with water and the solids were filtered. The filtered cake was dried and purified by silica gel column chromatography (DCM:MeOH, 100:1) to give the desired product (230 mg, 49%) as a yellow solid. LCMS: (Method A), R$_t$=4.97 min, [M+H]$^+$= 431.2. $^1$HNMR (400 MHz, DMSO-d$_6$) δ 8.67 (s, 2H), 7.39-7.31 (m, 4H), 6.53 (s, 1H), 4.94 (s, 4H), 4.45 (q, J=7.8 Hz, 2H), 1.56 (s, 9H), 1.44 (t, J=7.6 Hz, 3H).

Step 9: 3-(tert-butyl)-5-(isoindolin-2-yl)-7-(1H-pyrazol-4-yl)pyrazolo[1,5-a]pyrimidine-2-carboxylic acid (LIV)

To a solution of 3-(tert-butyl)-5-(isoindolin-2-yl)-7-(1H-pyrazol-4-yl)pyrazolo[1,5-a]pyrimidine-2-carboxylate (600 mg, 1.39 mmol) in THF (24 mL) and H$_2$O (24 mL) at 0° C. was slowly added an aqueous KOH solution (1 M, 12 mL) over 15 min. The reaction mixture was stirred to 90° C. overnight. The solution was concentrated under reduced pressure and the residue was partitioned between H$_2$O (20 mL) and Et2O (20 mL). The organics were discarded and the aqueous layer was acidified to pH 2 with an aqueous HCL solution (2M). The aqueous phase was extracted with CHCl$_3$ (100 mL×3) and the combined organics were dried over Na$_2$SO$_4$ and concentrated under reduced pressure to afford the title product (560 mg, 100%) as a yellow solid. LCMS: (Method A), R$_t$=4.22 min, [M+H]$^+$=403.1. $^1$HNMR (400 MHz, DMSO-d$_6$) δ 8.77 (s, 2H), 7.55-7.38 (m, 4H), 6.99 (s, 1H), 4.99 (s, 4H), 1.54 (s, 9H).

Step 10: 3-(tert-butyl)-N-(3-hydroxyphenyl)-5-(isoindolin-2-yl)-7-(1H-pyrazol-4-yl)pyrazolo[1,5-a]pyrimidine-2-carboxamide (LV)

A mixture of 3-(tert-butyl)-5-(isoindolin-2-yl)-7-(1H-pyrazol-4-yl)pyrazolo[1,5-a]pyrimidine-2-carboxylic acid (100 mg, 0.25 mmol), 3-aminophenol (34 mg, 0.28 mmol), HATU (142 mg, 0.37 mmol) and DIEA (931 mg, 9.20 mmol) in DMF (20 mL) was stirred at room temperature overnight. The mixture was diluted with water and the solids were removed by filtration. The combined solids were purified by silica gel column chromatography (DCM:MeOH, 99:1) to give the title product (50 mg, 39%) as a yellow solid. LCMS: (Method A), R$_t$=2.26 min, [M+H]$^+$=508.2. $^1$HNMR (400 MHz, DMSO-d$_6$) δ 13.47 (s, 1H), 10.55 (s, 1H), 9.01 (s, 1H), 8.63 (s, 1H), 7.50-7.47 (m, 3H), 7.37-7.35 (m, 3H), 7.26 (t, J=8.0 Hz, 1H), 7.0 (s, 1H), 6.70 (d, J=6.0 Hz, 1H), 4.96 (s, 4H), 3.76 (s, 3H), 1.55 (s, 9H).

The following compounds were similarly prepared using appropriate starting materials in step 8 and step 10 of scheme 7 according to the method described for the synthesis of compound 85.

Example 114—N-(3-acetamidophenyl)-3-(tert-butyl)-5-(isoindolin-2-yl)-7-(1H-pyrazol-4-yl)pyrazolo[1,5-a]pyrimidine-2-carboxamide (86)

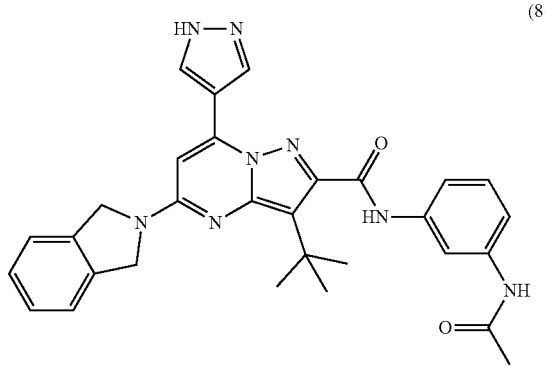

(86)

Starting material used in step 8—isoindoline, starting material used in step 10—N-(3-aminophenyl)acetamide, $^1$HNMR (400 MHz, DMSO-$d_6$) δ 13.44 (s, 1H), 10.57 (s, 1H), 9.98 (s, 1H), 9.01 (s, 1H), 8.64 (s, 1H), 8.08 (s, 1H), 7.46 (d, J=7.6 Hz, 3H), 7.37-7.35 (m, 3H), 7.26 (t, J=8.0 Hz, 1H), 7.0 (s, 1H), 4.96 (s, 4H), 2.05 (s, 3H), 1.55 (s, 9H). LCMS: (Method A), $R_t$=3.610 min, [M+H]$^+$=535.2.

Example 115—N-(3-(4-acetylpiperazin-1-yl)phenyl)-3-(tert-butyl)-5-(isoindolin-2-yl)-7-(1H-pyrazol-4-yl)pyrazolo[1,5-a]pyrimidine-2-carboxamide (87)

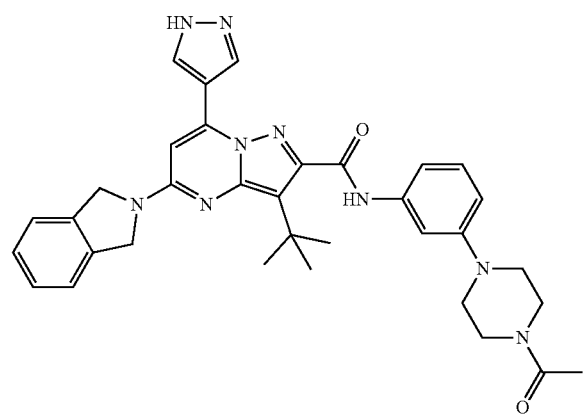

(87)

Starting material used in step 8—isoindoline, starting material used in step 10—1-(4-(3-aminophenyl)piperazin-1-yl)ethan-1-one, $^1$HNMR (400 MHz, DMSO-$d_6$) δ 13.44 (s, 1H), 10.43 (s, 1H), 9.00 (s, 1H), 8.66 (s, 1H), 7.51-7.47 (m, 3H), 7.37-7.35 (m, 3H), 7.27-7.18 (m, 2H), 7.0 (s, 1H), 6.74 (d, J=7.2 Hz, 1H), 4.96 (s, 4H), 3.60 (t, J=4.8 Hz, 4H), 3.17-3.08 (m, 4H), 2.05 (s, 3H), 1.55 (s, 9H). LCMS: (Method D), $R_t$=5.53 min, [M+H]$^+$=604.3.

Example 116—3-(tert-butyl)-N-(3-hydroxyphenyl)-5-(isoindolin-2-yl)-7-(1H-pyrazol-4-yl)pyrazolo[1,5-a]pyrimidine-2-carboxamide (88)

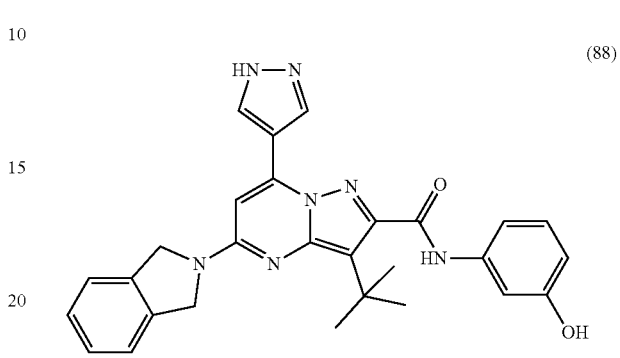

(88)

Starting material used in step 8—isoindoline. starting material used in step 10—3-aminophenol, $^1$HNMR (400 MHz, DMSO-$d_6$) δ 13.41 (s, 1H), 10.44 (s, 1H), 9.40 (s, 1H), 8.66 (s, 1H), 7.50-7.34 (m, 6H), 7.16-7.09 (m, 2H), 7.0 (s, 1H), 6.51 (d, J=7.2 Hz, 1H), 4.96 (s, 4H), 1.55 (s, 9H). LCMS: (Method A), $R_t$=3.67 min, [M+H]$^+$=494.2.

Example 117—3-(tert-butyl)-5-(5-chloroisoindolin-2-yl)-N-(3-methoxyphenyl)-7-(1H-pyrazol-4-yl)pyrazolo[1,5-a]pyrimidine-2-carboxamide (89)

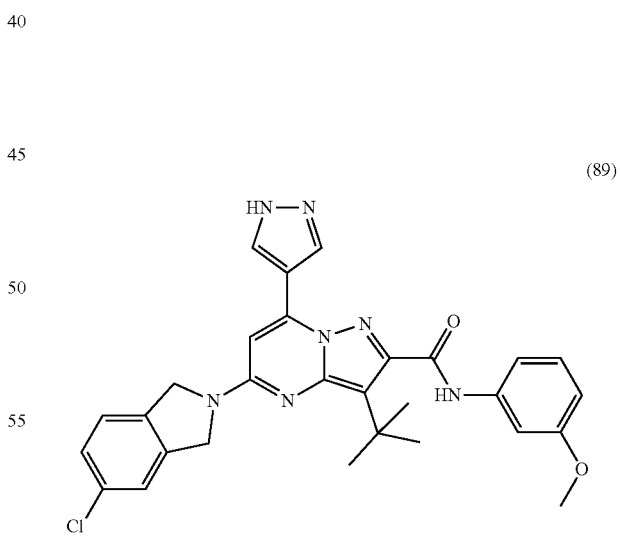

(89)

Starting material used in step 8—5-chloroisoindoline, starting material used in step 10—3-methoxyaniline, $^1$HNMR (400 MHz, DMSO-$d_6$) δ 13.44 (s, 1H), 10.55 (s, 1H), 8.94 (s, 1H), 8.63 (s, 1H), 7.50-7.23 (m, 6H), 6.98 (s, 1H), 6.70 (d, J=7.0 Hz, 1H), 4.96 (s, 4H), 3.76 (s, 3H), 1.55 (s, 9H). LCMS: (Method A), $R_t$=3.88 min. [M+H]$^+$=542.2.

Example 118—N-(3-(4-acetylpiperazin-1-yl)phenyl)-3-(tert-butyl)-5-(5-chloroisoindolin-2-yl)-7-(1H-pyrazol-4-yl)pyrazolo[1,5-a]pyrimidine-2-carboxamide (90)

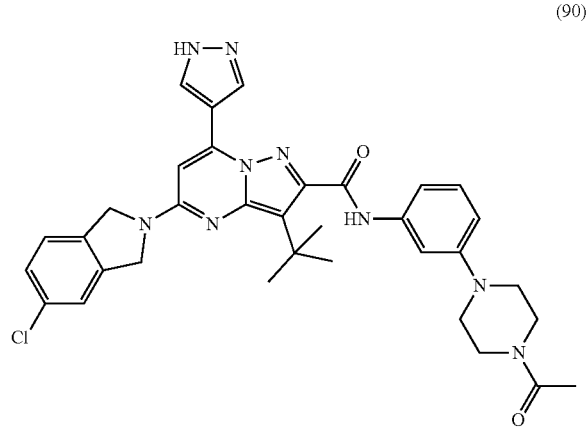 [SMILES: CC(=O)N1CCN(c2cccc(NC(=O)c3nn4c(-c5cn[nH]c5)cc(N5Cc6ccc(Cl)cc6C5)nc4c3C(C)(C)C)c2)CC1]

(90)

Starting material used in step 8—5-chloroisoindoline, Starting material used in step 10—Starting material: 1-(4-(3-aminophenyl)piperazin-1-yl)ethan-1-one. ¹HNMR (400 M Hz, DMSO-d$_6$) δ 13.42 (s, 1H), 10.43 (s, 1H), 8.81 (s, 2H), 7.51-7.18 (m, 6H), 6.98 (s, 1H), 6.74 (d, J=8 Hz, 1H), 4.95 (d, J=4.8 Hz, 4H), 3.59 (s, 4H), 3.16 (s, 2H), 3.10 (s, 2H), 2.05 (s, 3H), 1.55 (s, 9H). LCMS (Method D): R$_t$=5.86 min; [MH]$^+$=638.3.

Example 119—3-(tert-butyl)-5-(5-fluoroisoindolin-2-yl)-N-(3-methoxyphenyl)-7-(1H-pyrazol-4-yl)pyrazolo[1,5-a]pyrimidine-2-carboxamide (91)

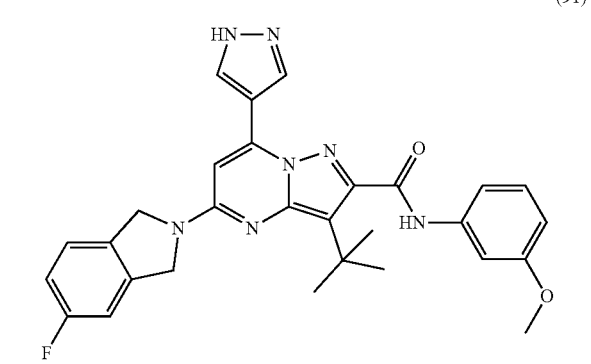

(91)

Starting material used in step 8—5-fluoroisoindoline, starting material used in step 10—3-methoxyaniline, ¹HNMR (400 MHz, DMSO-d$_6$) δ 13.44 (s, 1H), 10.55 (s, 1H), 9.0 (s, 1H), 8.63 (s, 1H), 7.50 (s, 2H), 7.36 (d, J=8.0 Hz, 2H), 7.26 (t, J=8.0 Hz, 1H), 7.19 (t, J=9.2 Hz, 1H), 6.98 (s, 1H), 6.70 (d, J=6.4 Hz, 1H), 4.96 (d, J=12.4 Hz, 4H), 3.76 (s, 3H), 1.55 (s, 9H). LCMS: (Method A), R$_t$=2.11 min, [M+H]$^+$=526.2.

Example 120—N-(3-(4-acetylpiperazin-1-yl)phenyl)-3-(tert-butyl)-5-(5-fluoroisoindolin-2-yl)-7-(1H-pyrazol-4-yl)pyrazolo[1,5-a]pyrimidine-2-carboxamide (92)

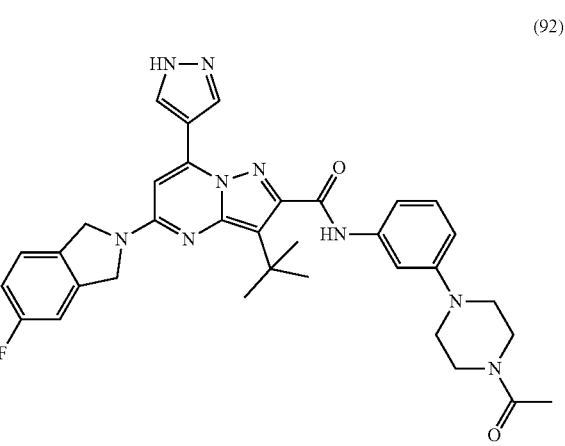 [SMILES: CC(=O)N1CCN(c2cccc(NC(=O)c3nn4c(-c5cn[nH]c5)cc(N5Cc6ccc(F)cc6C5)nc4c3C(C)(C)C)c2)CC1]

(92)

Starting material used in step 8—5-fluoroisoindoline, starting material used in step 10—1-(4-(3-aminophenyl)piperazin-1-yl)ethan-1-one, ¹HNMR (400 M Hz, DMSO-d$_6$) δ 13.45 (s, 1H), 10.42 (s, 1H), 8.99 (s, 1H), 8.62 (s, 1H), 7.5 (s, 2H), 7.39-7.18 (m, 4H), 6.98 (s, 1H), 6.74 (s, 1H), 4.93 (d, J=13.2 Hz, 4H), 3.59 (s, 4H), 3.16 (s, 2H), 3.10 (s, 2H), 2.05 (s, 3H), 1.55 (s, 9H). ¹HNMR (400 M Hz, DMSO-d$_6$) δ 13.45 (s, 1H), 10.42 (s, 1H), 8.99 (s, 1H), 8.62 (s, 1H), 7.5 (s, 2H), 7.39-7.18 (m, 4H), 6.98 (s, 1H), 6.74 (s, 1H), 4.93 (d, J=13.2 Hz, 4H), 3.59 (s, 4H), 3.16 (s, 2H), 3.10 (s, 2H), 2.05 (s, 3H), 1.55 (s, 9H).

Example 121—N-(3-chlorophenyl)-5-(isoindolin-2-yl)-7-(1H-pyrazol-4-yl)-3-(tetrahydro-2H-pyran-4-yl)pyrazolo[1,5-a]pyrimidine-2-carboxamide (110)

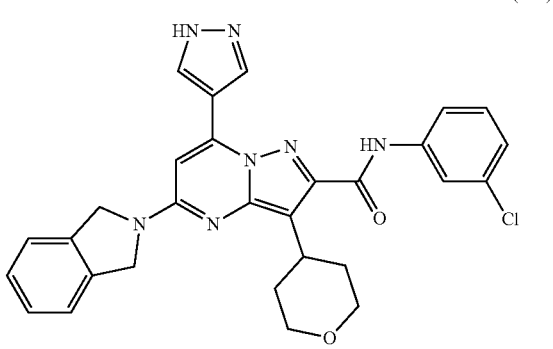

(110)

Compound 110 was made using the procedure outlined in scheme 8.

Scheme 8
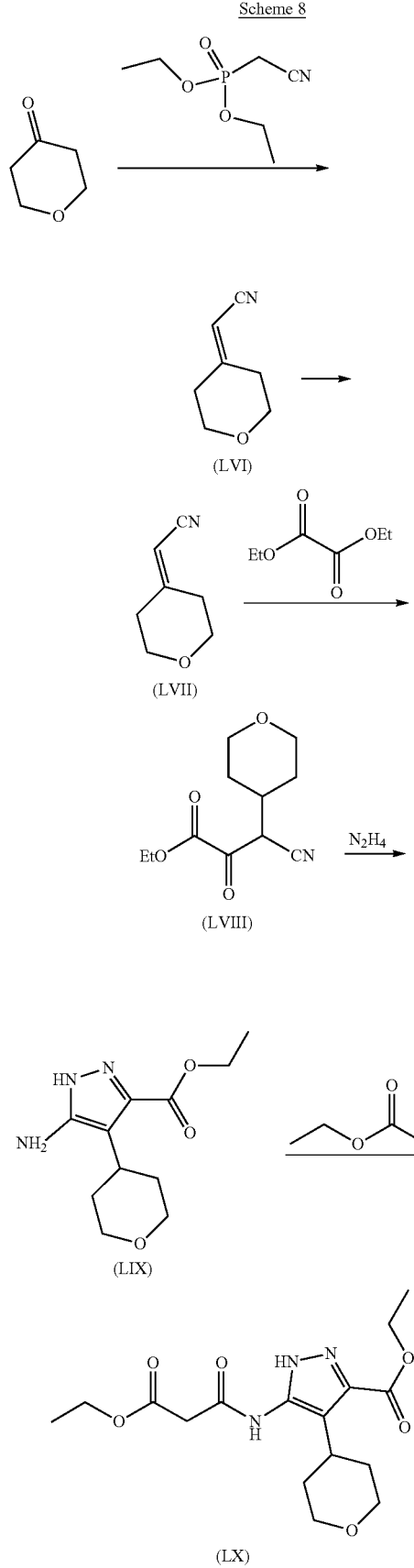
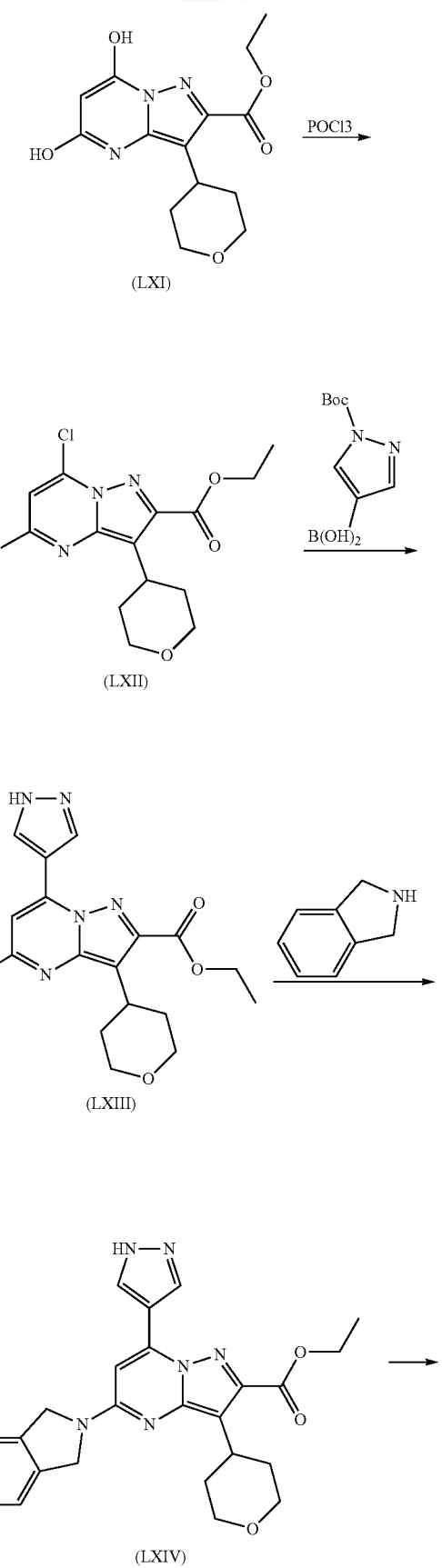

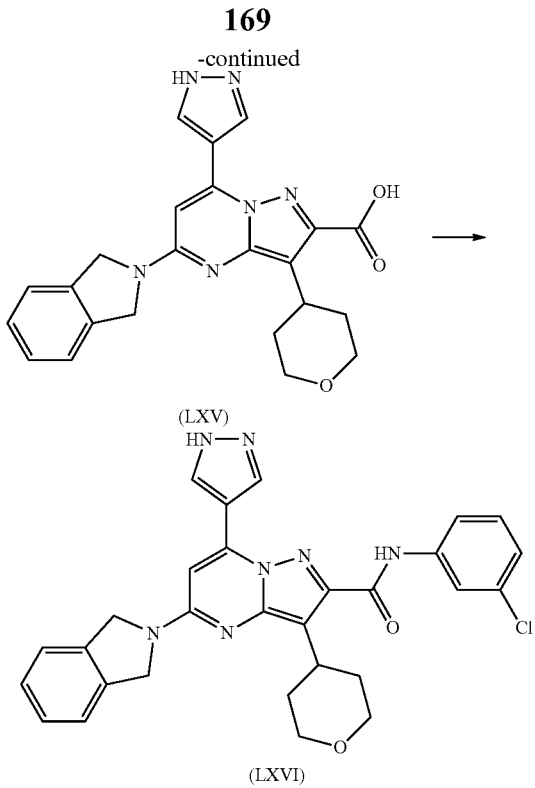

(LXV)

(LXVI)

Step 1: 2-(dihydro-2H-pyran-4(3H)-ylidene)acetonitrile (LVI)

To a suspension of NaH (60% in oil, 4.4 g, 0.11 mol) in diethyl ether (300 mL) cooled to 0° C. was added diethyl (cyanomethyl) phosphonate (19.5 g, 0.11 mol) dropwise, followed by a dropwise addition of a solution of tetrahydro-4H-pyran-4-one (10 g, 0.10 mol) in diethyl ether (300 mL). The reaction mixture was stirred at RT overnight. The mixture was partitioned between water (100 mL) and ethyl acetate (100 mL). The organic layer was washed with brine, dried over Na$_2$SO$_4$, filtered, and concentrated under reduced pressure to give the title product (7.0 g, 57%) as a yellow oil. LCMS (Method A): R$_t$=0.34 min; [M+H]$^+$=124.1, $^1$HNMR (400 MHz, CDCl$_3$) δ 5.10 (s, 1H), 3.72-3.66 (m, 4H), 2.63-2.50 (m, 2H), 2.36-2.27 (m, 2H).

Step 2: 2-(tetrahydro-2H-pyran-4-yl)acetonitrile (LVII)

To a solution of 2-(tetrahydro-4H-pyran-4-ylidene)acetonitrile (2.6 g, 21.14 mmol) in PE (25 mL) and acetic acid (1 mL) was added Pd/C (10%, 100 mg). The reaction mixture was purged with H$_2$ and stirred overnight under 1 atm of hydrogen. The reaction was filtered through Celite, and the filtrate was concentrated in vacuo to provide the title product as a yellow oil. LCMS (Method A): R$_t$=0.71 min; [M+H]$^+$=126.1. $^1$HNMR (400 MHz, CDCl$_3$) δ 4.02-3.98 (m, 2H), 3.43-3.37 (m, 2H), 2.32 (d, J=8.4 Hz, 2H), 2.08 (s, 1H), 1.99-1.86 (m, 1H), 1.77-1.72 (m, 2H).

Step 3: ethyl 3-cyano-2-oxo-3-(tetrahydro-2H-pyran-4-yl)propanoate (LVIII)

To a mixture of lithium bis(trimethylsilyl)amide (1.0 M in THF, 13.3 mL, 13.30 mmol) in dry THF (50 mL) under N$_2$ cooled to −78° C. was added 2-(tetrahydro-2H-pyran-4-yl)acetonitrile (2.0 g, 15.90 mmol) dropwise over 5 minutes, and the mixture was stirred for at −78° C. for 1 hour. Diethyl oxalate (1.95 g, 13.30 mmol) was added dropwise over 5 minutes at −78° C. and the solution was stirred for 45 minutes at 0° C. The mixture was diluted with H$_2$O (100 mL) and the organics were extracted with Et$_2$O (2×100 mL). The aqueous layer was adjusted to pH 5 with 6M HCl and then the organics were extracted with Et$_2$O (3×100 mL). The combined organics were washed with brine (300 mL), dried over Na$_2$SO$_4$, filtered and concentrated under reduced pressure to afford the title product (7.5 g, 89%) as a yellow oil. LCMS (Method A): R$_t$=0.868 min; [M+H]$^+$=226.1.

Step 4: ethyl 5-amino-4-(tetrahydro-2H-pyran-4-yl)-1H-pyrazole-3-carboxylate (LIX)

A mixture of ethyl 3-cyano-2-oxo-3-(tetrahydro-2H-pyran-4-yl)propanoate (24.22 g, 0.11 mol) and hydrazine hydrate (10.7 g, 0.21 mol) in a mixture AcOH (50 mL) and toluene (500 mL) was stirred at 110° C. overnight. The mixture was concentrated under reduced pressure and the residue was purified by column chromatography on silica gel (DCM:MeOH, 100:1) to give the product (8 g, 31%) as a yellow oil. LCMS (Method A): R$_t$=2.34 min; [M+H]$^+$=240.1

Step 5: ethyl 5-(3-ethoxy-3-oxopropanamido)-4-(tetrahydro-2H-pyran-4-yl)-1H-pyrazole-3-carboxylate (LX)

A mixture of ethyl 5-amino-4-(tetrahydro-2H-pyran-4-yl)-1H-pyrazole-3-carboxylate (7.0 g, 29.29 mmol), 3-ethoxy-3-oxopropanoic acid (4.05 g, 30.70 mmol), DCC (7.84 g, 38 mmol), pyridine (6.91 g, 87.80 mmol) and DMAP (357 mg, 2.92 mmol) in DCM (70 mL) was stirred at room temperature overnight. The mixture was filtered and the filtrate was concentrated under reduced pressure. The reside was purified by column chromatography on silica gel (DCM:MeOH, 100:1) to give the title product (6.6 g, 56%) as a yellow oil. LCMS (Method A): R$_t$=2.76 min; [M+H]$^+$=354.1

Step 6: ethyl 5,7-dihydroxy-3-(tetrahydro-2H-pyran-4-yl)pyrazolo[1,5-a]pyrimidine-2-carboxylate (LXI)

A mixture of ethyl 5-(3-ethoxy-3-oxopropanamido)-4-(tetrahydro-2H-pyran-4-yl)-1H-pyrazole-3-carboxylate (5.6 g, 15.86 mmol) and DMAP (5.8 g, 47.58 mmol) in ethanol (112 mL) and H$_2$O (112 mL) was stirred at 80° C. overnight. The mixture was concentrated and the residue was dissolved in EtOAc (200 mL) and washed with water (100 mL). The organics were dried over Na2SO4 and concentrated under reduced pressure to obtain the title product (3.5 g, 72%) as a white solid. LCMS (Method A): R$_t$=2.23 min; [M+H]$^+$=308.1

Step 7: ethyl 5,7-dichloro-3-(tetrahydro-2H-pyran-4-yl)pyrazolo[1,5-a]pyrimidine-2-carboxylate (LXII)

A mixture of 5,7-dihydroxy-3-(tetrahydro-2H-pyran-4-yl)pyrazolo[1,5-a]pyrimidine-2-carboxylate (2.0 g, 5.83 mmol) in phosphorus oxychloride (50 mL) was stirred at 110° C. overnight. The mixture was concentrated under reduced pressure. The residue was poured into ice-water, extracted with Et$_2$O (3×300 mL), and the combined organics were washed with brine (100 mL), dried (Na$_2$SO$_4$), filtered and concentrated under reduced pressure. The reside was purified by chromatography on silica gel (PE:EtOAc, 20:1) to give the title product (1.0 g, 45%) as a yellow solid. $^1$HNMR (400 MHz, DMSO-d$_6$) δ 7.05 (s, 1H), 4.51 (d, J=7.1 Hz, 2H), 4.13-4.06 (m, 2H), 3.75 (tt, J=12.8 Hz, 3.6 Hz, 1H), 3.56 (d, J=1.2 Hz, 2H), 2.47 (dd, J=13.1 Hz, 4.4 Hz, 2H), 1.69 (dd, J=12.8 Hz, 2.0 Hz, 2H), 1.47 (t, J=7.2 Hz, 3H).

Step 8: ethyl 5-chloro-7-(1H-pyrazol-4-yl)-3-(tetrahydro-2H-pyran-4-yl)pyrazolo [1,5-a]pyrimidine-2-carboxylate (LXIII)

A mixture of ethyl 5,7-dichloro-3(tetrahydro-2H-pyran-4-yl)pyrazolo [1,5-a]pyrimidine-2-carboxylate (1.2 g, 3.49 mmol), 1-Boc-pyrazole-4-boronic acid pinacol ester (1.02 g, 3.49 mmol), Na$_2$CO$_3$ (741 mg, 6.99 mmol) and Pd(dppf)$_2$Cl$_2$ (511 mg, 0.70 mmol) in 1,4-dioxane (35 mL) and H$_2$O (7 mL) was stirred at 80° C. overnight under N$_2$. The mixture was poured into water and extracted with EtOAc (100 mL×3). The combined organic layers were washed with brine, dried over Na$_2$SO$_4$, filtered and concentrated under reduced pressure. The residue was purified by chromatography on silica gel (MeOH:DCM, 1:100) to give the title product (600 mg, 61%) as a yellow solid. LCMS (Method A): R$_t$=3.71 min; [M+H]$^+$=376.1

Step 9: ethyl 5-(isoindolin-2-yl)-7-(1H-pyrazol-4-yl)-3-(tetrahydro-2H-pyran-4-yl)pyrazolo [1,5-a] pyrimidine-2-carboxylate (LXIV)

A mixture of ethyl 5-chloro-7-(1H-pyrazol-4-yl)-3-(tetrahydro-2H-pyran-4-yl)pyrazolo [1,5-a]pyrimidine-2-carboxylate (800 mg, 2.13 mmol), isoindoline (661 mg, 4.26 mmol) and triethylamine (861 mg, 8.53 mmol) in DMF (20 mL) was stirred at 80° C. overnight. The mixture was poured into water (20 mL) and the precipitate formed was collected by filtration. This reside was further purified by silica gel column chromatography (MeOH/DCM=1/100, v/v) to give the desired product (870 mg, 89%) as a yellow solid. LCMS: (Method A), R$_t$=4.25 min, [M+H]$^+$=459.2

Step 10: 5-(isoindolin-2-yl)-7-(1H-pyrazol-4-yl)-3-(tetrahydro-2H-pyran-4-yl)pyrazolo[1,5-a]pyrimidine-2-carboxylic acid (LXV)

To a solution of ethyl 5-(isoindolin-2-yl)-7-(1H-pyrazol-4-yl)-3-(tetrahydro-2H-pyran-4-yl) pyrazolo[1,5-a]pyrimidine-2-carboxylate (870 mg, 1.89 mmol) in THF (24 mL) and H$_2$O (24 mL) at 0° C. was slowly added aqueous KOH (1 M, 12 mL, 48 mmol) over 15 min. The reaction mixture was stirred at 70° C. overnight. The solvent was removed under reduced pressure and the residual aqueous solution was washed with Et$_2$O (2×30 mL), then acidified to pH 2 with an aqueous solution of HCl 1 M. The aqueous phase was extracted with CHCl$_3$ (3×100 mL) and the combined organics were dried over Na$_2$SO$_4$ and concentrated under reduced pressure to afford the title product (800 mg, 99%) as a solid. LCMS: (Method A), R$_t$=3.60 min, [M+H]$^+$=431.1

Step 11: N-(3-chlorophenyl)-5-(isoindolin-2-yl)-7-(1H-pyrazol-4-yl)-3-(tetrahydro-2H-pyran-4-yl)pyrazolo[1,5-a]pyrimidine-2-carboxamide (LXVI)

A mixture of 5-(isoindolin-2-yl)-7-(1H-pyrazol-4-yl)-3-(tetrahydro-2H-pyran-4-yl)pyrazolo[1,5-a]pyrimidine-2-carboxylic acid (100 mg, 0.25 mmol), 3-chloroaniline (36 mg, 0.28 mmol), HATU (142 mg, 0.37 mmol) and DIEA (120 mg, 0.93 mmol) in DMF (20 mL) was stirred at room temperature overnight. The mixture was diluted with water to form a suspension which was filtered. The filtered cake was dried and purified by silica gel column (MeOH/DCM=1/100, v/v) to give the desired product (60 mg, 48%) as a yellow solid. LCMS: (Method D), R$_1$=6.16 min, [M+H]$^+$=540.2. $^1$HNMR (400 MHz, DMSO-d$_6$) δ 13.50 (s, 1H), 10.37 (s, 1H), 9.30 (s, 1H), 8.72 (s, 1H), 8.03 (s, 1H), 7.82 (d, J=7.6 Hz, 1H) 7.51-7.35 (m, 5H), 7.19 (d, J=7.6 Hz, 1H), 7.07 (s, 1H), 4.98 (s, 4H), 3.99 (d, J=8.4 Hz, 2H), 3.68 (t, J=10.0 Hz, 1H), 3.44 (d, J=7.2 Hz, 2H), 2.54 (s, 2H), 1.59 (d, J=12.0 Hz, 2H)

The following compounds were similarly prepared using appropriate starting materials in step 9 and step 11 of scheme 8 according to the method described for the synthesis of compound 110.

Example 122—N-(3-hydroxyphenyl)-5-(isoindolin-2-yl)-7-(1H-pyrazol-4-yl)-3-(tetrahydro-2H-pyran-4-yl)pyrazolo[1,5-a]pyrimidine-2-carboxamide (111)

(111)

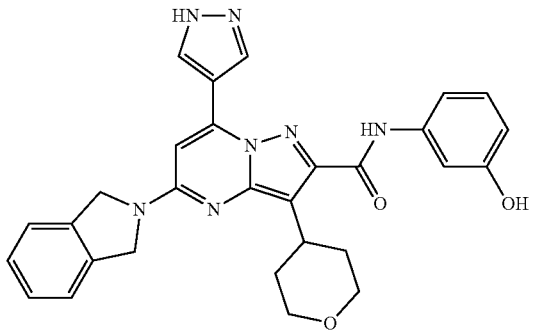

Starting material used in step 9-isoindoline, starting material used in step 11—3-aminophenol, $^1$HNMR (400 MHz, DMSO-d$_6$) δ 13.50 (s, 1H), 10.09 (s, 1H), 9.42 (s, 1H), 9.27 (s, 1H), 8.71 (s, 1H), 7.45-7.13 (m, 7H), 7.05 (s, 1H), 6.53 (d, J=8.8 Hz, 1H), 4.98 (s, 4H), 4.0 (d, J=10.4 Hz, 2H), 3.66 (s, 1H), 3.44 (d, J=11.6 Hz, 2H), 3.33 (s, 2H), 1.60 (d, J=12.0 Hz, 2H). LCMS: (Method B), R$_t$=2.27 min, [M+H]$^+$=522.2.

Example 123—5-(isoindolin-2-yl)-N-(3-methoxyphenyl)-7-(1H-pyrazol-4-yl)-3-(tetrahydro-2H-pyran-4-yl)pyrazolo[1,5-a]pyrimidine-2-carboxamide (112)

(112)

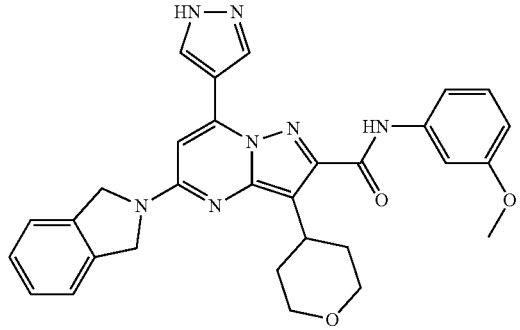

Starting material used in step 9—isoindoline, starting material used in step 11—3-methoxyaniline. ¹HNMR (400 MHz, DMSO-d₆) δ 13.50 (s, 1H), 10.17 (s, 1H), 9.28 (s, 1H), 8.72 (s, 1H), 7.45-7.42 (m, 4H), 7.38-7.35 (m, 2H), 7.28 (t, J=12.0 Hz, 1H), 7.06 (s, 1H), 6.72 (dd, J=5.6 Hz, 1.6 Hz, 1H), 4.98 (s, 4H), 3.98 (dd, J=7.2 Hz, 3.2 Hz, 2H), 3.78 (s, 3H), 3.72-3.64 (m, 1H), 3.44 (d, J=11.2 Hz, 2H), 3.33 (s, 2H), 2.57-2.53 (m, 1H), 1.60 (d, J=12.0 Hz, 2H). LCMS: (Method D), R₁=5.51 min, [M+H]⁺=536.2.

Example 124—5-(isoindolin-2-yl)-N-(4-methoxyphenyl)-7-(1H-pyrazol-4-yl)-3-(tetrahydro-2H-pyran-4-yl)pyrazolo[1,5-a]pyrimidine-2-carboxamide (113)

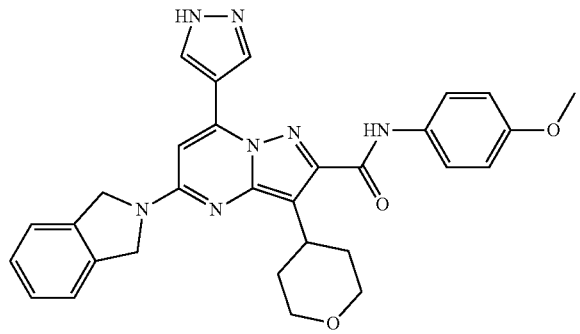

(113)

Starting material used in step 9—isoindoline, starting material used in step 11—4-methoxyaniline, ¹HNMR (400 M Hz, DMSO-d₆) δ 13.50 (s, 1H), 10.09 (s, 1H), 9.29 (s, 1H), 8.72 (s, 1H), 7.73 (d, J=9.2 Hz, 2H), 7.49-7.35 (m, 4H), 7.05 (s, 1H), 6.95 (d, J=6.8 Hz, 2H), 4.97 (s, 4H), 3.99 (d, J=7.2 Hz, 2H), 3.77 (s, 3H), 3.70 (s, 1H), 3.34 (t, J=11.2 Hz, 2H), 2.57-2.53 (m, 2H), 1.60 (d, J=12.0 Hz, 2H). LCMS: (Method A), R₁=2.45 min, [M+H]⁺=536.2.

Example 125—5-(benzyl(methyl)amino)-N-(3-hydroxyphenyl)-7-(1H-pyrazol-4-yl)-3-(tetrahydro-2H-pyran-4-yl)pyrazolo[1,5-a]pyrimidine-2-carboxamide (114)

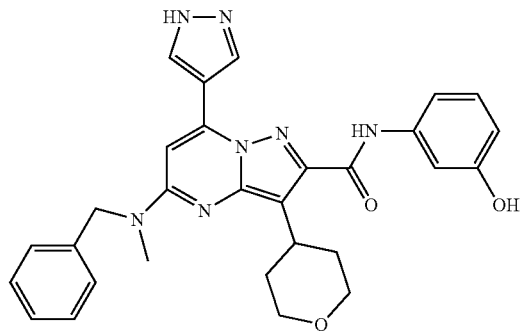

(114)

Starting material used in step 9—N-methyl-1-phenylmethanamine, starting material used in step 11—3-aminophenol, ¹HNMR (400 MHz, DMSO-d₆) δ 13.45 (s, 1H), 10.03 (s, 1H), 9.40 (s, 1H), 9.22 (s, 1H), 8.65 (s, 1H), 7.43 (t, J=3.2 Hz, 1H), 7.37-7.34 (m, 4H), 7.28-7.24 (m, 1H), 7.19 (d, J=8.4 Hz, 1H), 7.15-7.11 (m, 2H), 6.52 (d, J=6.4 Hz, 1H), 4.93 (s, 2H), 3.92 (dd, J=7.6 Hz, 4.4 Hz, 2H), 3.67-3.57 (m, 1H), 3.38 (t, J=11.2 Hz, 2H), 3.23 (s, 3H), 2.39 (dd, J=8.4 Hz, 4.0 Hz, 2H), 1.60 (d, J=12.0 Hz, 2H). LCMS: (Method A), R₁=1.91 min, [M+H]⁺=523.2.

Example 126—5-(5-fluoroisoindolin-2-yl)-N-(3-hydroxyphenyl)-7-(1H-pyrazol-4-yl)-3-(tetrahydro-2H-pyran-4-yl)pyrazolo[1,5-a]pyrimidine-2-carboxamide (115)

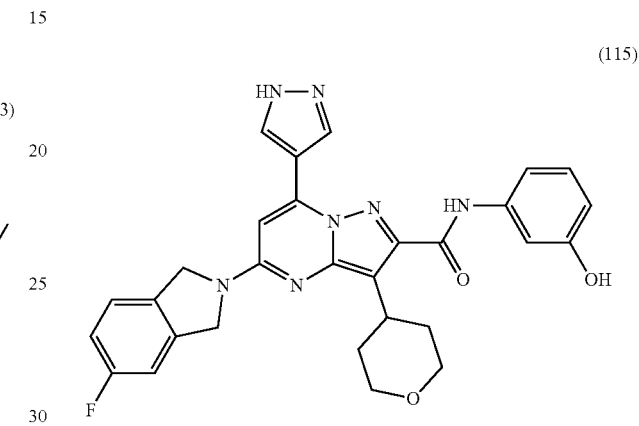

(115)

Starting material used in step 9—5-fluoroisoindoline, starting material used in step 11—3-aminophenol, ¹HNMR (400 MHz, DMSO-d₆) δ 13.45 (s, 1H), 10.05 (s, 1H), 8.94 (s, 2H), 7.41-7.12 (m, 7H), 6.99 (s, 1H), 6.53 (d, J=6.8 Hz, 1H), 4.95 (d, J=13.2 Hz, 4H), 3.98 (d, J=7.6 Hz, 2H), 3.69-3.63 (m, 2H), 3.43 (t, J=11.6 Hz, 3H), 1.60 (d, J=12.0 Hz, 2H). LCMS: (Method A), R₁=2.08 min, [M+H]⁺=540.1.

Example 127—5-(5-chloroisoindolin-2-yl)-N-(3-hydroxyphenyl)-7-(1H-pyrazol-4-yl)-3-(tetrahydro-2H-pyran-4-yl)pyrazolo[1,5-a]pyrimidine-2-carboxamide (116)

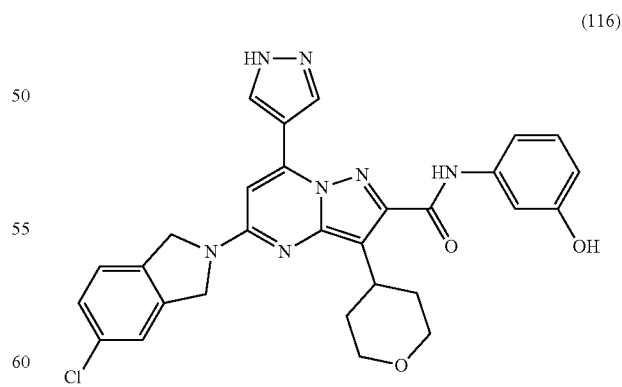

(116)

Starting material used in step 9—5-chloroisoindoline, starting material used in step 11—3-aminophenol, ¹HNMR (400 MHz, DMSO-d₆) δ 13.50 (s, 1H), 10.09 (s, 1H), 9.40 (s, 1H), 9.26 (s, 1H), 8.70 (s, 1H), 7.44-7.40 (m, 4H), 7.21-7.11 (m, 2H), 7.03 (s, 1H), 6.53 (d, J=7.2 Hz, 1H), 4.96

(s, 4H), 4.09 (q, J=2.8 Hz, 1.6 Hz, 2H), 4.0 (d, J=4.4 Hz, 2H), 3.70-3.61 (m, 1H), 3.43 (t, J=11.2 Hz, 2H), 1.60 (d, J=12.0 Hz, 2H). LCMS: (Method A), $R_t$=2.37 min, $[M+H]^+$= 556.2.

Example 128 Biological Activity 1.1 Cell Culture

The media antibiotics and serum were purchased from Invitrogen (Life Technologies). PC3 cells were purchased from ATCC (Granville, NSW, Australia). PC3 cells were expanded in cell culture T75 flasks with vented cap and then preserved in low passage number. The medium used for PC3 cells was RPMI (GlutaMAX) supplemented with 10% FCS and 1% penicillin/streptomycin (culture media). The cells were maintained at 37° C. in a humidified 95% (v/v) air/5% (v/v) CO2 environment and were grown up to 80% confluence.

1.2 xCELLigence Plates

XCELLigence® real-time cell analysis (RTCA) instrument (ACEA Biosciences), 16-well ACEA CIM-Plates, 16-well ACEA E-Plat and assembly tool were purchased from ELITechGroup empowering IVD (Braeside, Australia). The Matrigel was purchased from Corning (Australia).

1.2.1 Cell Seeding into CIM Plates and Cell Invasion and Proliferation on the xCELLigence RTCA DP To measure cell invasion under compound treatment the upper chamber of the CIM plate was coated with 5% Matrigel diluted in SF RPMI (20 μl) and incubated in a 37° C. tissue culture incubator for four hours. Using the assembly tool to support the chambers the lower chamber was filled with (160 μl) of culture media containing the compound in specific concertation from 25 uM to 1 uM and two controls (DMSO 0.1% and ESFAM 4C 10 uM) (see the schematic in FIG. 1). Once the upper chamber was placed on the top of the lower chamber it was loaded with (40 μl) serum-free (SF) RPMI containing the compound as previously stated. After one hour calibration in 37° C., plates were placed into the xCELLigence station, and the base-line electric impedance was measured to confirm that all wells and connections were working properly. In case of connection problem, the software automatically informs the researcher about the nature of the problem in the message section. Subsequently cells were trypsinized and upon harvesting and counting they were diluted in SF RPMI to desired density ($3 \times 10^4$) and seeded (100 μl) in the wells. After 30 minutes of incubation in room-temperature to allow cell attachment the plates were loaded in the xCELLigence RTCA DP machine. The cell invasion was monitored in real-time for the duration of 72 hours.

It is important to note that the same procedure but with minor changes was performed to measure cell proliferation under compound treatment, where cell proliferation was monitored in real-time using the E-plate and the xCELLigence station see FIG. 1.

1.3 Software and Data Analysis

The xCELLigence system automatically monitored the electrical impedance value of each well and expressed as a cell index (CI) value for the duration of 72 hours. The data for treatments was automatically grouped as the mean±standard deviation. The software version used in these experiments is 1.2.1. The electronic record of the experimental data is automatically saved in file that cannot be altered or changed by the researcher.

Statistical analysis was performed using Microsoft® Office EXCEL and GraphPad Prism 7. The IC50 was calculated from the four-parameter dose-response curve (log(inhibitor) vs. response-variable slopes). Where the row-data was inserted in GraphPad Prism 7 (Dose response x-log(dose)) and analysed for XY nonlinear regression (curve fit), dose response-inhibition, log(inhibitor) vs response variable slope (four parameters). For the IC90 calculation the log(IC50)=log(IC90)-(1/HillSlope)*log(9) equation was used in EXCEL based on the raw data extracted from xCELLigence system and the dose-response curve.

Representative inhibition data is given in the table below:

| Effect of compounds on the invention on prostate cancer cells (μM) | |
| --- | --- |
| Cmpd | IC50 |
| 1 | 6.9 |
| 2 | 16.89 |
| 3 | 11.9 |
| 4 | 0.81 |
| 5 | 1.198 |
| 6 | 11.67 |
| 7 | 9.49 |
| 8 | 5.198 |
| 9 | 4.28 |
| 10 | 3.71 |
| 11 | 9.71 |
| 12 | 6.64 |
| 13 | 4.71 |
| 14 | 1.96 |
| 15 | 1.022 |
| 16 | 150 |
| 17 | 9.67 |
| 18 | 7.95 |
| 19 | 12.78 |
| 20 | 3.56 |
| 21 | n/a |
| 22 | 3.71 |
| 23 | 2.83 |
| 24 | 1.42 |
| 25 | 2.43 |
| 26 | 9.74 |
| 27 | 1.99 |
| 28 | 2.03 |
| 29 | 3.58 |
| 30 | 1.61 |
| 31 | 2.215 |
| 32 | 3.044 |
| 33 | 2.59 |
| 34 | 8.97 |
| 35 | 1.40 |
| 36 | 1.47 |
| 37 | 3.1 |
| 38 | 4.36 |
| 39 | 8.46 |
| 40 | 3.96 |
| 41 | 9.86 |
| 42 | 2.86 |
| 43 | 6.09 |
| 44 | 12.23 |
| 45 | 10.78 |
| 46 | 7.0 |
| 47 | 6.18 |
| 48 | 2.77 |
| 49 | 5.85 |
| 50 | 1.46 |
| 51 | 3.55 |
| 52 | 5.52 |
| 53 | 2.76 |
| 54 | 1.65 |
| 55 | 7.86 |
| 56 | 2.83 |
| 57 | 2.586 |
| 58 | 10.07 |
| 59 | 4.38 |
| 60 | 7.39 |
| 61 | 3.68 |
| 62 | 5.22 |

-continued

| Effect of compounds on the invention on prostate cancer cells (μM) | |
|---|---|
| Cmpd | IC50 |
| 63 | 4.65 |
| 64 | 9.587 |
| 65 | 11.41 |
| 66 | 19.74 |
| 67 | 5.94 |
| 68 | 5.76 |
| 69 | 1.9 |
| 70 | 5.87 |
| 71 | 3.15 |
| 72 | 2.91 |
| 73 | 4.91 |
| 74 | 1.34 |
| 75 | 5.68 |
| 76 | 11.57 |
| 77 | 11.01 |
| 78 | 3.03 |
| 79 | 4.05 |
| 80 | 1.003 |
| 81 | 2.45 |
| 82 | 2.92 |
| 83 | 10.08 |
| 84 | 1.099 |
| 85 | 6.51 |
| 86 | n/a |
| 87 | n/a |
| 88 | n/a |
| 89 | 3.11 |
| 90 | n/a |
| 91 | n/a |
| 92 | n/a |
| 93 | n/a |
| 94 | 6.21 |
| 95 | 2.12 |
| 96 | 6.47 |
| 97 | 1.08 |
| 98 | 12.54 |
| 99 | 1.23 |
| 100 | 2.23 |
| 101 | 3.99 |
| 102 | 1.27 |
| 103 | n/a |
| 104 | 2.89 |
| 105 | n/a |
| 106 | 2.02 |
| 107 | 2.364 |
| 108 | 18.7 |
| 109 | 3.23 |
| 110 | n/a |
| 111 | n/a |
| 112 | n/a |
| 113 | n/a |
| 114 | n/a |
| 115 | n/a |
| 116 | n/a |
| 117 | n/a |
| 118 | n/a |
| 119 | 3.149 |
| 120 | 4.94 |
| 121 | 2.752 |
| 122 | 9.073 |
| 123 | 1.025 |
| 124 | 1.149 |
| 125 | 7.621 |
| 126 | 1.205 |
| 127 | n/a |

Finally, it will be appreciated that various modifications and variations of the methods and compositions of the invention described herein would be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that is apparent to those skilled in the art are intended to be within the scope of the present invention.

The invention claimed is:

1. A compound of Formula (I):

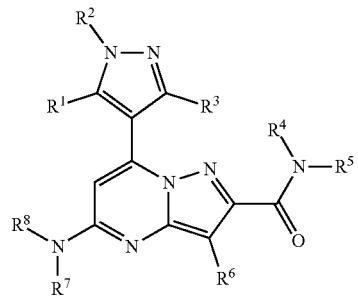

Formula (I)

wherein $R^1$, $R^2$, and $R^3$ are each independently selected from the group consisting of H and $C_1$-$C_{12}$alkyl, $R^4$ is selected from the group consisting of H and $C_1$-$C_{12}$alkyl, $R^5$ is selected from the group consisting of H, optionally substituted $C_6$-$C_{18}$aryl, optionally substituted $C_1$-$C_{18}$heteroaryl, optionally substituted $C_6$-$C_{18}$aryl$C_1$-$C_{12}$alkyl-, and optionally substituted $C_1$-$C_{18}$heteroaryl$C_1$-$C_{12}$alkyl-;

$R^6$ is selected from the group consisting of H, $C_1$-$C_{12}$alkyl, $C_3$-$C_6$ cycloalkyl, and $C_1$-$C_5$ heterocloalkyl, $R^7$ is selected from the group consisting of H and $C_1$-$C_{12}$alkyl;

$R^8$ is selected from the group consisting of H, $C_1$-$C_{12}$alkyl, optionally substituted $C_6$-$C_{18}$aryl, optionally substituted $C_1$-$C_{18}$heteroaryl, optionally substituted $C_6$-$C_{18}$aryl$C_1$-$C_{12}$alkyl-, and optionally substituted $C_1$-$C_{18}$heteroaryl$C_1$-$C_{12}$alkyl-;

or $R^7$ and $R^8$ when taken together with the nitrogen atom to which they are attached form an optionally substituted $C_2$-$C_{12}$heterocyclic group;

or a pharmaceutically acceptable salt thereof.

2. A compound according to claim 1, wherein $R^1$ and $R^3$ are H.

3. A compound according to claim 1, wherein $R^2$ is H.

4. A compound according to claim 1, wherein $R^4$ is H.

5. A compound according to claim 1, wherein $R^5$ is optionally substituted $C_6$-$C_{18}$aryl.

6. A compound according to claim 1, wherein $R^5$ is optionally substituted phenyl.

7. A compound according to claim 1, wherein $R^6$ is $C_1$-$C_{12}$alkyl.

8. A compound according to claim 1, wherein $R^6$ is isopropyl or tert-butyl.

9. A compound according to claim 1, wherein $R^7$ and $R^8$ when taken together with the nitrogen atom to which they are attached form an optionally substituted $C_2$-$C_{12}$heterocyclic group.

10. A compound according to claim 9, wherein the $C_2$-$C_{12}$heterocyclic group is a group of the formula:

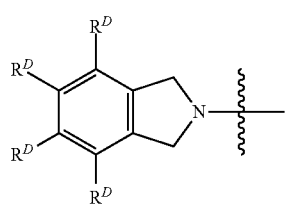

wherein $R^D$ is independently selected from the group consisting of H, halogen, OH, $NO_2$, CN, SH, $NH_2$, $CF_3$, $OCF_3$, optionally substituted $C_1$-$C_{12}$alkyl, optionally substituted $C_1$-$C_{12}$haloalkyl, optionally substituted $C_2$-$C_{12}$alkenyl, optionally substituted $C_2$-$C_{12}$alkynyl, optionally substituted $C_2$-$C_{12}$heteroalkyl, optionally substituted $C_3$-$C_{12}$cycloalkyl, optionally substituted $C_3$-$C_{12}$cycloalkenyl, optionally substituted $C_2$-$C_{12}$heterocycloalkyl, optionally substituted $C_2$-$C_{12}$heterocycloalkenyl, optionally substituted $C_6$-$C_{18}$aryl, optionally substituted $C_1$-$C_{18}$heteroaryl, optionally substituted $C_1$-$C_{12}$alkyloxy, optionally substituted $C_2$-$C_{12}$alkenyloxy, optionally substituted $C_2$-$C_{12}$alkynyloxy, optionally substituted $C_2$-$C_{10}$heteroalkyloxy, optionally substituted $C_3$-$C_{12}$cycloalkyloxy, optionally substituted $C_3$-$C_{12}$cycloalkenyloxy, optionally substituted $C_2$-$C_{12}$heterocycloalkyloxy, optionally substituted $C_2$-$C_{12}$heterocycloalkenyloxy, optionally substituted $C_6$-$C_{18}$aryloxy, optionally substituted $C_1$-$C_{18}$heteroaryloxy, optionally substituted $C_1$-$C_{12}$alkylamino, $SR^9$, $SO_3H$, $SO_2NR^9R^{10}$, $SO_2R^9$, $SONR^9R^{10}$, $SOR^9$, $COR^9$, COOH, $COOR^9$, $CONR^9R^{10}$, $NR^9COR^{10}$, $NR^9COOR^{10}$, $NR^9SO_2R^{10}$, $NR^9CONR^9R^{10}$, $NR^9R^{10}$, and acyl, and wherein each $R^9$ and $R^{10}$ are independently selected from the group consisting of H and $C_1$-$C_{12}$alkyl.

11. A compound according to claim 1, selected from the group consisting of:

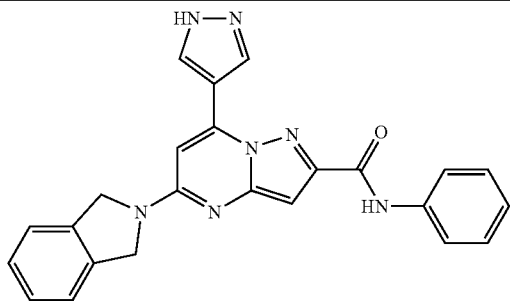

23

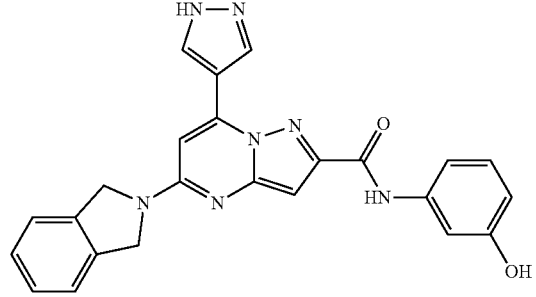 [SMILES: O=C(Nc1cccc(O)c1)c1cc2nc(N3Cc4ccccc4C3)cc(-c3cn[nH]c3)n2n1]

24

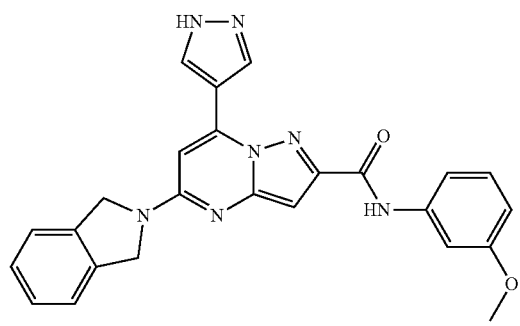 [SMILES: COc1cccc(NC(=O)c2cc3nc(N4Cc5ccccc5C4)cc(-c4cn[nH]c4)n3n2)c1]

25

26
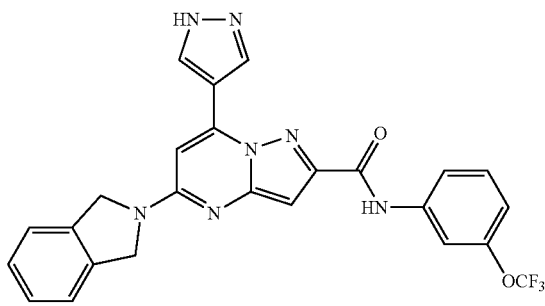 [SMILES: O=C(Nc1cccc(OC(F)(F)F)c1)c1cc2nc(N3Cc4ccccc4C3)cc(-c3cn[nH]c3)n2n1]
27
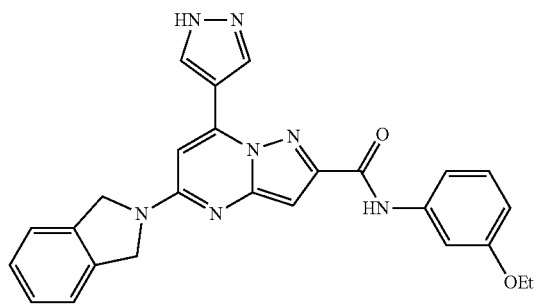 [SMILES: CCOc1cccc(NC(=O)c2cc3nc(N4Cc5ccccc5C4)cc(-c4cn[nH]c4)n3n2)c1]
28
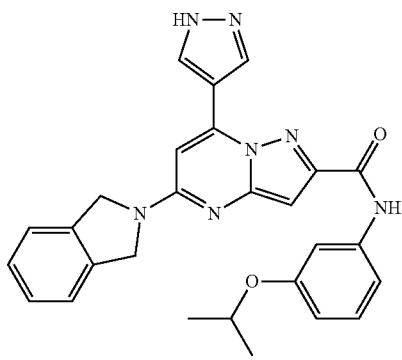 [SMILES: CC(C)Oc1cccc(NC(=O)c2cc3nc(N4Cc5ccccc5C4)cc(-c4cn[nH]c4)n3n2)c1]
47
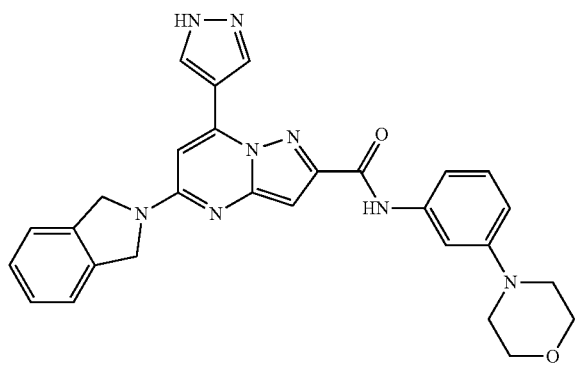 [SMILES: O=C(Nc1cccc(N2CCOCC2)c1)c1cc2nc(N3Cc4ccccc4C3)cc(-c3cn[nH]c3)n2n1]

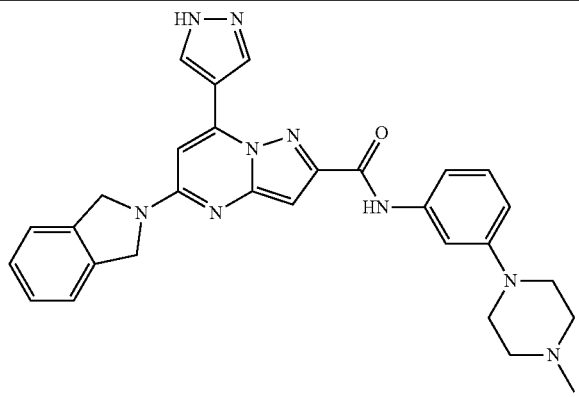
48
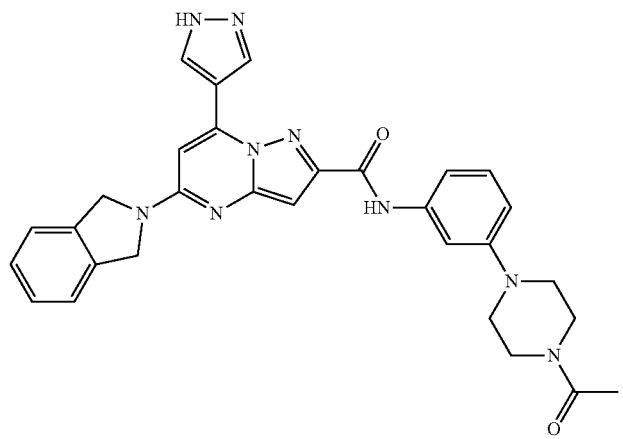 [SMILES: CC(=O)N1CCN(c2cccc(NC(=O)c3cc4nc(N5Cc6ccccc6C5)cc(-c5cn[nH]c5)n4n3)c2)CC1]
49
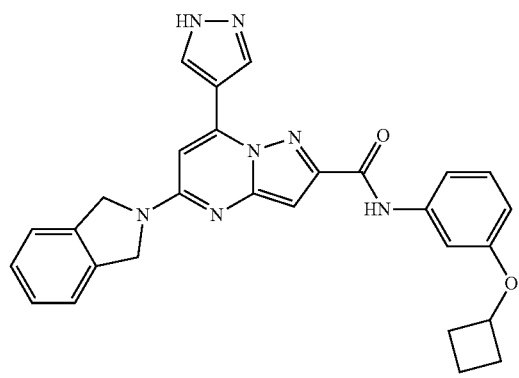 [SMILES: O=C(Nc1cccc(OC2CCC2)c1)c1cc2nc(N3Cc4ccccc4C3)cc(-c3cn[nH]c3)n2n1]
50
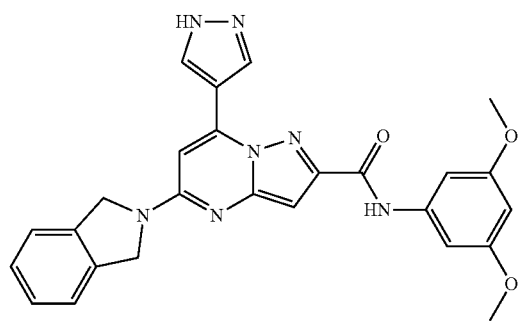 [SMILES: COc1cc(NC(=O)c2cc3nc(N4Cc5ccccc5C4)cc(-c4cn[nH]c4)n3n2)cc(OC)c1]
51

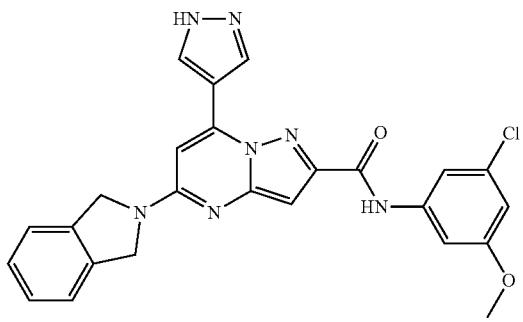 [SMILES: COc1cc(Cl)cc(NC(=O)c2cc3nc(N4Cc5ccccc5C4)cc(-c4cn[nH]c4)n3n2)c1]
52
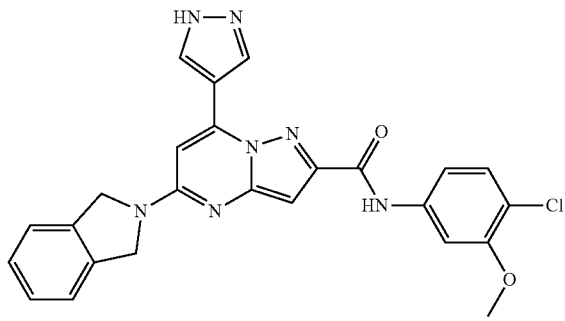 [SMILES: COc1cc(NC(=O)c2cc3nc(N4Cc5ccccc5C4)cc(-c4cn[nH]c4)n3n2)ccc1Cl]
53
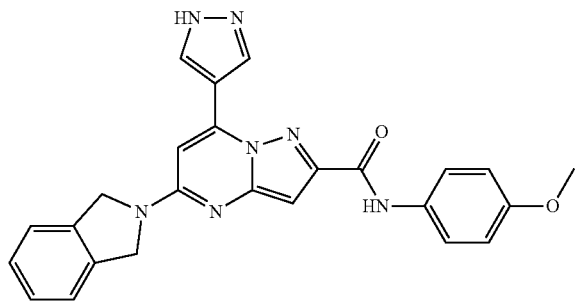 [SMILES: COc1ccc(NC(=O)c2cc3nc(N4Cc5ccccc5C4)cc(-c4cn[nH]c4)n3n2)cc1]
54
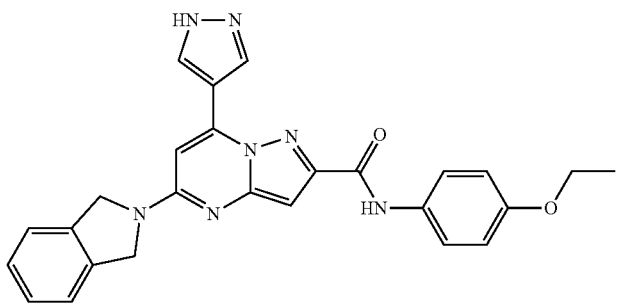 [SMILES: CCOc1ccc(NC(=O)c2cc3nc(N4Cc5ccccc5C4)cc(-c4cn[nH]c4)n3n2)cc1]
55
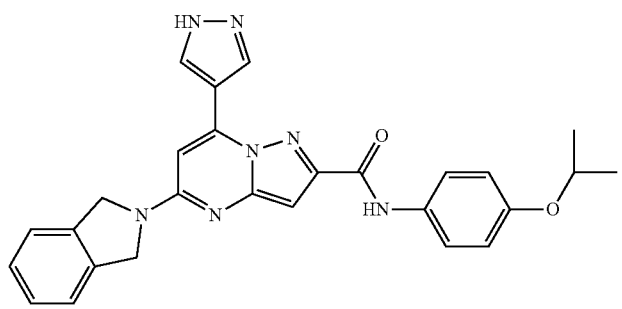
56

-continued
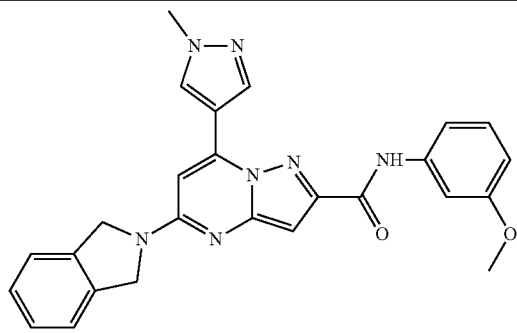
57
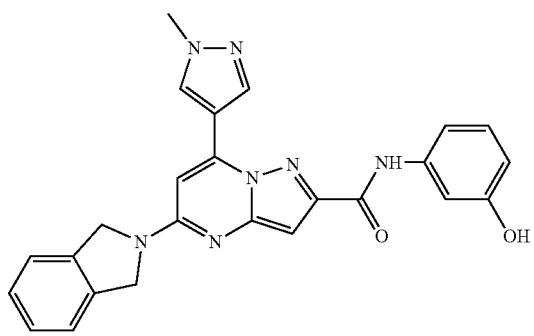 [SMILES: Cn1cc(-c2cc(N3Cc4ccccc4C3)nc3cc(C(=O)Nc4cccc(O)c4)nn23)cn1]
58
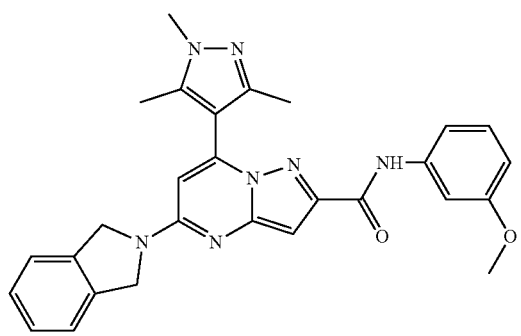 [SMILES: COc1cccc(NC(=O)c2cc3nc(N4Cc5ccccc5C4)cc(-c4c(C)nn(C)c4C)n3n2)c1]
59
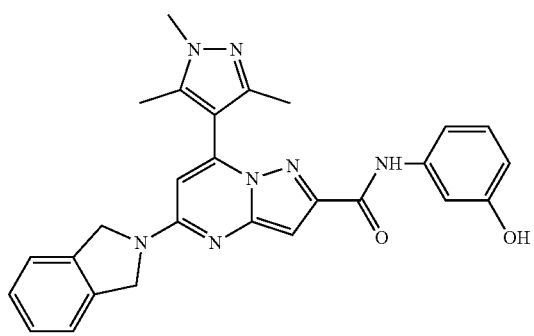 [SMILES: Cc1nn(C)c(C)c1-c1cc(N2Cc3ccccc3C2)nc2cc(C(=O)Nc3cccc(O)c3)nn12]
60
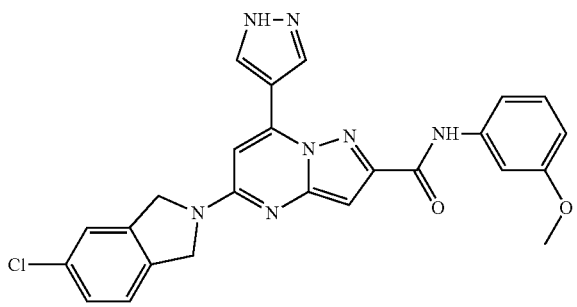 [SMILES: COc1cccc(NC(=O)c2cc3nc(N4Cc5ccc(Cl)cc5C4)cc(-c4cn[nH]c4)n3n2)c1]
61

-continued
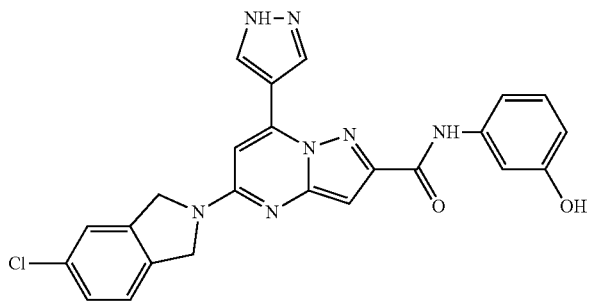 [SMILES: O=C(Nc1cccc(O)c1)c1cc2nc(N3Cc4ccc(Cl)cc4C3)cc(-c3cn[nH]c3)n2n1]
62
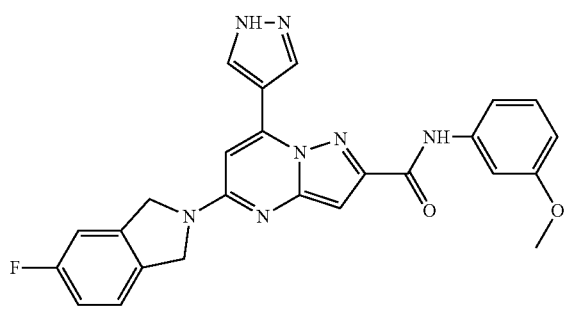 [SMILES: COc1cccc(NC(=O)c2cc3nc(N4Cc5ccc(F)cc5C4)cc(-c4cn[nH]c4)n3n2)c1]
63
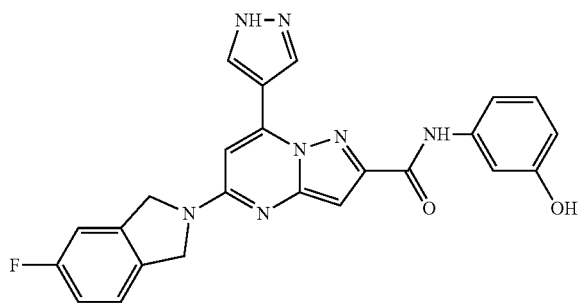 [SMILES: O=C(Nc1cccc(O)c1)c1cc2nc(N3Cc4ccc(F)cc4C3)cc(-c3cn[nH]c3)n2n1]
64
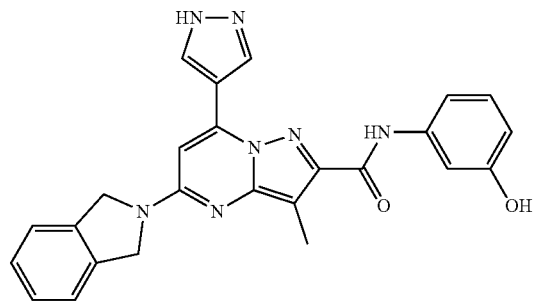 [SMILES: Cc1c(C(=O)Nc2cccc(O)c2)nn2c(-c3cn[nH]c3)cc(N3Cc4ccccc4C3)nc12]
65
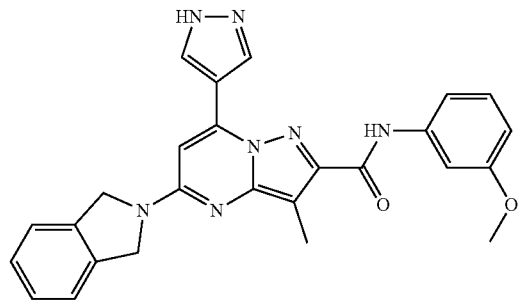 [SMILES: COc1cccc(NC(=O)c2nn3c(-c4cn[nH]c4)cc(N4Cc5ccccc5C4)nc3c2C)c1]
66

-continued
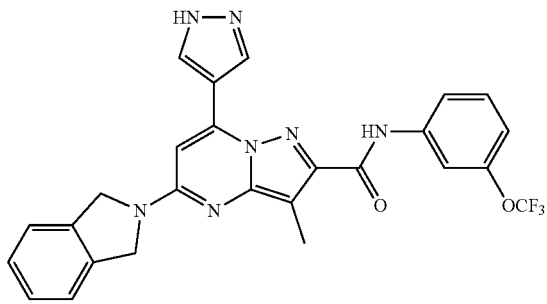 [SMILES: Cc1c(C(=O)Nc2cccc(OC(F)(F)F)c2)nn2c(-c3cn[nH]c3)cc(N3Cc4ccccc4C3)nc12]
67
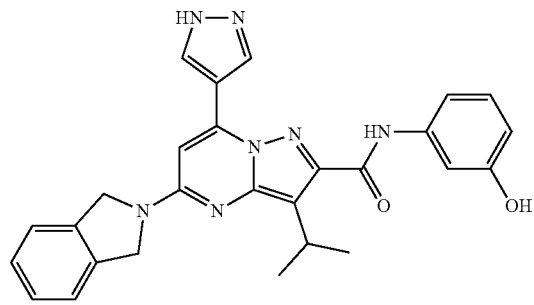 [SMILES: CC(C)c1c(C(=O)Nc2cccc(O)c2)nn2c(-c3cn[nH]c3)cc(N3Cc4ccccc4C3)nc12]
71
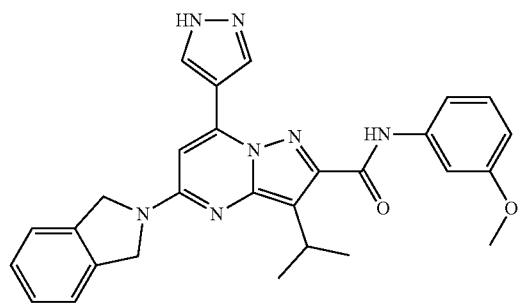 [SMILES: COc1cccc(NC(=O)c2nn3c(-c4cn[nH]c4)cc(N4Cc5ccccc5C4)nc3c2C(C)C)c1]
72
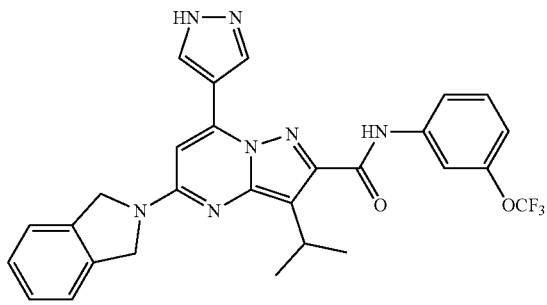 [SMILES: CC(C)c1c(C(=O)Nc2cccc(OC(F)(F)F)c2)nn2c(-c3cn[nH]c3)cc(N3Cc4ccccc4C3)nc12]
73
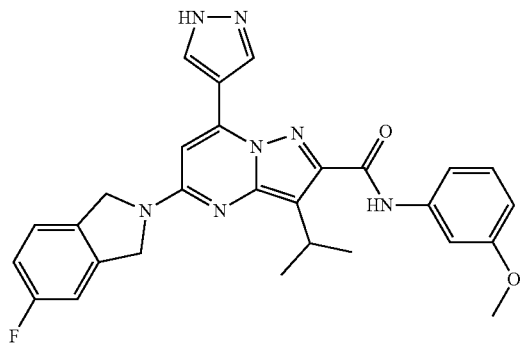
77

-continued
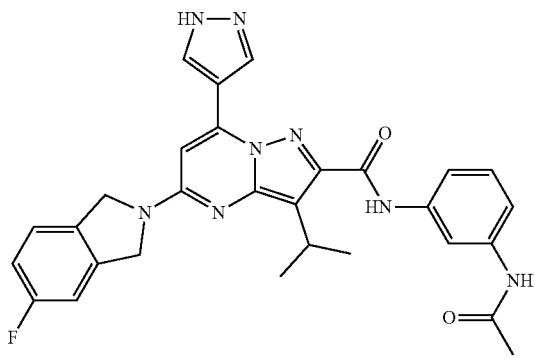 [SMILES: CC(=O)Nc1cccc(NC(=O)c2nn3c(-c4cn[nH]c4)cc(N4Cc5ccc(F)cc5C4)nc3c2C(C)C)c1]
78
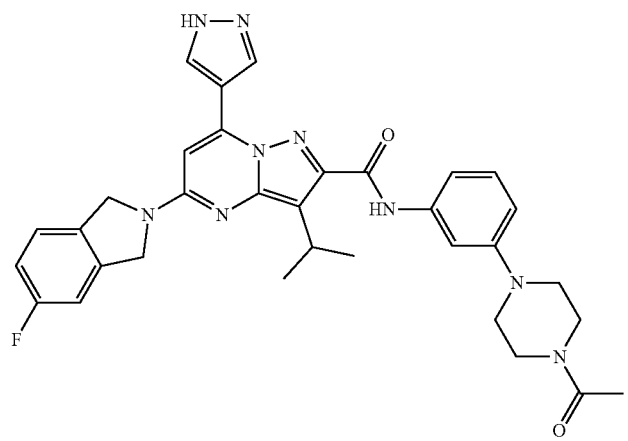 [SMILES: CC(=O)N1CCN(c2cccc(NC(=O)c3nn4c(-c5cn[nH]c5)cc(N5Cc6ccc(F)cc6C5)nc4c3C(C)C)c2)CC1]
79
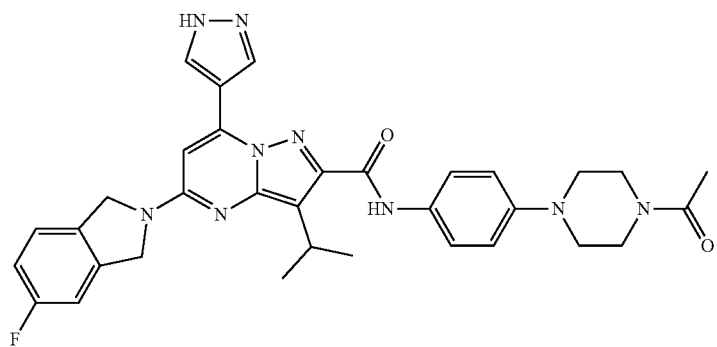 [SMILES: CC(=O)N1CCN(c2ccc(NC(=O)c3nn4c(-c5cn[nH]c5)cc(N5Cc6ccc(F)cc6C5)nc4c3C(C)C)cc2)CC1]
80
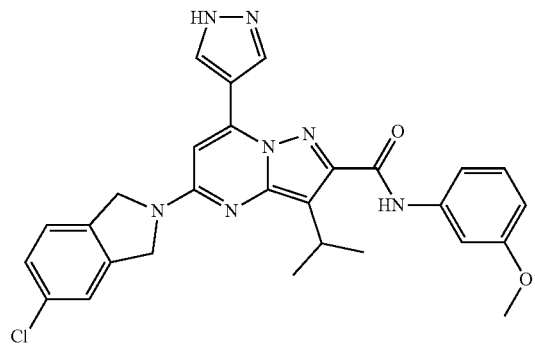 [SMILES: COc1cccc(NC(=O)c2nn3c(-c4cn[nH]c4)cc(N4Cc5ccc(Cl)cc5C4)nc3c2C(C)C)c1]
81

82
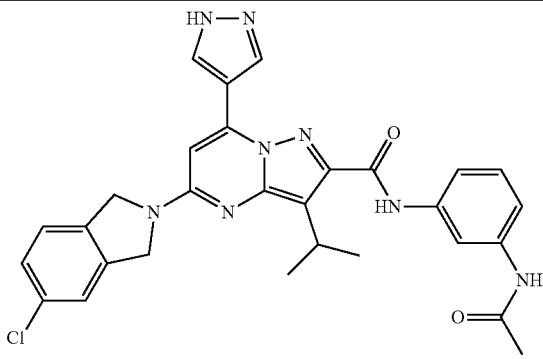
83
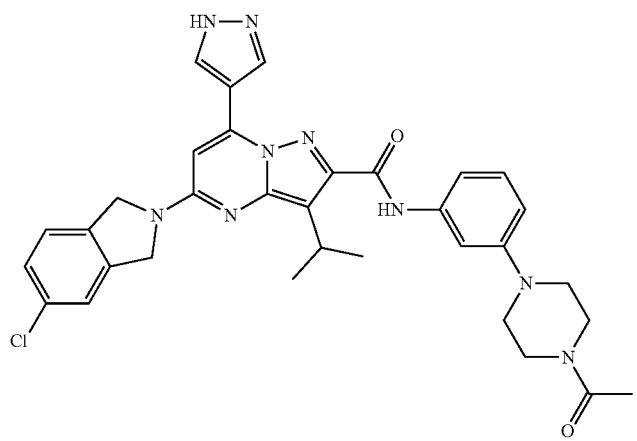 [SMILES: CC(=O)N1CCN(c2cccc(NC(=O)c3nn4c(-c5cn[nH]c5)cc(N5Cc6ccc(Cl)cc6C5)nc4c3C(C)C)c2)CC1]
84
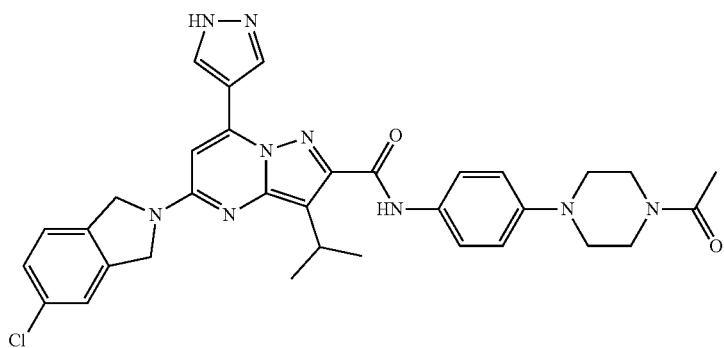 [SMILES: CC(=O)N1CCN(c2ccc(NC(=O)c3nn4c(-c5cn[nH]c5)cc(N5Cc6ccc(Cl)cc6C5)nc4c3C(C)C)cc2)CC1]
85
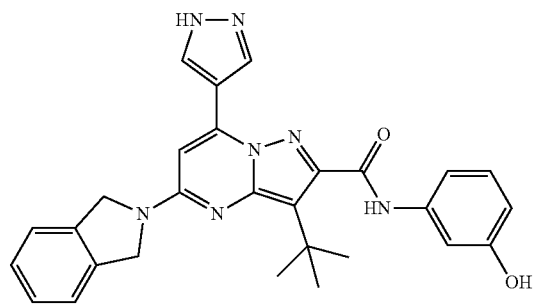 [SMILES: CC(C)(C)c1c(C(=O)Nc2cccc(O)c2)nn2c(-c3cn[nH]c3)cc(N3Cc4ccccc4C3)nc12]

86
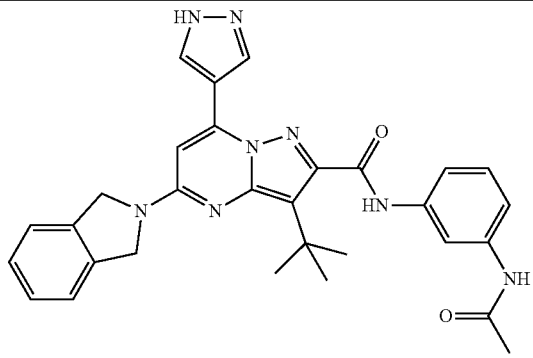
87
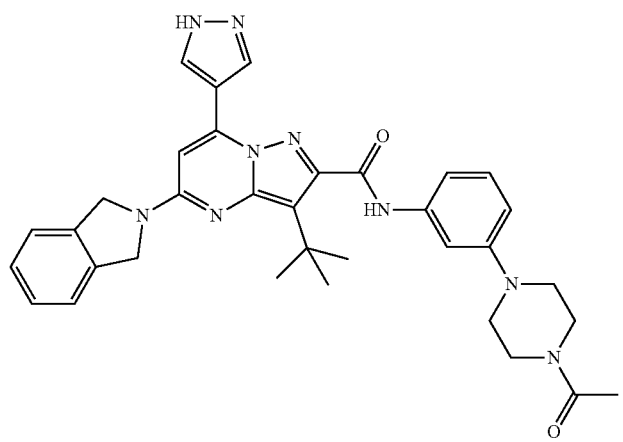 [SMILES: CC(=O)N1CCN(c2cccc(NC(=O)c3nn4c(-c5cn[nH]c5)cc(N5Cc6ccccc6C5)nc4c3C(C)(C)C)c2)CC1]
88
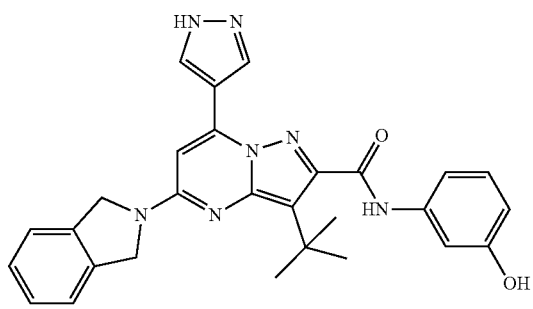 [SMILES: CC(C)(C)c1c(C(=O)Nc2cccc(O)c2)nn2c(-c3cn[nH]c3)cc(N3Cc4ccccc4C3)nc12]
89
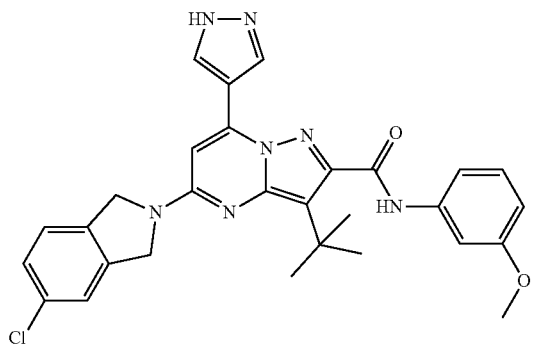 [SMILES: COc1cccc(NC(=O)c2nn3c(-c4cn[nH]c4)cc(N4Cc5ccc(Cl)cc5C4)nc3c2C(C)(C)C)c1]

90
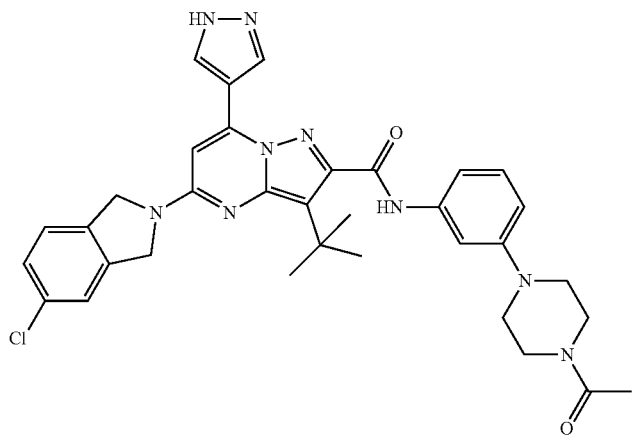
91
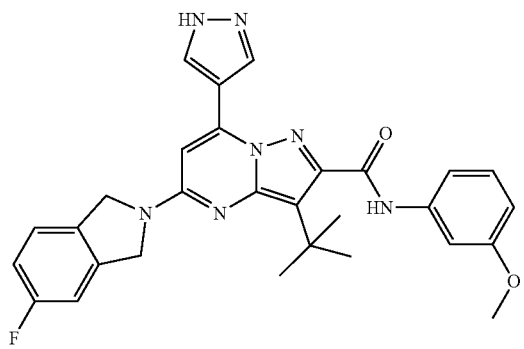 [SMILES: COc1cccc(NC(=O)c2nn3c(-c4cn[nH]c4)cc(N4Cc5ccc(F)cc5C4)nc3c2C(C)(C)C)c1]
92
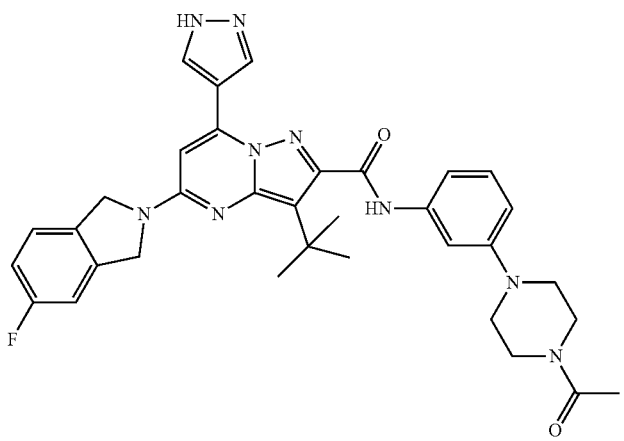 [SMILES: CC(=O)N1CCN(c2cccc(NC(=O)c3nn4c(-c5cn[nH]c5)cc(N5Cc6ccc(F)cc6C5)nc4c3C(C)(C)C)c2)CC1]
93
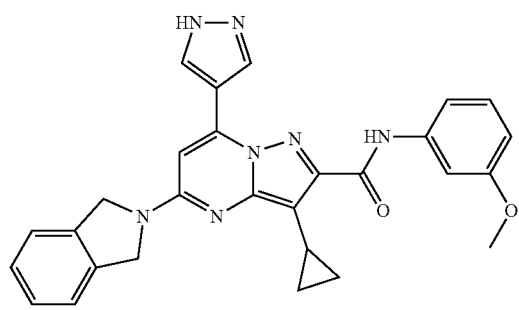 [SMILES: COc1cccc(NC(=O)c2nn3c(-c4cn[nH]c4)cc(N4Cc5ccccc5C4)nc3c2C2CC2)c1]

| | |
|---|---|
| 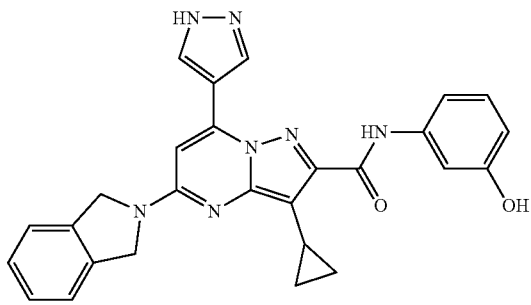 [SMILES: O=C(Nc1cccc(O)c1)c1nn2c(-c3cn[nH]c3)cc(N3Cc4ccccc4C3)nc2c1C1CC1] | 94 |
| 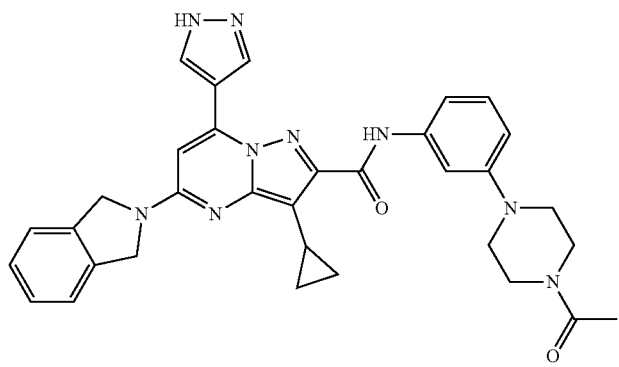 [SMILES: CC(=O)N1CCN(c2cccc(NC(=O)c3nn4c(-c5cn[nH]c5)cc(N5Cc6ccccc6C5)nc4c3C3CC3)c2)CC1] | 95 |
| 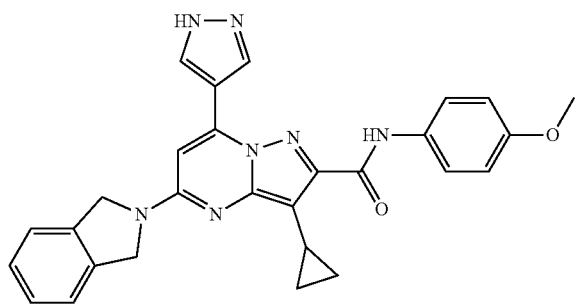 [SMILES: COc1ccc(NC(=O)c2nn3c(-c4cn[nH]c4)cc(N4Cc5ccccc5C4)nc3c2C2CC2)cc1] | 96 |
| 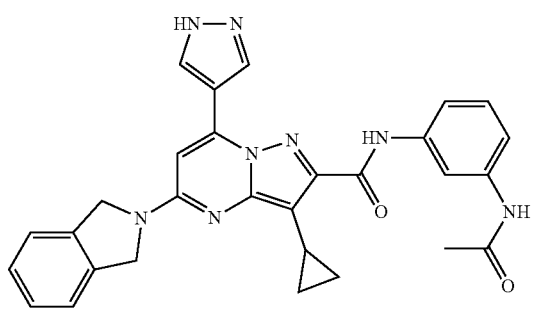 [SMILES: CC(=O)Nc1cccc(NC(=O)c2nn3c(-c4cn[nH]c4)cc(N4Cc5ccccc5C4)nc3c2C2CC2)c1] | 97 |
| 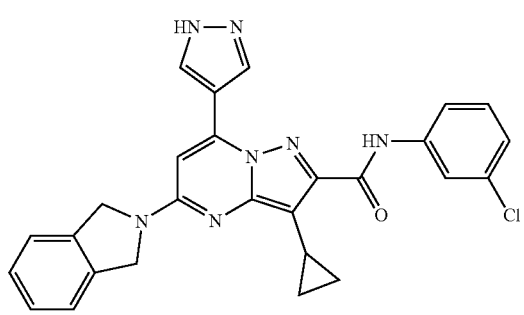 [SMILES: O=C(Nc1cccc(Cl)c1)c1nn2c(-c3cn[nH]c3)cc(N3Cc4ccccc4C3)nc2c1C1CC1] | 98 |

-continued
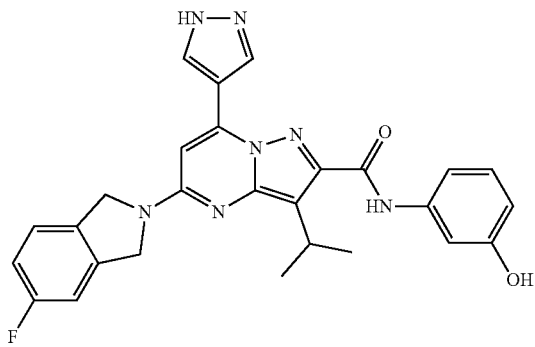 [SMILES: CC(C)c1c(C(=O)Nc2cccc(O)c2)nn2c(-c3cn[nH]c3)cc(N3Cc4ccc(F)cc4C3)nc12]
99
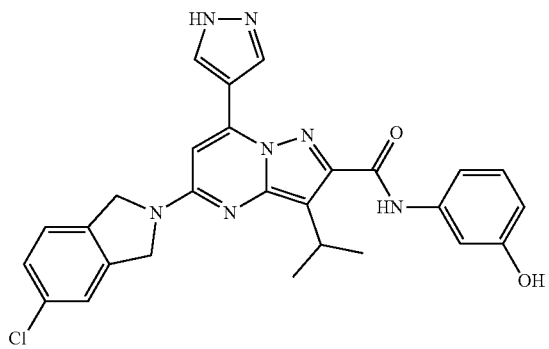 [SMILES: CC(C)c1c(C(=O)Nc2cccc(O)c2)nn2c(-c3cn[nH]c3)cc(N3Cc4ccc(Cl)cc4C3)nc12]
100
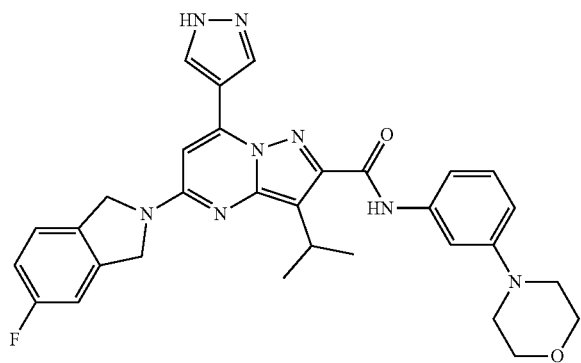 [SMILES: CC(C)c1c(C(=O)Nc2cccc(N3CCOCC3)c2)nn2c(-c3cn[nH]c3)cc(N3Cc4ccc(F)cc4C3)nc12]
101
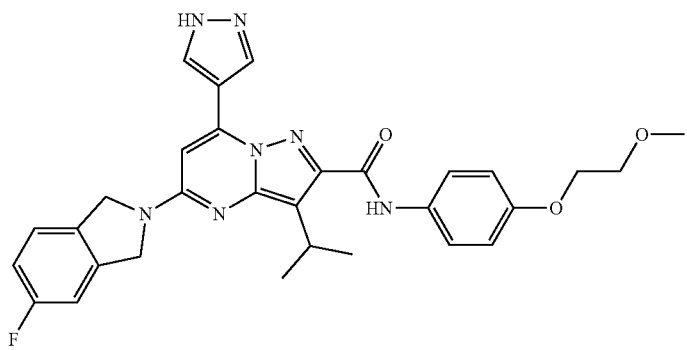 [SMILES: COCCOc1ccc(NC(=O)c2nn3c(-c4cn[nH]c4)cc(N4Cc5ccc(F)cc5C4)nc3c2C(C)C)cc1]
102

-continued
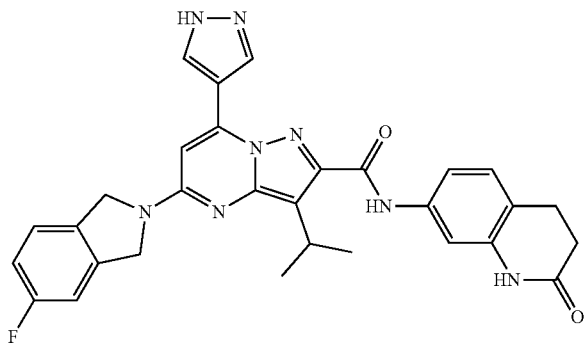 [SMILES: CC(C)c1c(C(=O)Nc2ccc3c(c2)NC(=O)CC3)nn2c(-c3cn[nH]c3)cc(N3Cc4ccc(F)cc4C3)nc12]
103
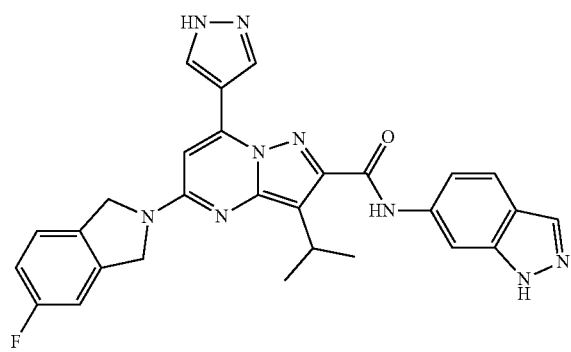 [SMILES: CC(C)c1c(C(=O)Nc2ccc3cn[nH]c3c2)nn2c(-c3cn[nH]c3)cc(N3Cc4ccc(F)cc4C3)nc12]
104
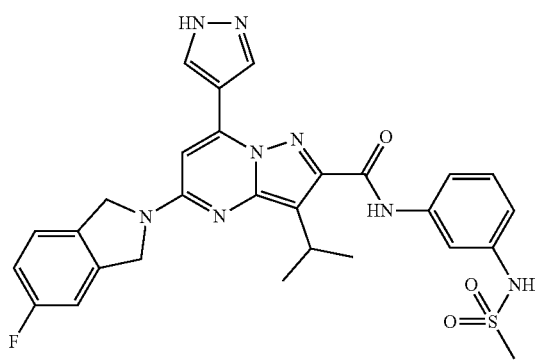 [SMILES: CC(C)c1c(C(=O)Nc2cccc(NS(C)(=O)=O)c2)nn2c(-c3cn[nH]c3)cc(N3Cc4ccc(F)cc4C3)nc12]
105
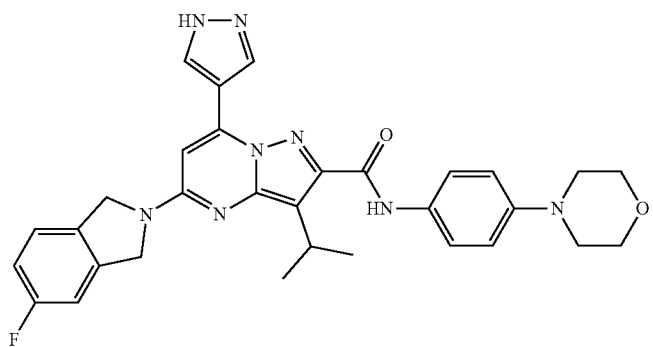 [SMILES: CC(C)c1c(C(=O)Nc2ccc(N3CCOCC3)cc2)nn2c(-c3cn[nH]c3)cc(N3Cc4ccc(F)cc4C3)nc12]
106

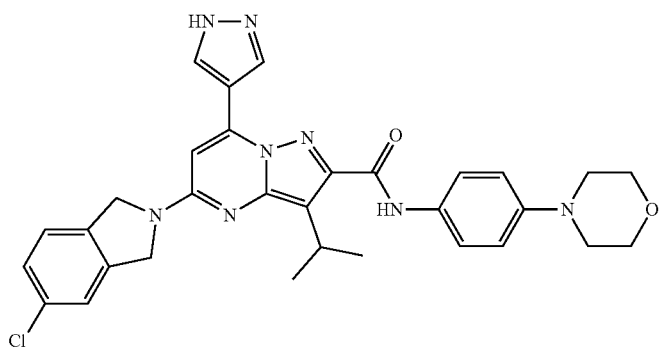 [SMILES: CC(C)c1c(C(=O)Nc2ccc(N3CCOCC3)cc2)nn2c(-c3cn[nH]c3)cc(N3Cc4ccc(Cl)cc4C3)nc12]
107
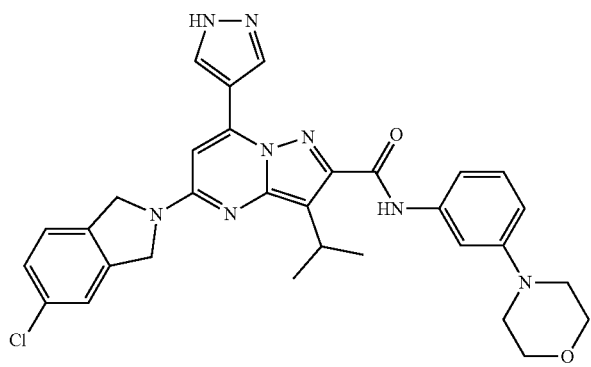 [SMILES: CC(C)c1c(C(=O)Nc2cccc(N3CCOCC3)c2)nn2c(-c3cn[nH]c3)cc(N3Cc4ccc(Cl)cc4C3)nc12]
108
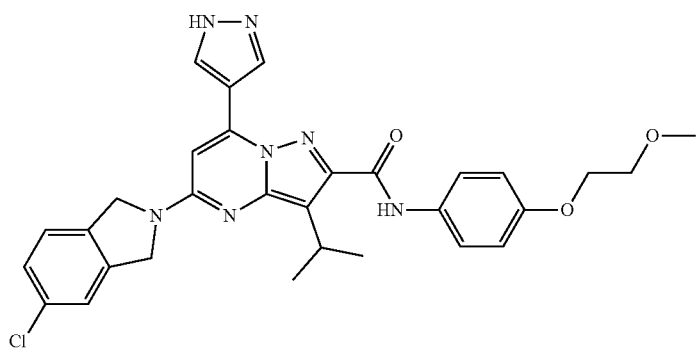 [SMILES: COCCOc1ccc(NC(=O)c2nn3c(-c4cn[nH]c4)cc(N4Cc5ccc(Cl)cc5C4)nc3c2C(C)C)cc1]
109
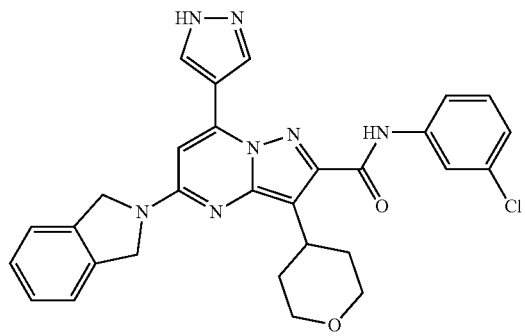 [SMILES: O=C(Nc1cccc(Cl)c1)c1nn2c(-c3cn[nH]c3)cc(N3Cc4ccccc4C3)nc2c1C1CCOCC1]
110

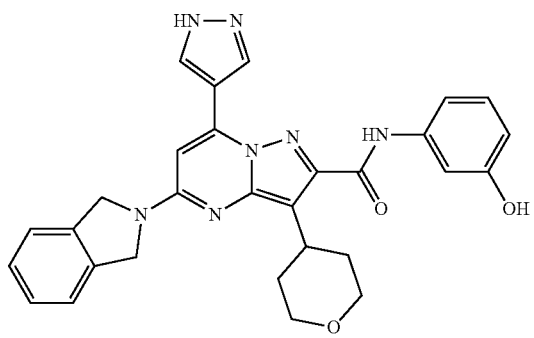 [SMILES: O=C(Nc1cccc(O)c1)c1nn2c(-c3cn[nH]c3)cc(N3Cc4ccccc4C3)nc2c1C1CCOCC1]
111
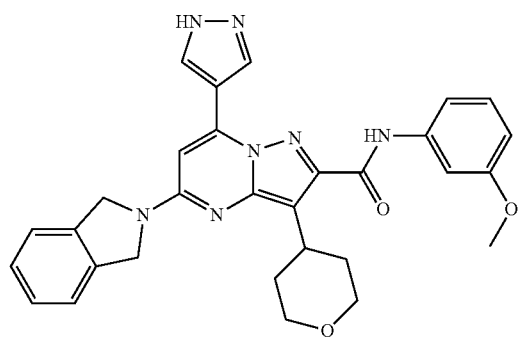 [SMILES: COc1cccc(NC(=O)c2nn3c(-c4cn[nH]c4)cc(N4Cc5ccccc5C4)nc3c2C2CCOCC2)c1]
112
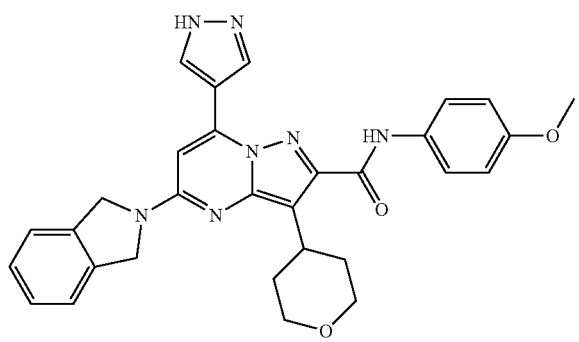 [SMILES: COc1ccc(NC(=O)c2nn3c(-c4cn[nH]c4)cc(N4Cc5ccccc5C4)nc3c2C2CCOCC2)cc1]
113
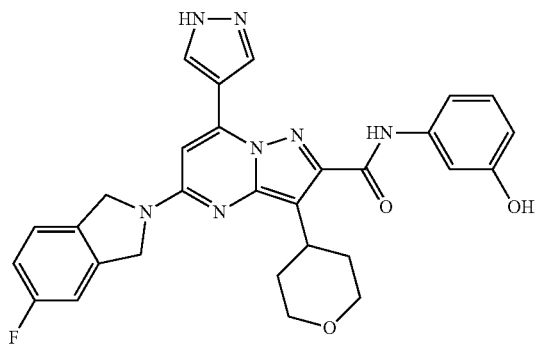 [SMILES: O=C(Nc1cccc(O)c1)c1nn2c(-c3cn[nH]c3)cc(N3Cc4ccc(F)cc4C3)nc2c1C1CCOCC1]
115

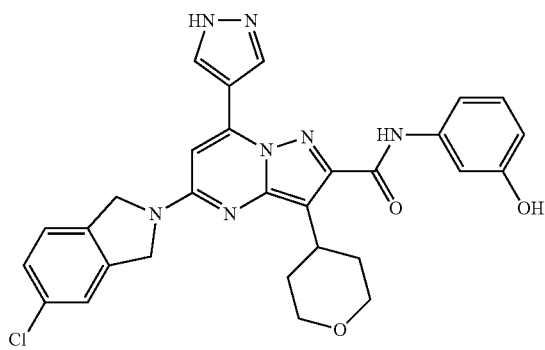 [SMILES: O=C(Nc1cccc(O)c1)c1nn2c(-c3cn[nH]c3)cc(N3Cc4ccc(Cl)cc4C3)nc2c1C1CCOCC1]
116
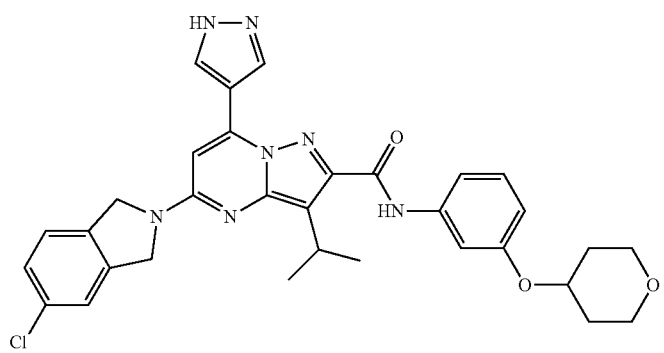 [SMILES: CC(C)c1c(C(=O)Nc2cccc(OC3CCOCC3)c2)nn2c(-c3cn[nH]c3)cc(N3Cc4ccc(Cl)cc4C3)nc12]
117
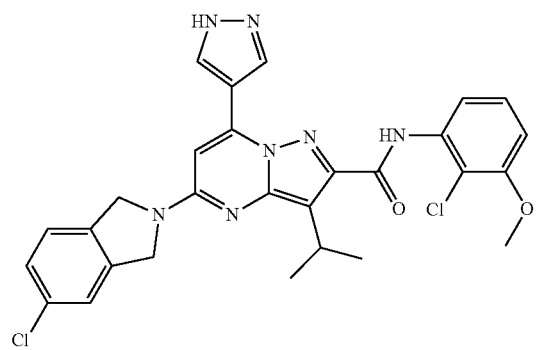 [SMILES: COc1cccc(NC(=O)c2nn3c(-c4cn[nH]c4)cc(N4Cc5ccc(Cl)cc5C4)nc3c2C(C)C)c1Cl]
118
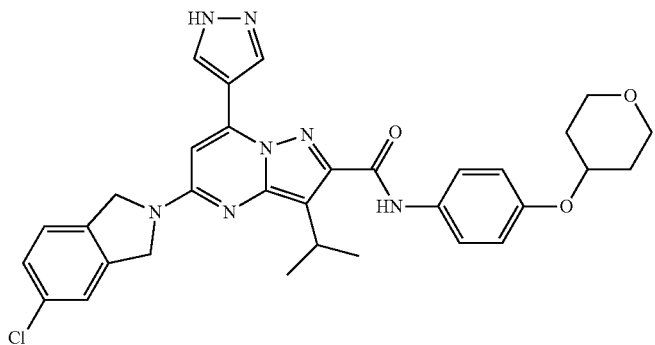 [SMILES: CC(C)c1c(C(=O)Nc2ccc(OC3CCOCC3)cc2)nn2c(-c3cn[nH]c3)cc(N3Cc4ccc(Cl)cc4C3)nc12]
119

120
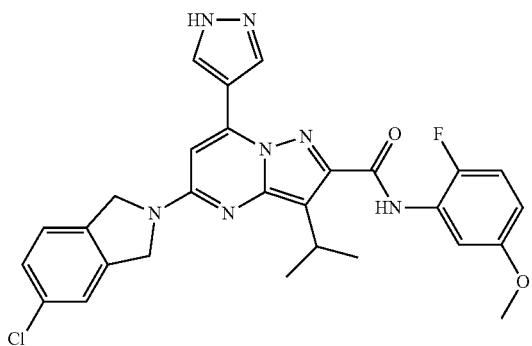 [SMILES: COc1ccc(F)c(NC(=O)c2nn3c(-c4cn[nH]c4)cc(N4Cc5ccc(Cl)cc5C4)nc3c2C(C)C)c1]
121
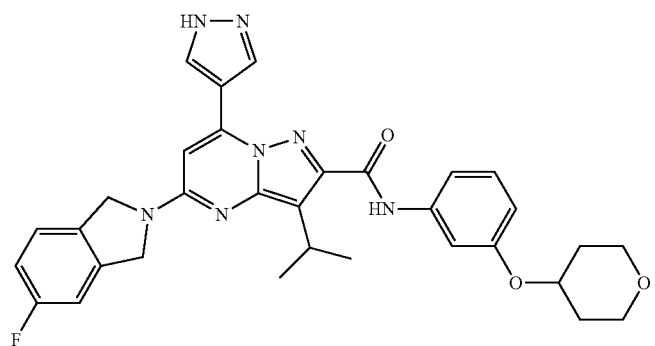 [SMILES: CC(C)c1c(C(=O)Nc2cccc(OC3CCOCC3)c2)nn2c(-c3cn[nH]c3)cc(N3Cc4ccc(F)cc4C3)nc12]
122
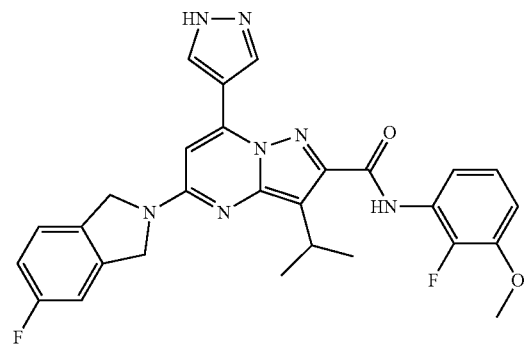
123
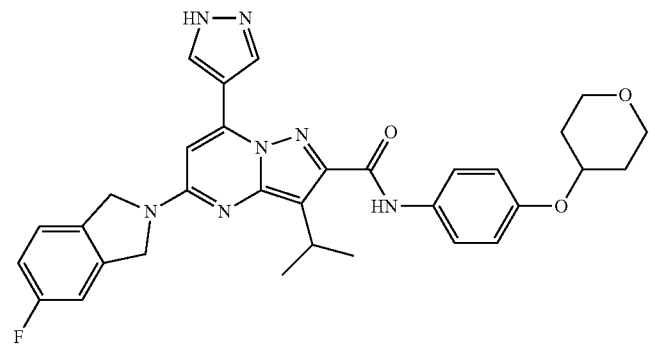 [SMILES: CC(C)c1c(C(=O)Nc2ccc(OC3CCOCC3)cc2)nn2c(-c3cn[nH]c3)cc(N3Cc4ccc(F)cc4C3)nc12]

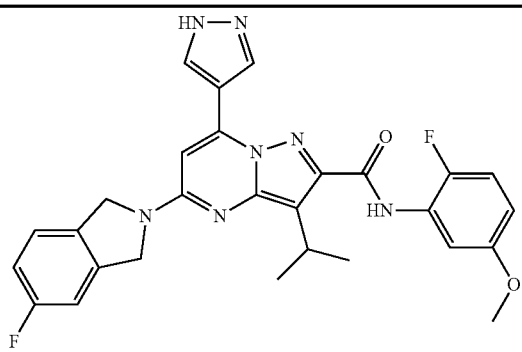
124
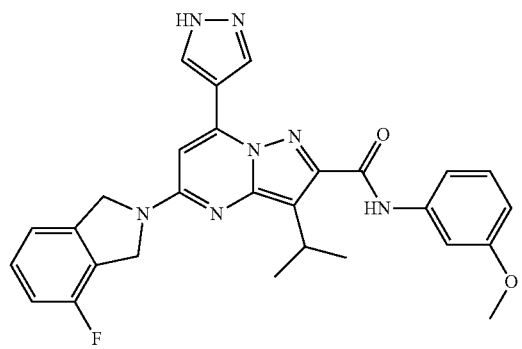 [SMILES: COc1cccc(NC(=O)c2nn3c(-c4cn[nH]c4)cc(N4Cc5cccc(F)c5C4)nc3c2C(C)C)c1]
125
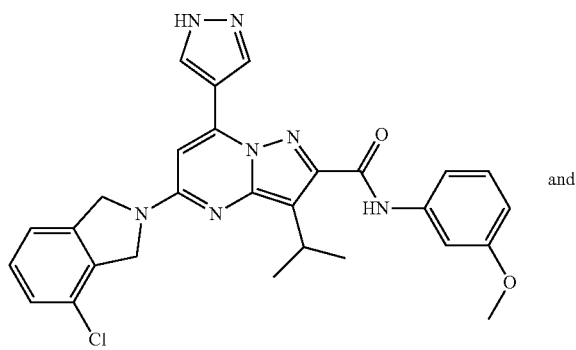 [SMILES: COc1cccc(NC(=O)c2nn3c(-c4cn[nH]c4)cc(N4Cc5cccc(Cl)c5C4)nc3c2C(C)C)c1]
126
and
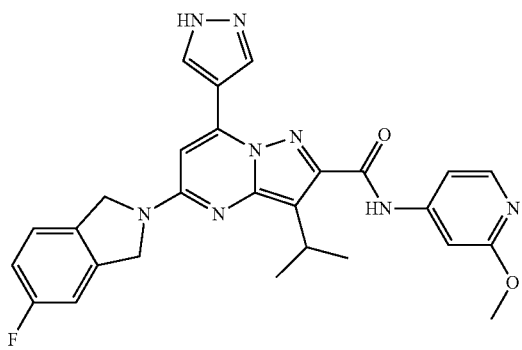 [SMILES: COc1cc(NC(=O)c2nn3c(-c4cn[nH]c4)cc(N4Cc5ccc(F)cc5C4)nc3c2C(C)C)ccn1]
127
or a pharmaceutically acceptable salt thereof.

12. A pharmaceutical composition comprising a compound according to claim 1, and a pharmaceutically acceptable diluent, excipient, or carrier.

13. A compound according to claim 1, wherein the compound is selected from the group consisting of:

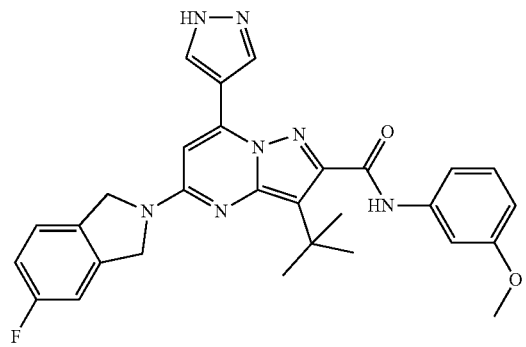

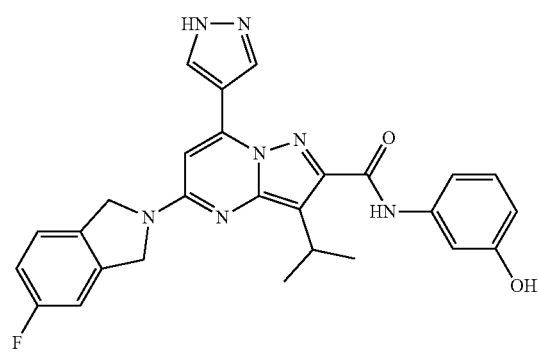

and or a pharmaceutically acceptable salt thereof.

14. A compound according to claim 1, wherein the compound is:

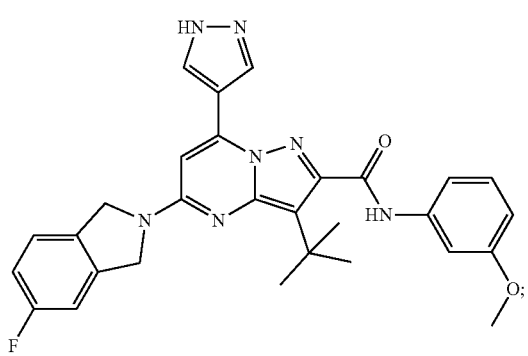

or a pharmaceutically acceptable salt thereof.

15. A compound according to claim 1, wherein the compound is:

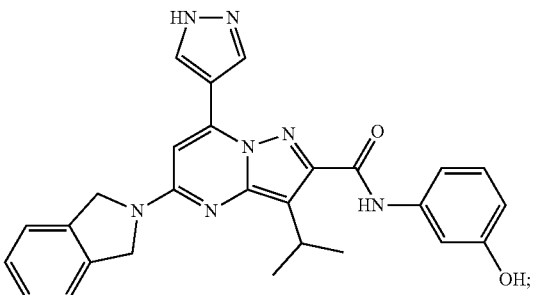

or a pharmaceutically acceptable salt thereof.

16. A compound according to claim 1, wherein the compound is:

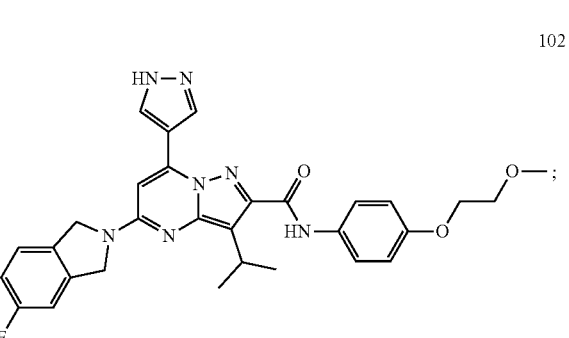

or a pharmaceutically acceptable salt thereof.

17. A compound according to claim 1, wherein the compound is:

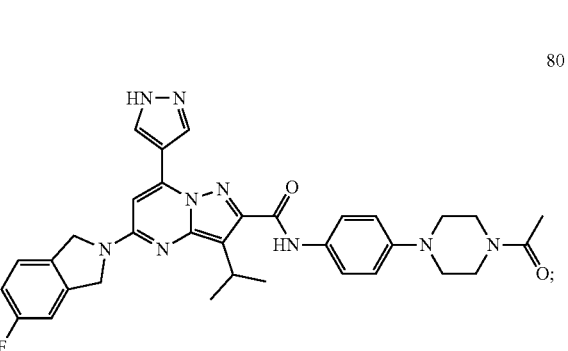

or a pharmaceutically acceptable salt thereof.

18. A compound according to claim 1, wherein the compound is:
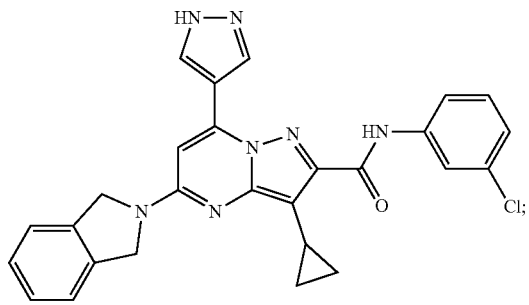
or a pharmaceutically acceptable salt thereof.
19. A compound according to claim 1, wherein the compound is:
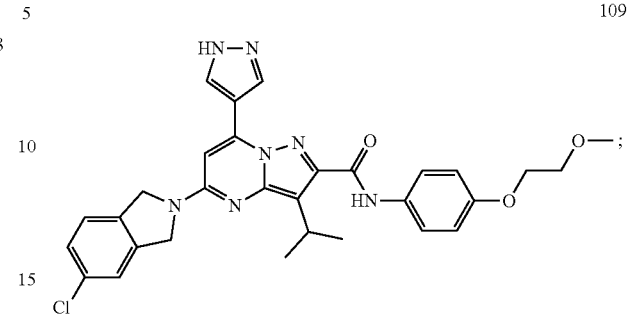
or a pharmaceutically acceptable salt thereof.
* * * * *